(12) United States Patent
Skaff et al.

(10) Patent No.: US 8,258,190 B2
(45) Date of Patent: *Sep. 4, 2012

(54) ENCAPSULATED CONTRAST AGENTS

(75) Inventors: Habib Skaff, Tampa, FL (US); Kurt Breitenkamp, Amherst, MA (US); Kevin N. Sill, Tampa, FL (US)

(73) Assignee: Intezyne Technologies, Inc., Tampa, FL (US)

(*) Notice: Subject to any disclaimer, the term of this patent is extended or adjusted under 35 U.S.C. 154(b) by 988 days.

This patent is subject to a terminal disclaimer.

(21) Appl. No.: 12/112,799

(22) Filed: Apr. 30, 2008

(65) Prior Publication Data

US 2009/0092554 A1    Apr. 9, 2009

Related U.S. Application Data

(60) Provisional application No. 60/915,014, filed on Apr. 30, 2007, provisional application No. 61/025,414, filed on Feb. 1, 2008.

(51) Int. Cl.
*A61K 47/00* (2006.01)
*A61B 5/055* (2006.01)
(52) U.S. Cl. .................... 514/772.1; 424/9.3
(58) Field of Classification Search .............. None
See application file for complete search history.

(56) References Cited

U.S. PATENT DOCUMENTS

| | | | |
|---|---|---|---|
| 4,650,750 A | 3/1987 | Giese | |
| 4,709,016 A | 11/1987 | Giese | |
| 5,360,819 A | 11/1994 | Giese | |
| 5,516,931 A | 5/1996 | Giese et al. | |
| 5,602,273 A | 2/1997 | Giese et al. | |
| 5,604,104 A | 2/1997 | Giese et al. | |
| 5,610,020 A | 3/1997 | Giese et al. | |
| 5,650,270 A | 7/1997 | Giese et al. | |
| 5,871,710 A | 2/1999 | Bogdanov et al. | |
| 2005/0058603 A1 | 3/2005 | Gao et al. | |
| 2006/0142506 A1 | 6/2006 | Breitenkamp et al. | |
| 2006/0172914 A1 | 8/2006 | Breitenkamp et al. | |
| 2006/0240092 A1* | 10/2006 | Breitenkamp et al. | 424/450 |
| 2008/0207913 A1 | 8/2008 | Breitenkamp et al. | |
| 2008/0274173 A1 | 11/2008 | Sill et al. | |
| 2008/0274965 A1 | 11/2008 | Breitenkamp et al. | |
| 2009/0110662 A1 | 4/2009 | Breitenkamp et al. | |

FOREIGN PATENT DOCUMENTS

| | | |
|---|---|---|
| WO | WO-2005/080032 | 9/2005 |
| WO | WO-2006/107903 | 10/2006 |
| WO | 2007069040 | 6/2007 |
| WO | 2007118884 | 10/2007 |

OTHER PUBLICATIONS

Trubetskoy VS, Gazelle GS, Wolf GL, Torchilin VP. Block-copolymer of polyethylene glycol and polylysine as a carrier of organic iodine: design of long-circulating particulate contrast medium for X-ray computed tomography. 1997 J. Drug Target. 4: 381-388.*

Thünemann AF, Schütt D, Kaufner L, Pison U, Möhwald H. Maghemite nanoparticles protectively coated with poly(ethylene imine) and poly(ethylene oxide)-block-poly(glutamic acid). 2006 Langmuir 22: 2351-2357. Published online Jan. 19, 2006.*

Vestal CR, Zhang ZJ. Synthesis and magnetic characterization of Mn and Co spinel ferrite-silica nanoparticles with tunable magnetic core. 2003 Nano Lett. 3: 1739-1743.*

Saravanan P, Alam S, Kandpal LD, Mathur GN. Effect of substitution of Mn ion on magnetic properties of Fe3O4 nanocrystallites. 2002 J. Mater. Sci. Lett. 21: 1135-1137.*

Said Hassane F, Frisch B, Schuber F. Targeted liposomes: convenient coupling of ligands to preformed vesicles using "click chemistry". 2006 Bioconjug. Chem. 17: 849-854. Published online Apr. 18, 2006.*

Markland P, Amidon GL, Yang VC. Modified polypeptides containing gamma-benzyl glutamic acid as drug delivery platforms. 1999 Int. J. Pharm. 178: 183-192.*

Torchilin VP. PEG-based micelles as carriers of contrast agents for different imaging modalities. 2002 Adv. Drug Deliv. Rev. 54: 235-252.*

Sakai et al. The structure of copolymers of L-proline with gamma-benzyl-L-glutamate in organic solvents, Bull Chem Soc. Japan. 1969, 42: 1332-1336.

Paolillo et al. "Nuclear magnetic resonance and optical spectroscopic studies of copolymers of polypeptides. II. Random copoly(benzyl-l-glutamate: benzyl-L-aspartate) and (benzyl-D-glutamate:benzyl-L-aspartate)" Biopolymers. 1972;11(10):2043-52.

Cho et al. "Synthesis and characterization of di- and triblock copolymers of poly(ethylene oxide) and poly(DL-valine-co-DL-leucine)" Polymer 44 (2003) 5497-5500.

Eby, GA. "Zinc ion availability—the determinant of efficacy in zinc lozenge treatment of common colds" J Antimicrob Chemother. Oct. 1997;40(4):483-93.

Salgado et al. "Controlling protein-protein interactions through metal coordination: assembly of a 16-helix bundle protein" J Am Chem. Soc. Nov. 7, 2007;129(44):13374-5.

Cannan et al. "Complex formation between carboxylic acids and divalent metal cations" J. Am. Chem. Soc. 1938, 60, 2314-2320.

Jeong et al. "Superparamagnetic colloids: controlled synthesis and niche applications" Adv. Mater. 2007, 19, 33-60.

Brus, L "Chemical Approaches to Semiconducting Nanoparticles" J. Phy. Chem. Solids 1998, 59, 459-465.

Wang et al. "Superparamagnetic Fe2O3 beads-CdSe/ZnS quantum dots core-shell nanocomposite particles for cell separation" Nano Letters 2004, 4, 409-413.

Yu et al. "Preparation and characterization of monodisperse PbSe semiconductor nanocrystals in a noncoordinating solvent" Chem. Mater. 2004, 16, 3318-3322.

Niederberger et al. "Organic reaction pathways in the nonaqueous synthesis of metal oxide nanoparticles" Chemistry European Journal. Sep. 25, 2006;12(28):7282-302.

(Continued)

*Primary Examiner* — Michael G Hartley
*Assistant Examiner* — Jennifer Lamberski

(57) ABSTRACT

The present invention relates to the field of polymer chemistry and more particularly to encapsulated contrast agents and methods for using the same.

15 Claims, 17 Drawing Sheets

OTHER PUBLICATIONS

Sun et al. "Size-controlled synthesis of magnetite nanoparticles" J Am Chem Soc. Jul. 17, 2002;124(28):8204-5.

Kumagai et al. "Iron hydroxide nanoparticles coated with poly(ethylene glycol)-poly(aspartic acid) block copolymer as novel magnetic resonance contrast agents for in vivo cancer imaging" Colloids Surf B Biointerfaces. Apr. 15, 2007;56 (1-2):174-81.

Kim et al. "Protective coating of superparamagnetic iron oxide nanoparticles" Chem. Mater. 2003, 15, 1617-1627.

AI et al. "Magnetite-loaded polymeric micelles as ultrasensitive magnetic-resonance probes" Adv. Mater. 2005, 17, 1949-1952.

Lee et al. "Artificially engineered magnetic nanoparticles for ultrasensitive molecular imaging" Nature Medicine, 2007, 13, 95-99.

Pan et al. "Folic acid-conjugated nanostructured materials designed for cancer cell targeting" Chem. Commun. 2003, 2400-2401.

Gabizon et al. "Tumor cell targeting of liposome-entrapped drugs with phospholipid-anchored folic acid-PEG conjugates" Adv Drug Deliv Rev. Apr. 29, 2004;56(8):1177-92.

Reynolds et al. "Insertion of an RGD motif into the HI loop of adenovirus fiber protein alters the distribution of transgene expression of the systemically administered vector" Gene Ther. Jul. 1999;6(7):1336-9.

Derycke et al. "Transferrin-conjugated liposome targeting of photosensitizer AlPcS4 to rat bladder carcinoma cells" J Natl Cancer Inst. Nov. 3, 2004;96(21):1620-30.

Nasongkla et al. "cRGD-functionalized polymer micelles for targeted doxorubicin delivery" Angew Chem Int Ed Engl. Nov. 26, 2004;43(46):6323-7.

Jule et al. "Lactose-installed poly(ethylene glycol)poly(d,l-lactide) block copolymer micelles exhibit fast-rate binding and high affinity toward a protein bed simulating a cell surface. A surface plasmon resonance study" Bioconjug Chem. Jan.-Feb. 2003;14(1):177-86.

Stubenrauch et al. "Conjugation of an antibody Fv fragment to a virus coat protein: cell-specific targeting of recombinant polyoma-virus-like particles" Biochem J. Jun. 15, 2001;356(Pt 3):867-73.

Kurschus et al. "Killing of target cells by redirected granzyme B in the absence of perforin" FEBS Lett. Mar. 26, 2004;562(1-3):87-92.

Jones et al. "Antibodies for targeted gene therapy: extracellular gene targeting and intracellular expression" Adv Drug Deliv Rev. Apr. 6, 1998;31(1-2):153-170.

Kolb et al. "Click Chemistry: Diverse Chemical Function from a Few Good Reactions" Angew. Chem. Int. Ed. 2001, 40, 2004-2021.

Wang et al. "Bioconjugation by Copper(I)-Catalyzed Azide-Alkyne [3+2] Cycloaddition" J. Am. Chem. Soc. 2003, 125, 3192-3193.

Link et al. "Presentation and detection of azide functionality in bacterial cell surface proteins" J Am Chem Soc. Sep. 1, 2004;126(34):10598-602.

Deiters et al. "Adding amino acids with novel reactivity to the genetic code of Saccharomyces cerevisiae" J Am Chem Soc. Oct. 1, 2003;125(39):11782-3.

Allen et al. "Nano-engineering block copolymer aggregates for drug delivery" Colloid Surface B 1999, 16, 3-27.

Nasongkla et al. "Multifunctional polymeric micelles as cancer-targeted, MRI-ultrasensitive drug delivery systems" Nano Lett. Nov. 2006;6(11):2427-30.

Torchilin VP PEG-based micelles as carriers of contrast agents for different imaging modalities. Adv Drug Deliv Rev. Feb. 21, 2002;54(2):235-52.

Khemtong et al. "In vivo off-resonance saturation magnetic resonance imaging of AVB3-targeted superparamagnetic nanoparticles" Cancer Res 2009;69(4):1651-8.

Barcena et al. "Zinc ferrite nanoparticles as MRI contrast agents" Chem Commun (Camb). May 21, 2008;(19):2224-6.

Lee et al. "Antibiofouling polymer-coated superparamagnetic iron oxide nanoparticles as potential magnetic resonance contrast agents for in vivo cancer imaging" J Am Chem Soc. Jun. 7, 2006;128(22):7383-9.

Nakamura et al. "A polymeric micelle MRI contrast agent with changeable relaxivity" J Control Release. Sep. 12, 2006;114(3):325-33.

Bakar, et al. "The chemical speciation of zinc in human saliva: possible correlation with reduction of the symptoms of the common cold produced by zinc gluconate-containing lozenges" Chem. Spec. Bioavail. 1999;11:95-101.

Office Action dated Feb. 17, 2009 for co-pending U.S. Appl. No. 11/325,020 published as US 20060172914.

Imai et al., "A Novel Contrast Medium Detects Increased Permeability of Rat Injured Carotid Arteries in Magnetic Resonance T2 Mapping Imaging," Journal of Atherosclerosis and Thrombosis, 14(2):65-71 (2007).

Kaufner et al., "Poly(ethylene oxide)-*block*- poly(glutamic acid) coated maghemite nanoparticles: in vitro characterization an in vivo behaviour," Nanotechnology, 18:1-10 (2007).

Park et al., "Polymeric nanomedicine for cancer therapy," Prog. Polym. Sci., 33:113-137 (2008).

Van Domeselaar et al., "Application of solid phase peptide synthesis to engineering PEO-peptide block copolymers for drug delivery," Colloids and Surfaces B: Biointerfaces, 30:323-334 (2003).

International Search Report from PCT/US2008/062038, mailed Apr. 27, 2009, 5 pages.

Written Opinion from PCT/US2008/062038, mailed Apr. 27, 2009, 7 pages.

\* cited by examiner

Example Images (R1):

1. 1/10 dilution
2. 1/50 dilution
3. 1/200 dilution
4. 1/1000 dilution
5. 1/500 dilution
6. 1/5000 dilution
7. Water TR = 0.1s TR = .7s TR = 1s TR = 5s Example Images (R2):

1. 1/10 dilution
2. 1/50 dilution
3. 1/200 dilution
4. 1/1000 dilution
5. 1/500 dilution
6. 1/5000 dilution
7. Water TE = 0.01s    TE = 0.025s TE = 0.05s    TE = 0.15s Example Images (R1):HS-2-165

1.) 0.01 x 15mg/ml
2.) 0.02 x 15mg/ml
3.) 0.04 x 15mg/ml
4.) 0.067 x 15mg/ml
5.) 0.1 x 15mg/ml

TR = 1s        TR = 2s

TR = 4s        TR = 7s

Example Images (R1):HS-2-166

1.) 0.01 x 15mg/ml
2.) 0.02 x 15mg/ml
3.) 0.04 x 15mg/ml
4.) 0.067 x 15mg/ml
5.) 0.1 x 15mg/ml

TR = 1s TR = 2s

TR = 4s TR = 7s

Example Images (R2):HS-2-166

1.) 0.01 x 15mg/ml
2.) 0.02 x 15mg/ml
3.) 0.04 x 15mg/ml
4.) 0.067 x 15mg/ml
5.) 0.1 x 15mg/ml

TE = 8ms          TE = 20ms

TE = 30ms         TE = 75ms

Example Images (R1):HS-2-177

1.) 0.300 mg/ml
2.) 0.200 mg/ml
3.) 0.120 mg/ml
4.) 0.060 mg/ml
5.) 0.030 mg/ml

TR = .1s TR = .75s

TR = 2s TR = .4s

ENCAPSULATED CONTRAST AGENTS

CROSS-REFERENCE TO RELATED APPLICATIONS

The present application claims priority to U.S. provisional patent application Ser. No. 60/915,014, filed Apr. 30, 2007, and U.S. provisional patent application Ser. No. 61/025,414, filed Feb. 1, 2008, the entirety of each of which is hereby incorporated herein by reference.

FIELD OF THE INVENTION

The present invention relates to the field of polymer chemistry and more particularly to encapsulated contrast agents and uses thereof.

BACKGROUND OF THE INVENTION

The development of new therapeutic agents has dramatically improved the quality of life and survival rate of patients suffering from a variety of disorders. However, drug delivery innovations are needed to improve the success rate of these treatments. Specifically, delivery systems are still needed which effectively minimize premature excretion and/or metabolism of therapeutic agents and deliver these agents specifically to diseased cells thereby reducing their toxicity to healthy cells.

Rationally-designed, nanoscopic drug carriers, or "nanovectors," offer a promising approach to achieving these goals due to their inherent ability to overcome many biological barriers. Moreover, their multi-functionality permits the incorporation of cell-targeting groups, diagnostic agents, and a multitude of drugs in a single delivery system. Polymer micelles, formed by the molecular assembly of functional, amphiphilic block copolymers, represent one notable type of multifunctional nanovector.

Polymer micelles are particularly attractive due to their ability to deliver large payloads of a variety of drugs (e.g. small molecule, proteins, and DNA/RNA therapeutics), their improved in vivo stability as compared to other colloidal carriers (e.g. liposomes), and their nanoscopic size which allows for passive accumulation in diseased tissues, such as solid tumors, by the enhanced permeation and retention (EPR) effect. Using appropriate surface functionality, polymer micelles are further decorated with cell-targeting groups and permeation enhancers that can actively target diseased cells and aid in cellular entry, resulting in improved cell-specific delivery.

While self assembly represents a convenient method for the bottom-up design of nanovectors, the forces that drive and sustain the assembly of polymer micelles are concentration dependent and inherently reversible. In clinical applications, where polymer micelles are rapidly diluted following administration, this reversibility, along with high concentrations of micelle-destabilizing blood components (e.g. proteins, lipids, and phospholipids), often leads to premature dissociation of the loaded micelle before active or passive targeting is effectively achieved. For polymer micelles to fully reach their cell-targeting potential and exploit their envisioned multi-functionality, in vivo circulation time must be improved. Drug delivery vehicles are needed, which are infinitely stable to post-administration dilution, can avoid biological barriers (e.g. reticuloendothelial system (RES) uptake), and deliver drugs, or other therapeutic agents, in response to the physiological environment encountered in diseased tissues, such as solid tumors.

DETAILED DESCRIPTION OF CERTAIN EMBODIMENTS OF THE INVENTION

Figure 1:
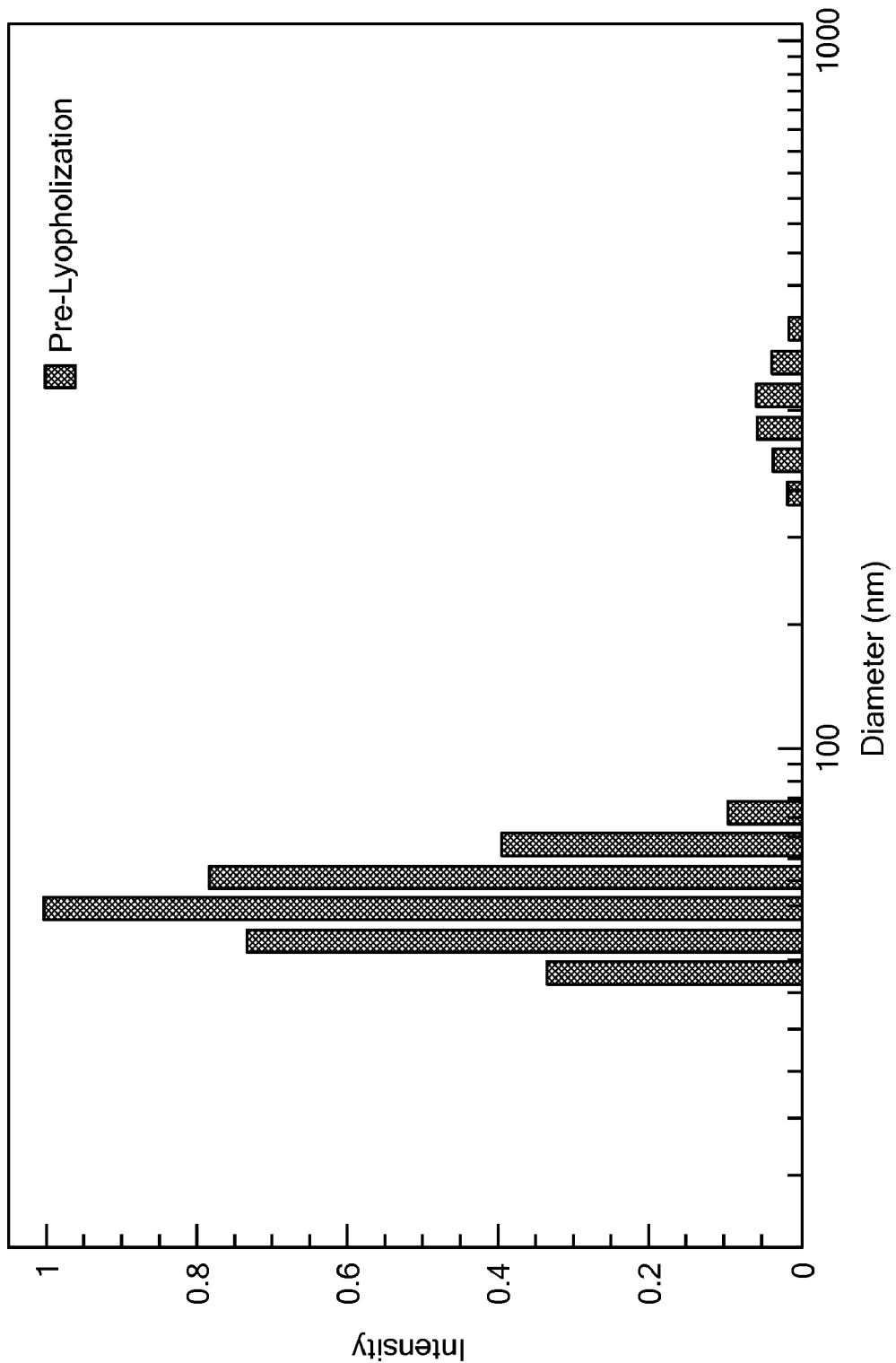
FIG. 1 depicts the results of dynamic light scattering on an exemplary iron oxide nanoparticle-loaded micelle in deionized water.

1. General Description:

Polymer micelles for use in the present invention are described in detail in International Patent Application publication number WO2006/107903, published Oct. 12, 2006, the entirety of which is incorporated herein by reference.

One embodiment of the present invention provides a micelle having a contrast agent encapsulated therein, comprising a multiblock copolymer which comprises a polymeric hydrophilic block, optionally a poly(amino acid block) that is optionally crosslinkable or crosslinked, and another poly(amino acid) block, characterized in that said micelle has an inner core, optionally a crosslinkable or crosslinked outer core, and a hydrophilic shell.

2. Definitions:

Compounds of this invention include those described generally above, and are further illustrated by the embodiments, sub-embodiments, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As used herein, the term "contrast agent" (also known as "contrast media" and "radiocontrast agents") refers to a compound used to improve the visibility of internal bodily structures during imaging. Such imaging methods are well known to one of ordinary skill in the art and include MRI, PET, ultrasound, X-ray, computed tomography, or Fluorescence imaging. Such agents include semiconductor materials, such as CdSe, CdS, CdTe, PdSe, CdSe/CdS, CdSe/ZnS, CdS/ZnS, and CdTe/ZnS. Contrast agents also include magnetic materials such as: Fe, $Fe_2O_3$, $Fe_3O_4$, $MnFe_2O_4$, $CoFe_2O_4$, $NiFe_2O_4$, Co, Ni, FePt, CoPt, CoO, $Fe_3Pt$, $Fe_2Pt$, $CO_3Pt$, $CO_2Pt$, and FeOOH.

As used herein, the term "sequential polymerization", and variations thereof, refers to the method wherein, after a first monomer (e.g. NCA, lactam, or imide) is incorporated into the polymer, thus forming an amino acid "block", a second monomer (e.g. NCA, lactam, or imide) is added to the reaction to form a second amino acid block, which process may be continued in a similar fashion to introduce additional amino acid blocks into the resulting multi-block copolymers.

As used herein, the term "multiblock copolymer" refers to a polymer comprising one synthetic polymer portion and two or more poly(amino acid) portions. Such multi-block copolymers include those having the format W—X'—X", wherein W is a synthetic polymer portion and X and X' are poly(amino acid) chains or "amino acid blocks". In certain embodiments, the multiblock copolymers of the present invention are triblock copolymers. As described herein, one or more of the amino acid blocks may be "mixed blocks", meaning that these blocks can contain a mixture of amino acid monomers thereby creating multiblock copolymers of the present invention. In some embodiments, the multiblock copolymers of the present invention comprise a mixed amino acid block and are tetrablock copolymers.

As used herein, the term "triblock copolymer" refers to a polymer comprising one synthetic polymer portion and two poly(amino acid) portions.

As used herein, the term "tetrablock copolymer" refers to a polymer comprising one synthetic polymer portion and either two poly(amino acid) portions, wherein 1 poly(amino acid) portion is a mixed block or a polymer comprising one synthetic polymer portion and three poly(amino acid) portions.

As used herein, the term "inner core" as it applies to a micelle of the present invention refers to the center of the micelle formed by the second (i.e., terminal) poly(amino acid) block. In accordance with the present invention, the inner core is not crosslinked. By way of illustration, in a triblock polymer of the format W—X'—X", as described above, the inner core corresponds to the X" block. It is contemplated that the X" block can be a mixed block.

As used herein, the term "outer core" as it applies to a micelle of the present invention refers to the layer formed by the first poly(amino acid) block. The outer core lies between the inner core and the hydrophilic shell. In accordance with the present invention, the outer core is either crosslinkable or is cross-linked. By way of illustration, in a triblock polymer of the format W—X'—X", as described above, the outer core corresponds to the X' block. It is contemplated that the X' block can be a mixed block.

As used herein, the terms "contrast agent-loaded" and "encapsulated", and derivatives thereof, are used interchangeably. In accordance with the present invention, a "contrast agent-loaded" micelle refers to a micelle having a contrast agent situated within the core of the micelle. This is also referred to as a contrast agent being "encapsulated" within the micelle.

As used herein, the term "polymeric hydrophilic block" refers to a polymer that is not a poly(amino acid) and is hydrophilic in nature. Such hydrophilic polymers are well known in the art and include polyethylene oxide (also referred to as polyethylene glycol or PEG), and derivatives thereof, poly(N-vinyl-2-pyrolidone), and derivatives thereof, poly(N-isopropylacrylamide), and derivatives thereof, poly(hydroxyethyl acrylate), and derivatives thereof, poly(hydroxyethyl methacrylate), and derivatives thereof, and polymers of N-(2-hydroxypropoyl)methacrylamide (HMPA) and derivatives thereof.

As used herein, the term "poly(amino acid)" or "amino acid block" refers to a covalently linked amino acid chain wherein each monomer is an amino acid unit. Such amino acid units include natural and unnatural amino acids. In certain embodiments, each amino acid unit is in the L-configuration. Such poly(amino acids) include those having suitably protected functional groups. For example, amino acid monomers may have hydroxyl or amino moieties which are optionally protected by a suitable hydroxyl protecting group or a suitable amine protecting group, as appropriate. Such suitable hydroxyl protecting groups and suitable amine protecting groups are described in more detail herein, infra. As used herein, an amino acid block comprises one or more monomers or a set of two or more monomers. In certain embodiments, an amino acid block comprises one or more monomers such that the overall block is hydrophilic. In other embodiments, an amino acid block comprises one or more monomers such that the overall block is hydrophobic. In still other embodiments, amino acid blocks of the present invention include random amino acid blocks, ie blocks comprising a mixture of amino acid residues.

As used herein, the phrase "natural amino acid side-chain group" refers to the side-chain group of any of the 20 amino acids naturally occurring in proteins. Such natural amino acids include the nonpolar, or hydrophobic amino acids, glycine, alanine, valine, leucine isoleucine, methionine, phenylalanine, tryptophan, and proline. Cysteine is sometimes classified as nonpolar or hydrophobic and other times as polar. Natural amino acids also include polar, or hydrophilic amino acids, such as tyrosine, serine, threonine, aspartic acid (also known as aspartate, when charged), glutamic acid (also known as glutamate, when charged), asparagine, and glutamine. Certain polar, or hydrophilic, amino acids have charged side-chains. Such charged amino acids include lysine, arginine, and histidine. One of ordinary skill in the art would recognize that protection of a polar or hydrophilic amino acid side-chain can render that amino acid nonpolar. For example, a suitably protected tyrosine hydroxyl group can render that tyroine nonpolar and hydrophobic by virtue of protecting the hydroxyl group.

As used herein, the phrase "unnatural amino acid side-chain group" refers to amino acids not included in the list of 20 amino acids naturally occurring in proteins, as described above. Such amino acids include the D-isomer of any of the 20 naturally occurring amino acids. Unnatural amino acids also include homoserine, DOPA (also referred to as levodopa or 3,4-dihydroxy phenyl alanine), ornithine, and thyroxine. Other unnatural amino acids side-chains are well know to one of ordinary skill in the art and include unnatural aliphatic side chains. Other unnatural amino acids include modified amino acids, including those that are N-alkylated, cyclized, phosphorylated, acetylated, amidated, azidylated, labelled, and the like.

As used herein, the phrase "living polymer chain-end" refers to the terminus resulting from a polymerization reaction which maintains the ability to react further with additional monomer or with a polymerization terminator.

As used herein, the term "termination" refers to attaching a terminal group to a polymer chain-end by the reaction of a living polymer with an appropriate compound. Alternatively, the term "termination" may refer to attaching a terminal group to an amine or hydroxyl end, or derivative thereof, of the polymer chain.

As used herein, the term "polymerization terminator" is used interchangeably with the term "polymerization terminating agent" and refers to a compound that reacts with a living polymer chain-end to afford a polymer with a terminal group. Alternatively, the term "polymerization terminator" may refer to a compound that reacts with an amine or hydroxyl end, or derivative thereof, of the polymer chain, to afford a polymer with a terminal group.

As used herein, the term "polymerization initiator" refers to a compound, which reacts with, or whose anion or free base form reacts with, the desired monomer in a manner which results in polymerization of that monomer. In certain embodiments, the polymerization initiator is the compound that reacts with an alkylene oxide to afford a polyalkylene oxide block. In other embodiments, the polymerization initiator is the amine salt described herein.

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-20 carbon atoms. In some embodiments, aliphatic groups contain 1-10 carbon atoms. In other embodiments, aliphatic groups contain 1-8 carbon atoms. In still other embodiments, aliphatic groups contain 1-6 carbon atoms, and in yet other embodiments aliphatic groups contain 1-4 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "heteroatom" means one or more of oxygen, sulfur, nitrogen, phosphorus, or silicon. This includes any oxidized form of nitrogen, sulfur, phosphorus, or silicon; the quaternized form of any basic nitrogen, or; a substitutable nitrogen of a heterocyclic ring including =N— as in 3,4-dihydro-2H-pyrrolyl, —NH— as in pyrrolidinyl, or =N(R$^\dagger$)— as in N-substituted pyrrolidinyl.

The term "unsaturated", as used herein, means that a moiety has one or more units of unsaturation.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains three to seven ring members. The term "aryl" may be used interchangeably with the term "aryl ring".

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R$^\circ$; —(CH$_2$)$_{0-4}$OR$^\circ$; —O—(CH$_2$)$_{0-4}$C(O)OR$^\circ$; —(CH$_2$)$_{0-4}$—CH(OR$^\circ$)$_2$; —(CH$_2$)$_{0-4}$SR$^\circ$; —(CH$_2$)$_{0-4}$Ph, which may be substituted with R$^\circ$; —(CH$_2$)$_{0-4}$O(CH$_2$)$_{0-1}$Ph which may be substituted with R$^\circ$; —CH=CHPh, which may be substituted with R$^\circ$; —NO$_2$; —CN; —N$_3$; —(CH$_2$)$_{0-4}$N(R$^\circ$)$_2$; —(CH$_2$)$_{0-4}$N(R$^\circ$)C(O)R$^\circ$; —N(R$^\circ$)C(S)R$^\circ$; —(CH$_2$)$_{0-4}$N(R$^\circ$)C(O)NR$^\circ_2$; —N(R$^\circ$)C(S)NR$^\circ_2$; —(CH$_2$)$_{0-4}$N(R$^\circ$)C(O)OR$^\circ$; —N(R$^\circ$)N(R$^\circ$)C(O)R$^\circ$; —N(R$^\circ$)N(R$^\circ$)C(O)NR$^\circ_2$; —N(R$^\circ$)N(R$^\circ$)C(O)OR$^\circ$; —(CH$_2$)$_{0-4}$C(O)R$^\circ$; —C(S)R$^\circ$; —(CH$_2$)$_{0-4}$C(O)OR$^\circ$; —(CH$_2$)$_{0-4}$C(O)SR$^\circ$; —(CH$_2$)$_{0-4}$C(O)OSiR$^\circ_3$; —(CH$_2$)$_{0-4}$OC(O)R$^\circ$; —OC(O)(CH$_2$)$_{0-4}$SR—, SC(S)SR$^\circ$; —(CH$_2$)$_{0-4}$SC(O)R$^\circ$; —(CH$_2$)$_{0-4}$C(O)NR$^\circ_2$; —C(S)NR$^\circ_2$; —C(S)SR$^\circ$; —SC(S)SR$^\circ$, —(CH$_2$)$_{0-4}$OC(O)NR$^\circ_2$; —C(O)N(OR$^\circ$)R$^\circ$; —C(O)C(O)R$^\circ$; —C(O)CH$_2$C(O)R$^\circ$; —C(NOR$^\circ$)R$^\circ$; —(CH$_2$)$_{0-4}$SSR$^\circ$; —(CH$_2$)$_{0-4}$S(O)$_2$R$^\circ$; —(CH$_2$)$_{0-4}$S(O)$_2$OR$^\circ$; —(CH$_2$)$_{0-4}$OS(O)$_2$R$^\circ$; —S(O)$_2$NR$^\circ_2$; —(CH$_2$)$_{0-4}$S(O)R$^\circ$; —N(R$^\circ$)S(O)$_2$NR$^\circ_2$; —N(R$^\circ$)S(O)$_2$R$^\circ$; —N(OR$^\circ$)R$^\circ$; —C(NH)NR$^\circ_2$; —P(O)$_2$R$^\circ$; —P(O)R$^\circ_2$; —OP(O)R$^\circ_2$; —OP(O)(OR$^\circ$)$_2$; SiR$^\circ_3$; —(C$_{1-4}$ straight or branched alkylene)O—N(R$^\circ$)$_2$; or —(C$_{1-4}$ straight or branched alkylene)C(O)O—N(R$^\circ$)$_2$, wherein each R$^\circ$ may be substituted as defined below and is independently hydrogen, C$_{1-6}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur, or, notwithstanding the definition above, two independent occurrences of R$^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R$^\circ$ (or the ring formed by taking two independent occurrences of R$^\circ$ together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet_2$, —NO$_2$, —SiR$^\bullet_3$, —OSiR$^\bullet_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R$^\circ$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. A suitable tetravalent substituent that is bound to vicinal substitutable methylene carbons of an "optionally substituted" group is the dicobalt hexacarbonyl cluster represented by

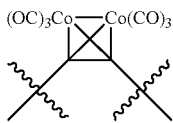

when depicted with the methylenes which bear it.

Suitable substituents on the aliphatic group of R* include halogen, —R$^\bullet$, -(haloR$^\bullet$), —OH, —OR$^\bullet$, —O(halo$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger_2$, —C(S)NR$^\dagger_2$, —C(NH)NR$^\dagger_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —ORE, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Protected hydroxyl groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Examples of suitably protected hydroxyl groups further include, but are not limited to, esters, carbonates, sulfonates allyl ethers, ethers, silyl ethers, alkyl ethers, arylalkyl ethers, and alkoxyalkyl ethers. Examples of suitable esters include formates, acetates, propionates, pentanoates, crotonates, and benzoates. Specific examples of suitable esters include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetate), crotonate, 4-methoxy-crotonate, benzoate, p-benzylbenzoate, 2,4,6-trimethylbenzoate. Examples of suitable carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of suitable silyl ethers include trimethylsilyl, triethylsilyl, t-butyldimethylsilyl, t-butyldiphenylsilyl, triisopropylsilyl ether, and other trialkylsilyl ethers. Examples of suitable alkyl ethers include methyl, benzyl, p-methoxybenzyl, 3,4-dimethoxybenzyl, trityl, t-butyl, and allyl ether, or derivatives thereof. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyran-2-yl ether. Examples of suitable arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

Protected amines are well known in the art and include those described in detail in Greene (1999). Suitable mono-protected amines further include, but are not limited to, aralkylamines, carbamates, allyl amines, amides, and the like. Examples of suitable mono-protected amino moieties include t-butyloxycarbonylamino (—NHBOC), ethyloxycarbonylamino, methyloxycarbonylamino, trichloroethyloxycarbonylamino, allyloxycarbonylamino (—NHAlloc), benzyloxocarbonylamino (—NHCBZ), allylamino, benzylamino (—NHBn), fluorenylmethylcarbonyl (—NHFmoc), formamido, acetamido, chloroacetamido, dichloroacetamido, trichloroacetamido, phenylacetamido, trifluoroacetamido, benzamido, t-butyldiphenylsilyl, and the like. Suitable di-protected amines include amines that are substituted with two substituents independently selected from those described above as mono-protected amines, and further include cyclic imides, such as phthalimide, maleimide, succinimide, and the like. Suitable di-protected amines also include pyrroles and the like, 2,2,5,5-tetramethyl-[1,2,5]azadisilolidine and the like, and azide.

Protected aldehydes are well known in the art and include those described in detail in Greene (1999). Suitable protected aldehydes further include, but are not limited to, acyclic acetals, cyclic acetals, hydrazones, imines, and the like. Examples of such groups include dimethyl acetal, diethyl acetal, diisopropyl acetal, dibenzyl acetal, bis(2-nitrobenzyl) acetal, 1,3-dioxanes, 1,3-dioxolanes, semicarbazones, and derivatives thereof.

Protected carboxylic acids are well known in the art and include those described in detail in Greene (1999). Suitable protected carboxylic acids further include, but are not limited to, optionally substituted C$_{1-6}$ aliphatic esters, optionally substituted aryl esters, silyl esters, activated esters, amides, hydrazides, and the like. Examples of such ester groups include methyl, ethyl, propyl, isopropyl, butyl, isobutyl, benzyl, and phenyl ester, wherein each group is optionally substituted. Additional suitable protected carboxylic acids include oxazolines and ortho esters.

Protected thiols are well known in the art and include those described in detail in Greene (1999). Suitable protected thiols further include, but are not limited to, disulfides, thioethers, silyl thioethers, thioesters, thiocarbonates, and thiocarbamates, and the like. Examples of such groups include, but are not limited to, alkyl thioethers, benzyl and substituted benzyl thioethers, triphenylmethyl thioethers, and trichloroethoxycarbonyl thioester, to name but a few.

A "crown ether moiety" is the radical of a crown ether. A crown ether is a monocyclic polyether comprised of repeating units of —$CH_2CH_2O$—. Examples of crown ethers include 12-crown-4, 15-crown-5, and 18-crown-6.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as in neutron scattering experiments, as analytical tools or probes in biological assays.

As used herein, the term "detectable moiety" is used interchangeably with the term "label" and relates to any moiety capable of being detected (e.g., primary labels and secondary labels). A "detectable moiety" or "label" is the radical of a detectable compound.

"Primary" labels include radioisotope-containing moieties (e.g., moieties that contain $^{32}P$, $^{33}P$, $^{35}S$, or $^{14}C$), mass-tags, and fluorescent labels, and are signal-generating reporter groups which can be detected without further modifications.

Other primary labels include those useful for positron emission tomography including molecules containing radioisotopes (e.g. $^{18}F$) or ligands with bound radioactive metals (e.g. $^{62}Cu$). In other embodiments, primary labels are contrast agents for magnetic resonance imaging such as gadolinium, gadolinium chelates, or iron oxide (e.g. $Fe_3O_4$ and $Fe_2O_3$) particles. Similarly, semiconducting nanoparticles (e.g. cadmium selenide, cadmium sulfide, cadmium telluride) are useful as fluorescent labels. Other metal nanoparticles (e.g. colloidal gold) also serve as primary labels.

"Secondary" labels include moieties such as biotin, or protein antigens, that require the presence of a second compound to produce a detectable signal. For example, in the case of a biotin label, the second compound may include streptavidin-enzyme conjugates. In the case of an antigen label, the second compound may include an antibody-enzyme conjugate. Additionally, certain fluorescent groups can act as secondary labels by transferring energy to another compound or group in a process of nonradiative fluorescent resonance energy transfer (FRET), causing the second compound or group to then generate the signal that is detected.

Unless otherwise indicated, radioisotope-containing moieties are optionally substituted hydrocarbon groups that contain at least one radioisotope. Unless otherwise indicated, radioisotope-containing moieties contain from 1-40 carbon atoms and one radioisotope. In certain embodiments, radioisotope-containing moieties contain from 1-20 carbon atoms and one radioisotope.

The terms "fluorescent label", "fluorescent group", "fluorescent compound", "fluorescent dye", and "fluorophore", as used herein, refer to compounds or moieties that absorb light energy at a defined excitation wavelength and emit light energy at a different wavelength. Examples of fluorescent compounds include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4', 5',7'-Tetra-bromosulfone-fluorescein, Tetramethylrhodamine (TMR), Carboxytetramethylrhodamine (TAMRA), Texas Red, Texas Red-X.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-Methoxytetrafluorobenzyl)oxy]phenyl]-3-methylglyceronyl]isonipecotic Acid, 4'-[2,3,5,6-Tetrafluoro-4-(pentafluorophenoxyl)]methyl acetophenone, and their derivatives. The synthesis and utility of these mass-tags is described in U.S. Pat. Nos. 4,650,750, 4,709,016, 5,360,8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags.

The term "substrate", as used herein refers to any material or macromolecular complex to which a functionalized endgroup of a block copolymer can be attached. Examples of commonly used substrates include, but are not limited to, glass surfaces, silica surfaces, plastic surfaces, metal surfaces, surfaces containing a metallic or chemical coating, membranes (e.g., nylon, polysulfone, silica), micro-beads (e.g., latex, polystyrene, or other polymer), porous polymer matrices (e.g., polyacrylamide gel, polysaccharide, polymethacrylate), macromolecular complexes (e.g., protein, polysaccharide).

3. Description of Exemplary Embodiments:

A. Multiblock Copolymers

As described generally above, one embodiment of the present invention provides a micelle having a contrast agent encapsulated therein, comprising a multiblock copolymer which comprises a polymeric hydrophilic block, optionally a poly(amino acid block) that is optionally crosslinkable or crosslinked, and another poly(amino acid) block, characterized in that said micelle has an inner core, optionally a crosslinkable or crosslinked outer core, and a hydrophilic shell.

Amphiphilic multiblock copolymers, as described herein, can self-assemble in aqueous solution to form nano- and micron-sized structures. In water, these amphiphilic multiblock copolymers assemble by multi-molecular micellization when present in solution above the critical micelle concentration (CMC). Without wishing to be bound by any particular theory, it is believed that the hydrophobic poly(amino acid) portion or "block" of the copolymer collapses to form the micellar core, while the hydrophilic PEG block forms a peripheral corona and imparts water solubility. In certain embodiments, the multiblock copolymers in accordance with the present invention possess distinct hydrophobic and hydrophilic segments that form micelles. In addition, these multiblock polymers comprise a poly(amino acid) block which contains functionality suitable for crosslinking. It will be appreciated that this functionality is found on the corresponding amino acid side-chain.

Multiblock copolymers of the present invention contain one or more poly(amino acid) blocks and a water-soluble polymer block. Poly(amino acid) (PAA) segments possess a wide range of functionality and are natural building blocks with inherent biocompatibility. In addition, PAA copolymers are hydrolytically stable and can tolerate most chemical transformation conditions yet can be enzymatically degradable.

In certain embodiments, the PEG block possesses a molecular weight of approx. 10,000 Da (225 repeat units) and contains at least one terminal ammonium salt used to initiate the synthesis of poly(amino acid) multi-block copolymers. In some embodiments, the PEG block possesses a molecular weight of approx. 12,000 Da (270 repeat units) and contains at least one terminal ammonium salt used to initiate the synthesis of poly(amino acid) multi-block copolymers. Without wishing to be bound by theory, it is believed that this particular PEG chain length imparts adequate water-solubility to the micelles and provides relatively long in vivo circulation times.

In certain embodiments, the present invention provides a micelle having a contrast agent encapsulated therein, wherein the micelle comprises a multiblock copolymer of formula I:

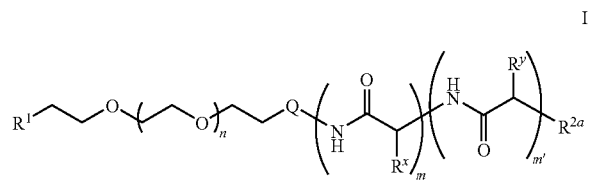

I wherein:
n is 10-2500;
m is 0 to 1000;
m' is 1 to 1000;
$R^x$ is a natural or unnatural amino acid side-chain group that is capable of crosslinking;
$R^y$ is a hydrophobic or ionic, natural or unnatural amino acid side-chain group;
$R^1$ is $-Z(CH_2CH_2Y)_p(CH_2)_tR^3$, wherein:
Z is —O—, —S—, —C≡C—, or —CH$_2$—;
each Y is independently —O— or —S—;
p is 0-10;
t is 0-10; and
$R^3$ is hydrogen, —N$_3$, —CN, a mono-protected amine, a di-protected amine, a protected aldehyde, a protected hydroxyl, a protected carboxylic acid, a protected thiol, a 9-30 membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;
Q is a valence bond or a bivalent, saturated or unsaturated, straight or branched C$_{1-12}$ hydrocarbon chain, wherein 0-6 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:
-Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;
$R^{2a}$ is a mono-protected amine, a di-protected amine, —N(R$^4$)$_2$, —NR$^4$C(O)R$^4$, —NR$^4$C(O)N(R$^4$)$_2$, —NR$^4$C(O)OR$^4$, or —NR$^4$SO$_2$R$^4$; and
each R$^4$ is independently an optionally substituted group selected from hydrogen, aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety, or:
two R$^4$ on the same nitrogen atom are taken together with said nitrogen atom to form an optionally substituted 4-7 membered saturated, partially unsaturated, or aryl ring having 1-4 heteroatoms independently selected from nitrogen, oxygen, or sulfur.

As defined generally above, the n group of formula I is 10-2500. In certain embodiments, the present invention provides compounds of formula I, as described above, wherein n is about 225. In other embodiments, n is about 275. In other embodiments, n is about 350. In other embodiments, n is about 10 to about 40. In other embodiments, n is about 40 to about 60. In other embodiments, n is about 60 to about 90. In still other embodiments, n is about 90 to about 150. In other embodiments, n is about 150 to about 200. In still other embodiments, n is about 200 to about 250. In other embodiments, n is about 300 to about 375. In other embodiments, n is about 400 to about 500. In still other embodiments, n is about 650 to about 750. In certain embodiments, n is selected from 50±10. In other embodiments, n is selected from 80±10, 115±10, 180±10, 225±10, 275±10, 315±10, or 340±10.

According to another embodiment, the present invention provides a compound of formula I, as described above, wherein said compound has a polydispersity index ("PDI") of about 1.0 to about 1.2. According to another embodiment, the present invention provides a compound of formula I, as described above, wherein said compound has a polydispersity index ("PDI") of about 1.02 to about 1.05. According to yet another embodiment, the present invention provides a compound of formula I, as described above, wherein said compound has a polydispersity index ("PDI") of about 1.05 to about 1.10. In other embodiments, said compound has a PDI of about 1.01 to about 1.03. In other embodiments, said compound has a PDI of about 1.10 to about 1.15. In still other embodiments, said compound has a PDI of about 1.15 to about 1.20.

In certain embodiments, the m' group of formula I is about 5 to about 500. In certain embodiments, the m' group of formula I is about 10 to about 250. In other embodiments, m' is about 10 to about 50. According to yet another embodiment, m' is about 15 to about 40. In other embodiments, m' is about 20 to about 40. According to yet another embodiment, m' is about 50 to about 75. According to other embodiments, m and m' are independently about 10 to about 100. In certain embodiments, m is 5-50. In other embodiments, m is 5-25. In certain embodiments, m' is 5-50. In other embodiments, m' is 5-10. In other embodiments, m' is 10-20. In certain embodiments, m and m' add up to about 30 to about 60. In still other embodiments, m is 1-20 repeat units and m' is 10-50 repeat units.

In certain embodiments, the m group of formula I is zero, thereby forming a diblock copolymer.

In certain embodiments, the $R^3$ moiety of the $R^1$ group of formula I is —$N_3$.

In certain embodiments, the $R^3$ moiety of the $R^1$ group of formula I is —$OCH_3$.

In other embodiments, the $R^3$ moiety of the $R^1$ group of formula I is —CN.

In still other embodiments, the $R^3$ moiety of the $R^1$ group of formula I is a mono-protected amine or a di-protected amine.

In certain embodiments, $R^3$ is hydrogen.

In certain embodiments, the $R^3$ moiety of the $R^1$ group of formula I is an optionally substituted aliphatic group. Examples include t-butyl, 5-norbornene-2-yl, octane-5-yl, acetylenyl, trimethylsilylacetylenyl, triisopropylsilylacetylenyl, and t-butyldimethylsilylacetylenyl. In some embodiments, said $R^3$ moiety is an optionally substituted alkyl group. In other embodiments, said $R^3$ moiety is an optionally substituted alkynyl or alkenyl group. When said $R^3$ moiety is a substituted aliphatic group, suitable substituents on $R^3$ include CN, $N_3$, trimethylsilyl, triisopropylsilyl, t-butyldimethylsilyl, N-methyl propiolamido, N-methyl-4-acetylenylanilino, N-methyl-4-acetylenylbenzoamido, bis-(4-ethynylbenzyl)-amino, dipropargylamino, di-hex-5-ynyl-amino, di-pent-4-ynyl-amino, di-but-3-ynyl-amino, propargyloxy, hex-5-ynyloxy, pent-4-ynyloxy, di-but-3-ynyloxy, N-methyl-propargylamino, N-methyl-hex-5-ynyl-amino, N-methyl-pent-4-ynyl-amino, N-methyl-but-3-ynyl-amino, 2-hex-5-ynyldisulfanyl, 2-pent-4-ynyldisulfanyl, 2-but-3-ynyldisulfanyl, and 2-propargyldisulfanyl. In certain embodiments, the $R^1$ group is 2-(N-methyl-N-(ethynylcarbonyl)amino)ethoxy, 4-ethynylbenzyloxy, or 2-(4-ethynylphenoxy)ethoxy.

In certain embodiments, the $R^3$ moiety of the $R^1$ group of formula I is an optionally substituted aryl group. Examples include optionally substituted phenyl and optionally substituted pyridyl. When said $R^3$ moiety is a substituted aryl group, suitable substituents on $R^3$ include CN, $N_3$, $NO_2$, —$CH_3$, —$CH_2N_3$, —CH=$CH_2$, —C≡CH, Br, I, F, bis-(4-ethynyl-benzyl)-amino, dipropargylamino, di-hex-5-ynyl-amino, di-pent-4-ynyl-amino, di-but-3-ynyl-amino, propargyloxy, hex-5-ynyloxy, pent-4-ynyloxy, di-but-3-ynyloxy, 2-hex-5-ynyloxy-ethyldisulfanyl, 2-pent-4-ynyloxy-ethyldisulfanyl, 2-but-3-ynyloxy-ethyldisulfanyl, 2-propargyloxy-ethyldisulfanyl, bis-benzyloxy-methyl, [1,3]dioxolan-2-yl, and [1,3]dioxan-2-yl.

In other embodiments, the $R^3$ moiety is an aryl group substituted with a suitably protected amino group. According to another aspect, the $R^3$ moiety is phenyl substituted with a suitably protected amino group.

In other embodiments, the $R^3$ moiety of the $R^1$ group of formula I is a protected hydroxyl group. In certain embodiments the protected hydroxyl of the $R^3$ moiety is an ester, carbonate, sulfonate, allyl ether, ether, silyl ether, alkyl ether, arylalkyl ether, or alkoxyalkyl ether. In certain embodiments, the ester is a formate, acetate, proprionate, pentanoate, crotonate, or benzoate. Exemplary esters include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio) pentanoate, pivaloate (trimethylacetate), crotonate, 4-methoxy-crotonate, benzoate, p-benzylbenzoate, 2,4,6-trimethylbenzoate. Exemplary carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of suitable silyl ethers include trimethylsilyl, triethylsilyl, t-butyldimethylsilyl, t-butyldiphenylsilyl, triisopropylsilyl ether, and other trialkylsilyl ethers. Exemplary alkyl ethers include methyl, benzyl, p-methoxybenzyl, 3,4-dimethoxybenzyl, trityl, t-butyl, and allyl ether, or derivatives thereof. Exemplary alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyran-2-yl ether. Exemplary arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

In certain embodiments, the $R^3$ moiety of the $R^1$ group of formula I is a mono-protected or di-protected amino group. In certain embodiments $R^3$ is a mono-protected amine. In certain embodiments $R^3$ is a mono-protected amine selected from aralkylamines, carbamates, allyl amines, or amides. Exemplary mono-protected amino moieties include t-butyloxycarbonylamino, ethyloxycarbonylamino, methyloxycarbonylamino, trichloroethyloxy-carbonylamino, allyloxycarbonylamino, benzyloxocarbonylamino, allylamino, benzylamino, fluorenylmethylcarbonyl, formamido, acetamido, chloroacetamido, dichloroacetamido, trichloroacetamido, phenylacetamido, trifluoroacetamido, benzamido, and t-butyldiphenylsilylamino. In other embodiments $R^3$ is a di-protected amine. Exemplary di-protected amines include di-benzylamine, di-allylamine, phthalimide, maleimide, succinimide, pyrrole, 2,2,5,5-tetramethyl-[1,2,5]azadisilolidine, and azide. In certain embodiments, the $R^3$ moiety is phthalimido. In other embodiments, the $R^3$ moiety is mono- or di-benzylamino or mono- or di-allylamino. In certain embodiments, the $R^1$ group is 2-dibenzylaminoethoxy.

In other embodiments, the $R^3$ moiety of the $R^1$ group of formula I is a protected aldehyde group. In certain embodiments the protected aldehydro moiety of $R^3$ is an acyclic acetal, a cyclic acetal, a hydrazone, or an imine. Exemplary $R^3$ groups include dimethyl acetal, diethyl acetal, diisopropyl acetal, dibenzyl acetal, bis(2-nitrobenzyl)acetal, 1,3-dioxane, 1,3-dioxolane, and semicarbazone. In certain embodiments, $R^3$ is an acyclic acetal or a cyclic acetal. In other embodiments, $R^3$ is a dibenzyl acetal.

In yet other embodiments, the $R^3$ moiety of the $R^1$ group of formula I is a protected carboxylic acid group. In certain embodiments, the protected carboxylic acid moiety of $R^3$ is an optionally substituted ester selected from $C_{1-6}$aliphatic or aryl, or a silyl ester, an activated ester, an amide, or a hydrazide. Examples of such ester groups include methyl, ethyl, propyl, isopropyl, butyl, isobutyl, benzyl, and phenyl ester. In other embodiments, the protected carboxylic acid moiety of $R^3$ is an oxazoline or an ortho ester. Examples of such protected carboxylic acid moieties include oxazolin-2-yl and 2-methoxy-[1,3]dioxin-2-yl. In certain embodiments, the $R^1$ group is oxazolin-2-ylmethoxy or 2-oxazolin-2-yl-1-propoxy.

According to another embodiments, the $R^3$ moiety of the $R^1$ group of formula I is a protected thiol group. In certain embodiments, the protected thiol of $R^3$ is a disulfide, thioether, silyl thioether, thioester, thiocarbonate, or a thiocarbamate. Examples of such protected thiols include triisopropylsilyl thioether, t-butyldimethylsilyl thioether, t-butyl thioether, benzyl thioether, p-methylbenzyl thioether, triphenylmethyl thioether, and p-methoxyphenyldiphenylmethyl thioether. In other embodiments, $R^3$ is an optionally substituted thioether selected from alkyl, benzyl, or triphenylmethyl, or trichloroethoxycarbonyl thioester. In certain embodiments, $R^3$ is —S—S-pyridin-2-yl, —S—SBn, —S—SCH$_3$, or —S—S(p-ethynylbenzyl). In other embodiments, $R^3$ is —S—S-pyridin-2-yl. In still other embodiments, the $R^1$ group is 2-triphenylmethylsulfanyl-ethoxy.

In certain embodiments, the $R^3$ moiety of the $R^1$ group of formula I is a crown ether. Examples of such crown ethers include 12-crown-4, 15-crown-5, and 18-crown-6.

In still other embodiments, the $R^3$ moiety of the $R^1$ group of formula I is a detectable moiety. According to one aspect of the invention, the $R^3$ moiety of the $R^1$ group of formula I is a fluorescent moiety. Such fluorescent moieties are well known in the art and include coumarins, quinolones, benzoisoquinolones, hostasol, and Rhodamine dyes, to name but a few. Exemplary fluorescent moieties of the $R^3$ group of $R^1$ include anthracen-9-yl, pyren-4-yl, 9-H-carbazol-9-yl, the carboxylate of rhodamine B, and the carboxylate of coumarin 343. In certain embodiments, the $R^3$ moiety of the $R^1$ group of formula I is a detectable moiety selected from:

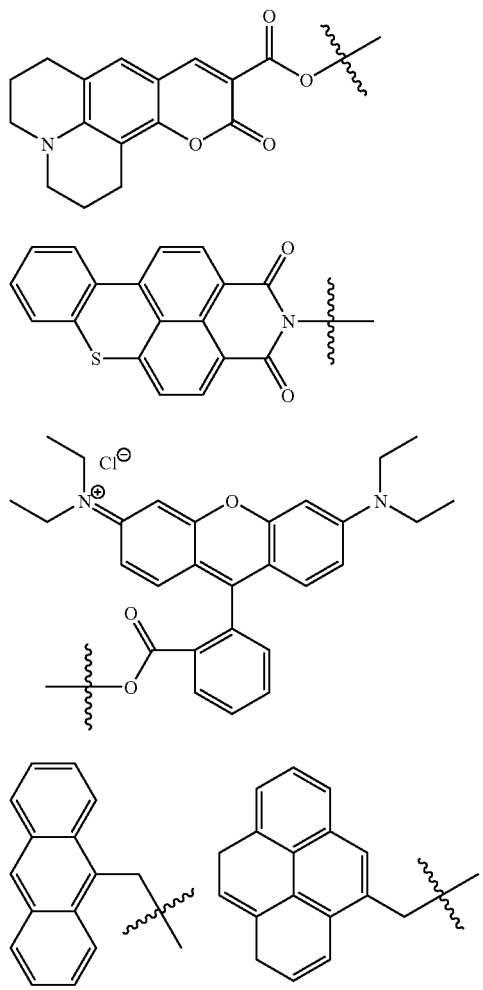

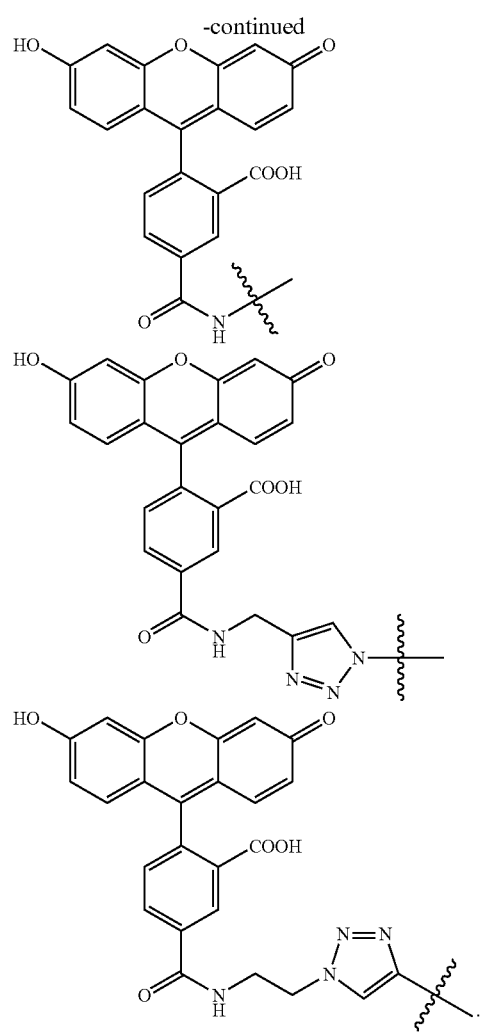

In certain embodiments, the $R^3$ moiety of the $R^1$ group of formula I is a group suitable for Click chemistry. Click reactions tend to involve high-energy ("spring-loaded") reagents with well-defined reaction coordinates, giving rise to selective bond-forming events of wide scope. Examples include the nucleophilic trapping of strained-ring electrophiles (epoxide, aziridines, aziridinium ions, episulfonium ions), certain forms of carbonyl reactivity (aldehydes and hydrazines or hydroxylamines, for example), and several types of cycloaddition reactions. The azide-alkyne 1,3-dipolar cycloaddition is one such reaction. Click chemistry is known in the art and one of ordinary skill in the art would recognize that certain $R^3$ moieties of the present invention are suitable for Click chemistry.

Compounds of formula I having $R^3$ moieties suitable for Click chemistry are useful for conjugating said compounds to biological systems or macromolecules such as proteins, viruses, and cells, to name but a few. The Click reaction is known to proceed quickly and selectively under physiological conditions. In contrast, most conjugation reactions are carried out using the primary amine functionality on proteins (e.g. lysine or protein end-group). Because most proteins contain a multitude of lysines and arginines, such conjugation occurs uncontrollably at multiple sites on the protein. This is particularly problematic when lysines or arginines are located around the active site of an enzyme or other biomolecule.

Thus, another embodiment of the present invention provides a method of conjugating the $R^1$ groups of a compound of formula I to a macromolecule via Click chemistry. Yet another embodiment of the present invention provides a macromolecule conjugated to a compound of formula I via the $R^1$ group.

According to one embodiment, the $R^3$ moiety of the $R^1$ group of formula I is an azide-containing group. According to another embodiment, the $R^3$ moiety of the $R^1$ group of formula I is an alkyne-containing group. In certain embodiments, the $R^3$ moiety of the $R^1$ group of formula I has a terminal alkyne moiety. In other embodiments, $R^3$ moiety of the $R^1$ group of formula I is an alkyne moiety having an electron withdrawing group. Accordingly, in such embodiments, the $R^3$ moiety of the $R^1$ group of formula I is

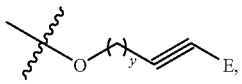

wherein E is an electron withdrawing group and y is 0-6. Such electron withdrawing groups are known to one of ordinary skill in the art. In certain embodiments, E is an ester. In other embodiments, the $R^3$ moiety of the $R^1$ group of formula I is

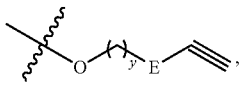

wherein E is an electron withdrawing group, such as a —C(O)O— group and y is 0-6.

As defined generally above, Q is a valence bond or a bivalent, saturated or unsaturated, straight or branched $C_{1-12}$ hydrocarbon chain, wherein 0-6 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein -Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur. In certain embodiments, Q is a valence bond. In other embodiments, Q is a bivalent, saturated $C_{1-12}$ hydrocarbon chain, wherein 0-6 methylene units of Q are independently replaced by -Cy-, —O—, —NH—, —S—, —OC(O)—, —C(O)O—, or —C(O)—, wherein -Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur.

In certain embodiments, Q is -Cy- (i.e. a $C_1$ alkylene chain wherein the methylene unit is replaced by -Cy-), wherein -Cy- is an optionally substituted 5-8 membered bivalent, saturated, partially unsaturated, or aryl ring having 0-4 heteroatoms independently selected from nitrogen, oxygen, or sulfur. According to one aspect of the present invention, -Cy- is an optionally substituted bivalent aryl group. According to another aspect of the present invention, -Cy- is an optionally substituted bivalent phenyl group. In other embodiments, -Cy- is an optionally substituted 5-8 membered bivalent, saturated carbocyclic ring. In still other embodiments, -Cy- is an optionally substituted 5-8 membered bivalent, saturated heterocyclic ring having 1-2 heteroatoms independently selected from nitrogen, oxygen, or sulfur. Exemplary -Cy- groups include bivalent rings selected from phenyl, pyridyl, pyrimidinyl, cyclohexyl, cyclopentyl, or cyclopropyl.

In certain embodiments, $R^x$ is a crosslinkable amino acid side-chain group and $R^y$ is a hydrophobic amino acid side-chain group. Such crosslinkable amino acid side-chain groups include tyrosine, serine, cysteine, threonine, aspartic acid (also known as aspartate, when charged), glutamic acid (also known as glutamate, when charged), asparagine, histidine, lysine, arginine, and glutamine. Such hydrophobic amino acid side-chain groups include a suitably protected tyrosine side-chain, a suitably protected serine side-chain, a suitably protected threonine side-chain, phenylalanine, alanine, valine, leucine, tryptophan, proline, benzyl and alkyl glutamates, or benzyl and alkyl aspartates or mixtures thereof. In other embodiments, $R^y$ is an ionic amino acid side-chain group. Such ionic amino acid side chain groups includes a lysine side-chain, arginine side-chain, or a suitably protected lysine or arginine side-chain, an aspartic acid side chain, glutamic acid side-chain, or a suitably protected aspartic acid or glutamic acid side-chain. One of ordinary skill in the art would recognize that protection of a polar or hydrophilic amino acid side-chain can render that amino acid nonpolar. For example, a suitably protected tyrosine hydroxyl group can render that tyrosine nonpolar and hydrophobic by virtue of protecting the hydroxyl group. Suitable protecting groups for the hydroxyl, amino, and thiol, and carboylate functional groups of $R^x$ and $R^y$ are as described herein.

In other embodiments, $R^y$ comprises a mixture of hydrophobic and hydrophilic amino acid side-chain groups such that the overall poly(amino acid) block comprising $R^y$ is hydrophobic. Such mixtures of amino acid side-chain groups include phenylalanine/tyrosine, phenalanine/serine, leucine/tyrosine, and the like. According to another embodiment, $R^y$ is a hydrophobic amino acid side-chain group selected from phenylalanine, alanine, or leucine, and one or more of tyrosine, serine, or threonine.

As defined above, $R^x$ is a natural or unnatural amino acid side-chain group capable of forming cross-links. It will be appreciated that a variety of amino acid side-chain functional groups are capable of such cross-linking, including, but not limited to, carboxylate, hydroxyl, thiol, and amino groups. Examples of $R^x$ moieties having functional groups capable of forming cross-links include a glutamic acid side-chain, —CH$_2$C(O)CH, an aspartic acid side-chain, —CH$_2$CH$_2$C(O) OH, a cysteine side-chain, —CH$_2$SH, a serine side-chain, —CH$_2$OH, an aldehyde containing side-chain, —CH$_2$C(O) H, a lysine side-chain, —(CH$_2$)$_4$NH$_2$, an arginine side-chain, —(CH$_2$)$_3$NHC(=NH)NH$_2$, a histidine side-chain, —CH$_2$-imidazol-4-yl, or benzimidazolyl.

As defined generally above, the $R^{2a}$ group of formula I is a mono-protected amine, a di-protected amine, —NHR$^4$, —N(R$^4$)$_2$, —NHC(O)R$^4$, —NR$^4$C(O)R$^4$, —NHC(O)NHR$^4$, —NHC(O)N(R$^4$)$_2$, —NR$^4$C(O)NHR$^4$, —NR$^4$C(O)N(R$^4$)$_2$, —NHC(O)OR$^4$, —NR$^4$C(O)OR$^4$, —NHSO$_2$R$^4$, or —NR$^4$SO$_2$R$^4$, wherein each R$^4$ is independently an optionally substituted group selected from aliphatic, a 5-8 membered saturated, partially unsaturated, or aryl ring having 0-4 heteroatoms independently selected from nitrogen, oxygen, or sulfur, an 8-10-membered saturated, partially unsaturated, or aryl bicyclic ring having 0-5 heteroatoms independently selected from nitrogen, oxygen, or sulfur, or a detectable moiety, or two R$^4$ on the same nitrogen atom are taken together with said nitrogen atom to form an optionally substituted 4-7 membered saturated, partially unsaturated, or aryl ring having 1-4 heteroatoms independently selected from nitrogen, oxygen, or sulfur.

In certain embodiments, the $R^{2a}$ group of formula I is —NHR$^4$ or —N(R$^4$)$_2$ wherein each R$^4$ is an optionally substituted aliphatic group. One exemplary R$^4$ group is 5-norbornen-2-yl-methyl. According to yet another aspect of the present invention, the $R^{2a}$ group of formula I is —NHR$^4$ wherein R$^4$ is a $C_{1-6}$ aliphatic group substituted with N$_3$. Examples include —CH$_2$N$_3$. In some embodiments, R$^4$ is an optionally substituted $C_{1-6}$ alkyl group. Examples include methyl, ethyl, propyl, butyl, pentyl, hexyl, 2-(tetrahydropyran-2-yloxy)ethyl, pyridin-2-yldisulfanylmethyl, methyldisulfanylmethyl, (4-acetylenylphenyl)methyl, 3-(methoxycarbonyl)-prop-2-ynyl, methoxycarbonylmethyl, 2-(N-methyl-N-(4-acetylenylphenyl)carbonylamino)-ethyl, 2-phthalimidoethyl, 4-bromobenzyl, 4-chlorobenzyl, 4-fluorobenzyl, 4-iodobenzyl, 4-propargyloxybenzyl, 2-nitrobenzyl, 4-(bis-4-acetylenylbenzyl)aminomethyl-benzyl, 4-propargyloxy-benzyl, 4-dipropargylamino-benzyl, 4-(2-propargyloxy-ethyldisulfanyl)benzyl, 2-propargyloxy-ethyl, 2-propargyldisulfanyl-ethyl, 4-propargyloxy-butyl, 2-(N-methyl-N-propargylamino)ethyl, and 2-(2-dipropargylaminoethoxy)-ethyl. In other embodiments, R$^4$ is an optionally substituted $C_{2-6}$ alkenyl group. Examples include vinyl, allyl, crotyl, 2-propenyl, and but-3-enyl. When R$^4$ group is a substituted aliphatic group, suitable substituents on R$^4$ include N$_3$, CN, and halogen. In certain embodiments, R$^4$ is —CH$_2$CN, —CH$_2$CH$_2$CN, —CH$_2$CH(OCH$_3$)$_2$, 4-(bisbenzyloxymethyl)phenylmethyl, and the like.

According to another aspect of the present invention, the $R^{2a}$ group of formula I is —NHR$^4$ wherein R$^4$ is an optionally substituted $C_{2-6}$ alkynyl group. Examples include —CC≡CH, —CH$_2$C≡CH, —CH$_2$C≡CCH$_3$, and —CH$_2$CH$_2$C≡CH.

In certain embodiments, the $R^{2a}$ group of formula I is —NHR$^4$ wherein R$^4$ is an optionally substituted 5-8-membered aryl ring. In certain embodiments, R$^4$ is optionally substituted phenyl or optionally substituted pyridyl. Examples include phenyl, 4-t-butoxycarbonylaminophenyl, 4-azidomethylphenyl, 4-propargyloxyphenyl, 2-pyridyl, 3-pyridyl, and 4-pyridyl. In certain embodiments, $R^{2a}$ is 4-t-butoxycarbonylaminophenylamino, 4-azidomethylphenamino, or 4-propargyloxyphenylamino.

In certain embodiments, the $R^{2a}$ group of formula I is —NHR$^4$ wherein R$^4$ is an optionally substituted phenyl ring. Suitable substituents on the R$^4$ phenyl ring include halogen; —(CH$_2$)$_{0-4}$R$^°$; —(CH$_2$)$_{0-4}$OR$^°$; —(CH$_2$)$_{0-4}$CH(OR$^°$)$_2$; —(CH$_2$)$_{0-4}$SR$^°$; —(CH$_2$)$_{0-4}$Ph, which may be substituted with R$^°$; —(CH$_2$)$_{0-4}$O(CH$_2$)$_{0-1}$Ph which may be substituted with R$^°$; —CH═CHPh, which may be substituted with R$^°$; —NO$_2$; —CN; —N$_3$; —(CH$_2$)$_{0-4}$N(R$^°$)$_2$; —(CH$_2$)$_{0-4}$N(R$^°$)C(O)R$^°$; —N(R$^°$)C(S)R$^°$; —(CH$_2$)$_{0-4}$N(R$^°$)C(O)NR$^°$$_2$; —N(R$^°$)C(S)NR$^°$$_2$; —(CH$_2$)$_{0-4}$N(R$^°$)C(O)OR$^°$; —N(R$^°$)N(R$^°$)C(O)R$^°$; —N(R$^°$)N(R$^°$)C(O)NR$^°$$_2$; —N(R$^°$)N(R$^°$)C(O)OR$^°$; —(CH$_2$)$_{0-4}$C(O)R$^°$; —C(S)R$^°$; —(CH$_2$)$_{0-4}$C(O)OR$^°$; —(CH$_2$)$_{0-4}$C(O)SR$^°$; —(CH$_2$)$_{0-4}$C(O)OSiR$^°$$_3$; —(CH$_2$)$_{0-4}$OC(O)R$^°$; —(CH$_2$)$_{0-4}$SC(O)R$^°$; —(CH$_2$)$_{0-4}$C(O)NR$^°$$_2$; —C(S)NR$^°$$_2$; —(CH$_2$)$_{0-4}$OC(O)NR$^°$$_2$; —C(O)N(OR$^°$)R$^°$; —C(O)C(O)R$^°$; —C(O)CH$_2$C(O)R$^°$; —C(NOR$^°$)R$^°$; —(CH$_2$)$_{0-4}$SSR$^°$; —(CH$_2$)$_{0-4}$S(O)$_2$R$^°$; —(CH$_2$)$_{0-4}$S(O)$_2$OR$^°$; —(CH$_2$)$_{0-4}$OS(O)$_2$R$^°$; —S(O)$_2$NR$^°$$_2$; —(CH$_2$)$_{0-4}$S(O)R$^°$; —N(R$^°$)S(O)$_2$NR$^°$$_2$; —N(R$^°$)S(O)$_2$R$^°$; —N(OR$^°$)R$^°$; —C(NH)NR$^°$$_2$; —P(O)$_2$R$^°$; —P(O)R$^°$$_2$; —OP(O)R$^°$$_2$; SiR$^°$$_3$; wherein each independent occurrence of R$^°$ is as defined herein supra. In other embodiments, the $R^{2a}$ group of formula I is —NHR$^4$ wherein R$^4$ is phenyl substituted with one or more optionally substituted $C_{1-6}$ aliphatic groups. In still other embodiments, R$^4$ is phenyl substituted with vinyl, allyl, acetylenyl, —CH$_2$N$_3$, —CH$_2$CH$_2$N$_3$, —CH$_2$C≡CCH$_3$, or —CH$_2$C≡CH.

In certain embodiments, the $R^{2a}$ group of formula I is —NHR$^4$ wherein R$^4$ is phenyl substituted with N$_3$, N(R$^°$)$_2$, CO$_2$R$^°$, or C(O)R$^°$ wherein each R$^°$ is independently as defined herein supra.

In certain embodiments, the $R^{2a}$ group of formula I is —N(R$^4$)$_2$ wherein each R$^4$ is independently an optionally substituted group selected from aliphatic, phenyl, naphthyl, a 5-6 membered aryl ring having 1-4 heteroatoms independently selected from nitrogen, oxygen, or sulfur, or a 8-10 membered bicyclic aryl ring having 1-5 heteroatoms independently selected from nitrogen, oxygen, or sulfur, or a detectable moiety.

In other embodiments, the $R^{2a}$ group of formula I is —N(R$^4$)$_2$ wherein the two R$^4$ groups are taken together with said nitrogen atom to form an optionally substituted 4-7 membered saturated, partially unsaturated, or aryl ring having 1-4 heteroatoms independently selected from nitrogen, oxygen, or sulfur. According to another embodiment, the two R$^4$ groups are taken together to form a 5-6-membered saturated or partially unsaturated ring having one nitrogen wherein said ring is substituted with one or two oxo groups. Such $R^{2a}$ groups include, but are not limited to, phthalimide, maleimide and succinimide.

In certain embodiments, the $R^{2a}$ group of formula I is a mono-protected or di-protected amino group. In certain embodiments $R^{2a}$ is a mono-protected amine. In certain embodiments $R^{2a}$ is a mono-protected amine selected from aralkylamines, carbamates, allyl amines, or amides. Exemplary mono-protected amino moieties include t-butyloxycarbonylamino, ethyloxycarbonylamino, methyloxycarbonylamino, trichloroethyloxy-carbonylamino, allyloxycarbonylamino, benzyloxocarbonylamino, allylamino, benzylamino, fluorenylmethylcarbonyl, formamido, acetamido, chloroacetamido, dichloroacetamido, trichloroacetamido, phenylacetamido, trifluoroacetamido, benzamido, and t-butyldiphenylsilylamino. In other embodiments $R^{2a}$ is a di-protected amine. Exemplary di-protected amino moieties include di-benzylamino, di-allylamino, phthalimide, maleimido, succinimido, pyrrolo, 2,2,5,5-tetramethyl-[1,2,5]azadisilolidino, and azido. In certain embodiments, the $R^{2a}$ moiety is phthalimido. In other embodiments, the $R^{2a}$ moiety is mono- or di-benzylamino or mono- or di-allylamino.

In certain embodiments, the $R^{2a}$ group of formula I comprises a group suitable for Click chemistry. One of ordinary skill in the art would recognize that certain $R^{2a}$ groups of the present invention are suitable for Click chemistry.

Compounds of formula I having $R^{2a}$ groups comprising groups suitable for Click chemistry are useful for conjugating said compounds to biological systems such as proteins, viruses, and cells, to name but a few. After conjugation to a biomolecule, drug, cell, substrate, or the like, the other end-group functionality, corresponding to the R$^1$ moiety of formula I, can be used to attach targeting groups for cell specific delivery including, but not limited to, fluorescent dyes, covalent attachment to surfaces, and incorporation into hydrogels. Thus, another embodiment of the present invention provides a method of conjugating the $R^{2a}$ group of a compound of formula I to a fluorescent dye, small molecule drug, or macromolecule via Click chemistry. Yet another embodiment of the present invention provides a macromolecule conjugated to a compound of formula I via the $R^{2a}$ group.

According to one embodiment, the $R^{2a}$ group of formula I is an azide-containing group. According to another embodiment, the $R^{2a}$ group of formula I is an alkyne-containing group.

In certain embodiments, the $R^{2a}$ group of formula I has a terminal alkyne moiety. In other embodiments, the $R^{2a}$ group of formula I is an alkyne-containing moiety having an electron withdrawing group. Accordingly, in such embodiments, the R group of formula I is

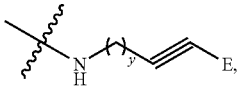

wherein E is an electron withdrawing group and y is 0-6. Such electron withdrawing groups are known to one of ordinary skill in the art. In certain embodiments, E is an ester. In other embodiments, the $R^{2a}$ group of formula I is

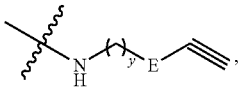

wherein E is an electron withdrawing group, such as a —C(O) O— group and y is 0-6.

In other embodiments, the present invention provides a micelle having a contrast agent encapsulated therein, wherein the micelle comprises multiblock copolymer of formula II:

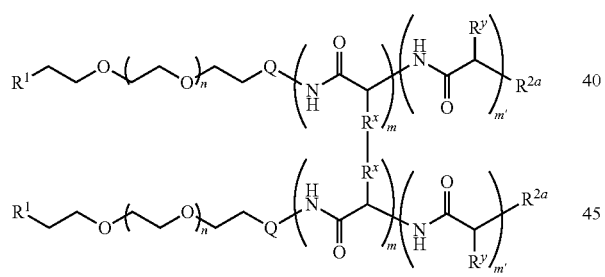

wherein:
n is 10-2500;
m is 1 to 1000;
m' is 1 to 1000;
$R^x$ is a crosslinked natural or unnatural amino acid side-chain group;
$R^y$ is a hydrophobic or ionic, natural or unnatural, amino acid side-chain group;
$R^1$ is $-Z(CH_2CH_2Y)_p(CH_2)_tR^3$, wherein:
Z is —O—, —S—, —C≡C—, or —CH$_2$—;
each Y is independently —O— or —S—;
p is 0-10;
t is 0-10; and
$R^3$ is hydrogen, —N$_3$, —CN, a mono-protected amine, a di-protected amine, a protected aldehyde, a protected hydroxyl, a protected carboxylic acid, a protected thiol, a 9-30 membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;

Q is a valence bond or a bivalent, saturated or unsaturated, straight or branched $C_{1-12}$ hydrocarbon chain, wherein 0-6 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:
-Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;

$R^{2a}$ is a mono-protected amine, a di-protected amine, —N(R$^4$)$_2$, —NR$^4$C(O)R$^4$, —NR$^4$C(O)N(R$^4$)$_2$, —NR$^4$C(O)OR$^4$, or —NR$^4$SO$_2$R$^4$; and each $R^4$ is independently an optionally substituted group selected from hydrogen, aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety, or:
two $R^4$ on the same nitrogen atom are taken together with said nitrogen atom to form an optionally substituted 4-7 membered saturated, partially unsaturated, or aryl ring having 1-4 heteroatoms independently selected from nitrogen, oxygen, or sulfur.

Embodiments for each of $R^1$, Q, n, m, m', $R^x$, $R^y$, and $R^{2a}$ for compounds of formula II are as described herein for compounds of formula I, singly and in combination.

According to another embodiment, the present invention provides compounds of formula II, as described above, wherein said compounds have a polydispersity index ("PDI") of about 1.0 to about 1.2. According to another embodiment, the present invention provides compounds of formula II, as described above, wherein said compound has a PDI of about 1.03 to about 1.15. According to yet another embodiment, the present invention provides compounds of formula II, as described above, wherein said compound has a PDI of about 1.10 to about 1.20. According to other embodiments, the present invention provides compounds of formula II having a PDI of less than about 1.10.

According to another embodiment, the present invention provides a micelle having a contrast agent encapsulated therein, wherein the micelle comprises a multiblock copolymer selected from those set forth in Tables 1 through 4, below. Table 1 sets forth exemplary compounds of the present invention having the formula:

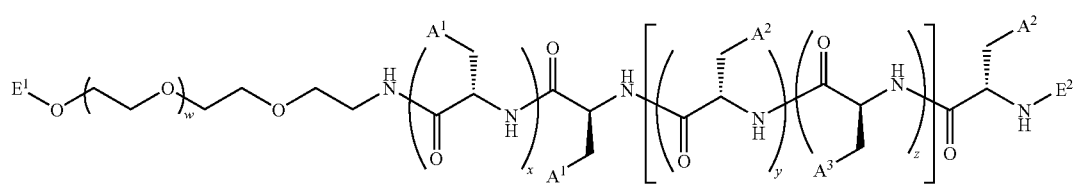

wherein each w is 25-1000, each x is 1-50, each y is 1-50, each z is 1-50, p is the sum of y and z, and each dotted bond represents the point of attachment to the rest of the molecule.

TABLE 1

| Compound | $A^1$ | $A^2$ | $A^3$ | $E^1$ | $E^2$ |
|---|---|---|---|---|---|
| 1 | COOH | phenyl | 4-hydroxyphenyl | HC≡C-CH2- | acetyl |
| 2 | COOH | phenyl | 4-hydroxyphenyl | N3-CH2CH2- | acetyl |
| 3 | COOH | phenyl | 4-hydroxyphenyl | H2N-CH2CH2- | acetyl |
| 4 | COOH | phenyl | 4-hydroxyphenyl | OHC-CH2CH2- | acetyl |
| 5 | COOH | phenyl | 4-hydroxyphenyl | H3C- | acetyl |
| 6 | COOH | phenyl | 4-hydroxyphenyl | N3-CH2CH2- | H |
| 7 | COOH | phenyl | 4-hydroxyphenyl | H2N-CH2CH2- | H |
| 8 | COOH | phenyl | 4-hydroxyphenyl | OHC-CH2CH2- | H |
| 9 | COOH | phenyl | 4-hydroxyphenyl | HC≡C-CH2- | H |
| 10 | COOH | phenyl | 4-hydroxyphenyl | H3C- | H |

TABLE 1-continued

| Compound | A¹ | A² | A³ | E¹ | E² |
|---|---|---|---|---|---|
| 11 | —SH | phenyl | 4-hydroxyphenyl | propargyl (HC≡C-CH₂-) | acetyl (C(=O)CH₃) |
| 12 | —SH | phenyl | 4-hydroxyphenyl | 2-azidoethyl (N₃-CH₂CH₂-) | acetyl |
| 13 | —SH | phenyl | 4-hydroxyphenyl | 2-aminoethyl (H₂N-CH₂CH₂-) | acetyl |
| 14 | —SH | phenyl | 4-hydroxyphenyl | 3-oxopropyl (OHC-CH₂CH₂-) | acetyl |
| 15 | —SH | phenyl | 4-hydroxyphenyl | methyl (H₃C-) | acetyl |
| 16 | —SH | phenyl | 4-hydroxyphenyl | 2-azidoethyl | H |
| 17 | —SH | phenyl | 4-hydroxyphenyl | 2-aminoethyl | H |
| 18 | —SH | phenyl | 4-hydroxyphenyl | 3-oxopropyl | H |
| 19 | —SH | phenyl | 4-hydroxyphenyl | propargyl | H |
| 20 | —SH | phenyl | 4-hydroxyphenyl | methyl | H |
| 21 | —COOH | phenyl | 3-aminopropyl | propargyl | acetyl |
| 22 | —COOH | phenyl | 3-aminopropyl | 2-azidoethyl | acetyl |
| 23 | —COOH | phenyl | 3-aminopropyl | 2-aminoethyl | acetyl |

TABLE 1-continued

| Compound | A¹ | A² | A³ | E¹ | E² |
|---|---|---|---|---|---|
| 24 | -COOH | phenyl | -CH₂CH₂CH₂NH₂ | H-C(=O)-CH₂-CH₂- | -C(=O)-CH₃ |
| 25 | -COOH | phenyl | -CH₂CH₂CH₂NH₂ | H₃C- | -C(=O)-CH₃ |
| 26 | -COOH | phenyl | -CH₂CH₂CH₂NH₂ | N₃-CH₂CH₂- | -H |
| 27 | -COOH | phenyl | -CH₂CH₂CH₂NH₂ | H₂N-CH₂CH₂- | -H |
| 28 | -COOH | phenyl | -CH₂CH₂CH₂NH₂ | H-C(=O)-CH₂-CH₂- | -H |
| 29 | -COOH | phenyl | -CH₂CH₂CH₂NH₂ | HC≡C- | -H |
| 30 | -COOH | phenyl | -CH₂CH₂CH₂NH₂ | H₃C- | -H |
| 31 | -SH | phenyl | -CH₂CH₂CH₂NH₂ | HC≡C- | -C(=O)-CH₃ |
| 32 | -SH | phenyl | -CH₂CH₂CH₂NH₂ | N₃-CH₂CH₂- | -C(=O)-CH₃ |
| 33 | -SH | phenyl | -CH₂CH₂CH₂NH₂ | H₂N-CH₂CH₂- | -C(=O)-CH₃ |
| 34 | -SH | phenyl | -CH₂CH₂CH₂NH₂ | H-C(=O)-CH₂-CH₂- | -C(=O)-CH₃ |
| 35 | -SH | phenyl | -CH₂CH₂CH₂NH₂ | H₃C- | -C(=O)-CH₃ |
| 36 | -SH | phenyl | -CH₂CH₂CH₂NH₂ | N₃-CH₂CH₂- | -H |
| 37 | -SH | phenyl | -CH₂CH₂CH₂NH₂ | H₂N-CH₂CH₂- | -H |

TABLE 1-continued

| Compound | A¹ | A² | A³ | E¹ | E² |
|---|---|---|---|---|---|
| 38 | -SH | phenyl | -CH₂CH₂CH₂-NH₂ | -C(=O)-CH₂CH₂- | -H |
| 39 | -SH | phenyl | -CH₂CH₂CH₂-NH₂ | -C≡C-CH₂- | -H |
| 40 | -SH | phenyl | -CH₂CH₂CH₂-NH₂ | H₃C- | -H |
| 41 | -CH₂-C(=O)OH | phenyl | 4-hydroxyphenyl | HC≡C-CH₂- | -C(=O)-CH₃ |
| 42 | -CH₂-C(=O)OH | phenyl | 4-hydroxyphenyl | N₃-CH₂CH₂- | -C(=O)-CH₃ |
| 43 | -CH₂-C(=O)OH | phenyl | 4-hydroxyphenyl | H₂N-CH₂CH₂- | -C(=O)-CH₃ |
| 44 | -CH₂-C(=O)OH | phenyl | 4-hydroxyphenyl | H-C(=O)-CH₂CH₂- | -C(=O)-CH₃ |
| 45 | -CH₂-C(=O)OH | phenyl | 4-hydroxyphenyl | H₃C- | -C(=O)-CH₃ |
| 46 | -CH₂-C(=O)OH | phenyl | 4-hydroxyphenyl | N₃-CH₂CH₂- | -H |
| 47 | -CH₂-C(=O)OH | phenyl | 4-hydroxyphenyl | H₂N-CH₂CH₂- | -H |
| 48 | -CH₂-C(=O)OH | phenyl | 4-hydroxyphenyl | H-C(=O)-CH₂CH₂- | -H |
| 49 | -CH₂-C(=O)OH | phenyl | 4-hydroxyphenyl | HC≡C-CH₂- | -H |
| 50 | -CH₂-C(=O)OH | phenyl | 4-hydroxyphenyl | H₃C- | -H |

TABLE 1-continued

| Compound | A¹ | A² | A³ | E¹ | E² |
|---|---|---|---|---|---|
| 51 | -CH₂-C(=O)-OH | phenyl | -(CH₂)₃-NH₂ | HC≡C-CH₂- | -C(=O)-CH₃ |
| 52 | -CH₂-C(=O)-OH | phenyl | -(CH₂)₃-NH₂ | N₃-CH₂-CH₂- | -C(=O)-CH₃ |
| 53 | -CH₂-C(=O)-OH | phenyl | -(CH₂)₃-NH₂ | H₂N-CH₂-CH₂- | -C(=O)-CH₃ |
| 54 | -CH₂-C(=O)-OH | phenyl | -(CH₂)₃-NH₂ | H-C(=O)-CH₂-CH₂- | -C(=O)-CH₃ |
| 55 | -CH₂-C(=O)-OH | phenyl | -(CH₂)₃-NH₂ | H₃C- | -C(=O)-CH₃ |
| 56 | -CH₂-C(=O)-OH | phenyl | -(CH₂)₃-NH₂ | N₃-CH₂-CH₂- | -H |
| 57 | -CH₂-C(=O)-OH | phenyl | -(CH₂)₃-NH₂ | H₂N-CH₂-CH₂- | -H |
| 58 | -CH₂-C(=O)-OH | phenyl | -(CH₂)₃-NH₂ | H-C(=O)-CH₂-CH₂- | -H |
| 59 | -CH₂-C(=O)-OH | phenyl | -(CH₂)₃-NH₂ | HC≡C-CH₂- | -H |
| 60 | -CH₂-C(=O)-OH | phenyl | -(CH₂)₃-NH₂ | H₃C- | -H |
| 61 | -C(=O)(OH)-OH | phenyl | -OH | HC≡C-CH₂- | -C(=O)-CH₃ |
| 62 | -C(=O)(OH)-OH | phenyl | -OH | N₃-CH₂-CH₂- | -C(=O)-CH₃ |
| 63 | -C(=O)(OH)-OH | phenyl | -OH | H₂N-CH₂-CH₂- | -C(=O)-CH₃ |
| 64 | -C(=O)(OH)-OH | phenyl | -OH | H-C(=O)-CH₂-CH₂- | -C(=O)-CH₃ |

TABLE 1-continued

| Compound | A¹ | A² | A³ | E¹ | E² |
|---|---|---|---|---|---|
| 65 | -CH₂-C(=O)OH | phenyl | -OH | H₃C- | -C(=O)CH₃ |
| 66 | -CH₂-C(=O)OH | phenyl | -OH | HC≡C-CH₂- | -C(=O)CH₃ |
| 67 | -CH₂-C(=O)OH | phenyl | -OH | N₃-CH₂CH₂- | -C(=O)CH₃ |
| 68 | -CH₂-C(=O)OH | phenyl | -OH | H₂N-CH₂CH₂- | -C(=O)CH₃ |
| 69 | -CH₂-C(=O)OH | phenyl | -OH | OHC-CH₂CH₂- | -C(=O)CH₃ |
| 70 | -CH₂-C(=O)OH | phenyl | -OH | H₃C- | -C(=O)CH₃ |
| 71 | -CH₂-C(=O)OH | phenyl | imidazolyl | HC≡C-CH₂- | -C(=O)CH₃ |
| 72 | -CH₂-C(=O)OH | phenyl | indolyl | HC≡C-CH₂- | -C(=O)CH₃ |
| 73 | -SH | phenyl | imidazolyl | HC≡C-CH₂- | -C(=O)CH₃ |
| 74 | -SH | phenyl | indolyl | HC≡C-CH₂- | -C(=O)CH₃ |
| 75 | -CH₂CH₂CH₂-NH- | phenyl | 4-hydroxyphenyl | HC≡C-CH₂- | -C(=O)CH₃ |
| 76 | -CH₂CH₂CH₂-NH- | phenyl | 4-hydroxyphenyl | N₃-CH₂CH₂- | -C(=O)CH₃ |
| 77 | -CH₂CH₂CH₂-NH- | phenyl | 4-hydroxyphenyl | H₂N-CH₂CH₂- | -C(=O)CH₃ |
| 78 | -CH₂CH₂CH₂-NH- | phenyl | 4-hydroxyphenyl | OHC-CH₂CH₂- | -C(=O)CH₃ |

TABLE 1-continued

| Compound | A¹ | A² | A³ | E¹ | E² |
|---|---|---|---|---|---|
| 79 | propyl-NH | phenyl | 4-hydroxyphenyl | H₃C- | -C(=O)- |
| 80 | propyl-NH | phenyl | 4-hydroxyphenyl | N₃-CH₂CH₂- | -H |
| 81 | propyl-NH | phenyl | 4-hydroxyphenyl | H₂N-CH₂CH₂- | -H |
| 82 | propyl-NH | phenyl | 4-hydroxyphenyl | OHC-CH₂CH₂- | -H |
| 83 | propyl-NH | phenyl | 4-hydroxyphenyl | HC≡C-CH₂- | -H |
| 84 | propyl-NH | phenyl | 4-hydroxyphenyl | H₃C- | -H |
| 85 | imidazolyl | phenyl | 4-hydroxyphenyl | HC≡C-CH₂- | -C(=O)- |
| 86 | imidazolyl | phenyl | 4-hydroxyphenyl | N₃-CH₂CH₂- | -C(=O)- |
| 87 | imidazolyl | phenyl | 4-hydroxyphenyl | H₂N-CH₂CH₂- | -C(=O)- |
| 88 | imidazolyl | phenyl | 4-hydroxyphenyl | OHC-CH₂CH₂- | -C(=O)- |
| 89 | imidazolyl | phenyl | 4-hydroxyphenyl | H₃C- | -C(=O)- |
| 90 | imidazolyl | phenyl | 4-hydroxyphenyl | N₃-CH₂CH₂- | -H |
| 91 | imidazolyl | phenyl | 4-hydroxyphenyl | H₂N-CH₂CH₂- | -H |

TABLE 1-continued

| Compound | A¹ | A² | A³ | E¹ | E² |
|---|---|---|---|---|---|
| 92 | imidazole | phenyl | 4-hydroxyphenyl | CHO-CH₂- | H |
| 93 | imidazole | phenyl | 4-hydroxyphenyl | HC≡C-CH₂- | H |
| 94 | imidazole | phenyl | 4-hydroxyphenyl | H₃C- | H |
| 95 | -CH₂-COOH | phenyl | 4-hydroxyphenyl | HS-CH₂-CH₂- | acetyl |
| 96 | -CH₂-COOH | phenyl | 4-hydroxyphenyl | HS-CH₂-CH₂- | acetyl |
| 97 | imidazole | phenyl | 4-hydroxyphenyl | HS-CH₂-CH₂- | acetyl |
| 98 | indole | phenyl | 4-hydroxyphenyl | HS-CH₂-CH₂- | acetyl |
| 99 | -CH₂-COOH | isopropyl | 4-hydroxyphenyl | HC≡C-CH₂- | acetyl |
| 100 | -CH₂-COOH | isopropyl | 4-hydroxyphenyl | N₃-CH₂-CH₂- | acetyl |
| 101 | -CH₂-COOH | isopropyl | 4-hydroxyphenyl | H₃C- | acetyl |
| 102 | -CH₂-COOH | isopropyl | 3,4-dihydroxyphenyl | HC≡C-CH₂- | acetyl |
| 103 | -CH₂-COOH | isopropyl | 3,4-dihydroxyphenyl | N₃-CH₂-CH₂- | acetyl |
| 104 | -CH₂-COOH | isopropyl | 3,4-dihydroxyphenyl | H₃C- | acetyl |

TABLE 1-continued

| Compound | A¹ | A² | A³ | E¹ | E² |
|---|---|---|---|---|---|
| 105 | COOH | iPr | COOH | HC≡C-CH₂- | C(=O)- |
| 106 | COOH | iPr | COOH | N₃-CH₂CH₂- | C(=O)- |
| 107 | COOH | iPr | COOH | H₃C- | C(=O)- |
| 108 | COOH | iPr | CH₂COOH | HC≡C-CH₂- | C(=O)- |
| 109 | COOH | iPr | CH₂COOH | N₃-CH₂CH₂- | C(=O)- |
| 110 | COOH | iPr | CH₂COOH | H₃C- | C(=O)- |
| 111 | COOH | iPr | CH₂CH₂NH₂ | HC≡C-CH₂- | C(=O)- |
| 112 | COOH | iPr | CH₂CH₂NH₂ | N₃-CH₂CH₂- | C(=O)- |
| 113 | COOH | iPr | CH₂CH₂NH₂ | H₃C- | C(=O)- |
| 114 | COOH | iPr | CH₂CH₂CH₂NH₂ | HC≡C-CH₂- | C(=O)- |
| 115 | COOH | iPr | CH₂CH₂CH₂NH₂ | N₃-CH₂CH₂- | C(=O)- |
| 116 | COOH | iPr | CH₂CH₂CH₂NH₂ | H₃C- | C(=O)- |
| 117 | COOH | iPr | imidazolyl-CH₂- | HC≡C-CH₂- | C(=O)- |
| 118 | COOH | iPr | imidazolyl-CH₂- | N₃-CH₂CH₂- | C(=O)- |
| 119 | COOH | iPr | imidazolyl-CH₂- | H₃C- | C(=O)- |

TABLE 1-continued

| Compound | A¹ | A² | A³ | E¹ | E² |
|---|---|---|---|---|---|
| 120 | COOH | isobutyl | SH | alkyne (propargyl) | C(=O) |
| 121 | COOH | isobutyl | SH | N₃-CH₂CH₂- | C(=O) |
| 122 | COOH | isobutyl | SH | H₃C- | C(=O) |
| 123 | COOH | -C(=O)O-CH₂-phenyl | 4-hydroxyphenyl | alkyne (propargyl) | C(=O) |
| 124 | COOH | -C(=O)O-CH₂-phenyl | 4-hydroxyphenyl | N₃-CH₂CH₂- | C(=O) |
| 125 | COOH | -C(=O)O-CH₂-phenyl | 4-hydroxyphenyl | H₃C- | C(=O) |
| 126 | COOH | -C(=O)O-CH₂-phenyl | 3,4-dihydroxyphenyl | alkyne (propargyl) | C(=O) |
| 127 | COOH | -C(=O)O-CH₂-phenyl | 3,4-dihydroxyphenyl | N₃-CH₂CH₂- | C(=O) |
| 128 | COOH | -C(=O)O-CH₂-phenyl | 3,4-dihydroxyphenyl | H₃C- | C(=O) |
| 129 | COOH | -C(=O)O-CH₂-phenyl | COOH | alkyne (propargyl) | C(=O) |
| 130 | COOH | -C(=O)O-CH₂-phenyl | COOH | N₃-CH₂CH₂- | C(=O) |

TABLE 1-continued

| Compound | A¹ | A² | A³ | E¹ | E² |
|---|---|---|---|---|---|
| 131 | -COOH | -C(O)O-CH₂-C₆H₅ | -COOH | H₃C- | -C(O)- |
| 132 | -COOH | -C(O)O-CH₂-C₆H₅ | -CH₂-COOH | HC≡C-CH₂- | -C(O)- |
| 133 | -COOH | -C(O)O-CH₂-C₆H₅ | -CH₂-COOH | N₃-CH₂-CH₂- | -C(O)- |
| 134 | -COOH | -C(O)O-CH₂-C₆H₅ | -CH₂-COOH | H₃C- | -C(O)- |
| 135 | -COOH | -C(O)O-CH₂-C₆H₅ | -CH₂-CH₂-NH₂ | HC≡C-CH₂- | -C(O)- |
| 136 | -COOH | -C(O)O-CH₂-C₆H₅ | -CH₂-CH₂-NH₂ | N₃-CH₂-CH₂- | -C(O)- |
| 137 | -COOH | -C(O)O-CH₂-C₆H₅ | -CH₂-CH₂-NH₂ | H₃C- | -C(O)- |
| 138 | -COOH | -C(O)O-CH₂-C₆H₅ | -CH₂-CH₂-CH₂-NH₂ | HC≡C-CH₂- | -C(O)- |
| 139 | -COOH | -C(O)O-CH₂-C₆H₅ | -CH₂-CH₂-CH₂-NH₂ | N₃-CH₂-CH₂- | -C(O)- |
| 140 | -COOH | -C(O)O-CH₂-C₆H₅ | -CH₂-CH₂-CH₂-NH₂ | H₃C- | -C(O)- |

TABLE 1-continued

| Compound | A[1] | A[2] | A[3] | E[1] | E[2] |
|---|---|---|---|---|---|
| 141 | -COOH | -C(=O)O-CH2-C6H5 | imidazol-4-yl | -CH2-C≡CH | -C(=O)CH3 |
| 142 | -COOH | -C(=O)O-CH2-C6H5 | imidazol-4-yl | -CH2CH2-N3 | -C(=O)CH3 |
| 143 | -COOH | -C(=O)O-CH2-C6H5 | imidazol-4-yl | -CH3 | -C(=O)CH3 |
| 144 | -COOH | -C(=O)O-CH2-C6H5 | -SH | -CH2-C≡CH | -C(=O)CH3 |
| 145 | -COOH | -C(=O)O-CH2-C6H5 | -SH | -CH2CH2-N3 | -C(=O)CH3 |
| 146 | -COOH | -C(=O)O-CH2-C6H5 | -SH | -CH3 | -C(=O)CH3 |
| 147 | -COOH | -CH2-C(=O)O-CH2-C6H5 | 4-hydroxyphenyl | -CH2-C≡CH | -C(=O)CH3 |
| 148 | -COOH | -CH2-C(=O)O-CH2-C6H5 | 4-hydroxyphenyl | -CH2CH2-N3 | -C(=O)CH3 |
| 149 | -COOH | -CH2-C(=O)O-CH2-C6H5 | 4-hydroxyphenyl | -CH3 | -C(=O)CH3 |
| 150 | -COOH | -CH2-C(=O)O-CH2-C6H5 | 3,4-dihydroxyphenyl | -CH2-C≡CH | -C(=O)CH3 |

TABLE 1-continued

| Compound | A¹ | A² | A³ | E¹ | E² |
|---|---|---|---|---|---|
| 151 | -COOH | -C(O)O-CH₂-C₆H₅ | 3,4-dihydroxyphenyl | N₃-CH₂CH₂- | -C(O)CH₃ |
| 152 | -COOH | -C(O)O-CH₂-C₆H₅ | 3,4-dihydroxyphenyl | H₃C- | -C(O)CH₃ |
| 153 | -COOH | -C(O)O-CH₂-C₆H₅ | -CH₂-COOH | HC≡C-CH₂- | -C(O)CH₃ |
| 154 | -COOH | -C(O)O-CH₂-C₆H₅ | -CH₂-COOH | N₃-CH₂CH₂- | -C(O)CH₃ |
| 155 | -COOH | -C(O)O-CH₂-C₆H₅ | -CH₂-COOH | H₃C- | -C(O)CH₃ |
| 156 | -COOH | -C(O)O-CH₂-C₆H₅ | -CH₂-COOH | HC≡C-CH₂- | -C(O)CH₃ |
| 157 | -COOH | -C(O)O-CH₂-C₆H₅ | -CH₂-COOH | N₃-CH₂CH₂- | -C(O)CH₃ |
| 158 | -COOH | -C(O)O-CH₂-C₆H₅ | -CH₂-COOH | H₃C- | -C(O)CH₃ |
| 159 | -COOH | -C(O)O-CH₂-C₆H₅ | -CH₂CH₂-NH₂ | HC≡C-CH₂- | -C(O)CH₃ |
| 160 | -COOH | -C(O)O-CH₂-C₆H₅ | -CH₂CH₂-NH₂ | N₃-CH₂CH₂- | -C(O)CH₃ |

TABLE 1-continued

| Compound | A¹ | A² | A³ | E¹ | E² |
|---|---|---|---|---|---|
| 161 | COOH | CH₂C(O)OCH₂Ph | CH₂CH₂NH₂ | CH₃ | C(O)CH₃ |
| 162 | COOH | CH₂C(O)OCH₂Ph | CH₂CH₂CH₂NH₂ | C≡CH | C(O)CH₃ |
| 163 | COOH | CH₂C(O)OCH₂Ph | CH₂CH₂CH₂NH₂ | CH₂CH₂N₃ | C(O)CH₃ |
| 164 | COOH | CH₂C(O)OCH₂Ph | CH₂CH₂CH₂NH₂ | CH₃ | C(O)CH₃ |
| 165 | COOH | CH₂C(O)OCH₂Ph | imidazolyl | C≡CH | C(O)CH₃ |
| 166 | COOH | CH₂C(O)OCH₂Ph | imidazolyl | CH₂CH₂N₃ | C(O)CH₃ |
| 167 | COOH | CH₂C(O)OCH₂Ph | imidazolyl | CH₃ | C(O)CH₃ |
| 168 | COOH | CH₂C(O)OCH₂Ph | SH | C≡CH | C(O)CH₃ |
| 169 | COOH | CH₂C(O)OCH₂Ph | SH | CH₂CH₂N₃ | C(O)CH₃ |
| 170 | COOH | CH₂C(O)OCH₂Ph | SH | CH₃ | C(O)CH₃ |

TABLE 1-continued

| Compound | A¹ | A² | A³ | E¹ | E² |
|---|---|---|---|---|---|
| 171 | -CH₂-COOH | phenyl | 3,4-dihydroxyphenyl | HC≡C-CH₂- | -C(O)CH₃ |
| 172 | -CH₂-COOH | phenyl | 3,4-dihydroxyphenyl | N₃-CH₂CH₂- | -C(O)CH₃ |
| 173 | -CH₂-COOH | phenyl | 3,4-dihydroxyphenyl | H₃C- | -C(O)CH₃ |
| 174 | -CH₂-COOH | isopropyl | 4-hydroxyphenyl | HC≡C-CH₂- | -C(O)CH₃ |
| 175 | -CH₂-COOH | isopropyl | 4-hydroxyphenyl | N₃-CH₂CH₂- | -C(O)CH₃ |
| 176 | -CH₂-COOH | isopropyl | 4-hydroxyphenyl | H₃C- | -C(O)CH₃ |
| 177 | -CH₂-COOH | isopropyl | 3,4-dihydroxyphenyl | HC≡C-CH₂- | -C(O)CH₃ |
| 178 | -CH₂-COOH | isopropyl | 3,4-dihydroxyphenyl | N₃-CH₂CH₂- | -C(O)CH₃ |
| 179 | -CH₂-COOH | isopropyl | 3,4-dihydroxyphenyl | H₃C- | -C(O)CH₃ |
| 180 | -CH₂-COOH | isopropyl | -CH₂-COOH | HC≡C-CH₂- | -C(O)CH₃ |
| 181 | -CH₂-COOH | isopropyl | -CH₂-COOH | N₃-CH₂CH₂- | -C(O)CH₃ |
| 182 | -CH₂-COOH | isopropyl | -CH₂-COOH | H₃C- | -C(O)CH₃ |
| 183 | -CH₂-COOH | isopropyl | -CH₂-COOH | HC≡C-CH₂- | -C(O)CH₃ |

TABLE 1-continued

| Compound | A¹ | A² | A³ | E¹ | E² |
|---|---|---|---|---|---|
| 184 | CH₂COOH | iPr | CH₂COOH | N₃-CH₂CH₂- | C(=O)CH₃ |
| 185 | CH₂COOH | iPr | CH₂COOH | H₃C- | C(=O)CH₃ |
| 186 | CH₂COOH | iPr | CH₂CH₂NH₂ | HC≡C-CH₂- | C(=O)CH₃ |
| 187 | CH₂COOH | iPr | CH₂CH₂NH₂ | N₃-CH₂CH₂- | C(=O)CH₃ |
| 188 | CH₂COOH | iPr | CH₂CH₂NH₂ | H₃C- | C(=O)CH₃ |
| 189 | CH₂COOH | iPr | CH₂CH₂CH₂NH₂ | HC≡C-CH₂- | C(=O)CH₃ |
| 190 | CH₂COOH | iPr | CH₂CH₂CH₂NH₂ | N₃-CH₂CH₂- | C(=O)CH₃ |
| 191 | CH₂COOH | iPr | CH₂CH₂CH₂NH₂ | H₃C- | C(=O)CH₃ |
| 192 | CH₂COOH | iPr | CH₂-imidazole | HC≡C-CH₂- | C(=O)CH₃ |
| 193 | CH₂COOH | iPr | CH₂-imidazole | N₃-CH₂CH₂- | C(=O)CH₃ |
| 194 | CH₂COOH | iPr | CH₂-imidazole | H₃C- | C(=O)CH₃ |
| 195 | CH₂COOH | iPr | CH₂SH | HC≡C-CH₂- | C(=O)CH₃ |
| 196 | CH₂COOH | iPr | CH₂SH | N₃-CH₂CH₂- | C(=O)CH₃ |
| 197 | CH₂COOH | iPr | CH₂SH | H₃C- | C(=O)CH₃ |
| 198 | CH₂COOH | CH₂-O-C(=O)-Ph | CH₂-C₆H₄-OH | HC≡C-CH₂- | C(=O)CH₃ |

TABLE 1-continued

| Compound | A¹ | A² | A³ | E¹ | E² |
|---|---|---|---|---|---|
| 199 | CH₂COOH | CH₂-O-C(O)- benzyl | 4-hydroxyphenyl | N₃-CH₂CH₂- | -C(O)CH₃ |
| 200 | CH₂COOH | CH₂-O-C(O)- benzyl | 4-hydroxyphenyl | H₃C- | -C(O)CH₃ |
| 201 | CH₂COOH | CH₂-O-C(O)- benzyl | 3,4-dihydroxyphenyl | HC≡C-CH₂- | -C(O)CH₃ |
| 202 | CH₂COOH | CH₂-O-C(O)- benzyl | 3,4-dihydroxyphenyl | N₃-CH₂CH₂- | -C(O)CH₃ |
| 203 | CH₂COOH | CH₂-O-C(O)- benzyl | 3,4-dihydroxyphenyl | H₃C- | -C(O)CH₃ |
| 204 | CH₂COOH | CH₂-O-C(O)- benzyl | CH₂COOH | HC≡C-CH₂- | -C(O)CH₃ |
| 205 | CH₂COOH | CH₂-O-C(O)- benzyl | CH₂COOH | N₃-CH₂CH₂- | -C(O)CH₃ |
| 206 | CH₂COOH | CH₂-O-C(O)- benzyl | CH₂COOH | H₃C- | -C(O)CH₃ |
| 207 | CH₂COOH | CH₂-O-C(O)- benzyl | CH₂COOH | HC≡C-CH₂- | -C(O)CH₃ |
| 208 | CH₂COOH | CH₂-O-C(O)- benzyl | CH₂COOH | N₃-CH₂CH₂- | -C(O)CH₃ |

TABLE 1-continued

| Compound | A¹ | A² | A³ | E¹ | E² |
|---|---|---|---|---|---|
| 209 | -CH2COOH | -C(O)OCH2Ph | -CH2COOH | H3C- | -C(O)CH3 |
| 210 | -CH2COOH | -C(O)OCH2Ph | -CH2CH2NH2 | HC≡C-CH2- | -C(O)CH3 |
| 211 | -CH2COOH | -C(O)OCH2Ph | -CH2CH2NH2 | N3-CH2CH2- | -C(O)CH3 |
| 212 | -CH2COOH | -C(O)OCH2Ph | -CH2CH2NH2 | H3C- | -C(O)CH3 |
| 213 | -CH2COOH | -C(O)OCH2Ph | -CH2CH2CH2NH2 | HC≡C-CH2- | -C(O)CH3 |
| 214 | -CH2COOH | -C(O)OCH2Ph | -CH2CH2CH2NH2 | N3-CH2CH2- | -C(O)CH3 |
| 215 | -CH2COOH | -C(O)OCH2Ph | -CH2CH2CH2NH2 | H3C- | -C(O)CH3 |
| 216 | -CH2COOH | -C(O)OCH2Ph | -CH2-(1H-imidazol-4-yl) | HC≡C-CH2- | -C(O)CH3 |
| 217 | -CH2COOH | -C(O)OCH2Ph | -CH2-(1H-imidazol-4-yl) | N3-CH2CH2- | -C(O)CH3 |
| 218 | -CH2COOH | -C(O)OCH2Ph | -CH2-(1H-imidazol-4-yl) | H3C- | -C(O)CH3 |

TABLE 1-continued

| Compound | A¹ | A² | A³ | E¹ | E² |
|---|---|---|---|---|---|
| 219 | -CH₂COOH | -C(O)OCH₂Ph | -SH | HC≡C-CH₂- | -C(O)CH₃ |
| 220 | -CH₂COOH | -C(O)OCH₂Ph | -SH | HC≡C-CH₂- | -C(O)CH₃ |
| 221 | -CH₂COOH | -C(O)OCH₂Ph | -SH | H₃C- | -C(O)CH₃ |
| 222 | -CH₂COOH | -C(O)OCH₂Ph | 4-HO-C₆H₄- | HC≡C-CH₂- | -C(O)CH₃ |
| 223 | -CH₂COOH | -C(O)OCH₂Ph | 4-HO-C₆H₄- | N₃CH₂CH₂- | -C(O)CH₃ |
| 224 | -CH₂COOH | -C(O)OCH₂Ph | 4-HO-C₆H₄- | H₃C- | -C(O)CH₃ |
| 225 | -CH₂COOH | -C(O)OCH₂Ph | 3,4-(HO)₂-C₆H₃- | HC≡C-CH₂- | -C(O)CH₃ |
| 226 | -CH₂COOH | -C(O)OCH₂Ph | 3,4-(HO)₂-C₆H₃- | N₃CH₂CH₂- | -C(O)CH₃ |
| 227 | -CH₂COOH | -C(O)OCH₂Ph | 3,4-(HO)₂-C₆H₃- | H₃C- | -C(O)CH₃ |
| 228 | -CH₂COOH | -C(O)OCH₂Ph | -COOH | HC≡C-CH₂- | -C(O)CH₃ |

TABLE 1-continued

| Compound | A$^1$ | A$^2$ | A$^3$ | E$^1$ | E$^2$ |
|---|---|---|---|---|---|
| 229 | -CH$_2$COOH | -CH$_2$C(O)OCH$_2$Ph | -CH$_2$COOH | N$_3$-CH$_2$CH$_2$- | -C(O)CH$_3$ |
| 230 | -CH$_2$COOH | -CH$_2$C(O)OCH$_2$Ph | -CH$_2$COOH | H$_3$C- | -C(O)CH$_3$ |
| 231 | -CH$_2$COOH | -CH$_2$C(O)OCH$_2$Ph | -CH$_2$COOH | HC≡C-CH$_2$- | -C(O)CH$_3$ |
| 232 | -CH$_2$COOH | -CH$_2$C(O)OCH$_2$Ph | -CH$_2$COOH | N$_3$-CH$_2$CH$_2$- | -C(O)CH$_3$ |
| 233 | -CH$_2$COOH | -CH$_2$C(O)OCH$_2$Ph | -CH$_2$COOH | H$_3$C- | -C(O)CH$_3$ |
| 234 | -CH$_2$COOH | -CH$_2$C(O)OCH$_2$Ph | -CH$_2$CH$_2$NH$_2$ | HC≡C-CH$_2$- | -C(O)CH$_3$ |
| 235 | -CH$_2$COOH | -CH$_2$C(O)OCH$_2$Ph | -CH$_2$CH$_2$NH$_2$ | N$_3$-CH$_2$CH$_2$- | -C(O)CH$_3$ |
| 236 | -CH$_2$COOH | -CH$_2$C(O)OCH$_2$Ph | -CH$_2$CH$_2$NH$_2$ | H$_3$C- | -C(O)CH$_3$ |
| 237 | -CH$_2$COOH | -CH$_2$C(O)OCH$_2$Ph | -CH$_2$CH$_2$CH$_2$NH$_2$ | HC≡C-CH$_2$- | -C(O)CH$_3$ |
| 238 | -CH$_2$COOH | -CH$_2$C(O)OCH$_2$Ph | -CH$_2$CH$_2$CH$_2$NH$_2$ | N$_3$-CH$_2$CH$_2$- | -C(O)CH$_3$ |

TABLE 1-continued

| Compound | A¹ | A² | A³ | E¹ | E² |
|---|---|---|---|---|---|
| 239 | -CH2-COOH | -CH2-C(O)O-CH2-Ph | -CH2CH2CH2-NH2 | H3C- | -C(O)CH2- |
| 240 | -CH2-COOH | -CH2-C(O)O-CH2-Ph | imidazol-4-yl | HC≡C-CH2- | -C(O)CH2- |
| 241 | -CH2-COOH | -CH2-C(O)O-CH2-Ph | imidazol-4-yl | N3-CH2CH2- | -C(O)CH2- |
| 242 | -CH2-COOH | -CH2-C(O)O-CH2-Ph | imidazol-4-yl | H3C- | -C(O)CH2- |
| 243 | -CH2-COOH | -CH2-C(O)O-CH2-Ph | -SH | HC≡C-CH2- | -C(O)CH2- |
| 244 | -CH2-COOH | -CH2-C(O)O-CH2-Ph | -SH | N3-CH2CH2- | -C(O)CH2- |
| 245 | -CH2-COOH | -CH2-C(O)O-CH2-Ph | -SH | H3C- | -C(O)CH2- |
| 246 | -CH2-COOH | -Ph | 3,4-dihydroxyphenyl | HC≡C-CH2- | -C(O)CH2- |
| 247 | -CH2-COOH | -Ph | 3,4-dihydroxyphenyl | N3-CH2CH2- | -C(O)CH2- |
| 248 | -CH2-COOH | -Ph | 3,4-dihydroxyphenyl | H3C- | -C(O)CH2- |
| 249 | imidazol-4-yl | -CH2-CH(CH3)2 | 4-hydroxyphenyl | HC≡C-CH2- | -C(O)CH2- |

TABLE 1-continued

| Compound | A¹ | A² | A³ | E¹ | E² |
|---|---|---|---|---|---|
| 250 | imidazole | isopropyl | 4-hydroxyphenyl | N₃-CH₂CH₂- | acetyl |
| 251 | imidazole | isopropyl | 4-hydroxyphenyl | H₃C- | acetyl |
| 252 | imidazole | isopropyl | 3,4-dihydroxyphenyl | HC≡C-CH₂- | acetyl |
| 253 | imidazole | isopropyl | 3,4-dihydroxyphenyl | N₃-CH₂CH₂- | acetyl |
| 254 | imidazole | isopropyl | 3,4-dihydroxyphenyl | H₃C- | acetyl |
| 255 | imidazole | isopropyl | -CH₂COOH | HC≡C-CH₂- | acetyl |
| 256 | imidazole | isopropyl | -CH₂COOH | N₃-CH₂CH₂- | acetyl |
| 257 | imidazole | isopropyl | -CH₂COOH | H₃C- | acetyl |
| 258 | imidazole | isopropyl | -CH₂CH₂COOH | HC≡C-CH₂- | acetyl |
| 259 | imidazole | isopropyl | -CH₂CH₂COOH | N₃-CH₂CH₂- | acetyl |
| 260 | imidazole | isopropyl | -CH₂CH₂COOH | H₃C- | acetyl |
| 261 | imidazole | isopropyl | -CH₂CH₂NH₂ | HC≡C-CH₂- | acetyl |
| 262 | imidazole | isopropyl | -CH₂CH₂NH₂ | N₃-CH₂CH₂- | acetyl |
| 263 | imidazole | isopropyl | -CH₂CH₂NH₂ | H₃C- | acetyl |

TABLE 1-continued

| Compound | A¹ | A² | A³ | E¹ | E² |
|---|---|---|---|---|---|
| 264 | imidazole | isopropyl | propyl-NH₂ | alkyne | C(=O) |
| 265 | imidazole | isopropyl | propyl-NH₂ | N₃-ethyl | C(=O) |
| 266 | imidazole | isopropyl | propyl-NH₂ | H₃C | C(=O) |
| 267 | imidazole | isopropyl | imidazole | alkyne | C(=O) |
| 268 | imidazole | isopropyl | imidazole | N₃-ethyl | C(=O) |
| 269 | imidazole | isopropyl | imidazole | H₃C | C(=O) |
| 270 | imidazole | isopropyl | SH | alkyne | C(=O) |
| 271 | imidazole | isopropyl | SH | N₃-ethyl | C(=O) |
| 272 | imidazole | isopropyl | SH | H₃C | C(=O) |
| 273 | imidazole | benzyl ester | 4-OH-phenyl | alkyne | C(=O) |
| 274 | imidazole | benzyl ester | 4-OH-phenyl | N₃-ethyl | C(=O) |
| 275 | imidazole | benzyl ester | 4-OH-phenyl | H₃C | C(=O) |
| 276 | imidazole | benzyl ester | 3,4-diOH-phenyl | alkyne | C(=O) |

TABLE 1-continued

| Compound | A¹ | A² | A³ | E¹ | E² |
|---|---|---|---|---|---|
| 277 | imidazole | benzyl ester | catechol (3,4-diOH phenyl) | N₃-CH₂CH₂- | acetyl |
| 278 | imidazole | benzyl ester | catechol (3,4-diOH phenyl) | H₃C- | acetyl |
| 279 | imidazole | benzyl ester | -CH₂-COOH | HC≡C-CH₂- | acetyl |
| 280 | imidazole | benzyl ester | -CH₂-COOH | N₃-CH₂CH₂- | acetyl |
| 281 | imidazole | benzyl ester | -CH₂-COOH | H₃C- | acetyl |
| 282 | imidazole | benzyl ester | -CH₂CH₂-COOH | HC≡C-CH₂- | acetyl |
| 283 | imidazole | benzyl ester | -CH₂CH₂-COOH | N₃-CH₂CH₂- | acetyl |
| 284 | imidazole | benzyl ester | -CH₂CH₂-COOH | H₃C- | acetyl |
| 285 | imidazole | benzyl ester | -CH₂CH₂-NH₂ | HC≡C-CH₂- | acetyl |
| 286 | imidazole | benzyl ester | -CH₂CH₂-NH₂ | N₃-CH₂CH₂- | acetyl |

TABLE 1-continued

| Compound | A¹ | A² | A³ | E¹ | E² |
|---|---|---|---|---|---|
| 287 | imidazole | benzyl ester | ethyl-NH₂ | H₃C- | acetyl |
| 288 | imidazole | benzyl ester | propyl-NH₂ | alkyne | acetyl |
| 289 | imidazole | benzyl ester | propyl-NH₂ | N₃-ethyl | acetyl |
| 290 | imidazole | benzyl ester | propyl-NH₂ | H₃C- | acetyl |
| 291 | imidazole | benzyl ester | imidazole | alkyne | acetyl |
| 292 | imidazole | benzyl ester | imidazole | N₃-ethyl | acetyl |
| 293 | imidazole | benzyl ester | imidazole | H₃C- | acetyl |
| 294 | imidazole | benzyl ester | SH | alkyne | acetyl |
| 295 | imidazole | benzyl ester | SH | N₃-ethyl | acetyl |
| 296 | imidazole | benzyl ester | SH | H₃C- | acetyl |

TABLE 1-continued

| Compound | A¹ | A² | A³ | E¹ | E² |
|---|---|---|---|---|---|
| 297 | imidazole (HN, N) | benzyl ester -CH₂-C(=O)-O-CH₂-Ph | 4-hydroxyphenyl | propargyl (HC≡C-CH₂-) | acetyl |
| 298 | imidazole | benzyl ester | 4-hydroxyphenyl | N₃-CH₂CH₂- | acetyl |
| 299 | imidazole | benzyl ester | 4-hydroxyphenyl | H₃C- | acetyl |
| 300 | imidazole | benzyl ester | 3,4-dihydroxyphenyl | propargyl | acetyl |
| 301 | imidazole | benzyl ester | 3,4-dihydroxyphenyl | N₃-CH₂CH₂- | acetyl |
| 302 | imidazole | benzyl ester | 3,4-dihydroxyphenyl | H₃C- | acetyl |
| 303 | imidazole | benzyl ester | -CH₂-COOH | propargyl | acetyl |
| 304 | imidazole | benzyl ester | -CH₂-COOH | N₃-CH₂CH₂- | acetyl |
| 305 | imidazole | benzyl ester | -CH₂-COOH | H₃C- | acetyl |
| 306 | imidazole | benzyl ester | -CH₂-COOH | propargyl | acetyl |

TABLE 1-continued

| Compound | A¹ | A² | A³ | E¹ | E² |
|---|---|---|---|---|---|
| 307 | imidazole | benzyl ester (–CH₂C(O)OCH₂Ph) | –CH₂C(O)OH | N₃–CH₂CH₂– | –C(O)CH₃ |
| 308 | imidazole | benzyl ester | –CH₂C(O)OH | H₃C– | –C(O)CH₃ |
| 309 | imidazole | benzyl ester | –CH₂CH₂NH₂ | HC≡C–CH₂– | –C(O)CH₃ |
| 310 | imidazole | benzyl ester | –CH₂CH₂NH₂ | N₃–CH₂CH₂– | –C(O)CH₃ |
| 311 | imidazole | benzyl ester | –CH₂CH₂NH₂ | H₃C– | –C(O)CH₃ |
| 312 | imidazole | benzyl ester | –CH₂CH₂CH₂NH₂ | HC≡C–CH₂– | –C(O)CH₃ |
| 313 | imidazole | benzyl ester | –CH₂CH₂CH₂NH₂ | N₃–CH₂CH₂– | –C(O)CH₃ |
| 314 | imidazole | benzyl ester | –CH₂CH₂CH₂NH₂ | H₃C– | –C(O)CH₃ |
| 315 | imidazole | benzyl ester | imidazole | HC≡C–CH₂– | –C(O)CH₃ |
| 316 | imidazole | benzyl ester | imidazole | N₃–CH₂CH₂– | –C(O)CH₃ |

TABLE 1-continued

| Compound | A¹ | A² | A³ | E¹ | E² |
|---|---|---|---|---|---|
| 317 | imidazole | -CH₂C(O)O-CH₂-phenyl | imidazole | H₃C- | -C(O)CH₃ |
| 318 | imidazole | -CH₂C(O)O-CH₂-phenyl | -SH | HC≡C-CH₂- | -C(O)CH₃ |
| 319 | imidazole | -CH₂C(O)O-CH₂-phenyl | -SH | N₃-CH₂CH₂- | -C(O)CH₃ |
| 320 | imidazole | -CH₂C(O)O-CH₂-phenyl | -SH | H₃C- | -C(O)CH₃ |
| 321 | imidazole | phenyl | 3,4-dihydroxyphenyl | HC≡C-CH₂- | -C(O)CH₃ |
| 322 | imidazole | phenyl | 3,4-dihydroxyphenyl | N₃-CH₂CH₂- | -C(O)CH₃ |
| 323 | imidazole | phenyl | 3,4-dihydroxyphenyl | H₃C- | -C(O)CH₃ |
| 324 | 2-benzimidazolyl | isobutyl | 4-hydroxyphenyl | HC≡C-CH₂- | -C(O)CH₃ |
| 325 | 2-benzimidazolyl | isobutyl | 4-hydroxyphenyl | N₃-CH₂CH₂- | -C(O)CH₃ |
| 326 | 2-benzimidazolyl | isobutyl | 4-hydroxyphenyl | H₃C- | -C(O)CH₃ |
| 327 | 2-benzimidazolyl | isobutyl | 3,4-dihydroxyphenyl | HC≡C-CH₂- | -C(O)CH₃ |

TABLE 1-continued

| Compound | A¹ | A² | A³ | E¹ | E² |
|---|---|---|---|---|---|
| 328 | 2-ethyl-1H-benzimidazole | isopropyl | 3,4-dihydroxyphenyl | N₃-CH₂CH₂- | acetyl |
| 329 | 2-ethyl-1H-benzimidazole | isopropyl | 3,4-dihydroxyphenyl | H₃C- | acetyl |
| 330 | 2-ethyl-1H-benzimidazole | isopropyl | -CH₂-COOH | HC≡C-CH₂- | acetyl |
| 331 | 2-ethyl-1H-benzimidazole | isopropyl | -CH₂-COOH | N₃-CH₂CH₂- | acetyl |
| 332 | 2-ethyl-1H-benzimidazole | isopropyl | -CH₂-COOH | H₃C- | acetyl |
| 333 | 2-ethyl-1H-benzimidazole | isopropyl | -CH₂CH₂-COOH | HC≡C-CH₂- | acetyl |
| 334 | 2-ethyl-1H-benzimidazole | isopropyl | -CH₂CH₂-COOH | N₃-CH₂CH₂- | acetyl |
| 335 | 2-ethyl-1H-benzimidazole | isopropyl | -CH₂CH₂-COOH | H₃C- | acetyl |
| 336 | 2-ethyl-1H-benzimidazole | isopropyl | -CH₂CH₂-NH₂ | HC≡C-CH₂- | acetyl |
| 337 | 2-ethyl-1H-benzimidazole | isopropyl | -CH₂CH₂-NH₂ | N₃-CH₂CH₂- | acetyl |
| 338 | 2-ethyl-1H-benzimidazole | isopropyl | -CH₂CH₂-NH₂ | H₃C- | acetyl |
| 339 | 2-ethyl-1H-benzimidazole | isopropyl | -CH₂CH₂CH₂-NH₂ | HC≡C-CH₂- | acetyl |
| 340 | 2-ethyl-1H-benzimidazole | isopropyl | -CH₂CH₂CH₂-NH₂ | N₃-CH₂CH₂- | acetyl |

TABLE 1-continued

| Compound | A¹ | A² | A³ | E¹ | E² |
|---|---|---|---|---|---|
| 341 | 2-ethyl-1H-benzimidazole | isobutyl | propylamine | H₃C– | acetyl |
| 342 | 2-ethyl-1H-benzimidazole | isobutyl | 1H-imidazol-4-yl | HC≡C–CH₂– | acetyl |
| 343 | 2-ethyl-1H-benzimidazole | isobutyl | 1H-imidazol-4-yl | N₃–CH₂CH₂– | acetyl |
| 344 | 2-ethyl-1H-benzimidazole | isobutyl | 1H-imidazol-4-yl | H₃C– | acetyl |
| 345 | 2-ethyl-1H-benzimidazole | isobutyl | SH | HC≡C– | acetyl |
| 346 | 2-ethyl-1H-benzimidazole | isobutyl | SH | N₃–CH₂CH₂– | acetyl |
| 347 | 2-ethyl-1H-benzimidazole | isobutyl | SH | H₃C– | acetyl |
| 348 | 2-ethyl-1H-benzimidazole | benzyl ester | 4-hydroxyphenyl | HC≡C– | acetyl |
| 349 | 2-ethyl-1H-benzimidazole | benzyl ester | 4-hydroxyphenyl | N₃–CH₂CH₂– | acetyl |
| 350 | 2-ethyl-1H-benzimidazole | benzyl ester | 4-hydroxyphenyl | H₃C– | acetyl |
| 351 | 2-ethyl-1H-benzimidazole | benzyl ester | 3,4-dihydroxyphenyl | HC≡C– | acetyl |

TABLE 1-continued

| Compound | A¹ | A² | A³ | E¹ | E² |
|---|---|---|---|---|---|
| 352 | 2-ethyl-1H-benzimidazole | benzyl ester | 3,4-dihydroxyphenyl | N₃-CH₂CH₂- | acetyl |
| 353 | 2-ethyl-1H-benzimidazole | benzyl ester | 3,4-dihydroxyphenyl | H₃C- | acetyl |
| 354 | 2-ethyl-1H-benzimidazole | benzyl ester | -CH₂COOH | HC≡C-CH₂- | acetyl |
| 355 | 2-ethyl-1H-benzimidazole | benzyl ester | -CH₂COOH | N₃-CH₂CH₂- | acetyl |
| 356 | 2-ethyl-1H-benzimidazole | benzyl ester | -CH₂COOH | H₃C- | acetyl |
| 357 | 2-ethyl-1H-benzimidazole | benzyl ester | -CH₂COOH | HC≡C-CH₂- | acetyl |
| 358 | 2-ethyl-1H-benzimidazole | benzyl ester | -CH₂COOH | N₃-CH₂CH₂- | acetyl |
| 359 | 2-ethyl-1H-benzimidazole | benzyl ester | -CH₂COOH | H₃C- | acetyl |
| 360 | 2-ethyl-1H-benzimidazole | benzyl ester | -CH₂CH₂NH₂ | HC≡C-CH₂- | acetyl |
| 361 | 2-ethyl-1H-benzimidazole | benzyl ester | -CH₂CH₂NH₂ | N₃-CH₂CH₂- | acetyl |

TABLE 1-continued
| Compound | A¹ | A² | A³ | E¹ | E² |
|---|---|---|---|---|---|
| 362 | 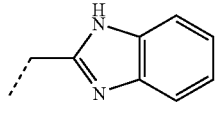 | 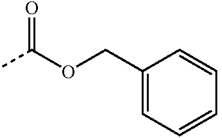 | 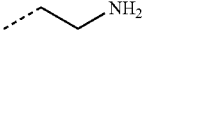 | 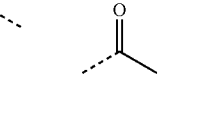 |  |
| 363 | 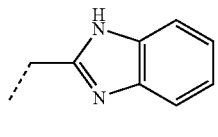 | 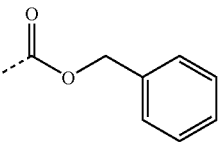 | 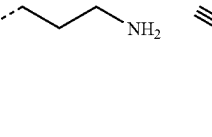 | 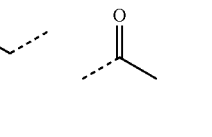 |  |
| 364 | 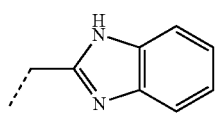 | 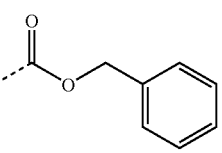 | 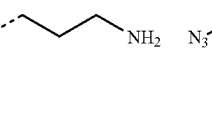 | 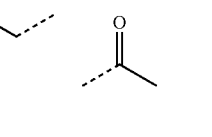 |  |
| 365 | 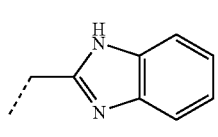 | 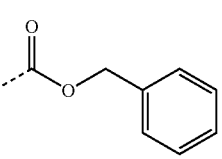 | 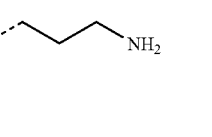 | 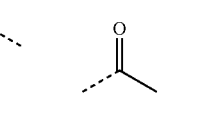 |  |
| 366 | 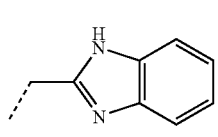 | 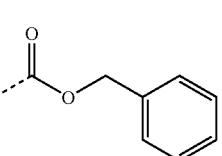 | 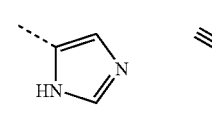 | 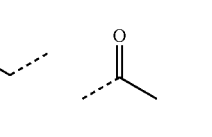 |  |
| 367 | 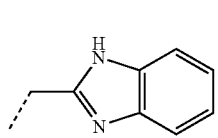 | 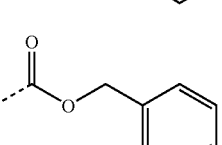 | 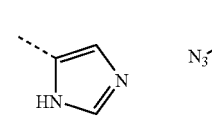 | 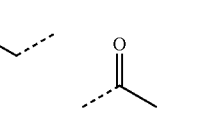 |  |
| 368 | 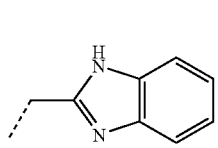 | 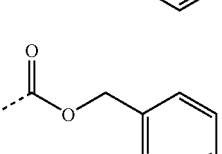 | 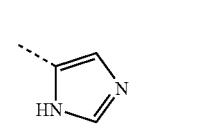 | 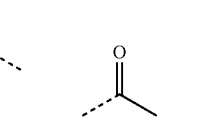 |  |
| 369 | 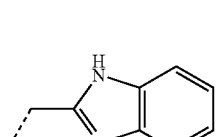 | 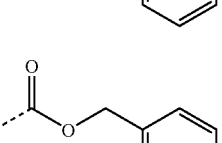 | 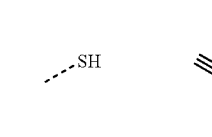 | 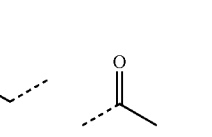 |  |
| 370 | 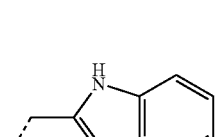 | 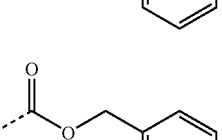 | 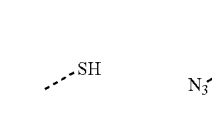 | 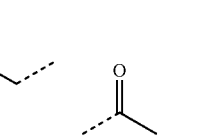 |  |
| 371 | 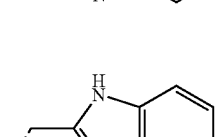 | 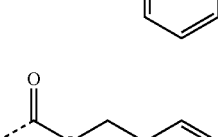 | 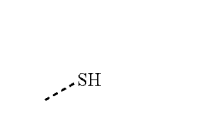 | 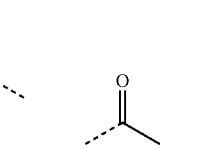 |  |

TABLE 1-continued
| Compound | A¹ | A² | A³ | E¹ | E² |
|---|---|---|---|---|---|
| 372 | 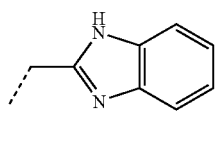 | 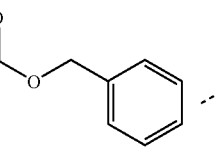 | 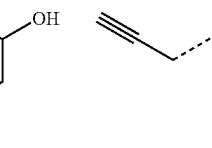 | 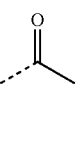 |  |
| 373 | 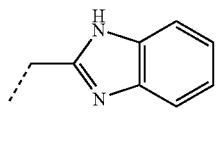 | 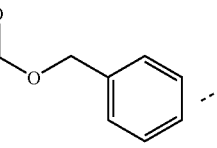 | 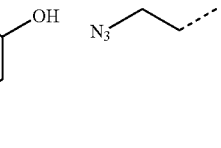 | 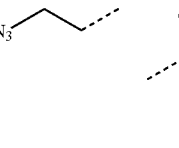 | 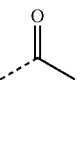 |
| 374 | 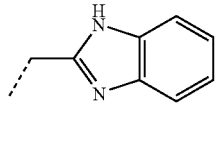 | 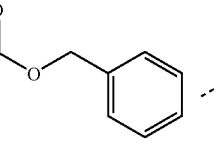 | 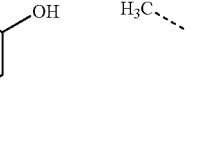 |  | 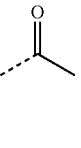 |
| 375 | 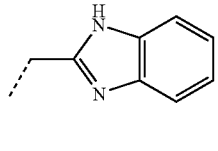 | 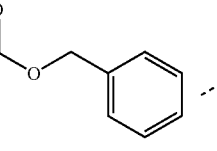 | 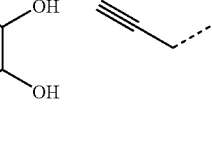 | 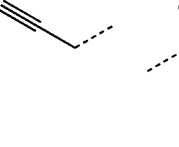 | 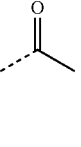 |
| 376 | 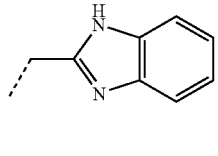 | 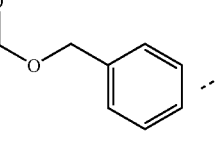 | 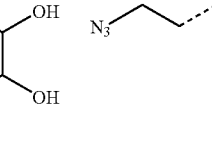 | 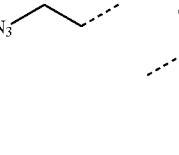 | 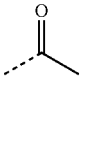 |
| 377 | 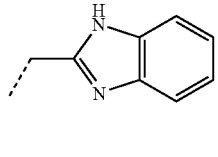 | 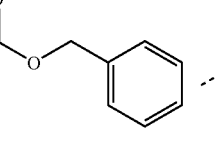 | 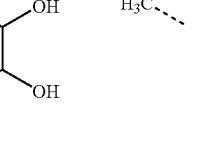 |  | 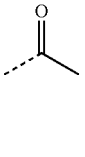 |
| 378 | 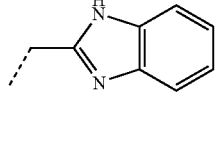 | 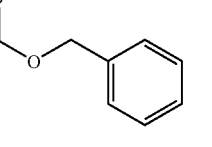 | 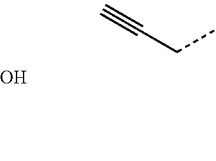 | 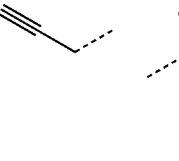 | 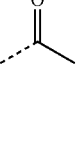 |
| 379 | 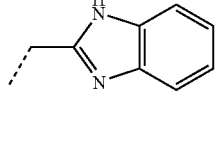 | 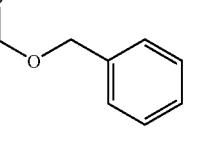 | 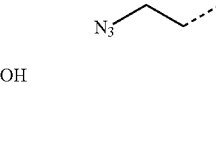 | 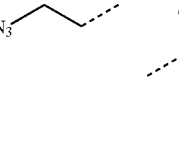 | 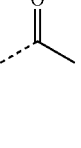 |
| 380 | 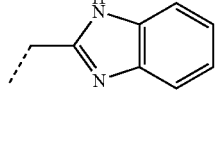 | 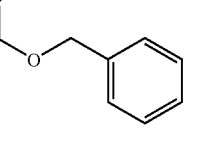 |  |  | 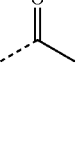 |
| 381 | 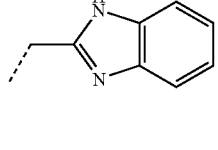 | 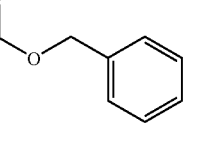 | 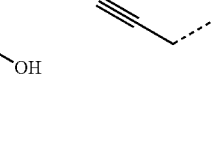 |  | 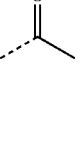 |

TABLE 1-continued
| Compound | A¹ | A² | A³ | E¹ | E² |
|---|---|---|---|---|---|
| 382 | 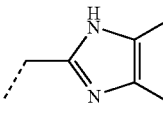 | 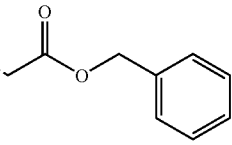 | 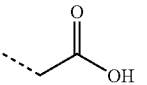 | 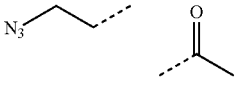 | 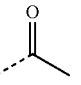 |
| 383 | 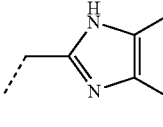 | 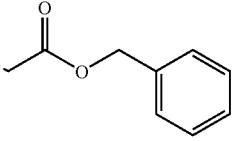 | 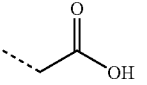 | 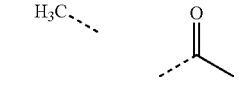 | 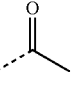 |
| 384 | 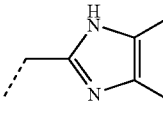 | 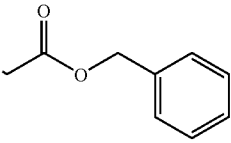 |  | 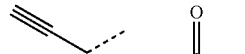 | 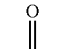 |
| 385 | 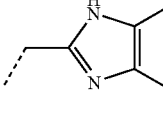 | 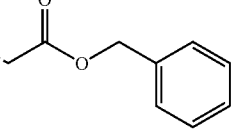 | 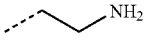 | 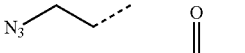 | 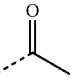 |
| 386 | 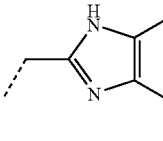 | 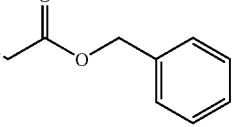 | 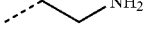 | 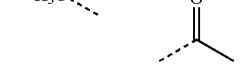 | 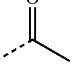 |
| 387 | 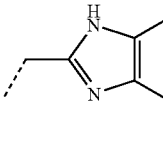 | 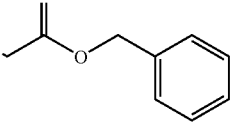 |  | 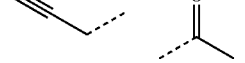 | 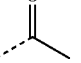 |
| 388 | 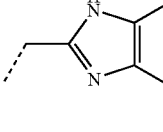 | 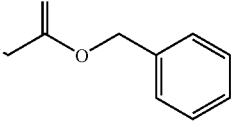 |  |  |  |
| 389 | 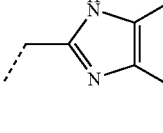 | 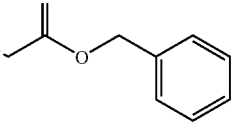 |  |  |  |
| 390 | 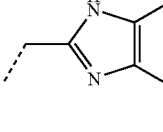 | 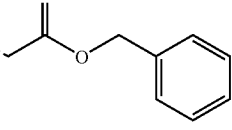 | 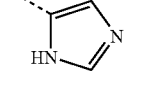 | 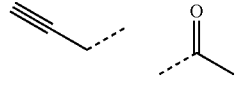 |  |
| 391 | 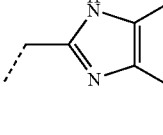 | 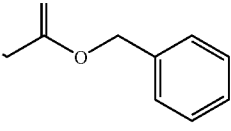 | 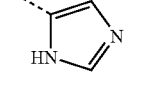 | 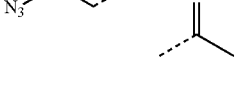 |  |

TABLE 1-continued

| Compound | A¹ | A² | A³ | E¹ | E² |
|---|---|---|---|---|---|
| 392 | 2-ethyl-1H-benzimidazole | benzyl acetate | 1H-imidazole | H₃C- | acetyl |
| 393 | 2-ethyl-1H-benzimidazole | benzyl acetate | -SH | propargyl | acetyl |
| 394 | 2-ethyl-1H-benzimidazole | benzyl acetate | -SH | N₃-CH₂CH₂- | acetyl |
| 395 | 2-ethyl-1H-benzimidazole | benzyl acetate | -SH | H₃C- | acetyl |
| 396 | 2-ethyl-1H-benzimidazole | phenyl | catechol (3,4-dihydroxyphenyl) | propargyl | acetyl |
| 397 | 2-ethyl-1H-benzimidazole | phenyl | catechol (3,4-dihydroxyphenyl) | N₃-CH₂CH₂- | acetyl |
| 398 | 2-ethyl-1H-benzimidazole | phenyl | catechol (3,4-dihydroxyphenyl) | H₃C- | acetyl |

Table 2 sets forth exemplary compounds of the present invention having the formula:
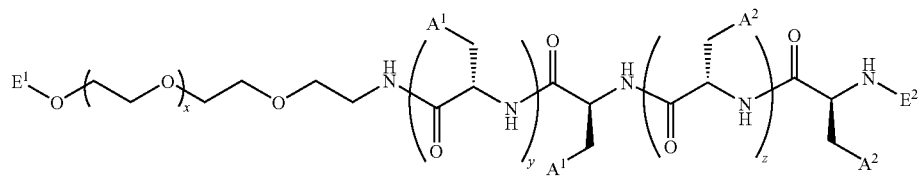
wherein each x is 100-500, each y is 1-50, each z is 1-50, and each dotted bond represents the point of attachment to the rest of the molecule.

TABLE 2-continued

| Compound | A¹ | A² | E¹ | E² |
|---|---|---|---|---|
| 408 | -CH₂-COOH | -(CH₂)₃-NH₂ | -C≡CH | -C(O)CH₃ |
| 409 | -CH₂-COOH | 1H-imidazol-4-yl | -C≡CH | -C(O)CH₃ |
| 410 | -CH₂-COOH | 1H-indol-2-yl | -C≡CH | -C(O)CH₃ |
| 411 | -SH | phenyl | -C≡CH | -C(O)CH₃ |
| 412 | -SH | -C(O)-O-CH₂-phenyl | -C≡CH | -C(O)CH₃ |
| 413 | -SH | -CH₂-C(O)-O-CH₂-phenyl | -C≡CH | -C(O)CH₃ |
| 414 | -SH | -(CH₂)₃-NH₂ | -C≡CH | -C(O)CH₃ |
| 415 | -SH | 1H-imidazol-4-yl | -C≡CH | -C(O)CH₃ |
| 416 | -SH | 1H-indol-2-yl | -C≡CH | -C(O)CH₃ |
| 417 | -COOH | phenyl | H₂N-CH₂CH₂- | -C(O)CH₃ |
| 418 | -COOH | -C(O)-O-CH₂-phenyl | H₂N-CH₂CH₂- | -C(O)CH₃ |
| 419 | -COOH | -CH₂-C(O)-O-CH₂-phenyl | H₂N-CH₂CH₂- | -C(O)CH₃ |
| 420 | -COOH | -(CH₂)₃-NH₂ | H₂N-CH₂CH₂- | -C(O)CH₃ |

TABLE 2-continued

| Compound | A¹ | A² | E¹ | E² |
|---|---|---|---|---|
| 421 | -COOH | imidazol-4-yl | H₂N- | -C(O)CH₃ |
| 422 | -COOH | 1H-indol-2-yl | H₂N- | -C(O)CH₃ |
| 423 | -CH₂COOH | phenyl | H₂N- | -C(O)CH₃ |
| 424 | -CH₂COOH | -C(O)O-CH₂-phenyl | H₂N- | -C(O)CH₃ |
| 425 | -CH₂COOH | -CH₂-C(O)O-CH₂-phenyl | H₂N- | -C(O)CH₃ |
| 426 | -CH₂COOH | -(CH₂)₃NH₂ | H₂N- | -C(O)CH₃ |
| 427 | -CH₂COOH | imidazol-4-yl | H₂N- | -C(O)CH₃ |
| 428 | -CH₂COOH | 1H-indol-2-yl | H₂N- | -C(O)CH₃ |
| 429 | -SH | phenyl | H₂N- | -C(O)CH₃ |
| 430 | -SH | -C(O)O-CH₂-phenyl | H₂N- | -C(O)CH₃ |
| 431 | -SH | -CH₂-C(O)O-CH₂-phenyl | H₂N- | -C(O)CH₃ |
| 432 | -SH | -(CH₂)₃NH₂ | H₂N- | -C(O)CH₃ |

TABLE 2-continued

| Compound | A¹ | A² | E¹ | E² |
|---|---|---|---|---|
| 433 | -SH | imidazol-4-yl | H₂N-CH₂CH₂- | -C(O)CH₃ |
| 434 | -SH | 1H-indol-2-yl | H₂N-CH₂CH₂- | -C(O)CH₃ |
| 435 | -C(O)OH | phenyl | N₃-CH₂CH₂- | -C(O)CH₃ |
| 436 | -C(O)OH | -C(O)O-CH₂-phenyl | N₃-CH₂CH₂- | -C(O)CH₃ |
| 437 | -C(O)OH | -CH₂-C(O)O-CH₂-phenyl | N₃-CH₂CH₂- | -C(O)CH₃ |
| 438 | -C(O)OH | -CH₂CH₂CH₂-NH₂ | N₃-CH₂CH₂- | -C(O)CH₃ |
| 439 | -C(O)OH | imidazol-4-yl | N₃-CH₂CH₂- | -C(O)CH₃ |
| 440 | -C(O)OH | 1H-indol-2-yl | N₃-CH₂CH₂- | -C(O)CH₃ |
| 441 | -CH₂-C(O)OH | phenyl | N₃-CH₂CH₂- | -C(O)CH₃ |
| 442 | -CH₂-C(O)OH | -C(O)O-CH₂-phenyl | N₃-CH₂CH₂- | -C(O)CH₃ |
| 443 | -CH₂-C(O)OH | -CH₂-C(O)O-CH₂-phenyl | N₃-CH₂CH₂- | -C(O)CH₃ |
| 444 | -CH₂-C(O)OH | -CH₂CH₂CH₂-NH₂ | N₃-CH₂CH₂- | -C(O)CH₃ |
| 445 | -CH₂-C(O)OH | imidazol-4-yl | N₃-CH₂CH₂- | -C(O)CH₃ |

TABLE 2-continued

| Compound | A¹ | A² | E¹ | E² |
|---|---|---|---|---|
| 446 | CH₂COOH | 1H-indol-2-yl | N₃-CH₂CH₂- | -C(O)CH₃ |
| 447 | SH | phenyl | N₃-CH₂CH₂- | -C(O)CH₃ |
| 448 | SH | benzyl ester (-C(O)OCH₂Ph) | N₃-CH₂CH₂- | -C(O)CH₃ |
| 449 | SH | -CH₂C(O)OCH₂Ph | N₃-CH₂CH₂- | -C(O)CH₃ |
| 450 | SH | -CH₂CH₂CH₂NH₂ | N₃-CH₂CH₂- | -C(O)CH₃ |
| 451 | SH | 1H-imidazol-4-yl | N₃-CH₂CH₂- | -C(O)CH₃ |
| 452 | SH | 1H-indol-2-yl | N₃-CH₂CH₂- | -C(O)CH₃ |
| 453 | 1H-imidazol-4-yl | phenyl | HC≡C-CH₂- | -C(O)CH₃ |
| 454 | 1H-imidazol-4-yl | -C(O)OCH₂Ph | HC≡C-CH₂- | -C(O)CH₃ |
| 455 | 1H-imidazol-4-yl | -CH₂C(O)OCH₂Ph | HC≡C-CH₂- | -C(O)CH₃ |
| 456 | 1H-imidazol-4-yl | -CH₂CH₂CH₂NH₂ | HC≡C-CH₂- | -C(O)CH₃ |
| 457 | 1H-imidazol-4-yl | phenyl | N₃-CH₂CH₂- | -C(O)CH₃ |

TABLE 2-continued

| Compound | A¹ | A² | E¹ | E² |
|---|---|---|---|---|
| 458 | imidazole | benzyl ester (C(=O)O-CH2-Ph) | N3-CH2CH2- | C(=O)CH3 |
| 459 | imidazole | benzyl ester with CH2 (C(=O)O-CH2-Ph, with extra CH2) | N3-CH2CH2- | C(=O)CH3 |
| 460 | imidazole | -CH2CH2CH2-NH2 | N3-CH2CH2- | C(=O)CH3 |
| 461 | -C(=O)OH | phenyl | HS-CH2CH2- | C(=O)CH3 |
| 462 | -C(=O)OH | -C(=O)O-CH2-Ph | HS-CH2CH2- | C(=O)CH3 |
| 463 | -C(=O)OH | -CH2-C(=O)O-CH2-Ph | HS-CH2CH2- | C(=O)CH3 |
| 464 | -C(=O)OH | -CH2CH2CH2-NH2 | HS-CH2CH2- | C(=O)CH3 |
| 465 | -C(=O)OH | imidazole | HS-CH2CH2- | C(=O)CH3 |
| 466 | -C(=O)OH | indole | HS-CH2CH2- | C(=O)CH3 |
| 467 | -CH2-C(=O)OH | phenyl | HS-CH2CH2- | C(=O)CH3 |
| 468 | -CH2-C(=O)OH | -C(=O)O-CH2-Ph | HS-CH2CH2- | C(=O)CH3 |
| 469 | -CH2-C(=O)OH | -CH2-C(=O)O-CH2-Ph | HS-CH2CH2- | C(=O)CH3 |

TABLE 2-continued

| Compound | A¹ | A² | E¹ | E² |
|---|---|---|---|---|
| 470 | —CH₂C(O)OH | —CH₂CH₂NH₂ | —CH₂CH₂SH | —C(O)CH₃ |
| 471 | —CH₂C(O)OH | (1H-imidazol-4-yl)methyl | —CH₂CH₂SH | —C(O)CH₃ |
| 472 | —CH₂C(O)OH | (1H-indol-2-yl)methyl | —CH₂CH₂SH | —C(O)CH₃ |
| 473 | —CH₂CH₂NH₂ | phenyl | —CH₂CH₂SH | —C(O)CH₃ |
| 474 | —CH₂CH₂NH₂ | benzyloxycarbonyl | —CH₂CH₂SH | —C(O)CH₃ |
| 475 | —CH₂CH₂NH₂ | benzyloxycarbonylmethyl | —CH₂CH₂SH | —C(O)CH₃ |
| 476 | —CH₂CH₂NH₂ | (1H-imidazol-4-yl)methyl | —CH₂CH₂SH | —C(O)CH₃ |
| 477 | —CH₂CH₂NH₂ | (1H-indol-2-yl)methyl | —CH₂CH₂SH | —C(O)CH₃ |
| 478 | —CH₂CH₂NH₂ | phenyl | —CH₂C≡CH | —C(O)CH₃ |
| 479 | —CH₂CH₂NH₂ | benzyloxycarbonyl | —CH₂C≡CH | —C(O)CH₃ |
| 480 | —CH₂CH₂NH₂ | benzyloxycarbonylmethyl | —CH₂C≡CH | —C(O)CH₃ |
| 481 | —CH₂CH₂NH₂ | (1H-imidazol-4-yl)methyl | —CH₂C≡CH | —C(O)CH₃ |

TABLE 2-continued

| Compound | A¹ | A² | E¹ | E² |
|---|---|---|---|---|
| 482 | propylamine | 1H-indol-2-yl | ethynyl | acetyl |
| 483 | propylamine | phenyl | azidoethyl | acetyl |
| 484 | propylamine | benzyloxycarbonyl | azidoethyl | acetyl |
| 485 | propylamine | benzyloxycarbonylmethyl | azidoethyl | acetyl |
| 486 | propylamine | 1H-imidazol-4-yl | azidoethyl | acetyl |
| 487 | propylamine | 1H-indol-2-yl | azidoethyl | acetyl |
| 488 | propylamine | phenyl | 3-oxopropyl | acetyl |
| 489 | propylamine | benzyloxycarbonyl | 3-oxopropyl | acetyl |
| 490 | propylamine | benzyloxycarbonylmethyl | 3-oxopropyl | acetyl |
| 491 | propylamine | 1H-imidazol-4-yl | 3-oxopropyl | acetyl |
| 492 | propylamine | 1H-indol-2-yl | 3-oxopropyl | acetyl |

Table 3 sets forth exemplary compounds of the present invention having the formula:

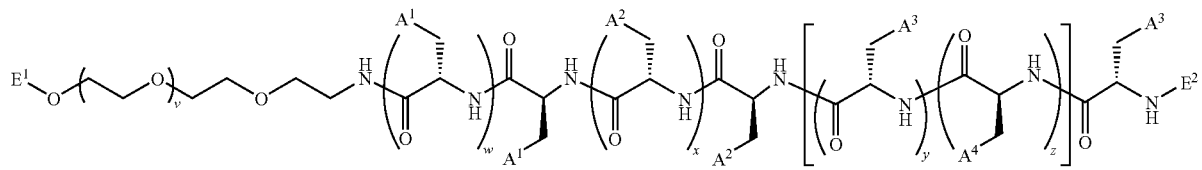

wherein each v is 100-500, each w is 4-20, x is 4-20, each y is 5-50, each z is 5-50, p is the sum of y and z, and each dotted bond represents the point of attachment to the rest of the molecule.

TABLE 3

| Compound | $A^1$ | $A^2$ | $A^3$ | $A^4$ | $E^1$ | $E^2$ |
|---|---|---|---|---|---|---|
| 493 | -C(=O)OH | -SH | phenyl | 4-hydroxyphenyl | HC≡C- | -C(=O)CH3 |
| 494 | -C(=O)OH | -SH | phenyl | 4-hydroxyphenyl | H2N-CH2CH2- | -C(=O)CH3 |
| 495 | -C(=O)OH | -SH | phenyl | 4-hydroxyphenyl | N3-CH2CH2- | -C(=O)CH3 |
| 496 | -C(=O)OH | -SH | phenyl | 4-hydroxyphenyl | H-C(=O)-CH2CH2- | -C(=O)CH3 |
| 497 | -C(=O)OH | -SH | phenyl | 4-hydroxyphenyl | H3C- | -C(=O)CH3 |
| 498 | -CH2-C(=O)OH | -SH | phenyl | 4-hydroxyphenyl | HC≡C- | -C(=O)CH3 |
| 499 | -CH2-C(=O)OH | -SH | phenyl | 4-hydroxyphenyl | H2N-CH2CH2- | -C(=O)CH3 |
| 500 | -CH2-C(=O)OH | -SH | phenyl | 4-hydroxyphenyl | N3-CH2CH2- | -C(=O)CH3 |
| 501 | -CH2-C(=O)OH | -SH | phenyl | 4-hydroxyphenyl | H-C(=O)-CH2CH2- | -C(=O)CH3 |
| 502 | -CH2-C(=O)OH | -SH | phenyl | 4-hydroxyphenyl | H3C- | -C(=O)CH3 |

TABLE 3-continued

| Compound | A¹ | A² | A³ | A⁴ | E¹ | E² |
|---|---|---|---|---|---|---|
| 503 | COOH | SH | phenyl | 4-hydroxyphenyl | HC≡C-CH₂- | H |
| 504 | COOH | SH | phenyl | 4-hydroxyphenyl | H₂N-CH₂-CH₂- | H |
| 505 | COOH | SH | phenyl | 4-hydroxyphenyl | N₃-CH₂-CH₂- | H |
| 506 | COOH | SH | phenyl | 4-hydroxyphenyl | OHC-CH₂-CH₂- | H |
| 507 | COOH | SH | phenyl | 4-hydroxyphenyl | H₃C- | H |
| 508 | CH₂COOH | SH | phenyl | 4-hydroxyphenyl | HC≡C-CH₂- | H |
| 509 | CH₂COOH | SH | phenyl | 4-hydroxyphenyl | H₂N-CH₂-CH₂- | H |
| 510 | CH₂COOH | SH | phenyl | 4-hydroxyphenyl | N₃-CH₂-CH₂- | H |
| 511 | CH₂COOH | SH | phenyl | 4-hydroxyphenyl | OHC-CH₂-CH₂- | H |
| 512 | CH₂COOH | SH | phenyl | 4-hydroxyphenyl | H₃C- | H |

Table 4 sets forth exemplary compounds of the present invention having the formula:

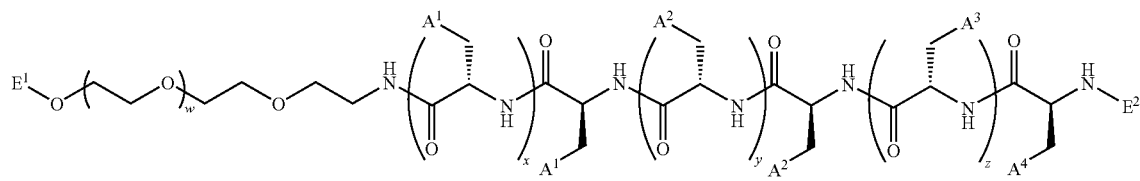

wherein each w is 25-1000, each x is 1-50, y is 1-50, each z is 1-100, and each dotted bond represents the point of attachment to the rest of the molecule.

TABLE 4

| Compound | $A^1$ | $A^2$ | $A^3$ | $E^1$ | $E^2$ |
|---|---|---|---|---|---|
| 513 | -C(O)OH | -SH | phenyl | -C≡CH | -C(O)CH3 |
| 514 | -C(O)OH | -SH | 4-hydroxyphenyl | -C≡CH | -C(O)CH3 |
| 515 | -C(O)OH | -SH | -CH2CH2CH2NH2 | -C≡CH | -C(O)CH3 |
| 516 | -C(O)OH | -SH | imidazolyl | -C≡CH | -C(O)CH3 |
| 517 | -C(O)OH | -SH | indolyl | -C≡CH | -C(O)CH3 |
| 518 | -C(O)OH | -SH | -C(O)OCH2Ph | -C≡CH | -C(O)CH3 |
| 519 | -C(O)OH | -SH | -CH2C(O)OCH2Ph | -C≡CH | -C(O)CH3 |
| 520 | -CH2C(O)OH | -SH | phenyl | -C≡CH | -C(O)CH3 |
| 521 | -CH2C(O)OH | -SH | 4-hydroxyphenyl | -C≡CH | -C(O)CH3 |
| 522 | -CH2C(O)OH | -SH | -CH2CH2CH2NH2 | -C≡CH | -C(O)CH3 |

TABLE 4-continued

| Compound | A¹ | A² | A³ | E¹ | E² |
|---|---|---|---|---|---|
| 523 | CH₂COOH | SH | imidazol-4-yl | ethynyl | acetyl |
| 524 | CH₂COOH | SH | 1H-indol-2-yl | ethynyl | acetyl |
| 525 | CH₂COOH | SH | benzyloxycarbonyl | ethynyl | acetyl |
| 526 | CH₂COOH | SH | benzyloxycarbonylmethyl | ethynyl | acetyl |
| 527 | COOH | SH | phenyl | ethynyl | H |
| 528 | COOH | SH | 4-hydroxyphenyl | ethynyl | H |
| 529 | COOH | SH | CH₂CH₂CH₂NH₂ | ethynyl | H |
| 530 | COOH | SH | imidazol-4-yl | ethynyl | H |
| 531 | COOH | SH | 1H-indol-2-yl | ethynyl | H |
| 532 | COOH | SH | benzyloxycarbonyl | ethynyl | H |
| 533 | COOH | SH | benzyloxycarbonylmethyl | ethynyl | H |
| 534 | CH₂COOH | SH | phenyl | ethynyl | H |

TABLE 4-continued

| Compound | A¹ | A² | A³ | E¹ | E² |
|---|---|---|---|---|---|
| 535 | -CH₂-C(=O)OH | -SH | 4-hydroxyphenyl | -C≡CH | -H |
| 536 | -CH₂-C(=O)OH | -SH | -CH₂CH₂NH₂ | -C≡CH | -H |
| 537 | -CH₂-C(=O)OH | -SH | imidazol-4-yl | -C≡CH | -H |
| 538 | -CH₂-C(=O)OH | -SH | 1H-indol-2-yl | -C≡CH | -H |
| 539 | -CH₂-C(=O)OH | -SH | -C(=O)O-CH₂-phenyl | -C≡CH | -H |
| 540 | -CH₂-C(=O)OH | -SH | -CH₂-C(=O)O-CH₂-phenyl | -C≡CH | -H |
| 541 | -C(=O)OH | -SH | phenyl | -CH₂CH₂-N₃ | -C(=O)CH₃ |
| 542 | -C(=O)OH | -SH | 4-hydroxyphenyl | -CH₂CH₂-N₃ | -C(=O)CH₃ |
| 543 | -C(=O)OH | -SH | -CH₂CH₂NH₂ | -CH₂CH₂-N₃ | -C(=O)CH₃ |
| 544 | -C(=O)OH | -SH | imidazol-4-yl | -CH₂CH₂-N₃ | -C(=O)CH₃ |
| 545 | -C(=O)OH | -SH | 1H-indol-2-yl | -CH₂CH₂-N₃ | -C(=O)CH₃ |
| 546 | -C(=O)OH | -SH | -C(=O)O-CH₂-phenyl | -CH₂CH₂-N₃ | -C(=O)CH₃ |

TABLE 4-continued

| Compound | A¹ | A² | A³ | E¹ | E² |
|---|---|---|---|---|---|
| 547 | COOH | SH | CH₂C(O)O-CH₂-phenyl | N₃-CH₂CH₂- | C(O)CH₃ |
| 548 | CH₂COOH | SH | phenyl | N₃-CH₂CH₂- | C(O)CH₃ |
| 549 | CH₂COOH | SH | 4-hydroxyphenyl | N₃-CH₂CH₂- | C(O)CH₃ |
| 550 | CH₂COOH | SH | CH₂CH₂CH₂NH₂ | N₃-CH₂CH₂- | C(O)CH₃ |
| 551 | CH₂COOH | SH | imidazol-4-yl | N₃-CH₂CH₂- | C(O)CH₃ |
| 552 | CH₂COOH | SH | 1H-indol-2-yl | N₃-CH₂CH₂- | C(O)CH₃ |
| 553 | CH₂COOH | SH | C(O)O-CH₂-phenyl | N₃-CH₂CH₂- | C(O)CH₃ |
| 554 | CH₂COOH | SH | CH₂C(O)O-CH₂-phenyl | N₃-CH₂CH₂- | C(O)CH₃ |
| 555 | COOH | SH | phenyl | N₃-CH₂CH₂- | H |
| 556 | COOH | SH | 4-hydroxyphenyl | N₃-CH₂CH₂- | H |
| 557 | COOH | SH | CH₂CH₂CH₂NH₂ | N₃-CH₂CH₂- | H |
| 558 | COOH | SH | imidazol-4-yl | N₃-CH₂CH₂- | H |
| 559 | COOH | SH | 1H-indol-2-yl | N₃-CH₂CH₂- | H |

TABLE 4-continued

| Compound | A¹ | A² | A³ | E¹ | E² |
|---|---|---|---|---|---|
| 560 | COOH | SH | C(=O)O-CH2-phenyl | N3-CH2CH2- | H |
| 561 | COOH | SH | CH2-C(=O)O-CH2-phenyl | N3-CH2CH2- | H |
| 562 | -CH2-COOH | SH | phenyl | N3-CH2CH2- | H |
| 563 | -CH2-COOH | SH | 4-hydroxyphenyl | N3-CH2CH2- | H |
| 564 | -CH2-COOH | SH | -CH2CH2-NH2 | N3-CH2CH2- | H |
| 565 | -CH2-COOH | SH | imidazol-4-yl | N3-CH2CH2- | H |
| 566 | -CH2-COOH | SH | 1H-indol-2-yl | N3-CH2CH2- | H |
| 567 | -CH2-COOH | SH | C(=O)O-CH2-phenyl | N3-CH2CH2- | H |
| 568 | -CH2-COOH | SH | CH2-C(=O)O-CH2-phenyl | N3-CH2CH2- | H |
| 569 | COOH | SH | phenyl | OHC-CH2CH2- | C(=O)-CH3 |
| 570 | COOH | SH | 4-hydroxyphenyl | OHC-CH2CH2- | C(=O)-CH3 |
| 571 | COOH | SH | -CH2CH2-NH2 | OHC-CH2CH2- | C(=O)-CH3 |

TABLE 4-continued

| Compound | A¹ | A² | A³ | E¹ | E² |
|---|---|---|---|---|---|
| 572 | COOH | SH | imidazole | CH₂CHO | C(O)CH₃ |
| 573 | COOH | SH | indole (2-yl) | CH₂CHO | C(O)CH₃ |
| 574 | COOH | SH | OC(O)-CH₂-C₆H₅ (benzyl ester) | CH₂CHO | C(O)CH₃ |
| 575 | COOH | SH | CH₂C(O)O-CH₂-C₆H₅ | CH₂CHO | C(O)CH₃ |
| 576 | CH₂COOH | SH | phenyl | CH₂CHO | C(O)CH₃ |
| 577 | CH₂COOH | SH | 4-hydroxyphenyl | CH₂CHO | C(O)CH₃ |
| 578 | CH₂COOH | SH | CH₂CH₂NH₂ | CH₂CHO | C(O)CH₃ |
| 579 | CH₂COOH | SH | imidazole | CH₂CHO | C(O)CH₃ |
| 580 | CH₂COOH | SH | indole (2-yl) | CH₂CHO | C(O)CH₃ |
| 581 | CH₂COOH | SH | OC(O)-CH₂-C₆H₅ | CH₂CHO | C(O)CH₃ |
| 582 | CH₂COOH | SH | CH₂C(O)O-CH₂-C₆H₅ | CH₂CHO | C(O)CH₃ |
| 583 | COOH | SH | phenyl | CH₂CHO | H |

TABLE 4-continued

| Compound | A¹ | A² | A³ | E¹ | E² |
|---|---|---|---|---|---|
| 584 | COOH | SH | 4-hydroxyphenyl | CH₂CHO | H |
| 585 | COOH | SH | CH₂CH₂NH₂ | CH₂CHO | H |
| 586 | COOH | SH | imidazol-4-yl | CH₂CHO | H |
| 587 | COOH | SH | 1H-indol-2-yl | CH₂CHO | H |
| 588 | COOH | SH | C(O)OCH₂Ph | CH₂CHO | H |
| 589 | COOH | SH | CH₂C(O)OCH₂Ph | CH₂CHO | H |
| 590 | CH₂COOH | SH | phenyl | CH₂CHO | H |
| 591 | CH₂COOH | SH | 4-hydroxyphenyl | CH₂CHO | H |
| 592 | CH₂COOH | SH | CH₂CH₂NH₂ | CH₂CHO | H |
| 593 | CH₂COOH | SH | imidazol-4-yl | CH₂CHO | H |
| 594 | CH₂COOH | SH | 1H-indol-2-yl | CH₂CHO | H |
| 595 | CH₂COOH | SH | CH₂C(O)OCH₂Ph | CH₂CHO | H |

TABLE 4-continued

| Compound | A¹ | A² | A³ | E¹ | E² |
|---|---|---|---|---|---|
| 596 | ⋯COOH (acetic acid) | ⋯SH | ⋯CH₂C(=O)O-CH₂-C₆H₅ (benzyl ester) | H-C(=O)-CH₂-CH₂⋯ | ⋯H |

According to another embodiment, the present invention provides a micelle having a contrast agent encapsulated therein, wherein the micelle comprises a multiblock copolymer which comprises a polymeric hydrophilic block, optionally a crosslinkable or crosslinked poly(amino acid block), and a hydrophobic D,L-mixed poly(amino acid) block, characterized in that said micelle has an inner core, optionally a crosslinkable or crosslinked outer core, and a hydrophilic shell. It will be appreciated that the polymeric hydrophilic block corresponds to the hydrophilic shell, the optionally crosslinkable or crosslinked poly(amino acid block) corresponds to the optionally crosslinked outer core, and the hydrophobic poly(amino acid) block corresponds to the inner core.

The "hydrophobic D,L-mixed poly(amino acid)" block, as described herein, consists of a mixture of D and L enantiomers to facilitate the encapsulation of hydrophobic moieties. It is well established that homopolymers and copolymers of amino acids, consisting of a single stereoisomer, may exhibit secondary structures such as the α-helix or β-sheet. See α-*Aminoacid-N-Caroboxy-Anhydrides and Related Heterocycles*, H. R. Kricheldorf, Springer-Verlag, 1987. For example, poly(L-benzyl glutatmate) typically exhibits an α-helical conformation; however this secondary structure can be disrupted by a change of solvent or temperature (see *Advances in Protein Chemistry XVI*, P. Urnes and P. Doty, Academic Press, New York 1961). The secondary structure can also be disrupted by the incorporation of structurally dissimilar amino acids such as β-sheet forming amino acids (e.g. proline) or through the incorporation of amino acids with dissimilar stereochemistry (e.g. mixture of D and L stereoisomers), which results in poly(amino acids) with a random coil conformation. See Sakai, R.; Ikeda; S.; Isemura, T. *Bull Chem. Soc. Japan* 1969, 42, 1332-1336, Paolillo, L.; Temussi, P. A.; Bradbury, E. M.; Crane-Robinson, C. *Biopolymers* 1972, 11, 2043-2052, and Cho, I.; Kim, J. B.; Jung, H. J. *Polymer* 2003, 44, 5497-5500.

While the methods to influence secondary structure of poly(amino acids) have been known for some time, it has been suprisingly discovered that block copolymers possessing a random coil conformation are particularly useful for the encapsulation of hydrophobic molecules and nanoparticles when compared to similar block copolymers possessing a helical segment. Without wishing to be bound to any particular theory, it is believed that the block copolymers consisting of a coil-coil conformation allow for efficient packing and loading of hydrophobic moieties within the micelle core, while the steric demands of a rod-coil conformation for a helix-containing block copolymer results in less effective encapsulation.

As used herein, the term "D,L-mixed poly(amino acid) block" refers to a poly(amino acid) block wherein the poly (amino acid) consists of a mixture of amino acids in both the D- and L-configurations. In certain embodiments, the D,L-mixed poly(amino acid) block is hydrophobic. In other embodiments, the D,L-mixed poly(amino acid) block consists of a mixture of D-configured hydrophobic amino acids and L-configured hydrophilic amino acid side-chain groups such that the overall poly(amino acid) block comprising is hydrophobic.

Thus, in certain embodiments, the $R^y$ group of any of formulae I, II, and III forms a hydrophobic D,L-mixed poly (amino acid) block. Hydrophobic amino acid side-chain groups are well known in the art and include those described herein. In other embodiments, $R^y$ consists of a mixture of D-hydrophobic and L-hydrophilic amino acid side-chain groups such that the overall poly(amino acid) block comprising $R^y$ is hydrophobic and is a mixture of D- and L-configured amino acids. Such mixtures of amino acid side-chain groups include D-leucine/L-tyrosine, D-leucine/L-aspartic acid, D-leucine/L-glutamic acid, D-phenylalanine/L-tyrosine, D-phenylalanine/L-aspartic acid, D-phenylalanine/L-glutamic acid, D-phenylalanine/L-serine, D-benzyl aspartate/L-tyrosine, D-benzyl aspartate/L-aspartic acid, D-benzyl aspartate/L-glutamic acid, D-benzyl glutamate/L-tyrosine, D-benzyl glutamate/L-aspartic acid and the like. According to another embodiment, $R^y$ is a hydrophobic amino acid side-chain group selected from D-leucine, D-phenylalanine, D-alanine, D-benzyl aspartate, or D-benzyl glutamate, and one or more of L-tyrosine, L-cysteine, L-aspartic acid, L-glutamic acid, L-DOPA, L-histidine, L-lysine, or L-ornithine.

In other embodiments, the $R^y$ group of any of formulae I, II, and III forms a mixture of D-hydrophobic and L-hydrophilic amino acid side-chain groups such that the overall poly (amino acid) block comprising $R^y$ is hydrophobic and is a mixture of D- and L-configured amino acids. Such mixtures of amino acid side-chain groups include D-leucine/L-tyrosine, D-leucine/L-aspartic acid, D-leucine/L-glutamic acid, D-phenylalanine/L-tyrosine, D-phenylalanine/L-aspartic acid, D-phenylalanine/L-glutamic acid, D-phenylalanine/L-cysteine, D-benzyl aspartate/L-tyrosine, D-benzyl aspartate/L-aspartic acid, D-benzyl aspartate/L-glutamic acid, D-benzyl glutamate/L-tyrosine, D-benzyl glutamate/L-aspartic acid and the like. Ratios (D-hydrophobic to L-hydrophilic) of such mixtures include 6:1, 5:1, 4:1, 3:1, 2:1, 1:1, 1:2, 1:3, 1:4; 1:5, and 1:6.

According to another embodiment, the present invention provides a micelle having a contrast agent encapsulated therein, wherein the micelle comprises a multiblock copolymer selected from those set forth in Tables 5 through 11. Table 5 sets forth exemplary compounds of the present invention having the formula:

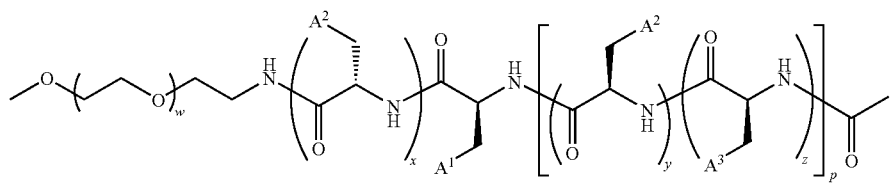
wherein each w is 25-1000, each x is 1-50, each y is 1-50, each z is 1-100, p is the sum of y and z, and each dotted bond represents the point of attachment to the rest of the molecule.
TABLE 5
| Compound | A¹ | A² | A³ |
|---|---|---|---|
| 597 | -COOH | -CH₂C(O)OCH₂-phenyl | -COOH |
| 598 | -COOH | -C(O)OCH₂-phenyl | -COOH |
| 599 | -COOH | -phenyl | -COOH |
| 600 | -COOH | -CH₂C(O)OCH₂-phenyl | -SH |
| 601 | -COOH | -C(O)OCH₂-phenyl | -SH |
| 602 | -COOH | -phenyl | -SH |
| 603 | -COOH | -CH₂C(O)OCH₂-phenyl | -CH₂C(O)OH |
| 604 | -COOH | -C(O)OCH₂-phenyl | -CH₂C(O)OH |

TABLE 5-continued

| Compound | A¹ | A² | A³ |
| --- | --- | --- | --- |
| 605 | -COOH | -C₆H₅ (phenyl) | -CH₂COOH |
| 606 | -COOH | -C(=O)OCH₂-C₆H₅ | -C₆H₄-OH (4-hydroxyphenyl) |
| 607 | -COOH | -C(=O)OCH₂-C₆H₅ | -C₆H₄-OH (4-hydroxyphenyl) |
| 608 | -COOH | -C₆H₅ (phenyl) | -C₆H₄-OH (4-hydroxyphenyl) |
| 609 | -CH₂COOH | -C(=O)OCH₂-C₆H₅ | -COOH |
| 610 | -CH₂COOH | -C(=O)OCH₂-C₆H₅ | -COOH |
| 611 | -CH₂COOH | -C₆H₅ (phenyl) | -COOH |
| 612 | -CH₂COOH | -C(=O)OCH₂-C₆H₅ | -SH |
| 613 | -CH₂COOH | -C(=O)OCH₂-C₆H₅ | -SH |
| 614 | -CH₂COOH | -C₆H₅ (phenyl) | -SH |
| 615 | -CH₂COOH | -C(=O)OCH₂-C₆H₅ | -CH₂COOH |

TABLE 5-continued

| Compound | A¹ | A² | A³ |
|---|---|---|---|
| 616 | -CH₂COOH | -C(O)OCH₂-phenyl | -CH₂COOH |
| 617 | -CH₂COOH | -phenyl- | -CH₂COOH |
| 618 | -CH₂COOH | -CH₂C(O)OCH₂-phenyl | -C₆H₄-OH (p) |
| 619 | -CH₂COOH | -C(O)OCH₂-phenyl | -C₆H₄-OH (p) |
| 620 | -CH₂COOH | -phenyl- | -C₆H₄-OH (p) |
| 621 | -SH | -CH₂C(O)OCH₂-phenyl | -CH₂COOH |
| 622 | -SH | -C(O)OCH₂-phenyl | -CH₂COOH |
| 623 | -SH | -phenyl- | -CH₂COOH |
| 624 | -SH | -CH₂C(O)OCH₂-phenyl | -SH |
| 625 | -SH | -C(O)OCH₂-phenyl | -SH |
| 626 | -SH | -phenyl- | -SH |

TABLE 5-continued

| Compound | A¹ | A² | A³ |
|---|---|---|---|
| 627 | -SH | -CH₂C(O)OCH₂-phenyl | -CH₂COOH |
| 628 | -SH | -C(O)OCH₂-phenyl | -CH₂COOH |
| 629 | -SH | -phenyl | -CH₂COOH |
| 630 | -SH | -CH₂C(O)OCH₂-phenyl | -C₆H₄-OH |
| 631 | -SH | -C(O)OCH₂-phenyl | -C₆H₄-OH |
| 632 | -SH | -phenyl | -C₆H₄-OH |
| 633 | -imidazolyl | -CH₂C(O)OCH₂-phenyl | -COOH |
| 634 | -imidazolyl | -C(O)OCH₂-phenyl | -COOH |
| 635 | -imidazolyl | -phenyl | -COOH |
| 636 | -imidazolyl | -CH₂C(O)OCH₂-phenyl | -SH |
| 637 | -imidazolyl | -C(O)OCH₂-phenyl | -SH |

TABLE 5-continued
| Compound | A¹ | A² | A³ |
|---|---|---|---|
| 638 |  | 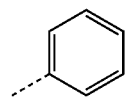 |  |
| 639 |  | 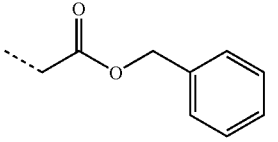 | 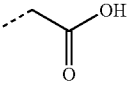 |
| 640 |  | 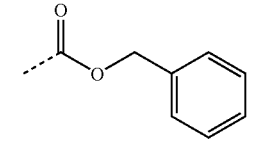 | 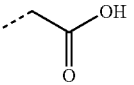 |
| 641 |  | 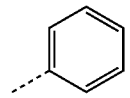 | 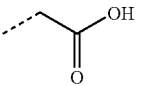 |
| 642 |  | 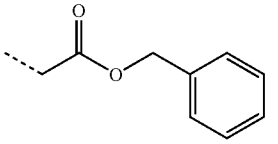 | 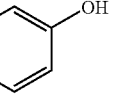 |
| 643 |  | 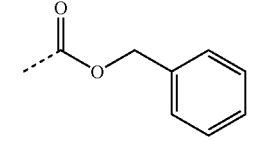 | 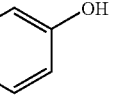 |
| 644 |  | 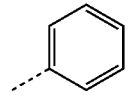 | 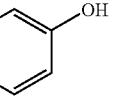 |
| 645 |  | 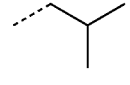 | 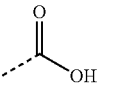 |
| 646 |  | 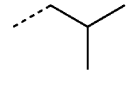 | 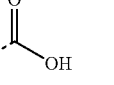 |
| 647 |  |  | 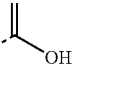 |
| 648 |  | 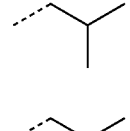 | 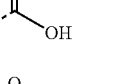 |
| 649 | 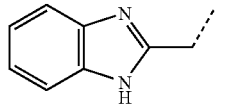 | 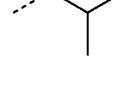 | 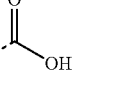 |

TABLE 5-continued

| Compound | A¹ | A² | A³ |
|---|---|---|---|
| 650 | -COOH | -CH(CH₃)₂ | 4-hydroxyphenyl |
| 651 | -CH₂COOH | -CH(CH₃)₂ | 4-hydroxyphenyl |
| 652 | -SH | -CH(CH₃)₂ | 4-hydroxyphenyl |
| 653 | 1H-imidazol-4-yl | -CH(CH₃)₂ | 4-hydroxyphenyl |
| 654 | 1H-benzimidazol-2-ylmethyl | -CH(CH₃)₂ | 4-hydroxyphenyl |
| 655 | -COOH | -CH(CH₃)₂ | -CH₂COOH |
| 656 | -CH₂COOH | -CH(CH₃)₂ | -CH₂COOH |
| 657 | -SH | -CH(CH₃)₂ | -CH₂COOH |
| 658 | 1H-imidazol-4-yl | -CH(CH₃)₂ | -CH₂COOH |
| 659 | 1H-benzimidazol-2-ylmethyl | -CH(CH₃)₂ | -CH₂COOH |
| 660 | -COOH | -CH(CH₃)₂ | -SH |
| 661 | -CH₂COOH | -CH(CH₃)₂ | -SH |
| 662 | -SH | -CH(CH₃)₂ | -SH |
| 663 | 1H-imidazol-4-yl | -CH(CH₃)₂ | -SH |

TABLE 5-continued

| Compound | A¹ | A² | A³ |
|---|---|---|---|
| 664 | benzimidazol-2-yl | isobutyl | -SH |
| 665 | benzimidazol-2-yl | -CH₂C(O)OCH₂Ph | -C(O)OH |
| 666 | benzimidazol-2-yl | -C(O)OCH₂Ph | -C(O)OH |
| 667 | benzimidazol-2-yl | phenyl | -C(O)OH |
| 668 | benzimidazol-2-yl | -CH₂C(O)OCH₂Ph | -SH |
| 669 | benzimidazol-2-yl | -C(O)OCH₂Ph | -SH |
| 670 | benzimidazol-2-yl | phenyl | -SH |
| 671 | benzimidazol-2-yl | -CH₂C(O)OCH₂Ph | -CH₂C(O)OH |
| 672 | benzimidazol-2-yl | -C(O)OCH₂Ph | -CH₂C(O)OH |
| 673 | benzimidazol-2-yl | phenyl | -CH₂C(O)OH |
| 674 | benzimidazol-2-yl | -CH₂C(O)OCH₂Ph | 4-hydroxyphenyl |

TABLE 5-continued

| Compound | A¹ | A² | A³ |
|---|---|---|---|
| 675 | 2-ethyl-1H-benzimidazole | benzyl ester | 4-hydroxyphenyl |
| 676 | 2-ethyl-1H-benzimidazole | phenyl | 4-hydroxyphenyl |
| 677 | COOH | benzyl ester | CH₂CH₂NH₂ |
| 678 | COOH | benzyl ester | CH₂CH₂NH₂ |
| 679 | COOH | phenyl | CH₂CH₂NH₂ |
| 680 | COOH | benzyl ester | 1H-imidazol-4-yl |
| 681 | COOH | benzyl ester | 1H-imidazol-4-yl |
| 682 | COOH | phenyl | 1H-imidazol-4-yl |
| 683 | COOH | benzyl ester | CH₂CH₂CH₂NH₂ |
| 684 | COOH | benzyl ester | CH₂CH₂CH₂NH₂ |
| 685 | COOH | phenyl | CH₂CH₂CH₂NH₂ |

TABLE 5-continued

| Compound | A¹ | A² | A³ |
| --- | --- | --- | --- |
| 686 | -COOH | -CH₂C(O)OCH₂-phenyl | 3,4-dihydroxyphenyl |
| 687 | -COOH | -CH₂C(O)OCH₂-phenyl | 3,4-dihydroxyphenyl |
| 688 | -COOH | -phenyl- | 3,4-dihydroxyphenyl |
| 689 | -CH₂COOH | -CH₂C(O)OCH₂-phenyl | -CH₂CH₂NH₂ |
| 690 | -CH₂COOH | -CH₂C(O)OCH₂-phenyl | -CH₂CH₂NH₂ |
| 691 | -CH₂COOH | -phenyl- | -CH₂CH₂NH₂ |
| 692 | -CH₂COOH | -CH₂C(O)OCH₂-phenyl | 1H-imidazol-4-yl |
| 693 | -CH₂COOH | -CH₂C(O)OCH₂-phenyl | 1H-imidazol-4-yl |
| 694 | -CH₂COOH | -phenyl- | 1H-imidazol-4-yl |
| 695 | -CH₂COOH | -CH₂C(O)OCH₂-phenyl | -CH₂CH₂CH₂NH₂ |
| 696 | -CH₂COOH | -CH₂C(O)OCH₂-phenyl | -CH₂CH₂CH₂NH₂ |

TABLE 5-continued

| Compound | A¹ | A² | A³ |
|---|---|---|---|
| 697 | acetic acid | phenyl | propylamine |
| 698 | acetic acid | benzyl ester | 3,4-dihydroxyphenyl |
| 699 | acetic acid | benzyl ester | 3,4-dihydroxyphenyl |
| 700 | acetic acid | phenyl | 3,4-dihydroxyphenyl |
| 701 | SH | benzyl ester | ethylamine |
| 702 | SH | benzyl ester | ethylamine |
| 703 | SH | phenyl | ethylamine |
| 704 | SH | benzyl ester | 1H-imidazol-4-yl |
| 705 | SH | benzyl ester | 1H-imidazol-4-yl |
| 706 | SH | phenyl | 1H-imidazol-4-yl |
| 707 | SH | benzyl ester | propylamine |

TABLE 5-continued

| Compound | A¹ | A² | A³ |
| --- | --- | --- | --- |
| 708 | —SH | —C(=O)O—CH₂—C₆H₅ | —(CH₂)₃—NH₂ |
| 709 | —SH | —C₆H₅— | —(CH₂)₃—NH₂ |
| 710 | —SH | —CH₂—C(=O)O—CH₂—C₆H₅ | 3,4-dihydroxyphenyl |
| 711 | —SH | —C(=O)O—CH₂—C₆H₅ | 3,4-dihydroxyphenyl |
| 712 | —SH | —C₆H₅— | 3,4-dihydroxyphenyl |
| 713 | 1H-imidazol-4-yl | —CH₂—C(=O)O—CH₂—C₆H₅ | —(CH₂)₂—NH₂ |
| 714 | 1H-imidazol-4-yl | —C(=O)O—CH₂—C₆H₅ | —(CH₂)₂—NH₂ |
| 715 | 1H-imidazol-4-yl | —C₆H₅— | —(CH₂)₂—NH₂ |
| 716 | 1H-imidazol-4-yl | —CH₂—C(=O)O—CH₂—C₆H₅ | 1H-imidazol-4-yl |
| 717 | 1H-imidazol-4-yl | —C(=O)O—CH₂—C₆H₅ | 1H-imidazol-4-yl |
| 718 | 1H-imidazol-4-yl | —C₆H₅— | 1H-imidazol-4-yl |

TABLE 5-continued

| Compound | A¹ | A² | A³ |
| --- | --- | --- | --- |
| 719 | imidazole | -CH2-C(=O)-O-CH2-phenyl | -CH2CH2CH2-NH2 |
| 720 | imidazole | -C(=O)-O-CH2-phenyl | -CH2CH2CH2-NH2 |
| 721 | imidazole | phenyl | -CH2CH2CH2-NH2 |
| 722 | imidazole | -CH2-C(=O)-O-CH2-phenyl | 3,4-dihydroxyphenyl |
| 723 | imidazole | -C(=O)-O-CH2-phenyl | 3,4-dihydroxyphenyl |
| 724 | imidazole | phenyl | 3,4-dihydroxyphenyl |
| 725 | -CH2-COOH | isobutyl | -CH2CH2-NH2 |
| 726 | -CH2-COOH | isobutyl | -CH2CH2-NH2 |
| 727 | -SH | isobutyl | -CH2CH2-NH2 |
| 728 | imidazole | isobutyl | -CH2CH2-NH2 |
| 729 | benzimidazol-2-yl-methyl | isobutyl | -CH2CH2-NH2 |
| 730 | -CH2-COOH | isobutyl | 3,4-dihydroxyphenyl |

TABLE 5-continued

| Compound | A¹ | A² | A³ |
| --- | --- | --- | --- |
| 731 | CH₂COOH | isobutyl | 3,4-dihydroxyphenyl |
| 732 | SH | isobutyl | 3,4-dihydroxyphenyl |
| 733 | imidazolyl | isobutyl | 3,4-dihydroxyphenyl |
| 734 | 2-benzimidazolyl-ethyl | isobutyl | 3,4-dihydroxyphenyl |
| 735 | COOH | isobutyl | CH₂CH₂CH₂NH₂ |
| 736 | CH₂COOH | isobutyl | CH₂CH₂CH₂NH₂ |
| 737 | SH | isobutyl | CH₂CH₂CH₂NH₂ |
| 738 | imidazolyl | isobutyl | CH₂CH₂CH₂NH₂ |
| 739 | 2-benzimidazolyl-ethyl | isobutyl | CH₂CH₂CH₂NH₂ |
| 740 | COOH | isobutyl | imidazolyl |
| 741 | CH₂COOH | isobutyl | imidazolyl |
| 742 | SH | isobutyl | imidazolyl |
| 743 | imidazolyl | isobutyl | imidazolyl |
| 744 | 2-benzimidazolyl-ethyl | isobutyl | imidazolyl |

TABLE 5-continued

| Compound | A¹ | A² | A³ |
|---|---|---|---|
| 745 | benzimidazol-2-yl-CH₂- | -CH₂C(O)O-CH₂-phenyl | -CH₂CH₂NH₂ |
| 746 | benzimidazol-2-yl-CH₂- | -C(O)O-CH₂-phenyl | -CH₂CH₂NH₂ |
| 747 | benzimidazol-2-yl-CH₂- | phenyl | -CH₂CH₂NH₂ |
| 748 | benzimidazol-2-yl-CH₂- | -CH₂C(O)O-CH₂-phenyl | 1H-imidazol-4-yl |
| 749 | benzimidazol-2-yl-CH₂- | -C(O)O-CH₂-phenyl | 1H-imidazol-4-yl |
| 750 | benzimidazol-2-yl-CH₂- | phenyl | 1H-imidazol-4-yl |
| 751 | benzimidazol-2-yl-CH₂- | -CH₂C(O)O-CH₂-phenyl | -CH₂CH₂CH₂NH₂ |
| 752 | benzimidazol-2-yl-CH₂- | -C(O)O-CH₂-phenyl | -CH₂CH₂CH₂NH₂ |
| 753 | benzimidazol-2-yl-CH₂- | phenyl | -CH₂CH₂CH₂NH₂ |
| 754 | benzimidazol-2-yl-CH₂- | -CH₂C(O)O-CH₂-phenyl | 3,4-dihydroxyphenyl |

TABLE 5-continued

| Compound | A¹ | A² | A³ |
|---|---|---|---|
| 755 | benzimidazol-2-yl-ethyl | benzyl ester | 3,4-dihydroxyphenyl |
| 756 | benzimidazol-2-yl-ethyl | phenyl | 3,4-dihydroxyphenyl |

Table 6 sets forth exemplary compounds of the present invention having the formula:

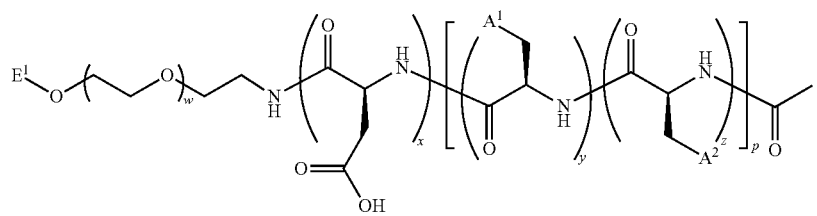

wherein each w is 25-1000, each x is 1-50, each y is 1-50, each z is 1-100, p is the sum of y and z, and each dotted bond represents the point of attachment to the rest of the molecule.

TABLE 6

| Compound | A¹ | A² | E¹ |
|---|---|---|---|
| 757 | benzyl ester | 4-hydroxyphenyl | propargyl |
| 758 | benzyl ester | 4-hydroxyphenyl | 2-azidoethyl |
| 759 | benzyl ester | 4-hydroxyphenyl | 2-aminoethyl |
| 760 | benzyl ester | 4-hydroxyphenyl | 3-oxopropyl |

TABLE 6-continued
| Compound | A¹ | A² | E¹ |
|---|---|---|---|
| 761 | 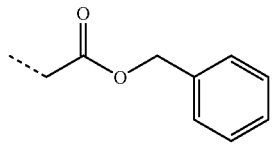 | 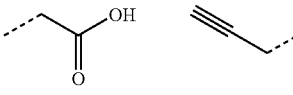 | 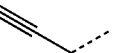 |
| 762 | 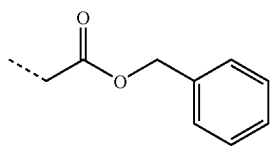 | 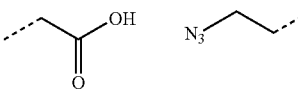 | 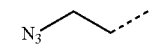 |
| 763 | 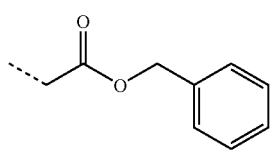 | 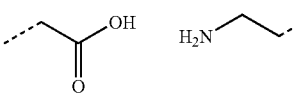 | 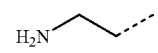 |
| 764 | 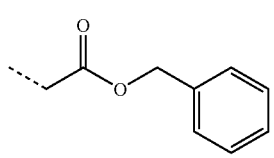 | 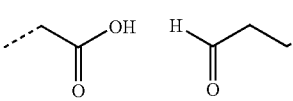 | 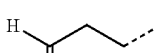 |
| 765 | 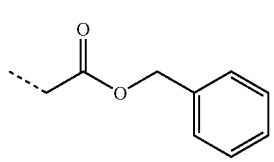 |  |  |
| 766 | 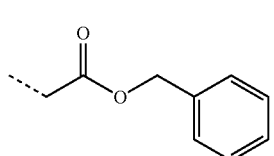 | 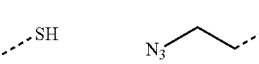 | 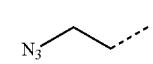 |
| 767 | 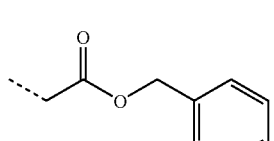 |  | 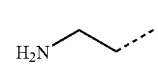 |
| 768 | 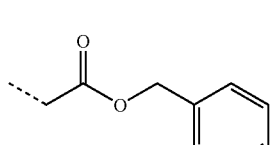 | 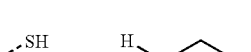 | 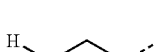 |
| 769 | 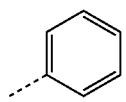 | 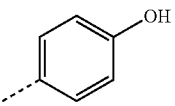 | 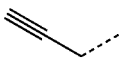 |
| 770 | 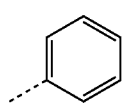 | 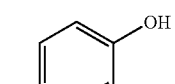 | 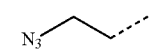 |

TABLE 6-continued

| Compound | A¹ | A² | E¹ |
|---|---|---|---|
| 771 | phenyl | 4-hydroxyphenyl | H₂N-CH₂CH₂- |
| 772 | phenyl | 4-hydroxyphenyl | OHC-CH₂CH₂- |
| 773 | phenyl | -CH₂-C(=O)OH | HC≡C-CH₂- |
| 774 | phenyl | -CH₂-C(=O)OH | N₃-CH₂CH₂- |
| 775 | phenyl | -CH₂-C(=O)OH | H₂N-CH₂CH₂- |
| 776 | phenyl | -CH₂-C(=O)OH | OHC-CH₂CH₂- |
| 777 | phenyl | -SH | HC≡C-CH₂- |
| 778 | phenyl | -SH | N₃-CH₂CH₂- |
| 779 | phenyl | -SH | H₂N-CH₂CH₂- |
| 780 | phenyl | -SH | OHC-CH₂CH₂- |
| 781 | benzyl ester (-C(=O)O-CH₂-C₆H₅) | 4-hydroxyphenyl | HC≡C-CH₂- |
| 782 | benzyl ester (-C(=O)O-CH₂-C₆H₅) | 4-hydroxyphenyl | N₃-CH₂CH₂- |
| 783 | benzyl ester (-C(=O)O-CH₂-C₆H₅) | 4-hydroxyphenyl | H₂N-CH₂CH₂- |

TABLE 6-continued

| Compound | A¹ | A² | E¹ |
|---|---|---|---|
| 784 | benzyl ester | 4-hydroxyphenyl | -CH₂-CH₂-CHO |
| 785 | benzyl ester | -CH₂-COOH | -CH₂-C≡CH |
| 786 | benzyl ester | -CH₂-COOH | -CH₂-CH₂-N₃ |
| 787 | benzyl ester | -CH₂-COOH | -CH₂-CH₂-NH₂ |
| 788 | benzyl ester | -CH₂-COOH | -CH₂-CH₂-CHO |
| 789 | benzyl ester | -SH | -CH₂-C≡CH |
| 790 | benzyl ester | -SH | -CH₂-CH₂-N₃ |
| 791 | benzyl ester | -SH | -CH₂-CH₂-NH₂ |
| 792 | benzyl ester | -SH | -CH₂-CH₂-CHO |
| 793 | benzyl ester | -COOH | -CH₂-C≡CH |

TABLE 6-continued

| Compound | A¹ | A² | E¹ |
|---|---|---|---|
| 794 | benzyl ester | COOH | N₃-CH₂CH₂- |
| 795 | benzyl ester | COOH | H₂N-CH₂CH₂- |
| 796 | benzyl ester | COOH | OHC-CH₂CH₂- |
| 797 | phenyl | COOH | HC≡C-CH₂- |
| 798 | phenyl | COOH | N₃-CH₂CH₂- |
| 799 | phenyl | COOH | H₂N-CH₂CH₂- |
| 800 | phenyl | COOH | OHC-CH₂CH₂- |
| 801 | isobutyl | COOH | HC≡C-CH₂- |
| 802 | isobutyl | COOH | N₃-CH₂CH₂- |
| 803 | isobutyl | COOH | H₂N-CH₂CH₂- |
| 804 | isobutyl | COOH | OHC-CH₂CH₂- |
| 805 | isobutyl | 4-hydroxyphenyl | HC≡C-CH₂- |
| 806 | isobutyl | 4-hydroxyphenyl | N₃-CH₂CH₂- |

TABLE 6-continued
| Compound | A¹ | A² | E¹ |
|---|---|---|---|
| 807 | 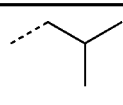 | 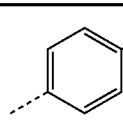 | 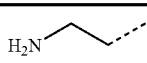 |
| 808 | 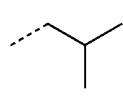 | 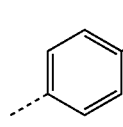 | 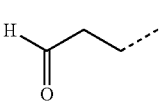 |
| 809 | 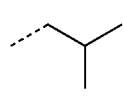 | 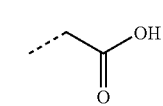 | 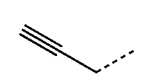 |
| 810 | 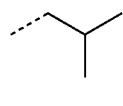 | 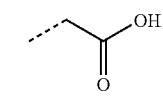 | 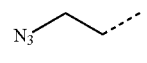 |
| 811 | 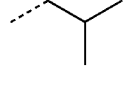 | 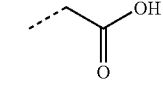 | 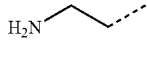 |
| 812 | 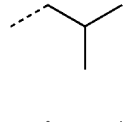 | 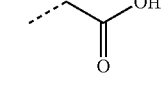 | 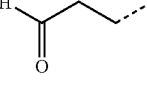 |
| 813 | 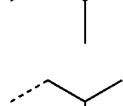 |  | 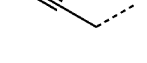 |
| 814 | 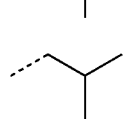 |  | 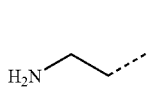 |
| 815 | 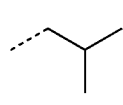 |  | 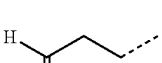 |
| 816 | 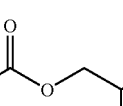 |  | 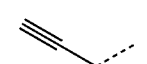 |
| 817 | 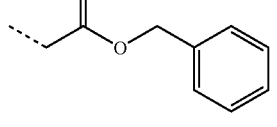 | 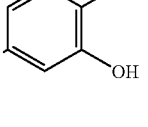 | 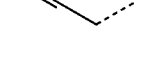 |
| 818 | 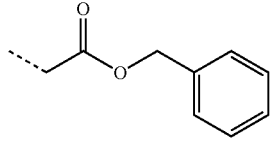 | 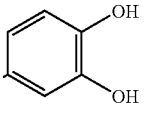 | 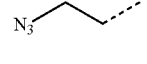 |
| 819 | 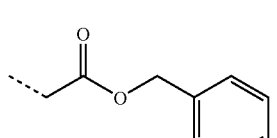 | 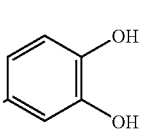 | 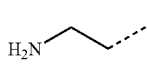 |

TABLE 6-continued

| Compound | A¹ | A² | E¹ |
|---|---|---|---|
| 820 | benzyl ester | 3,4-dihydroxyphenyl | propanal |
| 821 | benzyl ester | propylamine | propynyl |
| 822 | benzyl ester | propylamine | azidoethyl |
| 823 | benzyl ester | propylamine | aminoethyl |
| 824 | benzyl ester | propylamine | propanal |
| 825 | benzyl ester | 1H-imidazol-4-yl | propynyl |
| 826 | benzyl ester | 1H-imidazol-4-yl | azidoethyl |
| 827 | benzyl ester | 1H-imidazol-4-yl | aminoethyl |
| 828 | benzyl ester | 1H-imidazol-4-yl | propanal |
| 829 | phenyl | 3,4-dihydroxyphenyl | propynyl |

TABLE 6-continued

| Compound | A¹ | A² | E¹ |
|---|---|---|---|
| 830 | phenyl | catechol (3,4-dihydroxyphenyl) | -CH₂CH₂-N₃ |
| 831 | phenyl | catechol (3,4-dihydroxyphenyl) | -CH₂CH₂-NH₂ |
| 832 | phenyl | catechol (3,4-dihydroxyphenyl) | -CH₂CH₂-CHO |
| 833 | phenyl | -CH₂CH₂CH₂-NH₂ | -C≡CH |
| 834 | phenyl | -CH₂CH₂CH₂-NH₂ | -CH₂CH₂-N₃ |
| 835 | phenyl | -CH₂CH₂CH₂-NH₂ | -CH₂CH₂-NH₂ |
| 836 | phenyl | -CH₂CH₂CH₂-NH₂ | -CH₂CH₂-CHO |
| 837 | phenyl | 1H-imidazol-4-yl | -C≡CH |
| 838 | phenyl | 1H-imidazol-4-yl | -CH₂CH₂-N₃ |
| 839 | phenyl | 1H-imidazol-4-yl | -CH₂CH₂-NH₂ |
| 840 | phenyl | 1H-imidazol-4-yl | -CH₂CH₂-CHO |
| 841 | benzyl ester | catechol (3,4-dihydroxyphenyl) | -C≡CH |
| 842 | benzyl ester | catechol (3,4-dihydroxyphenyl) | -CH₂CH₂-N₃ |

TABLE 6-continued

| Compound | A¹ | A² | E¹ |
|---|---|---|---|
| 843 | benzyl ester | 3,4-dihydroxyphenyl | H₂N-CH₂CH₂- |
| 844 | benzyl ester | 3,4-dihydroxyphenyl | OHC-CH₂CH₂- |
| 845 | benzyl ester | -CH₂CH₂CH₂-NH₂ | HC≡C-CH₂- |
| 846 | benzyl ester | -CH₂CH₂CH₂-NH₂ | N₃-CH₂CH₂- |
| 847 | benzyl ester | -CH₂CH₂CH₂-NH₂ | H₂N-CH₂CH₂- |
| 848 | benzyl ester | -CH₂CH₂CH₂-NH₂ | OHC-CH₂CH₂- |
| 849 | benzyl ester | 1H-imidazol-4-yl | HC≡C-CH₂- |
| 850 | benzyl ester | 1H-imidazol-4-yl | N₃-CH₂CH₂- |
| 851 | benzyl ester | 1H-imidazol-4-yl | H₂N-CH₂CH₂- |
| 852 | benzyl ester | 1H-imidazol-4-yl | OHC-CH₂CH₂- |

TABLE 6-continued

| Compound | A¹ | A² | E¹ |
|---|---|---|---|
| 853 | benzyl ester | ethylamine | propargyl |
| 854 | benzyl ester | ethylamine | azidoethyl |
| 855 | benzyl ester | ethylamine | aminoethyl |
| 856 | benzyl ester | ethylamine | oxopropyl |
| 857 | phenyl | ethylamine | propargyl |
| 858 | phenyl | ethylamine | azidoethyl |
| 859 | phenyl | ethylamine | aminoethyl |
| 860 | phenyl | ethylamine | oxopropyl |
| 861 | isobutyl | ethylamine | propargyl |
| 862 | isobutyl | ethylamine | azidoethyl |
| 863 | isobutyl | ethylamine | aminoethyl |
| 864 | isobutyl | ethylamine | oxopropyl |
| 865 | isobutyl | dihydroxyphenyl | propargyl |

TABLE 6-continued

| Compound | A¹ | A² | E¹ |
|---|---|---|---|
| 866 | isopropyl | 3,4-dihydroxyphenyl | N₃-CH₂CH₂- |
| 867 | isopropyl | 3,4-dihydroxyphenyl | H₂N-CH₂CH₂- |
| 868 | isopropyl | 3,4-dihydroxyphenyl | OHC-CH₂CH₂- |
| 869 | isopropyl | -CH₂CH₂CH₂-NH₂ | HC≡C- |
| 870 | isopropyl | -CH₂CH₂CH₂-NH₂ | N₃-CH₂CH₂- |
| 871 | isopropyl | -CH₂CH₂CH₂-NH₂ | H₂N-CH₂CH₂- |
| 872 | isopropyl | -CH₂CH₂CH₂-NH₂ | OHC-CH₂CH₂- |
| 873 | isopropyl | 1H-imidazol-4-yl | HC≡C- |
| 874 | isopropyl | 1H-imidazol-4-yl | N₃-CH₂CH₂- |
| 875 | isopropyl | 1H-imidazol-4-yl | H₂N-CH₂CH₂- |
| 876 | isopropyl | 1H-imidazol-4-yl | OHC-CH₂CH₂- |

Table 7 sets forth exemplary compounds of the present invention having the formula:

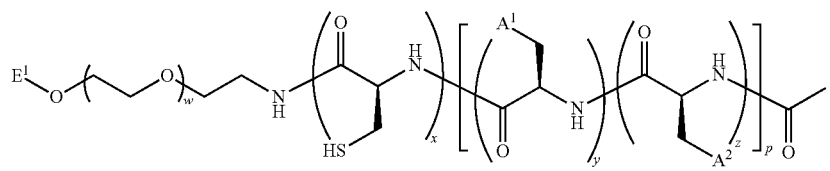

wherein each w is 25-1000, each x is 1-50, each y is 1-50, each z is 1-100, p is the sum of y and z, and each dotted bond represents the point of attachment to the rest of the molecule.

TABLE 7

| Compound | $A^1$ | $A^2$ | $E^1$ |
|---|---|---|---|
| 877 | benzyl ester acetate | 4-hydroxyphenyl | propargyl |
| 878 | benzyl ester acetate | 4-hydroxyphenyl | 2-azidoethyl |
| 879 | benzyl ester acetate | 4-hydroxyphenyl | 2-aminoethyl |
| 880 | benzyl ester acetate | 4-hydroxyphenyl | 3-oxopropyl |
| 881 | benzyl ester acetate | carboxymethyl | propargyl |
| 882 | benzyl ester acetate | carboxymethyl | 2-azidoethyl |
| 883 | benzyl ester acetate | carboxymethyl | 2-aminoethyl |

TABLE 7-continued
| Compound | A¹ | A² | E¹ |
|---|---|---|---|
| 884 | 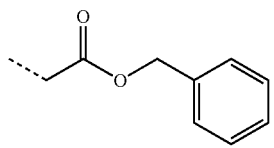 | 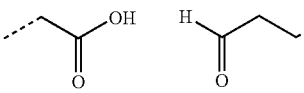 |  |
| 885 | 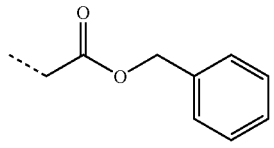 |  | 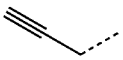 |
| 886 | 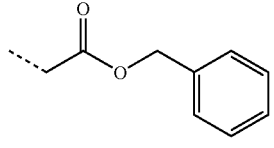 |  | 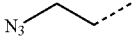 |
| 887 | 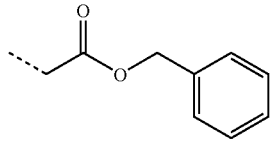 | 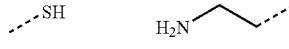 | 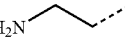 |
| 888 | 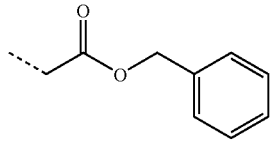 |  |  |
| 889 | 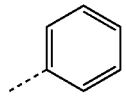 | 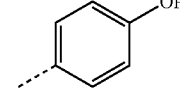 | 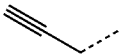 |
| 890 | 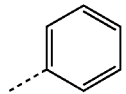 | 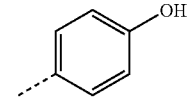 | 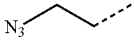 |
| 891 | 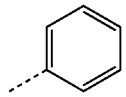 | 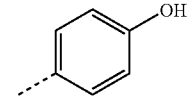 |  |
| 892 | 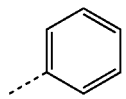 | 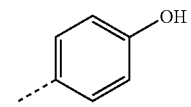 |  |
| 893 | 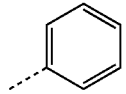 | 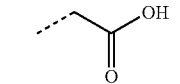 | 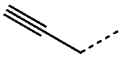 |
| 894 | 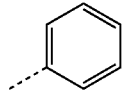 | 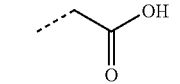 | 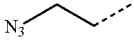 |
| 895 | 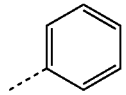 | 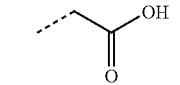 | 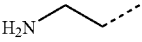 |

TABLE 7-continued

| Compound | A¹ | A² | E¹ |
|---|---|---|---|
| 896 | phenyl | -CH₂-COOH | -C(O)-CH₂-CH₂- (aldehyde) |
| 897 | phenyl | -SH | -C≡CH |
| 898 | phenyl | -SH | -CH₂-CH₂-N₃ |
| 899 | phenyl | -SH | -CH₂-CH₂-NH₂ |
| 900 | phenyl | -SH | -C(O)-CH₂-CH₂- (aldehyde) |
| 901 | benzyl ester | 4-hydroxyphenyl | -C≡CH |
| 902 | benzyl ester | 4-hydroxyphenyl | -CH₂-CH₂-N₃ |
| 903 | benzyl ester | 4-hydroxyphenyl | -CH₂-CH₂-NH₂ |
| 904 | benzyl ester | 4-hydroxyphenyl | -C(O)-CH₂-CH₂- (aldehyde) |
| 905 | benzyl ester | -CH₂-COOH | -C≡CH |
| 906 | benzyl ester | -CH₂-COOH | -CH₂-CH₂-N₃ |

TABLE 7-continued

| Compound | A¹ | A² | E¹ |
|---|---|---|---|
| 907 | benzyl ester (–C(O)O–CH₂–C₆H₅) | –CH₂–C(O)OH | H₂N–CH₂CH₂– |
| 908 | benzyl ester | –CH₂–C(O)OH | OHC–CH₂CH₂– |
| 909 | benzyl ester | –SH | HC≡C–CH₂– |
| 910 | benzyl ester | –SH | N₃–CH₂CH₂– |
| 911 | benzyl ester | –SH | H₂N–CH₂CH₂– |
| 912 | benzyl ester | –SH | OHC–CH₂CH₂– |
| 913 | benzyl ester | –C(O)OH | HC≡C–CH₂– |
| 914 | benzyl ester | –C(O)OH | N₃–CH₂CH₂– |
| 915 | benzyl ester | –C(O)OH | H₂N–CH₂CH₂– |
| 916 | benzyl ester | –C(O)OH | OHC–CH₂CH₂– |

TABLE 7-continued
| Compound | A¹ | A² | E¹ |
|---|---|---|---|
| 917 | 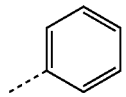 |  | 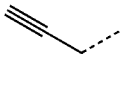 |
| 918 | 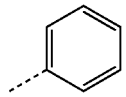 |  | 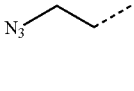 |
| 919 | 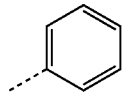 |  | 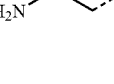 |
| 920 | 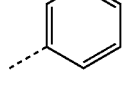 |  | 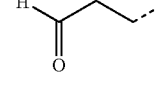 |
| 921 | 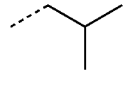 |  | 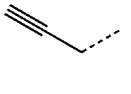 |
| 922 |  |  | 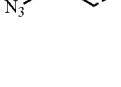 |
| 923 | 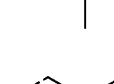 |  |  |
| 924 | 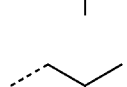 |  | 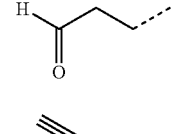 |
| 925 | 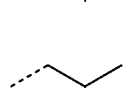 | 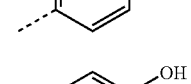 | 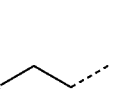 |
| 926 | 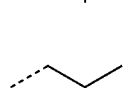 | 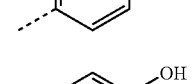 | 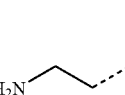 |
| 927 | 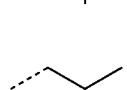 | 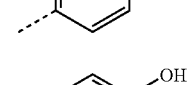 | 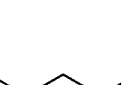 |
| 928 | 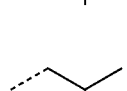 | 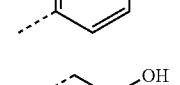 | 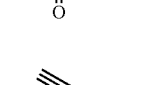 |
| 929 | 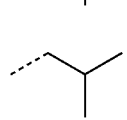 | 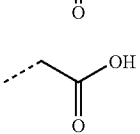 | 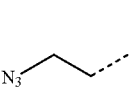 |
| 930 |  |  |  |

TABLE 7-continued
| Compound | A¹ | A² | E¹ |
|---|---|---|---|
| 931 | 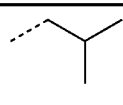 | 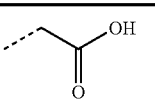 | 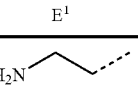 |
| 932 | 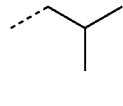 | 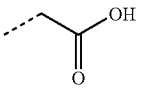 | 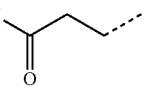 |
| 933 | 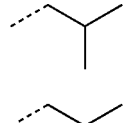 |  | 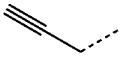 |
| 934 | 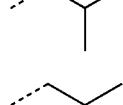 |  | 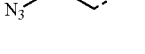 |
| 935 | 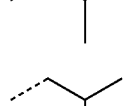 |  |  |
| 936 | 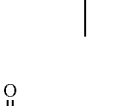 |  | 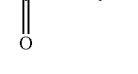 |
| 937 | 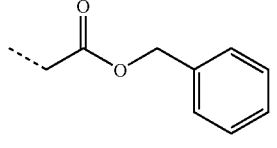 | 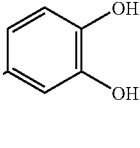 | 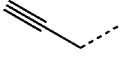 |
| 938 | 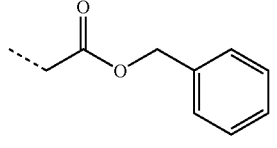 | 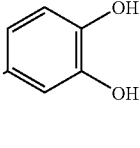 | 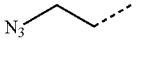 |
| 939 | 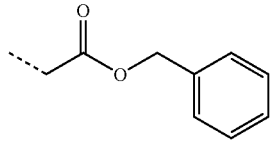 | 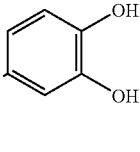 | 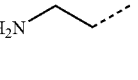 |
| 940 | 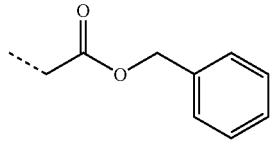 | 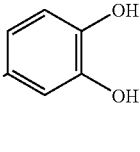 | 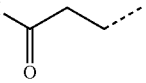 |
| 941 | 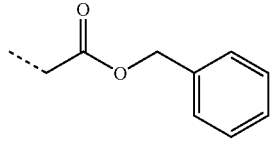 | 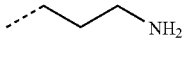 | 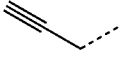 |
| 942 | 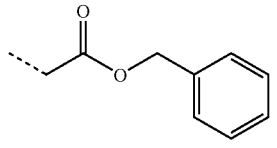 | 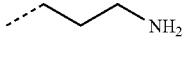 | 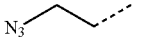 |

TABLE 7-continued
| Compound | A¹ | A² | E¹ |
|---|---|---|---|
| 943 | 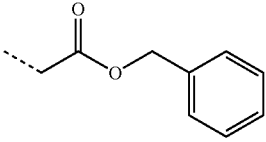 | 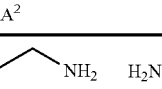 |  |
| 944 | 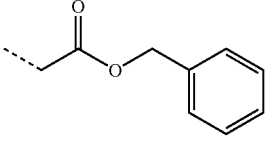 | 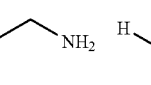 |  |
| 945 | 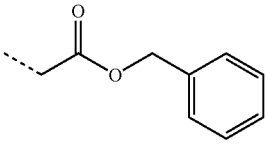 |  |  |
| 946 | 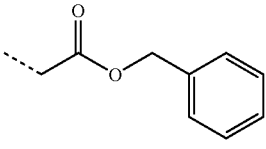 |  |  |
| 947 | 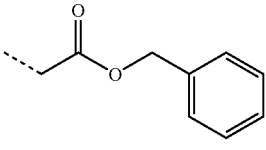 |  |  |
| 948 | 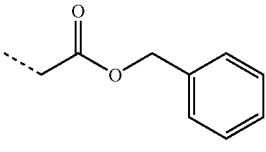 |  |  |
| 949 | 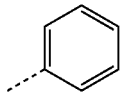 | 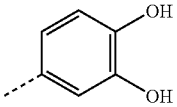 |  |
| 950 | 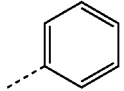 | 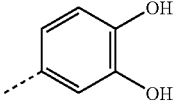 |  |
| 951 | 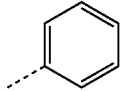 | 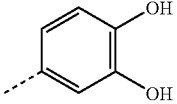 |  |
| 952 | 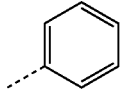 | 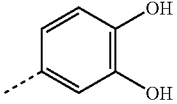 |  |
| 953 | 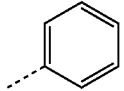 | 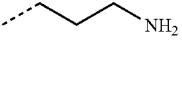 |  |

TABLE 7-continued

| Compound | A¹ | A² | E¹ |
| --- | --- | --- | --- |
| 954 | phenyl | -CH2CH2CH2NH2 | -CH2CH2N3 |
| 955 | phenyl | -CH2CH2CH2NH2 | -CH2CH2NH2 |
| 956 | phenyl | -CH2CH2CH2NH2 | -CH2CH2CHO |
| 957 | phenyl | 1H-imidazol-4-yl | -C≡CH |
| 958 | phenyl | 1H-imidazol-4-yl | -CH2CH2N3 |
| 959 | phenyl | 1H-imidazol-4-yl | -CH2CH2NH2 |
| 960 | phenyl | 1H-imidazol-4-yl | -CH2CH2CHO |
| 961 | benzyloxycarbonyl | 3,4-dihydroxyphenyl | -C≡CH |
| 962 | benzyloxycarbonyl | 3,4-dihydroxyphenyl | -CH2CH2N3 |
| 963 | benzyloxycarbonyl | 3,4-dihydroxyphenyl | -CH2CH2NH2 |
| 964 | benzyloxycarbonyl | 3,4-dihydroxyphenyl | -CH2CH2CHO |
| 965 | benzyloxycarbonyl | -CH2CH2CH2NH2 | -C≡CH |

TABLE 7-continued
| Compound | A¹ | A² | E¹ |
|---|---|---|---|
| 966 | 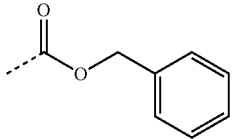 | 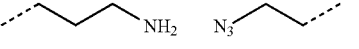 |  |
| 967 | 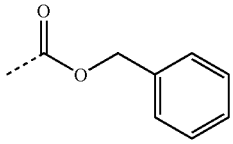 | 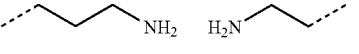 |  |
| 968 | 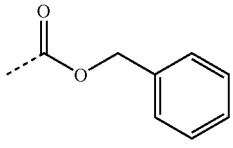 | 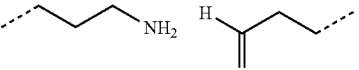 |  |
| 969 | 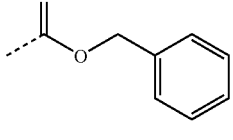 |  |  |
| 970 | 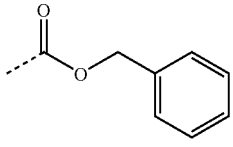 |  |  |
| 971 | 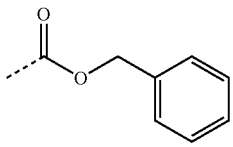 |  |  |
| 972 | 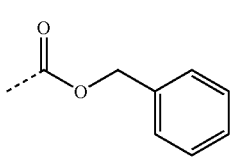 |  |  |
| 973 | 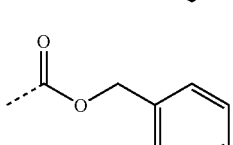 |  |  |
| 974 | 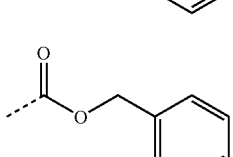 |  |  |
| 975 | 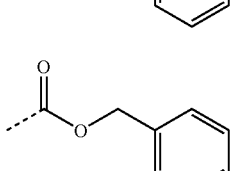 |  |  |

TABLE 7-continued

| Compound | A¹ | A² | E¹ |
|---|---|---|---|
| 976 | benzyl ester (–C(=O)O–CH₂–C₆H₅) | –CH₂CH₂NH₂ | –CH₂CH₂C(=O)H |
| 977 | phenyl | –CH₂CH₂NH₂ | –C≡CH |
| 978 | phenyl | –CH₂CH₂NH₂ | –CH₂CH₂N₃ |
| 979 | phenyl | –CH₂CH₂NH₂ | –CH₂CH₂NH₂ |
| 980 | phenyl | –CH₂CH₂NH₂ | –CH₂CH₂C(=O)H |
| 981 | isopropyl | –CH₂CH₂NH₂ | –C≡CH |
| 982 | isopropyl | –CH₂CH₂NH₂ | –CH₂CH₂N₃ |
| 983 | isopropyl | –CH₂CH₂NH₂ | –CH₂CH₂NH₂ |
| 984 | isopropyl | –CH₂CH₂NH₂ | –CH₂CH₂C(=O)H |
| 985 | isopropyl | 3,4-dihydroxyphenyl | –C≡CH |
| 986 | isopropyl | 3,4-dihydroxyphenyl | –CH₂CH₂N₃ |
| 987 | isopropyl | 3,4-dihydroxyphenyl | –CH₂CH₂NH₂ |
| 988 | isopropyl | 3,4-dihydroxyphenyl | –CH₂CH₂C(=O)H |
| 989 | isopropyl | –CH₂CH₂CH₂NH₂ | –C≡CH |

TABLE 7-continued

| Compound | A¹ | A² | E¹ |
|---|---|---|---|
| 990 | isopropyl | propyl-NH₂ | N₃-CH₂CH₂- |
| 991 | isopropyl | propyl-NH₂ | H₂N-CH₂CH₂- |
| 992 | isopropyl | propyl-NH₂ | OHC-CH₂CH₂- |
| 993 | isopropyl | imidazolyl | HC≡C-CH₂- |
| 994 | isopropyl | imidazolyl | N₃-CH₂CH₂- |
| 995 | isopropyl | imidazolyl | H₂N-CH₂CH₂- |
| 996 | isopropyl | imidazolyl | OHC-CH₂CH₂- |

Table 8 sets forth exemplary compounds of the present invention having the formula:

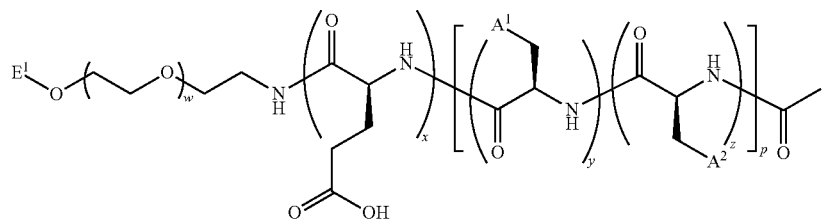

wherein each w is 25-1000, each x is 1-50, each y is 1-50, each z is 1-100, p is the sum of y and z, and each dotted bond represents the point of attachment to the rest of the molecule.

TABLE 8

| Compound | A¹ | A² | E¹ |
|---|---|---|---|
| 997 | -CH₂C(O)O-CH₂-Ph | -C₆H₄-OH | HC≡C-CH₂- |
| 998 | -CH₂C(O)O-CH₂-Ph | -C₆H₄-OH | N₃-CH₂CH₂- |

TABLE 8-continued

| Compound | A¹ | A² | E¹ |
|---|---|---|---|
| 999 | benzyl ester (-CH₂-C(=O)-O-CH₂-C₆H₅) | 4-hydroxyphenyl | H₂N-CH₂-CH₂- |
| 1000 | benzyl ester | 4-hydroxyphenyl | OHC-CH₂-CH₂- |
| 1001 | benzyl ester | -CH₂-C(=O)-OH | HC≡C-CH₂- |
| 1002 | benzyl ester | -CH₂-C(=O)-OH | N₃-CH₂-CH₂- |
| 1003 | benzyl ester | -CH₂-C(=O)-OH | H₂N-CH₂-CH₂- |
| 1004 | benzyl ester | -CH₂-C(=O)-OH | OHC-CH₂-CH₂- |
| 1005 | benzyl ester | -SH | HC≡C-CH₂- |
| 1006 | benzyl ester | -SH | N₃-CH₂-CH₂- |
| 1007 | benzyl ester | -SH | H₂N-CH₂-CH₂- |
| 1008 | benzyl ester | -SH | OHC-CH₂-CH₂- |

TABLE 8-continued

| Compound | A¹ | A² | E¹ |
|---|---|---|---|
| 1009 | phenyl | 4-hydroxyphenyl | propargyl |
| 1010 | phenyl | 4-hydroxyphenyl | azidoethyl (N₃-CH₂CH₂-) |
| 1011 | phenyl | 4-hydroxyphenyl | aminoethyl (H₂N-CH₂CH₂-) |
| 1012 | phenyl | 4-hydroxyphenyl | -CH₂CH₂-CHO |
| 1013 | phenyl | -CH₂-C(=O)-OH | propargyl |
| 1014 | phenyl | -CH₂-C(=O)-OH | azidoethyl |
| 1015 | phenyl | -CH₂-C(=O)-OH | aminoethyl |
| 1016 | phenyl | -CH₂-C(=O)-OH | -CH₂CH₂-CHO |
| 1017 | phenyl | -SH | propargyl |
| 1018 | phenyl | -SH | azidoethyl |
| 1019 | phenyl | -SH | aminoethyl |
| 1020 | phenyl | -SH | -CH₂CH₂-CHO |
| 1021 | -C(=O)-O-CH₂-phenyl | 4-hydroxyphenyl | propargyl |

TABLE 8-continued
| Compound | A¹ | A² | E¹ |
|---|---|---|---|
| 1022 | 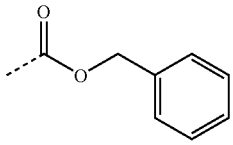 | 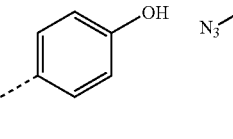 | 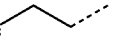 |
| 1023 | 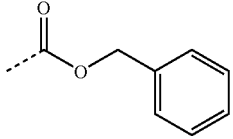 | 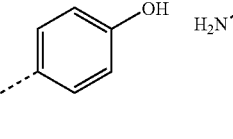 | 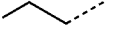 |
| 1024 | 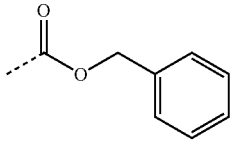 | 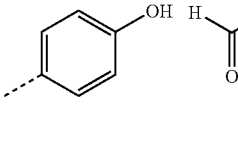 | 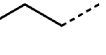 |
| 1025 | 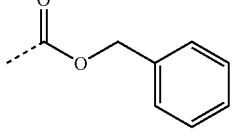 | 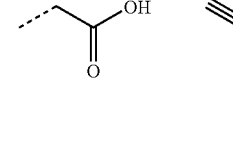 | 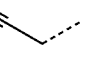 |
| 1026 | 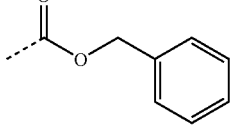 | 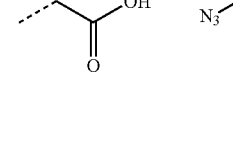 | 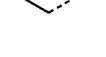 |
| 1027 | 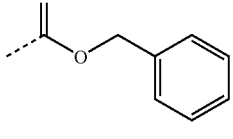 | 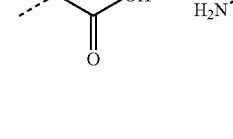 |  |
| 1028 | 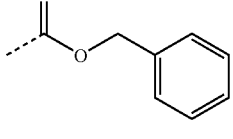 | 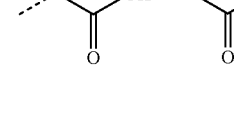 | 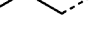 |
| 1029 | 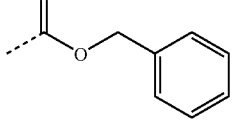 |  | 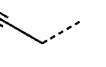 |
| 1030 | 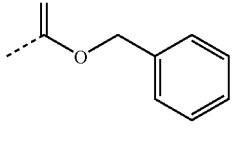 |  |  |
| 1031 | 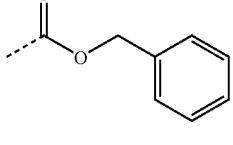 |  |  |

TABLE 8-continued
| Compound | A¹ | A² | E¹ |
|---|---|---|---|
| 1032 | 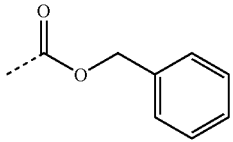 | 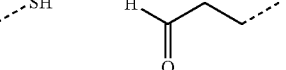—SH | 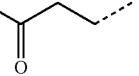 |
| 1033 | 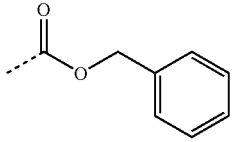 |  | 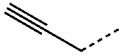 |
| 1034 | 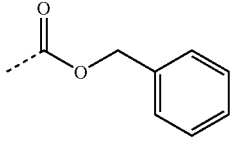 |  | 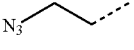 |
| 1035 | 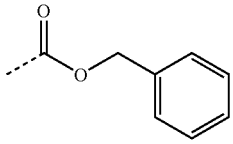 |  | 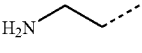 |
| 1036 | 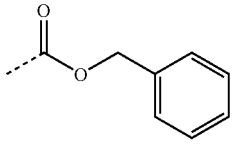 |  | 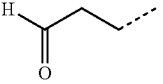 |
| 1037 | 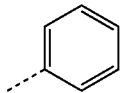 |  | 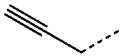 |
| 1038 | 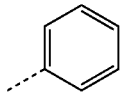 |  | 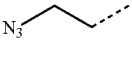 |
| 1039 | 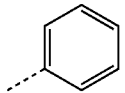 |  | 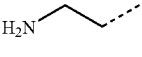 |
| 1040 | 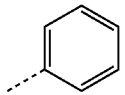 |  | 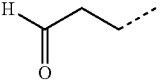 |
| 1041 | 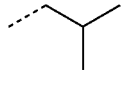 |  | 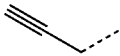 |
| 1042 | 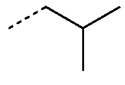 |  | 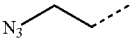 |
| 1043 | 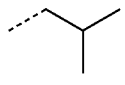 |  | 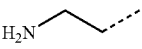 |

TABLE 8-continued

| Compound | A¹ | A² | E¹ |
|---|---|---|---|
| 1044 | isopropyl | -C(=O)OH | -CH₂CH₂C(=O)H |
| 1045 | isopropyl | 4-hydroxyphenyl | -CH₂C≡CH |
| 1046 | isopropyl | 4-hydroxyphenyl | -CH₂CH₂N₃ |
| 1047 | isopropyl | 4-hydroxyphenyl | -CH₂CH₂NH₂ |
| 1048 | isopropyl | 4-hydroxyphenyl | -CH₂CH₂C(=O)H |
| 1049 | isopropyl | -CH₂C(=O)OH | -CH₂C≡CH |
| 1050 | isopropyl | -CH₂C(=O)OH | -CH₂CH₂N₃ |
| 1051 | isopropyl | -CH₂C(=O)OH | -CH₂CH₂NH₂ |
| 1052 | isopropyl | -CH₂C(=O)OH | -CH₂CH₂C(=O)H |
| 1053 | isopropyl | -SH | -CH₂C≡CH |
| 1054 | isopropyl | -SH | -CH₂CH₂N₃ |
| 1055 | isopropyl | -SH | -CH₂CH₂NH₂ |
| 1056 | isopropyl | -SH | -CH₂CH₂C(=O)H |
| 1057 | -CH₂C(=O)OCH₂Ph | 3,4-dihydroxyphenyl | -CH₂C≡CH |

TABLE 8-continued

| Compound | A¹ | A² | E¹ |
| --- | --- | --- | --- |
| 1058 | benzyl ester (–CH₂C(O)OCH₂-C₆H₅) | 3,4-dihydroxyphenyl | –CH₂CH₂–N₃ |
| 1059 | benzyl ester | 3,4-dihydroxyphenyl | –CH₂CH₂–NH₂ |
| 1060 | benzyl ester | 3,4-dihydroxyphenyl | –CH₂CH₂–C(O)H |
| 1061 | benzyl ester | –CH₂CH₂CH₂–NH₂ | –CH₂–C≡CH |
| 1062 | benzyl ester | –CH₂CH₂CH₂–NH₂ | –CH₂CH₂–N₃ |
| 1063 | benzyl ester | –CH₂CH₂CH₂–NH₂ | –CH₂CH₂–NH₂ |
| 1064 | benzyl ester | –CH₂CH₂CH₂–NH₂ | –CH₂CH₂–C(O)H |
| 1065 | benzyl ester | 1H-imidazol-4-yl | –CH₂–C≡CH |
| 1066 | benzyl ester | 1H-imidazol-4-yl | –CH₂CH₂–N₃ |
| 1067 | benzyl ester | 1H-imidazol-4-yl | –CH₂CH₂–NH₂ |

TABLE 8-continued

| Compound | A¹ | A² | E¹ |
| --- | --- | --- | --- |
| 1068 | benzyl propanoate | 1H-imidazol-4-yl | propanal |
| 1069 | phenyl | 3,4-dihydroxyphenyl | but-3-yn-1-yl |
| 1070 | phenyl | 3,4-dihydroxyphenyl | 3-azidopropyl |
| 1071 | phenyl | 3,4-dihydroxyphenyl | 2-aminoethyl |
| 1072 | phenyl | 3,4-dihydroxyphenyl | propanal |
| 1073 | phenyl | 3-aminopropyl | but-3-yn-1-yl |
| 1074 | phenyl | 3-aminopropyl | 3-azidopropyl |
| 1075 | phenyl | 3-aminopropyl | 2-aminoethyl |
| 1076 | phenyl | 3-aminopropyl | propanal |
| 1077 | phenyl | 1H-imidazol-4-yl | but-3-yn-1-yl |
| 1078 | phenyl | 1H-imidazol-4-yl | 3-azidopropyl |
| 1079 | phenyl | 1H-imidazol-4-yl | 2-aminoethyl |
| 1080 | phenyl | 1H-imidazol-4-yl | propanal |

TABLE 8-continued

| Compound | A¹ | A² | E¹ |
|---|---|---|---|
| 1081 | benzyl ester | 3,4-dihydroxyphenyl | ethynyl |
| 1082 | benzyl ester | 3,4-dihydroxyphenyl | azidoethyl |
| 1083 | benzyl ester | 3,4-dihydroxyphenyl | aminoethyl |
| 1084 | benzyl ester | 3,4-dihydroxyphenyl | oxopropyl |
| 1085 | benzyl ester | aminopropyl | ethynyl |
| 1086 | benzyl ester | aminopropyl | azidoethyl |
| 1087 | benzyl ester | aminopropyl | aminoethyl |
| 1088 | benzyl ester | aminopropyl | oxopropyl |
| 1089 | benzyl ester | 1H-imidazol-4-yl | ethynyl |
| 1090 | benzyl ester | 1H-imidazol-4-yl | azidoethyl |

TABLE 8-continued
| Compound | A¹ | A² | E¹ |
|---|---|---|---|
| 1091 | 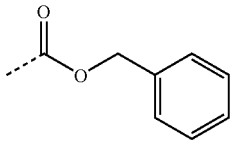 | 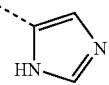 | 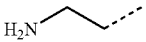 |
| 1092 | 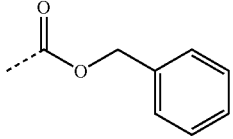 | 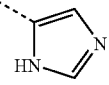 | 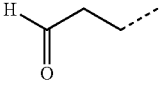 |
| 1093 | 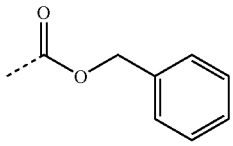 | 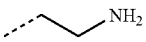 | 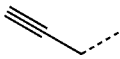 |
| 1094 | 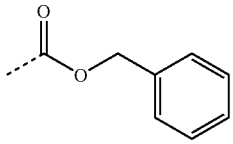 | 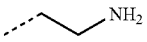 | 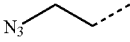 |
| 1095 | 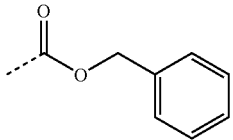 | 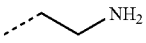 | 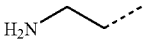 |
| 1096 | 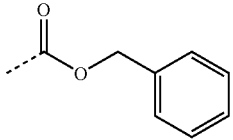 | 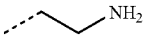 | 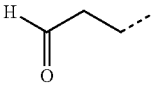 |
| 1097 | 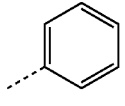 | 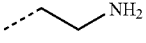 |  |
| 1098 | 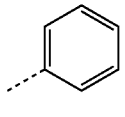 | 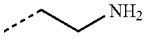 | 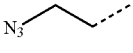 |
| 1099 | 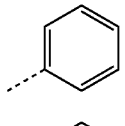 | 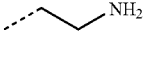 |  |
| 1100 | 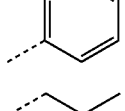 |  | 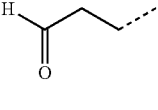 |
| 1101 | 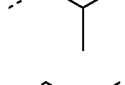 | 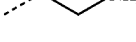 | 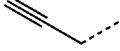 |
| 1102 | 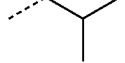 | 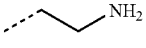 | 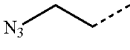 |

TABLE 8-continued
| Compound | A¹ | A² | E¹ |
|---|---|---|---|
| 1103 | 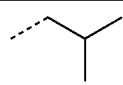 | 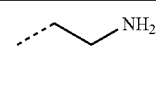 NH₂ | H₂N 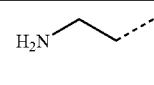 |
| 1104 | 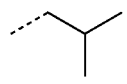 | 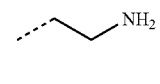 NH₂ | 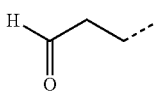 |
| 1105 | 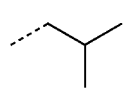 | 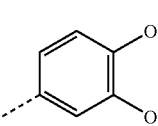 | 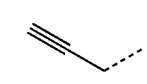 |
| 1106 | 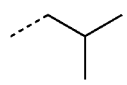 | 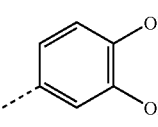 | N₃ 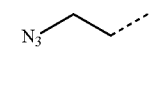 |
| 1107 | 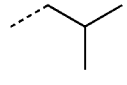 | 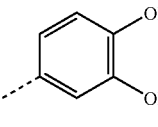 | H₂N 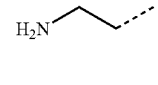 |
| 1108 | 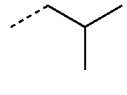 | 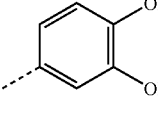 | 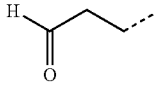 |
| 1109 | 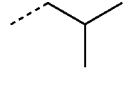 |  NH₂ | 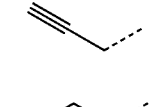 |
| 1110 | 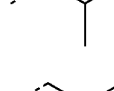 |  NH₂ | N₃ 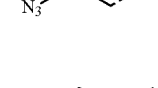 |
| 1111 | 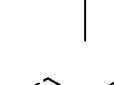 | 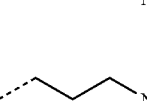 NH₂ | H₂N 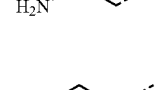 |
| 1112 | 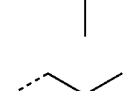 |  NH₂ | H₂N 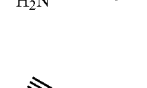 |
| 1113 | 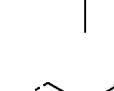 | 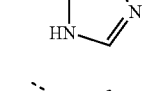 | 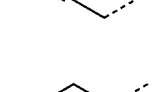 |
| 1114 | 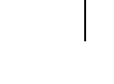 | 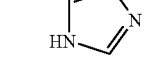 | N₃ 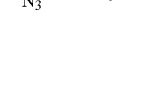 |
| 1115 | 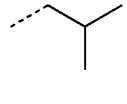 | 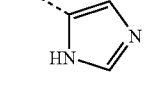 | H₂N 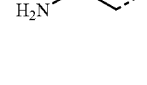 |
| 1116 | 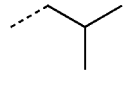 | 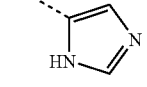 | 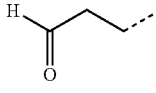 |

Table 9 sets forth exemplary compounds of the present invention having the formula:

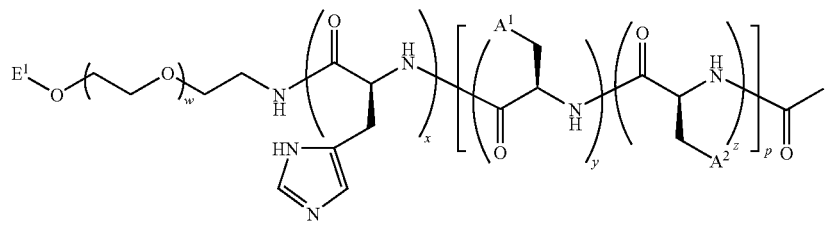

wherein each w is 25-1000, each x is 1-50, each y is 1-50, each z is 1-100, p is the sum of y and z, and each dotted bond represents the point of attachment to the rest of the molecule.

TABLE 9

| Compound | $A^1$ | $A^2$ | $E^1$ |
|---|---|---|---|
| 1117 | benzyl ester acetate | 4-hydroxyphenyl | propargyl |
| 1118 | benzyl ester acetate | 4-hydroxyphenyl | N₃-ethyl |
| 1119 | benzyl ester acetate | 4-hydroxyphenyl | H₂N-ethyl |
| 1120 | benzyl ester acetate | 4-hydroxyphenyl | HC(O)-ethyl |
| 1121 | benzyl ester acetate | carboxylate | propargyl |
| 1122 | benzyl ester acetate | carboxylate | N₃-ethyl |
| 1123 | benzyl ester acetate | carboxylate | H₂N-ethyl |

TABLE 9-continued

| Compound | A¹ | A² | E¹ |
|---|---|---|---|
| 1124 | benzyl ester | -CH₂COOH | -CH₂CHO |
| 1125 | benzyl ester | -SH | alkyne |
| 1126 | benzyl ester | -SH | -CH₂CH₂N₃ |
| 1127 | benzyl ester | -SH | -CH₂CH₂NH₂ |
| 1128 | benzyl ester | -SH | -CH₂CHO |
| 1129 | phenyl | 4-hydroxyphenyl | alkyne |
| 1130 | phenyl | 4-hydroxyphenyl | -CH₂CH₂N₃ |
| 1131 | phenyl | 4-hydroxyphenyl | -CH₂CH₂NH₂ |
| 1132 | phenyl | 4-hydroxyphenyl | -CH₂CHO |
| 1133 | phenyl | -CH₂COOH | alkyne |
| 1134 | phenyl | -CH₂COOH | -CH₂CH₂N₃ |
| 1135 | phenyl | -CH₂COOH | -CH₂CH₂NH₂ |

TABLE 9-continued

| Compound | A¹ | A² | E¹ |
|---|---|---|---|
| 1136 | phenyl | CH₂COOH | CH₂CH₂CHO |
| 1137 | phenyl | SH | C≡CCH₂ |
| 1138 | phenyl | SH | N₃CH₂CH₂ |
| 1139 | phenyl | SH | H₂NCH₂CH₂ |
| 1140 | phenyl | SH | CH₂CH₂CHO |
| 1141 | benzyl ester | 4-hydroxyphenyl | C≡CCH₂ |
| 1142 | benzyl ester | 4-hydroxyphenyl | N₃CH₂CH₂ |
| 1143 | benzyl ester | 4-hydroxyphenyl | H₂NCH₂CH₂ |
| 1144 | benzyl ester | 4-hydroxyphenyl | CH₂CH₂CHO |
| 1145 | benzyl ester | CH₂COOH | C≡CCH₂ |
| 1146 | benzyl ester | CH₂COOH | N₃CH₂CH₂ |

TABLE 9-continued
| Compound | A¹ | A² | E¹ |
|---|---|---|---|
| 1147 | 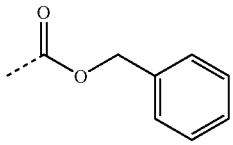 | 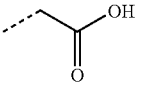 | 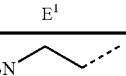 |
| 1148 | 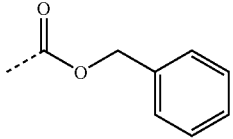 | 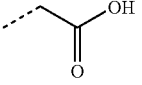 | 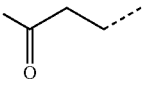 |
| 1149 | 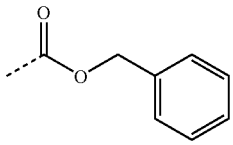 | ⋯SH |  |
| 1150 | 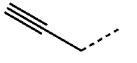 | ⋯SH | 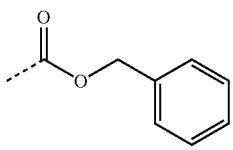 |
| 1151 |  | ⋯SH | 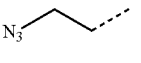 |
| 1152 | 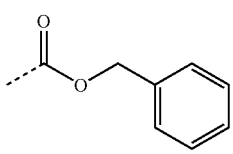 | ⋯SH |  |
| 1153 | 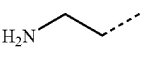 | 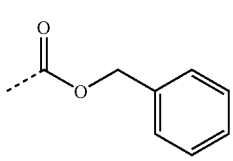 |  |
| 1154 | 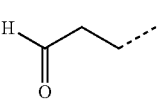 | 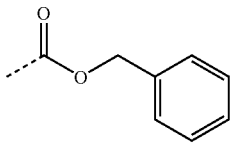 | 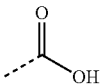 |
| 1155 | 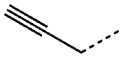 | 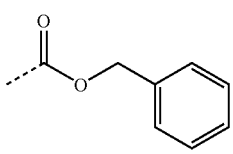 | 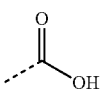 |
| 1156 | 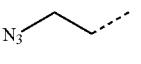 | 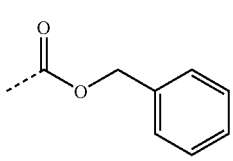 | 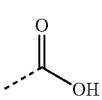 |

TABLE 9-continued

| Compound | A¹ | A² | E¹ |
|---|---|---|---|
| 1157 | phenyl | COOH | alkyne |
| 1158 | phenyl | COOH | CH₂CH₂N₃ |
| 1159 | phenyl | COOH | CH₂CH₂NH₂ |
| 1160 | phenyl | COOH | CH₂CH₂CHO |
| 1161 | isopropyl | COOH | alkyne |
| 1162 | isopropyl | COOH | CH₂CH₂N₃ |
| 1163 | isopropyl | COOH | CH₂CH₂NH₂ |
| 1164 | isopropyl | COOH | CH₂CH₂CHO |
| 1165 | isopropyl | 4-hydroxyphenyl | alkyne |
| 1166 | isopropyl | 4-hydroxyphenyl | CH₂CH₂N₃ |
| 1167 | isopropyl | 4-hydroxyphenyl | CH₂CH₂NH₂ |
| 1168 | isopropyl | 4-hydroxyphenyl | CH₂CH₂CHO |
| 1169 | isopropyl | CH₂COOH | alkyne |
| 1170 | isopropyl | CH₂COOH | CH₂CH₂N₃ |

TABLE 9-continued

| Compound | A¹ | A² | E¹ |
|---|---|---|---|
| 1171 | isobutyl | CH₂COOH | H₂N-CH₂CH₂- |
| 1172 | isobutyl | CH₂COOH | OHC-CH₂CH₂- |
| 1173 | isobutyl | -SH | HC≡C-CH₂- |
| 1174 | isobutyl | -SH | N₃-CH₂CH₂- |
| 1175 | isobutyl | -SH | H₂N-CH₂CH₂- |
| 1176 | isobutyl | -SH | OHC-CH₂CH₂- |
| 1177 | benzyl ester -CH₂C(O)OCH₂Ph | 3,4-dihydroxyphenyl | HC≡C-CH₂- |
| 1178 | benzyl ester -CH₂C(O)OCH₂Ph | 3,4-dihydroxyphenyl | N₃-CH₂CH₂- |
| 1179 | benzyl ester -CH₂C(O)OCH₂Ph | 3,4-dihydroxyphenyl | H₂N-CH₂CH₂- |
| 1180 | benzyl ester -CH₂C(O)OCH₂Ph | 3,4-dihydroxyphenyl | OHC-CH₂CH₂- |
| 1181 | benzyl ester -CH₂C(O)OCH₂Ph | -CH₂CH₂CH₂NH₂ | HC≡C-CH₂- |
| 1182 | benzyl ester -CH₂C(O)OCH₂Ph | -CH₂CH₂CH₂NH₂ | N₃-CH₂CH₂- |

TABLE 9-continued

| Compound | A¹ | A² | E¹ |
| --- | --- | --- | --- |
| 1183 | benzyl ester | propyl-NH₂ | H₂N-ethyl |
| 1184 | benzyl ester | propyl-NH₂ | CHO-propyl |
| 1185 | benzyl ester | imidazole | alkyne |
| 1186 | benzyl ester | imidazole | N₃-ethyl |
| 1187 | benzyl ester | imidazole | H₂N-ethyl |
| 1188 | benzyl ester | imidazole | CHO-propyl |
| 1189 | phenyl | catechol (3,4-diOH) | alkyne |
| 1190 | phenyl | catechol (3,4-diOH) | N₃-ethyl |
| 1191 | phenyl | catechol (3,4-diOH) | H₂N-ethyl |
| 1192 | phenyl | catechol (3,4-diOH) | CHO-propyl |
| 1193 | phenyl | propyl-NH₂ | alkyne |

TABLE 9-continued
| Compound | A¹ | A² | E¹ |
|---|---|---|---|
| 1194 | 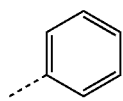 | 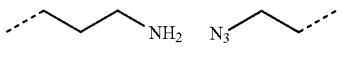 NH₂ |  N₃ |
| 1195 | 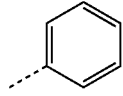 | 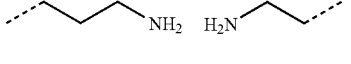 NH₂ | H₂N  |
| 1196 | 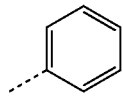 | 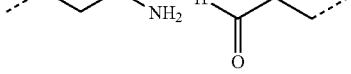 NH₂ |  |
| 1197 | 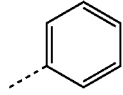 | 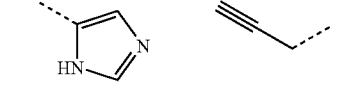 |  |
| 1198 | 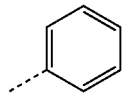 | 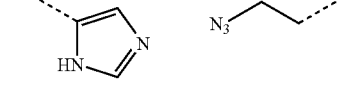 |  N₃ |
| 1199 | 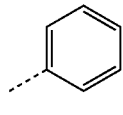 | 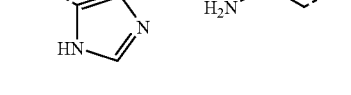 | H₂N  |
| 1200 | 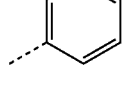 | 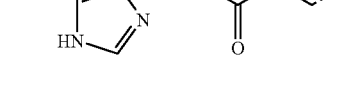 |  |
| 1201 | 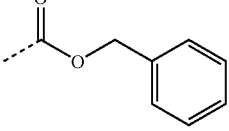 | 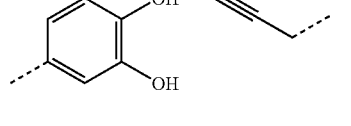 |  |
| 1202 | 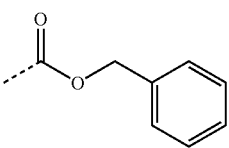 | 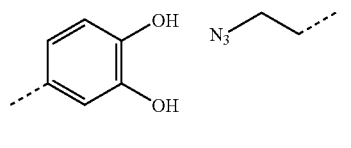 |  N₃ |
| 1203 | 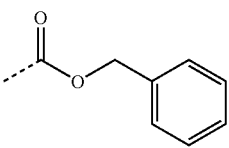 | 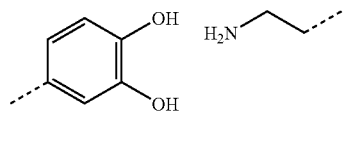 | H₂N  |
| 1204 | 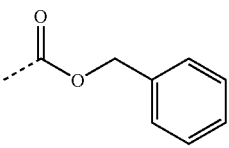 | 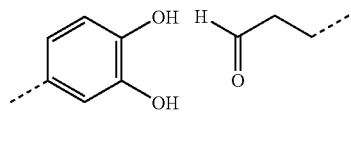 |  |
| 1205 | 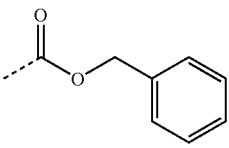 | 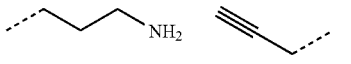 NH₂ |  |

TABLE 9-continued
| Compound | A¹ | A² | E¹ |
|---|---|---|---|
| 1206 | 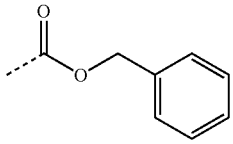 | 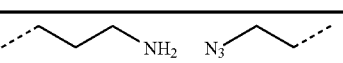 NH₂ |  N₃ |
| 1207 | 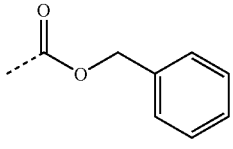 | 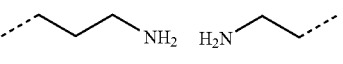 NH₂ |  H₂N |
| 1208 | 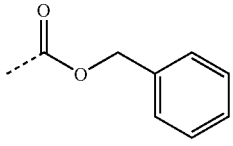 | 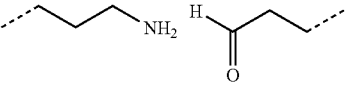 NH₂ |  |
| 1209 | 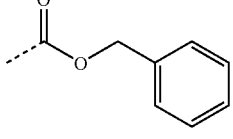 |  |  |
| 1210 | 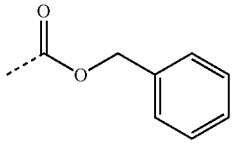 |  |  N₃ |
| 1211 | 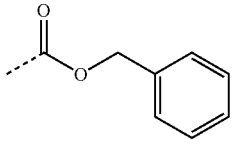 | 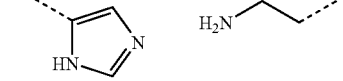 |  H₂N |
| 1212 | 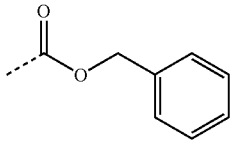 | 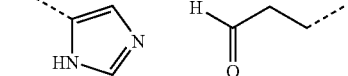 |  |
| 1213 | 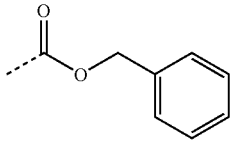 | 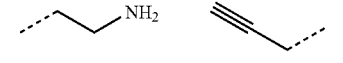 NH₂ |  |
| 1214 | 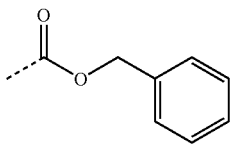 | 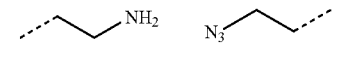 NH₂ |  N₃ |
| 1215 | 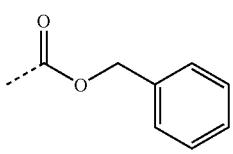 | 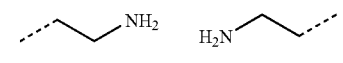 NH₂ |  H₂N |

TABLE 9-continued

| Compound | A[1] | A[2] | E[1] |
|---|---|---|---|
| 1216 | benzyl ester (–C(O)O–CH2–Ph) | –CH2CH2–NH2 | –CH2CH2–C(O)H |
| 1217 | phenyl | –CH2CH2–NH2 | –C≡CH |
| 1218 | phenyl | –CH2CH2–NH2 | –CH2CH2–N3 |
| 1219 | phenyl | –CH2CH2–NH2 | –CH2CH2–NH2 |
| 1220 | phenyl | –CH2CH2–NH2 | –CH2CH2–C(O)H |
| 1221 | isopropyl | –CH2CH2–NH2 | –C≡CH |
| 1222 | isopropyl | –CH2CH2–NH2 | –CH2CH2–N3 |
| 1223 | isopropyl | –CH2CH2–NH2 | –CH2CH2–NH2 |
| 1224 | isopropyl | –CH2CH2–NH2 | –CH2CH2–C(O)H |
| 1225 | isopropyl | 3,4-dihydroxyphenyl | –C≡CH |
| 1226 | isopropyl | 3,4-dihydroxyphenyl | –CH2CH2–N3 |
| 1227 | isopropyl | 3,4-dihydroxyphenyl | –CH2CH2–NH2 |
| 1228 | isopropyl | 3,4-dihydroxyphenyl | –CH2CH2–C(O)H |
| 1229 | isopropyl | –CH2CH2CH2–NH2 | –C≡CH |

TABLE 9-continued

| Compound | A¹ | A² | E¹ |
|---|---|---|---|
| 1230 | isopropyl | propyl-NH₂ | N₃-ethyl |
| 1231 | isopropyl | propyl-NH₂ | H₂N-ethyl |
| 1232 | isopropyl | propyl-NH₂ | CHO-ethyl |
| 1233 | isopropyl | imidazolyl | propargyl |
| 1234 | isopropyl | imidazolyl | N₃-ethyl |
| 1235 | isopropyl | imidazolyl | H₂N-ethyl |
| 1236 | isopropyl | imidazolyl | CHO-ethyl |

Table 10 sets forth exemplary compounds of the present invention having the formula:

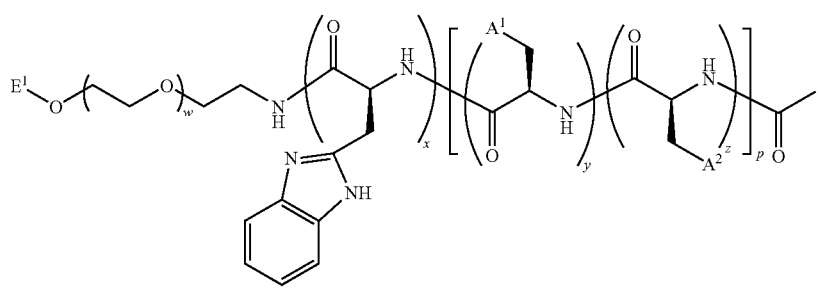

wherein each w is 25-1000, each x is 1-50, each y is 1-50, each z is 1-100, p is the sum of y and z, and each dotted bond represents the point of attachment to the rest of the molecule.

TABLE 10

| Compound | A¹ | A² | E² |
|---|---|---|---|
| 1237 | benzyl ester-CH₂C(O)O-CH₂-Ph | 4-hydroxyphenyl | propargyl |

TABLE 10-continued

| Compound | A¹ | A² | E² |
| --- | --- | --- | --- |
| 1238 | benzyl ester | 4-hydroxyphenyl | N₃-CH₂CH₂- |
| 1239 | benzyl ester | 4-hydroxyphenyl | H₂N-CH₂CH₂- |
| 1240 | benzyl ester | 4-hydroxyphenyl | OHC-CH₂CH₂- |
| 1241 | benzyl ester | -CH₂-COOH | HC≡C-CH₂- |
| 1242 | benzyl ester | -CH₂-COOH | N₃-CH₂CH₂- |
| 1243 | benzyl ester | -CH₂-COOH | H₂N-CH₂CH₂- |
| 1244 | benzyl ester | -CH₂-COOH | OHC-CH₂CH₂- |
| 1245 | benzyl ester | -SH | HC≡C-CH₂- |
| 1246 | benzyl ester | -SH | N₃-CH₂CH₂- |
| 1247 | benzyl ester | -SH | H₂N-CH₂CH₂- |

TABLE 10-continued

| Compound | A¹ | A² | E² |
|---|---|---|---|
| 1248 | benzyl propanoate ester group | SH | butanal group |
| 1249 | phenyl | 4-hydroxyphenyl | but-1-ynyl |
| 1250 | phenyl | 4-hydroxyphenyl | 3-azidopropyl |
| 1251 | phenyl | 4-hydroxyphenyl | 2-aminoethyl |
| 1252 | phenyl | 4-hydroxyphenyl | butanal group |
| 1253 | phenyl | carboxymethyl (CH₂COOH) | but-1-ynyl |
| 1254 | phenyl | carboxymethyl | 3-azidopropyl |
| 1255 | phenyl | carboxymethyl | 2-aminoethyl |
| 1256 | phenyl | carboxymethyl | butanal group |
| 1257 | phenyl | SH | but-1-ynyl |
| 1258 | phenyl | SH | 3-azidopropyl |
| 1259 | phenyl | SH | 2-aminoethyl |
| 1260 | phenyl | SH | propanal group |

TABLE 10-continued
| Compound | A¹ | A² | E² |
|---|---|---|---|
| 1261 | 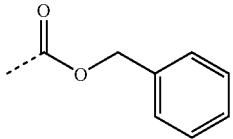 | 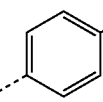 | 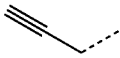 |
| 1262 | 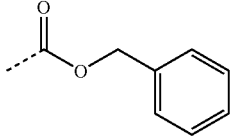 | 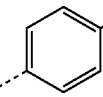 | 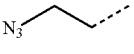 |
| 1263 | 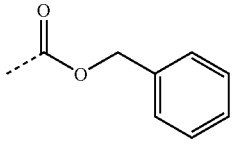 | 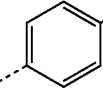 | 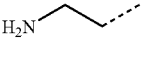 |
| 1264 | 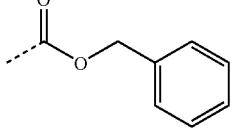 | 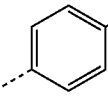 | 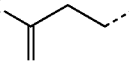 |
| 1265 | 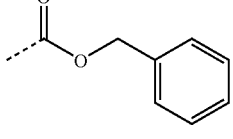 | 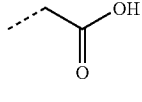 | 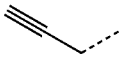 |
| 1266 | 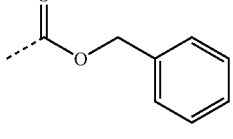 | 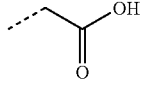 | 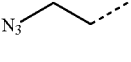 |
| 1267 | 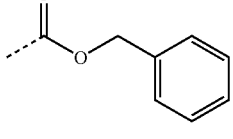 | 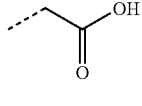 |  |
| 1268 | 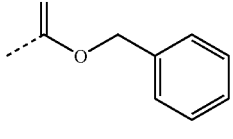 | 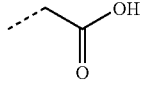 | 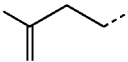 |
| 1269 | 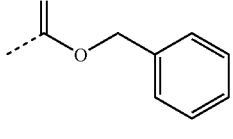 |  | 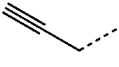 |
| 1270 | 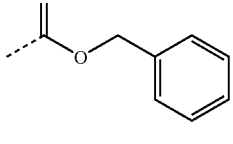 |  |  |

TABLE 10-continued

| Compound | A¹ | A² | E² |
|---|---|---|---|
| 1271 | benzyl ester | SH | H₂N-ethyl |
| 1272 | benzyl ester | SH | CHO-propyl |
| 1273 | benzyl ester | COOH | propynyl |
| 1274 | benzyl ester | COOH | N₃-ethyl |
| 1275 | benzyl ester | COOH | H₂N-ethyl |
| 1276 | benzyl ester | COOH | CHO-propyl |
| 1277 | phenyl | COOH | propynyl |
| 1278 | phenyl | COOH | N₃-ethyl |
| 1279 | phenyl | COOH | H₂N-ethyl |
| 1280 | phenyl | COOH | CHO-propyl |
| 1281 | isobutyl | COOH | propynyl |
| 1282 | isobutyl | COOH | N₃-ethyl |

TABLE 10-continued

| Compound | A¹ | A² | E² |
|---|---|---|---|
| 1283 | isopropyl | -COOH | H₂N-CH₂CH₂- |
| 1284 | isopropyl | -COOH | OHC-CH₂CH₂- |
| 1285 | isopropyl | 4-hydroxyphenyl | HC≡C-CH₂- |
| 1286 | isopropyl | 4-hydroxyphenyl | N₃-CH₂CH₂- |
| 1287 | isopropyl | 4-hydroxyphenyl | H₂N-CH₂CH₂- |
| 1288 | isopropyl | 4-hydroxyphenyl | OHC-CH₂CH₂- |
| 1289 | isopropyl | -CH₂COOH | HC≡C-CH₂- |
| 1290 | isopropyl | -CH₂COOH | N₃-CH₂CH₂- |
| 1291 | isopropyl | -CH₂COOH | H₂N-CH₂CH₂- |
| 1292 | isopropyl | -CH₂COOH | OHC-CH₂CH₂- |
| 1293 | isopropyl | -SH | HC≡C-CH₂- |
| 1294 | isopropyl | -SH | N₃-CH₂CH₂- |
| 1295 | isopropyl | -SH | H₂N-CH₂CH₂- |
| 1296 | isopropyl | -SH | OHC-CH₂CH₂- |

TABLE 10-continued

| Compound | A¹ | A² | E² |
| --- | --- | --- | --- |
| 1297 | benzyl ester | 3,4-dihydroxyphenyl | propargyl |
| 1298 | benzyl ester | 3,4-dihydroxyphenyl | azidoethyl |
| 1299 | benzyl ester | 3,4-dihydroxyphenyl | aminoethyl |
| 1300 | benzyl ester | 3,4-dihydroxyphenyl | oxopropyl |
| 1301 | benzyl ester | aminopropyl | propargyl |
| 1302 | benzyl ester | aminopropyl | azidoethyl |
| 1303 | benzyl ester | aminopropyl | aminoethyl |
| 1304 | benzyl ester | aminopropyl | oxopropyl |
| 1305 | benzyl ester | 1H-imidazol-4-yl | propargyl |
| 1306 | benzyl ester | 1H-imidazol-4-yl | azidoethyl |

TABLE 10-continued
| Compound | A¹ | A² | E² |
|---|---|---|---|
| 1307 | 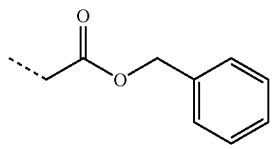 | 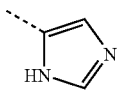 | 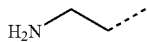 |
| 1308 | 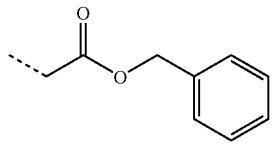 | 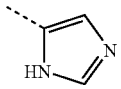 | 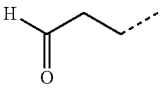 |
| 1309 | 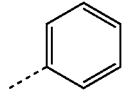 | 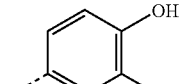 | 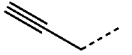 |
| 1310 | 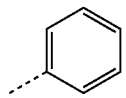 | 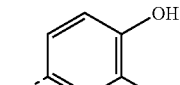 | 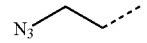 |
| 1311 | 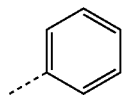 | 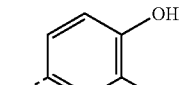 | 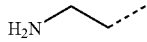 |
| 1312 | 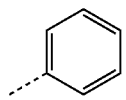 | 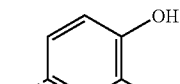 | 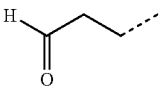 |
| 1313 | 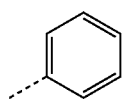 | 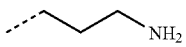 |  |
| 1314 | 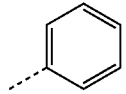 | 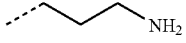 | 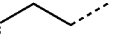 |
| 1315 | 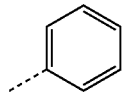 | 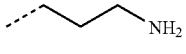 | 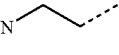 |
| 1316 | 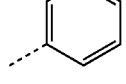 |  | 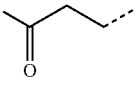 |
| 1317 | 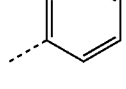 | 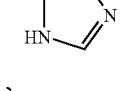 | 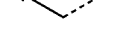 |
| 1318 | 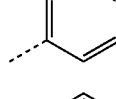 | 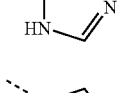 |  |
| 1319 | 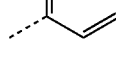 | 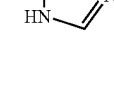 |  |

TABLE 10-continued

| Compound | A¹ | A² | E² |
|---|---|---|---|
| 1320 | phenyl | imidazole | CHO-CH₂- |
| 1321 | benzyl ester | 3,4-dihydroxyphenyl | alkyne |
| 1322 | benzyl ester | 3,4-dihydroxyphenyl | -CH₂CH₂N₃ |
| 1323 | benzyl ester | 3,4-dihydroxyphenyl | -CH₂CH₂NH₂ |
| 1324 | benzyl ester | 3,4-dihydroxyphenyl | -CH₂CH₂CHO |
| 1325 | benzyl ester | -CH₂CH₂CH₂NH₂ | alkyne |
| 1326 | benzyl ester | -CH₂CH₂CH₂NH₂ | -CH₂CH₂N₃ |
| 1327 | benzyl ester | -CH₂CH₂CH₂NH₂ | -CH₂CH₂NH₂ |
| 1328 | benzyl ester | -CH₂CH₂CH₂NH₂ | -CH₂CH₂CHO |
| 1329 | benzyl ester | imidazole | alkyne |

TABLE 10-continued

| Compound | A¹ | A² | E² |
|---|---|---|---|
| 1330 | benzyl ester (–C(O)O–CH₂–C₆H₅) | 1H-imidazol-4-yl | –CH₂CH₂–N₃ |
| 1331 | benzyl ester | 1H-imidazol-4-yl | –CH₂CH₂–NH₂ |
| 1332 | benzyl ester | 1H-imidazol-4-yl | –CH₂CH₂–CHO |
| 1333 | benzyl ester | –CH₂CH₂–NH₂ | –C≡CH |
| 1334 | benzyl ester | –CH₂CH₂–NH₂ | –CH₂CH₂–N₃ |
| 1335 | benzyl ester | –CH₂CH₂–NH₂ | –CH₂CH₂–NH₂ |
| 1336 | benzyl ester | –CH₂CH₂–NH₂ | –CH₂CH₂–CHO |
| 1337 | phenyl | –CH₂CH₂–NH₂ | –C≡CH |
| 1338 | phenyl | –CH₂CH₂–NH₂ | –CH₂CH₂–N₃ |
| 1339 | phenyl | –CH₂CH₂–NH₂ | –CH₂CH₂–NH₂ |
| 1340 | phenyl | –CH₂CH₂–NH₂ | –CH₂CH₂–CHO |

TABLE 10-continued

| Compound | A¹ | A² | E² |
|---|---|---|---|
| 1341 | isopropyl | -CH₂CH₂NH₂ | -C≡CH |
| 1342 | isopropyl | -CH₂CH₂NH₂ | -CH₂CH₂N₃ |
| 1343 | isopropyl | -CH₂CH₂NH₂ | -CH₂CH₂NH₂ |
| 1344 | isopropyl | -CH₂CH₂NH₂ | -CH₂CH₂C(O)H |
| 1345 | isopropyl | 3,4-dihydroxyphenyl | -C≡CH |
| 1346 | isopropyl | 3,4-dihydroxyphenyl | -CH₂CH₂N₃ |
| 1347 | isopropyl | 3,4-dihydroxyphenyl | -CH₂CH₂NH₂ |
| 1348 | isopropyl | 3,4-dihydroxyphenyl | -CH₂CH₂C(O)H |
| 1349 | isopropyl | -CH₂CH₂CH₂NH₂ | -C≡CH |
| 1350 | isopropyl | -CH₂CH₂CH₂NH₂ | -CH₂CH₂N₃ |
| 1351 | isopropyl | -CH₂CH₂CH₂NH₂ | -CH₂CH₂NH₂ |
| 1352 | isopropyl | -CH₂CH₂CH₂NH₂ | -CH₂CH₂C(O)H |
| 1353 | isopropyl | 1H-imidazol-4-yl | -C≡CH |
| 1354 | isopropyl | 1H-imidazol-4-yl | -CH₂CH₂N₃ |
| 1355 | isopropyl | 1H-imidazol-4-yl | -CH₂CH₂NH₂ |

TABLE 10-continued

| Compound | A¹ | A² | E² |
|---|---|---|---|
| 1356 | 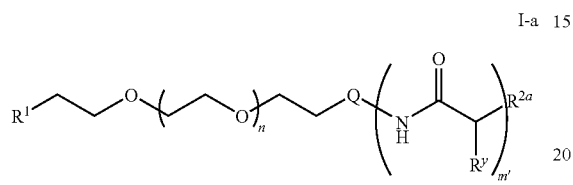 | | |

In certain embodiments, the present invention provides a micelle comprising a multiblock copolymer of formula I, wherein m is 0 thus forming a compound of formula I-a:

I-a $$R^1 \diagup O \diagdown \left( \diagup O \diagdown \right)_n \diagup Q \left( \begin{array}{c} O \\ \| \\ N \\ H \end{array} \diagup \begin{array}{c} R^{2a} \\ R^y \end{array} \right)_{m'}$$

wherein:
n is 10-2500;
m' is 2 to 1000;
$R^y$ forms a hydrophobic D,L-mixed poly(amino acid) block;
$R^1$ is $-Z(CH_2CH_2Y)_p(CH_2)_tR^3$, wherein:
  Z is $-O-$, $-S-$, $-C\equiv C-$, or $-CH_2-$;
  each Y is independently $-O-$ or $-S-$;
  p is 0-10;
  t is 0-10; and
$R^3$ is hydrogen, $-N_3$, $-CN$, a mono-protected amine, a di-protected amine, a protected aldehyde, a protected hydroxyl, a protected carboxylic acid, a protected thiol, a 9-30 membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;
Q is a valence bond or a bivalent, saturated or unsaturated, straight or branched $C_{1-12}$ hydrocarbon chain, wherein 0-6 methylene units of Q are independently replaced by -Cy-, $-O-$, $-NH-$, $-S-$, $-OC(O)-$, $-C(O)O-$, $-C(O)-$, $-SO-$, $-SO_2-$, $-NHSO_2-$, $-SO_2NH-$, $-NHC(O)-$, $-C(O)NH-$, $-OC(O)NH-$, or $-NHC(O)O-$, wherein:
-Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;
$R^{2a}$ is a mono-protected amine, a di-protected amine, $-N(R^4)_2$, $-NR^4C(O)R^4$, $-NR^4C(O)N(R^4)_2$, $-NR^4C(O)OR^4$, or $-NR^4SO_2R^4$; and
each $R^4$ is independently hydrogen or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety, or: two $R^4$ on the same nitrogen atom are taken together with said nitrogen atom to form an optionally substituted 4-7 membered saturated, partially unsaturated, or aryl ring having 1-4 heteroatoms independently selected from nitrogen, oxygen, or sulfur, wherein each of $R^1$, n, m', $R^y$, and $R^{2a}$, is as described herein singly and in combination.

Exemplary compounds of formula I-a include those set forth in Table 11, below, having the formula:

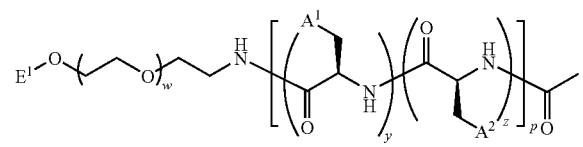

wherein each w is 25-1000, each x is 1-50, each y is 1-50, each z is 1-100, p is the sum of y and z, and each dotted bond represents the point of attachment to the rest of the molecule.

TABLE 11

| Compound | E¹ | A¹ | A² |
|---|---|---|---|
| 1357 | H₃C- | | OH (phenol) |
| 1358 | alkyne | | OH (phenol) |

TABLE 11-continued

| Compound | E¹ | A¹ | A² |
|---|---|---|---|
| 1359 | N₃-CH₂CH₂- | isopropyl | 4-hydroxyphenyl |
| 1360 | OHC-CH₂CH₂- | isopropyl | 4-hydroxyphenyl |
| 1361 | H₂N-CH₂CH₂- | isopropyl | 4-hydroxyphenyl |
| 1362 | H₃C- | isopropyl | 3,4-dihydroxyphenyl |
| 1363 | HC≡C-CH₂- | isopropyl | 3,4-dihydroxyphenyl |
| 1364 | N₃-CH₂CH₂- | isopropyl | 3,4-dihydroxyphenyl |
| 1365 | OHC-CH₂CH₂- | isopropyl | 3,4-dihydroxyphenyl |
| 1366 | H₂N-CH₂CH₂- | isopropyl | 3,4-dihydroxyphenyl |
| 1367 | H₃C- | isopropyl | -COOH |
| 1368 | HC≡C-CH₂- | isopropyl | -COOH |
| 1369 | N₃-CH₂CH₂- | isopropyl | -COOH |
| 1370 | OHC-CH₂CH₂- | isopropyl | -COOH |
| 1371 | H₂N-CH₂CH₂- | isopropyl | -COOH |
| 1372 | H₃C- | isopropyl | -CH₂COOH |

TABLE 11-continued

| Compound | E¹ | A¹ | A² |
|---|---|---|---|
| 1373 | HC≡C-CH₂- | -CH(CH₃)₂ | -CH₂-COOH |
| 1374 | N₃-CH₂-CH₂- | -CH(CH₃)₂ | -CH₂-COOH |
| 1375 | OHC-CH₂-CH₂- | -CH(CH₃)₂ | -CH₂-COOH |
| 1376 | H₂N-CH₂-CH₂- | -CH(CH₃)₂ | -CH₂-COOH |
| 1377 | H₃C- | -CH(CH₃)₂ | -SH |
| 1378 | HC≡C-CH₂- | -CH(CH₃)₂ | -SH |
| 1379 | N₃-CH₂-CH₂- | -CH(CH₃)₂ | -SH |
| 1380 | OHC-CH₂-CH₂- | -CH(CH₃)₂ | -SH |
| 1381 | H₂N-CH₂-CH₂- | -CH(CH₃)₂ | -SH |
| 1382 | H₃C- | -CH(CH₃)₂ | -CH₂-NH₂ |
| 1383 | HC≡C-CH₂- | -CH(CH₃)₂ | -CH₂-NH₂ |
| 1384 | N₃-CH₂-CH₂- | -CH(CH₃)₂ | -CH₂-NH₂ |
| 1385 | OHC-CH₂-CH₂- | -CH(CH₃)₂ | -CH₂-NH₂ |
| 1386 | H₂N-CH₂-CH₂- | -CH(CH₃)₂ | -CH₂-NH₂ |
| 1387 | H₃C- | -CH(CH₃)₂ | -CH₂-CH₂-NH₂ |
| 1388 | HC≡C-CH₂- | -CH(CH₃)₂ | -CH₂-CH₂-NH₂ |
| 1389 | N₃-CH₂-CH₂- | -CH(CH₃)₂ | -CH₂-CH₂-NH₂ |

TABLE 11-continued
| Compound | E¹ | A¹ | A² |
|---|---|---|---|
| 1390 | 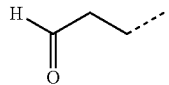 | 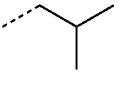 | 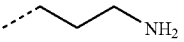 |
| 1391 | 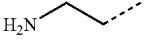 | 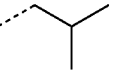 | 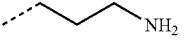 |
| 1392 |  | 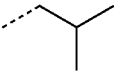 |  |
| 1393 | 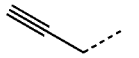 | 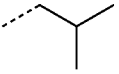 |  |
| 1394 | 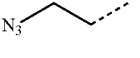 |  |  |
| 1395 | 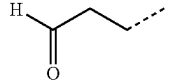 | 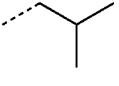 |  |
| 1396 | 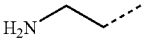 | 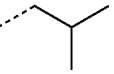 |  |
| 1397 |  |  |  |
| 1398 |  | 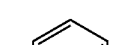 | 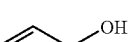 |
| 1399 | 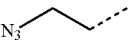 | 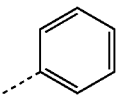 | 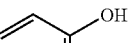 |
| 1400 | 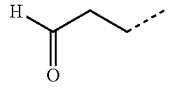 | 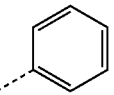 | 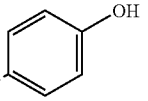 |
| 1401 | 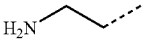 | 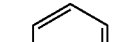 | 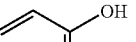 |
| 1402 |  | 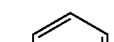 | 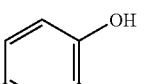 |
| 1403 | 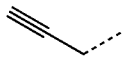 | 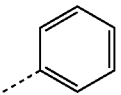 | 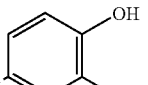 |

TABLE 11-continued

| Compound | E¹ | A¹ | A² |
|---|---|---|---|
| 1404 | N₃-CH₂CH₂- | phenyl | 3,4-dihydroxyphenyl |
| 1405 | OHC-CH₂CH₂- | phenyl | 3,4-dihydroxyphenyl |
| 1406 | H₂N-CH₂CH₂- | phenyl | 3,4-dihydroxyphenyl |
| 1407 | H₃C- | phenyl | -C(=O)OH |
| 1408 | HC≡C-CH₂- | phenyl | -C(=O)OH |
| 1409 | N₃-CH₂CH₂- | phenyl | -C(=O)OH |
| 1410 | OHC-CH₂CH₂- | phenyl | -C(=O)OH |
| 1411 | H₂N-CH₂CH₂- | phenyl | -C(=O)OH |
| 1412 | H₃C- | phenyl | -CH₂C(=O)OH |
| 1413 | HC≡C-CH₂- | phenyl | -CH₂C(=O)OH |
| 1414 | N₃-CH₂CH₂- | phenyl | -CH₂C(=O)OH |
| 1415 | OHC-CH₂CH₂- | phenyl | -CH₂C(=O)OH |
| 1416 | H₂N-CH₂CH₂- | phenyl | -CH₂C(=O)OH |
| 1417 | H₃C- | phenyl | -SH |

TABLE 11-continued
| Compound | E¹ | A¹ | A² |
|---|---|---|---|
| 1418 | 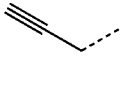 | 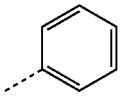 | 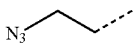 SH |
| 1419 | 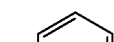 N₃ | 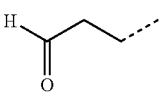 | SH |
| 1420 | 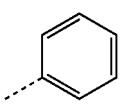 | 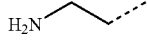 | SH |
| 1421 | H₂N 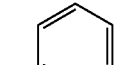 |  | SH |
| 1422 | H₃C 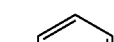 | 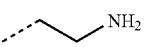 |  NH₂ |
| 1423 | 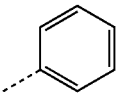 | 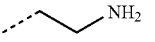 | 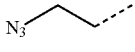 NH₂ |
| 1424 | N₃  | 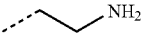 | 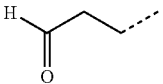 NH₂ |
| 1425 | 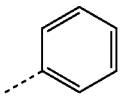 | 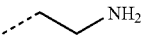 | 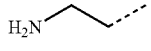 NH₂ |
| 1426 | H₂N 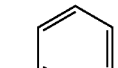 | 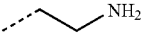 |  NH₂ |
| 1427 | H₃C 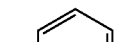 | 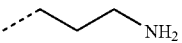 | 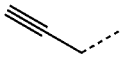 NH₂ |
| 1428 | 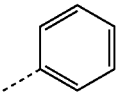 | 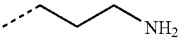 |  NH₂ |
| 1429 | N₃ 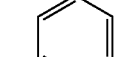 | 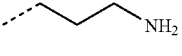 | 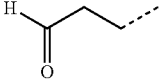 NH₂ |
| 1430 | 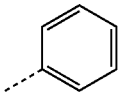 | 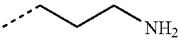 | 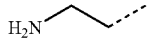 NH₂ |
| 1431 | H₂N 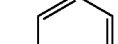 |  | NH₂ |

TABLE 11-continued
| Compound | E¹ | A¹ | A² |
|---|---|---|---|
| 1432 | 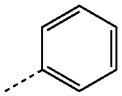 | 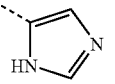 | 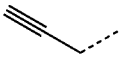 |
| 1433 | 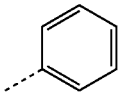 | 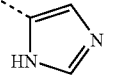 | 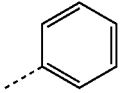 |
| 1434 | 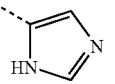 | 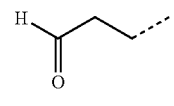 | 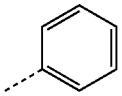 |
| 1435 | 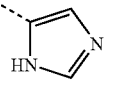 | 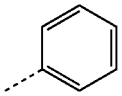 | 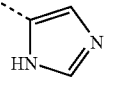 |
| 1436 | 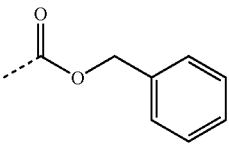 | 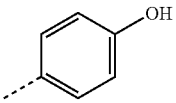 | 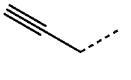 |
| 1437 | 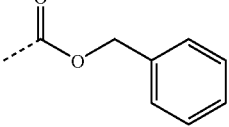 | 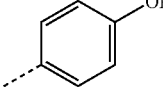 | 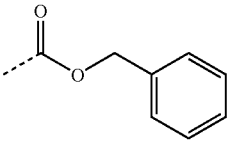 |
| 1438 | 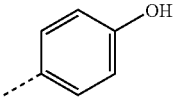 | 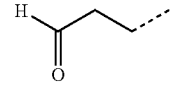 | 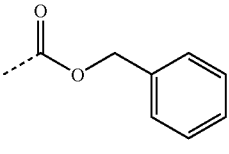 |
| 1439 | 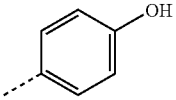 | 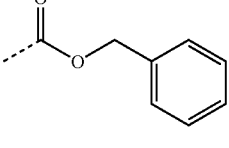 | 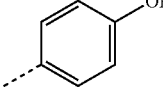 |
| 1440 | 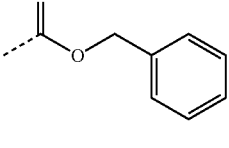 | 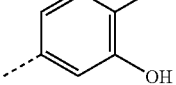 | |
| 1441 | | | |
| 1442 | | | |

TABLE 11-continued

| Compound | E¹ | A¹ | A² |
|---|---|---|---|
| 1443 | ethynyl-CH₂- | benzyl ester | 3,4-dihydroxyphenyl |
| 1444 | N₃-CH₂CH₂- | benzyl ester | 3,4-dihydroxyphenyl |
| 1445 | OHC-CH₂CH₂- | benzyl ester | 3,4-dihydroxyphenyl |
| 1446 | H₂N-CH₂CH₂- | benzyl ester | 3,4-dihydroxyphenyl |
| 1447 | H₃C- | benzyl ester | -COOH |
| 1448 | ethynyl-CH₂- | benzyl ester | -COOH |
| 1449 | N₃-CH₂CH₂- | benzyl ester | -COOH |
| 1450 | OHC-CH₂CH₂- | benzyl ester | -COOH |
| 1451 | H₂N-CH₂CH₂- | benzyl ester | -COOH |
| 1452 | H₃C- | benzyl ester | -CH₂COOH |

TABLE 11-continued

| Compound | E¹ | A¹ | A² |
| --- | --- | --- | --- |
| 1453 | HC≡C-CH₂- | -C(O)O-CH₂-C₆H₅ | -CH₂-C(O)OH |
| 1454 | N₃-CH₂-CH₂- | -C(O)O-CH₂-C₆H₅ | -CH₂-C(O)OH |
| 1455 | OHC-CH₂-CH₂- | -C(O)O-CH₂-C₆H₅ | -CH₂-C(O)OH |
| 1456 | H₂N-CH₂-CH₂- | -C(O)O-CH₂-C₆H₅ | -CH₂-C(O)OH |
| 1457 | H₃C- | -C(O)O-CH₂-C₆H₅ | -SH |
| 1458 | HC≡C-CH₂- | -C(O)O-CH₂-C₆H₅ | -SH |
| 1459 | N₃-CH₂-CH₂- | -C(O)O-CH₂-C₆H₅ | -SH |
| 1460 | OHC-CH₂-CH₂- | -C(O)O-CH₂-C₆H₅ | -SH |
| 1461 | H₂N-CH₂-CH₂- | -C(O)O-CH₂-C₆H₅ | -SH |
| 1462 | H₃C- | -C(O)O-CH₂-C₆H₅ | -CH₂-CH₂-NH₂ |

TABLE 11-continued
| Compound | E¹ | A¹ | A² |
|---|---|---|---|
| 1463 | 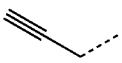 | 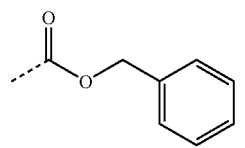 | 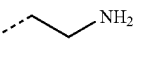 |
| 1464 | 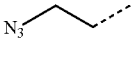 | 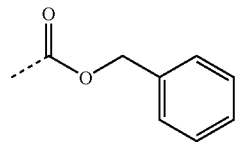 | 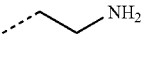 |
| 1465 | 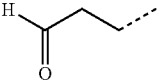 | 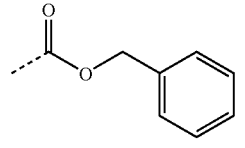 | 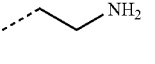 |
| 1466 | 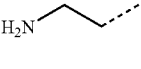 | 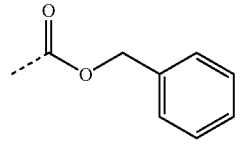 | 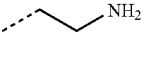 |
| 1467 | 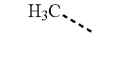 | 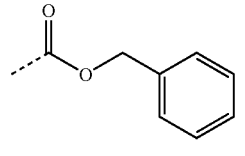 | 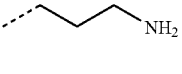 |
| 1468 | 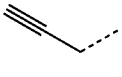 | 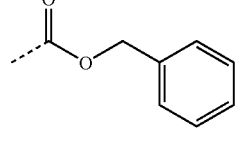 | 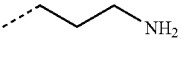 |
| 1469 | 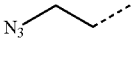 | 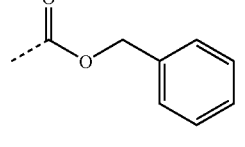 | 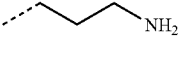 |
| 1470 | 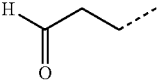 | 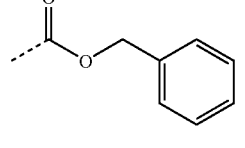 | 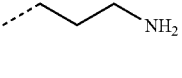 |
| 1471 | 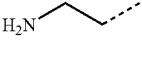 | 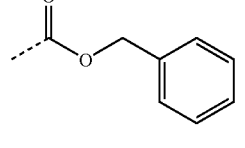 | 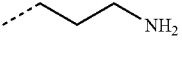 |
| 1472 | 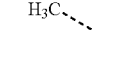 | 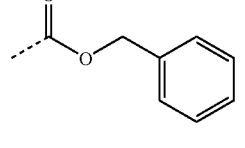 | 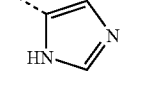 |

TABLE 11-continued

| Compound | E¹ | A¹ | A² |
|---|---|---|---|
| 1473 | alkyne (HC≡C-CH₂-) | benzyl ester (-C(O)O-CH₂-C₆H₅) | 1H-imidazol-4-yl |
| 1474 | 2-azidoethyl (N₃-CH₂-CH₂-) | benzyl ester | 1H-imidazol-4-yl |
| 1475 | 3-oxopropyl (OHC-CH₂-CH₂-) | benzyl ester | 1H-imidazol-4-yl |
| 1476 | 2-aminoethyl (H₂N-CH₂-CH₂-) | benzyl ester | 1H-imidazol-4-yl |
| 1477 | methyl (H₃C-) | benzyl ester (-CH₂-C(O)O-CH₂-C₆H₅) | 4-hydroxyphenyl |
| 1478 | alkyne | benzyl ester | 4-hydroxyphenyl |
| 1479 | 2-azidoethyl | benzyl ester | 4-hydroxyphenyl |
| 1480 | 3-oxopropyl | benzyl ester | 4-hydroxyphenyl |
| 1481 | 2-aminoethyl | benzyl ester | 4-hydroxyphenyl |
| 1482 | methyl | benzyl ester | 3,4-dihydroxyphenyl |

TABLE 11-continued

| Compound | E¹ | A¹ | A² |
|---|---|---|---|
| 1483 | alkyne (HC≡C-CH₂-) | benzyl ester (-CH₂-C(=O)-O-CH₂-C₆H₅) | 3,4-dihydroxyphenyl |
| 1484 | N₃-CH₂-CH₂- | benzyl ester | 3,4-dihydroxyphenyl |
| 1485 | OHC-CH₂-CH₂- | benzyl ester | 3,4-dihydroxyphenyl |
| 1486 | H₂N-CH₂-CH₂- | benzyl ester | 3,4-dihydroxyphenyl |
| 1487 | H₃C- | benzyl ester | -CH₂-COOH |
| 1488 | HC≡C-CH₂- | benzyl ester | -CH₂-COOH |
| 1489 | N₃-CH₂-CH₂- | benzyl ester | -CH₂-COOH |
| 1490 | OHC-CH₂-CH₂- | benzyl ester | -CH₂-COOH |
| 1491 | H₂N-CH₂-CH₂- | benzyl ester | -CH₂-COOH |
| 1492 | H₃C- | benzyl ester | -CH₂-COOH |

TABLE 11-continued

| Compound | E¹ | A¹ | A² |
| --- | --- | --- | --- |
| 1493 | HC≡C-CH₂- | -CH₂-C(=O)-O-CH₂-C₆H₅ | -CH₂-C(=O)-OH |
| 1494 | N₃-CH₂-CH₂- | -CH₂-C(=O)-O-CH₂-C₆H₅ | -CH₂-C(=O)-OH |
| 1495 | H(C=O)-CH₂-CH₂- | -CH₂-C(=O)-O-CH₂-C₆H₅ | -CH₂-C(=O)-OH |
| 1496 | H₂N-CH₂-CH₂- | -CH₂-C(=O)-O-CH₂-C₆H₅ | -CH₂-C(=O)-OH |
| 1497 | H₃C- | -CH₂-C(=O)-O-CH₂-C₆H₅ | -SH |
| 1498 | HC≡C-CH₂- | -CH₂-C(=O)-O-CH₂-C₆H₅ | -SH |
| 1499 | N₃-CH₂-CH₂- | -CH₂-C(=O)-O-CH₂-C₆H₅ | -SH |
| 1500 | H(C=O)-CH₂-CH₂- | -CH₂-C(=O)-O-CH₂-C₆H₅ | -SH |
| 1501 | H₂N-CH₂-CH₂- | -CH₂-C(=O)-O-CH₂-C₆H₅ | -SH |
| 1502 | H₃C- | -CH₂-C(=O)-O-CH₂-C₆H₅ | -CH₂-CH₂-NH₂ |

TABLE 11-continued
| Compound | E¹ | A¹ | A² |
|---|---|---|---|
| 1503 | 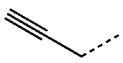 | 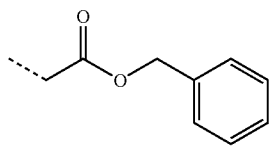 | 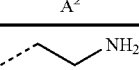 |
| 1504 | 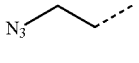 | 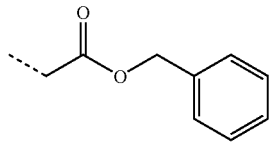 | 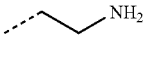 |
| 1505 | 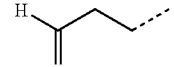 | 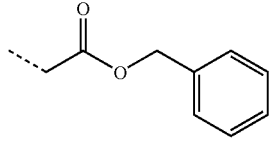 | 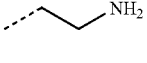 |
| 1506 | 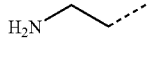 | 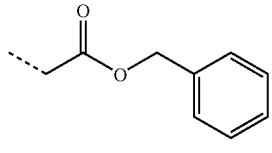 | 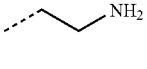 |
| 1507 |  | 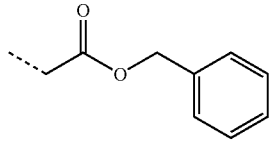 | 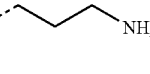 |
| 1508 | 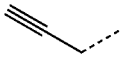 | 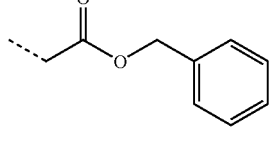 | 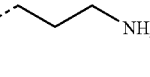 |
| 1509 | 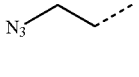 | 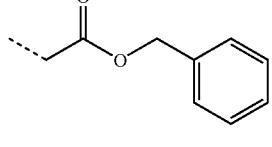 | 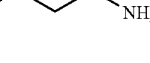 |
| 1510 | 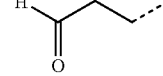 | 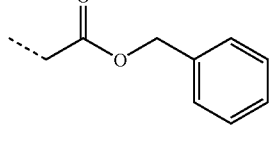 | 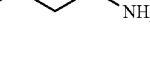 |
| 1511 | 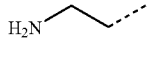 | 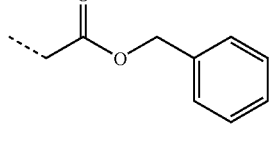 | 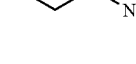 |
| 1512 |  | 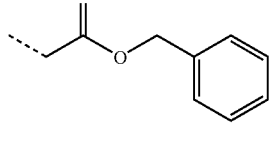 | 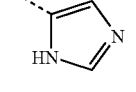 |

TABLE 11-continued

| Compound | E¹ | A¹ | A² |
|---|---|---|---|
| 1513 | alkyne | benzyl ester | imidazole |
| 1514 | azidoethyl | benzyl ester | imidazole |
| 1515 | oxopropyl (aldehyde) | benzyl ester | imidazole |
| 1516 | aminoethyl | benzyl ester | imidazole |

In certain embodiments, the present invention provides a micelle having a contrast agent encapsulated therein, wherein the micelle comprises a multiblock copolymer selected from:

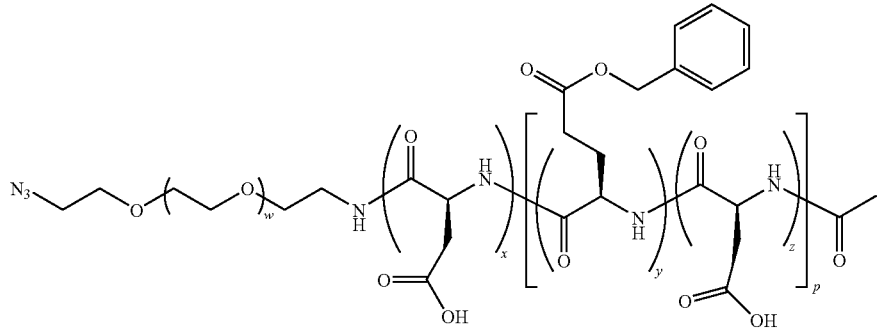

I-1

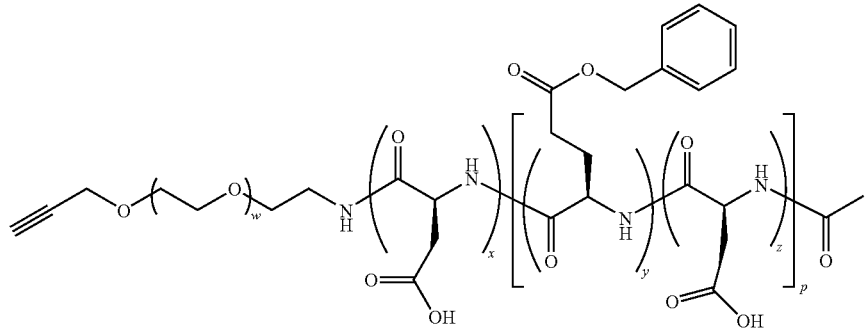

I-2

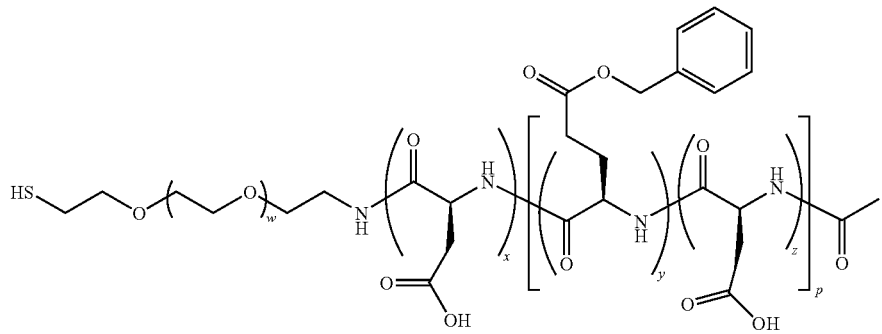
I-3
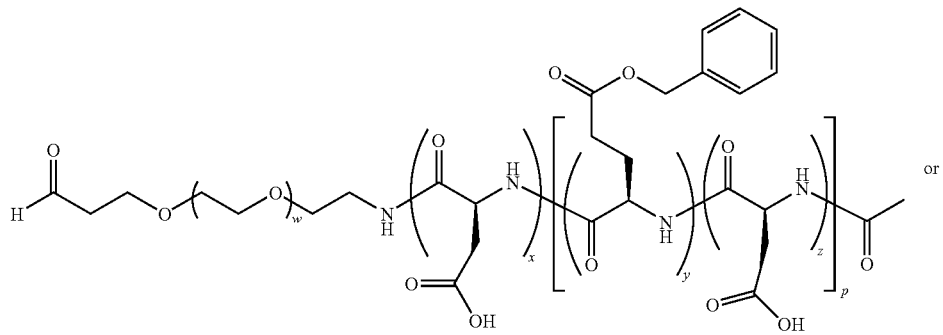
I-4
or
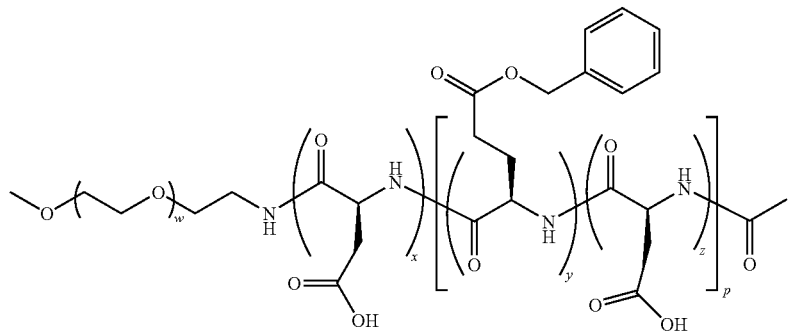
I-5
wherein each w is 25-1000, each x is 1-50, each y is 1-50, each z is 1-100, and p is the sum of y and z.
In certain embodiments, the present invention provides a micelle having a contrast agent encapsulated therein, wherein the micelle comprises a multiblock copolymer selected from:
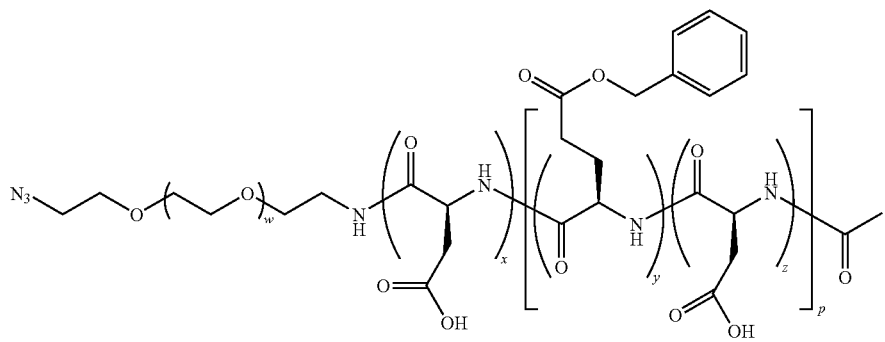
I-6

I-7
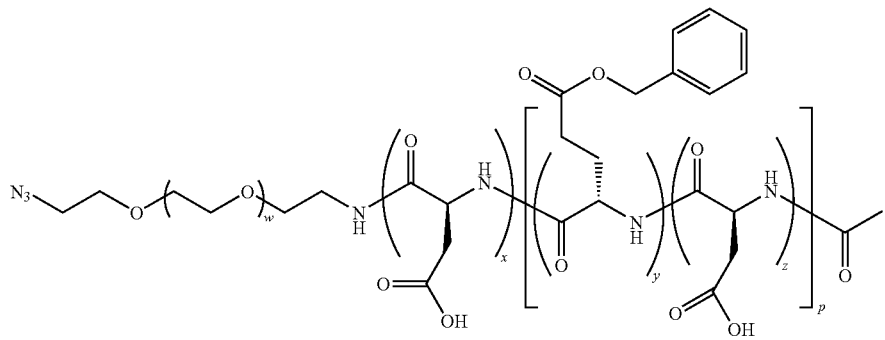
I-8
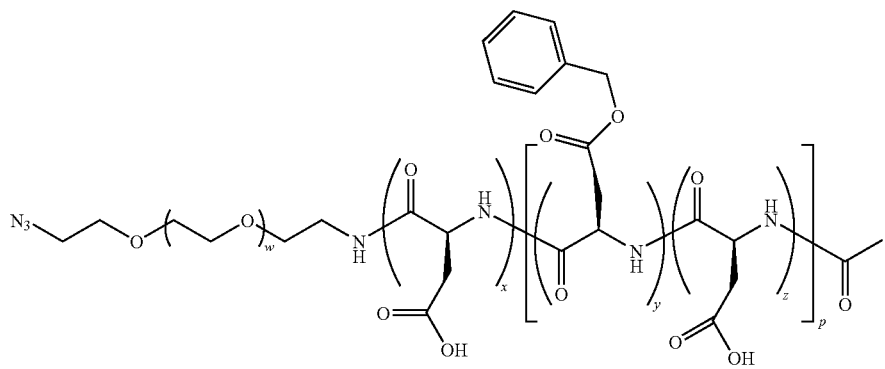
I-9
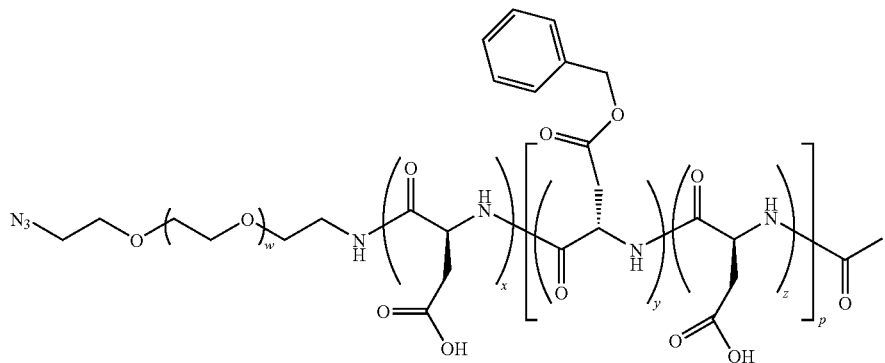
I-10
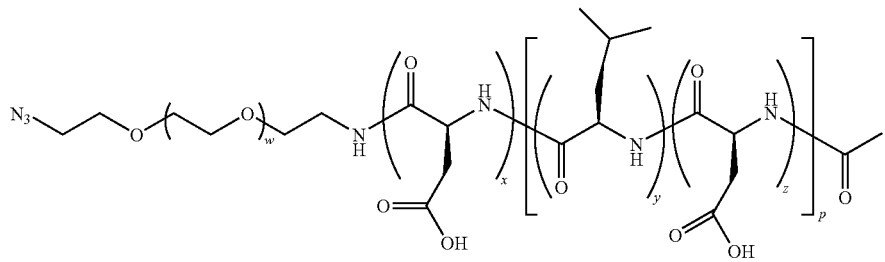
I-11
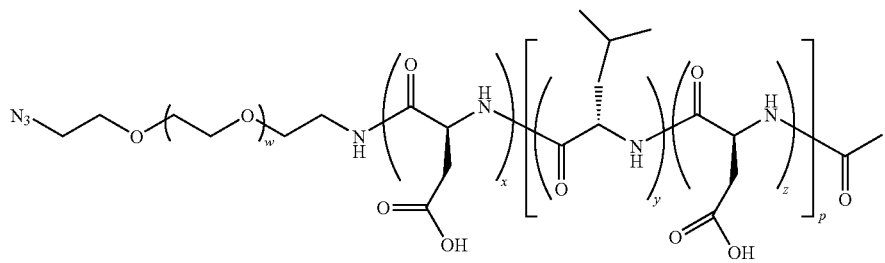

I-12
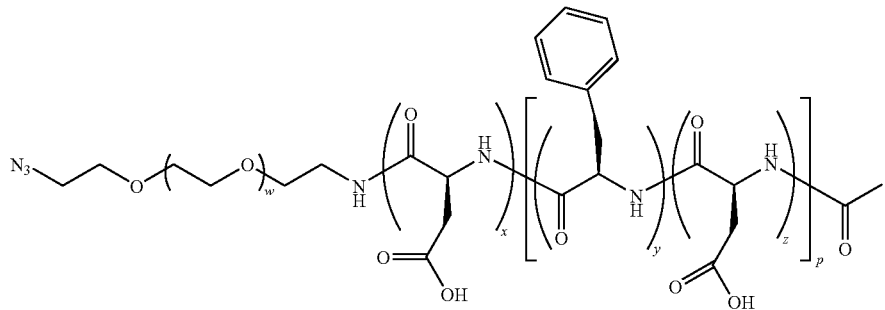
I-13
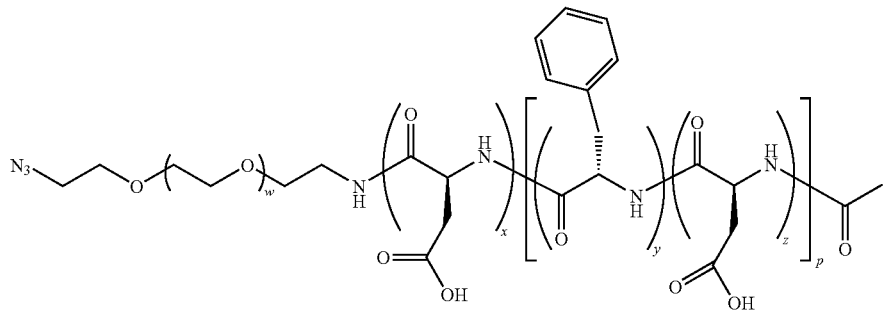
wherein each w is 150-350, x is 3-20, y is 3-50, z is 3-50, and p is y+z.
In some embodiments, the present invention provides a micelle having a contrast agent encapsulated therein, wherein the micelle comprises a multiblock copolymer selected from:
I-14
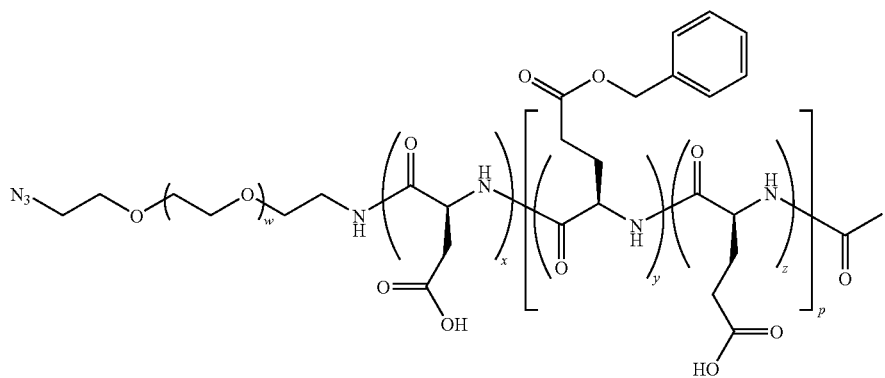
I-15
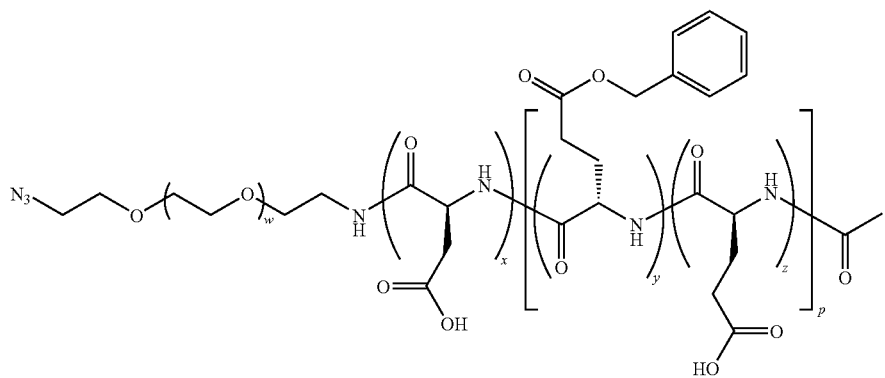

I-16
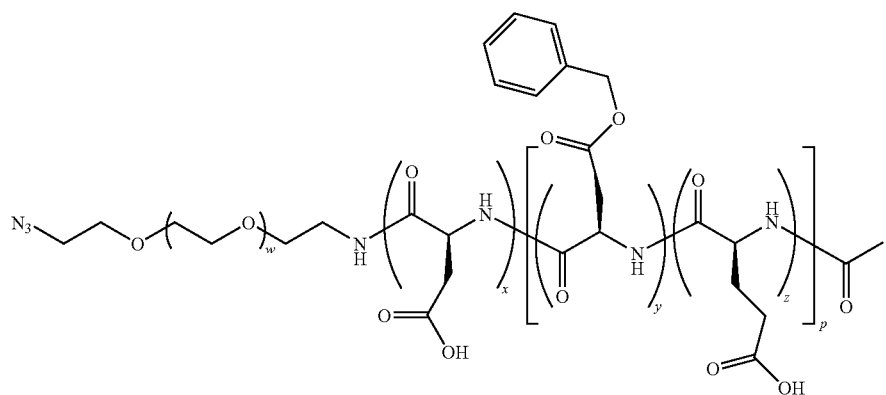
I-17
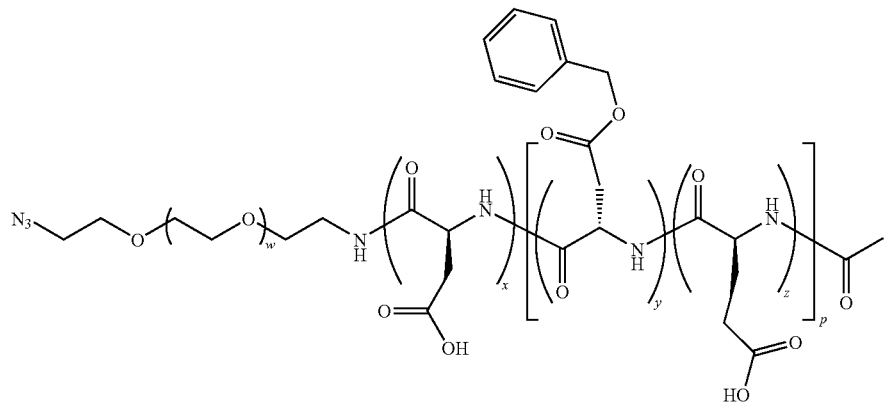
I-18
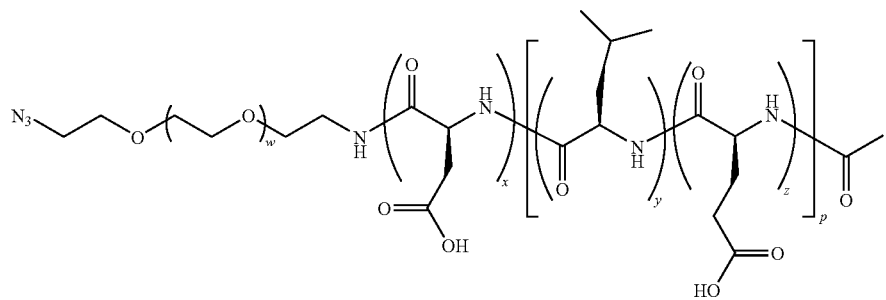
I-19
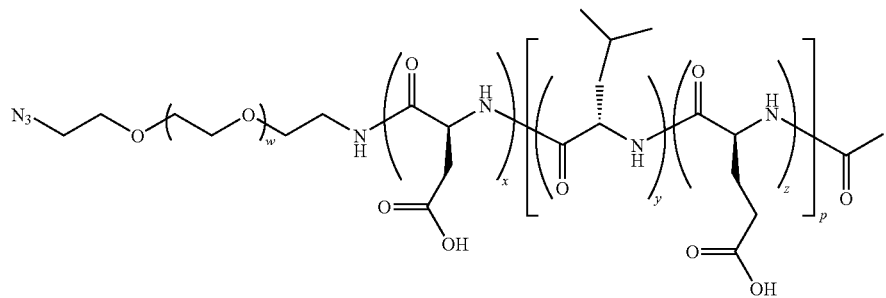

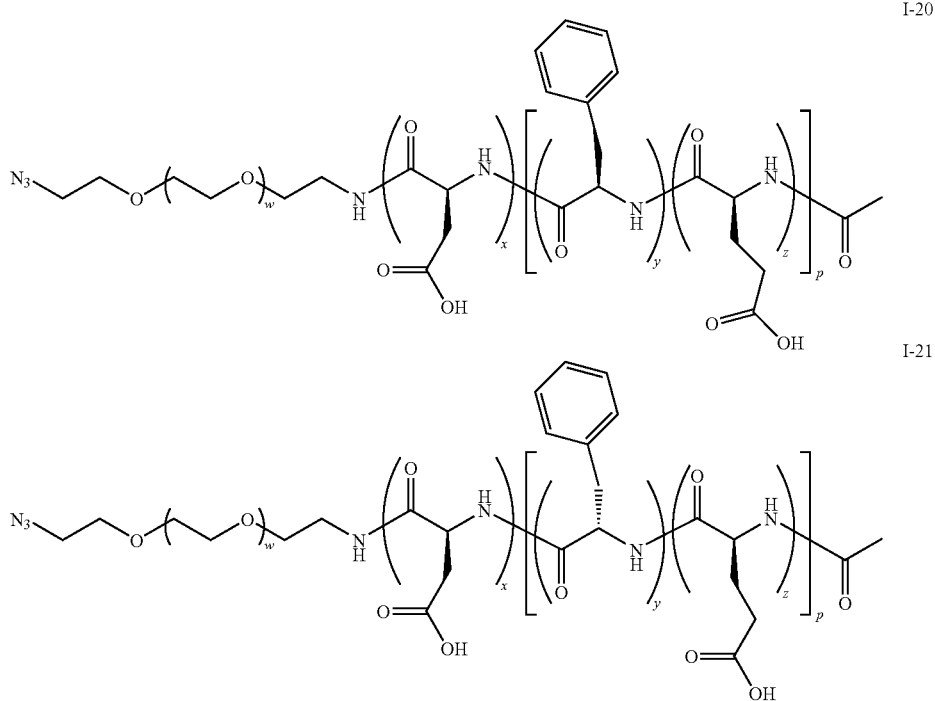
wherein each of w is 150-350, x is 3-20, y is 3-50, z is 3-50, and p is y+z.
In certain embodiments, the present invention provides a micelle having a contrast agent encapsulated therein, wherein the micelle comprises a multiblock copolymer selected from:
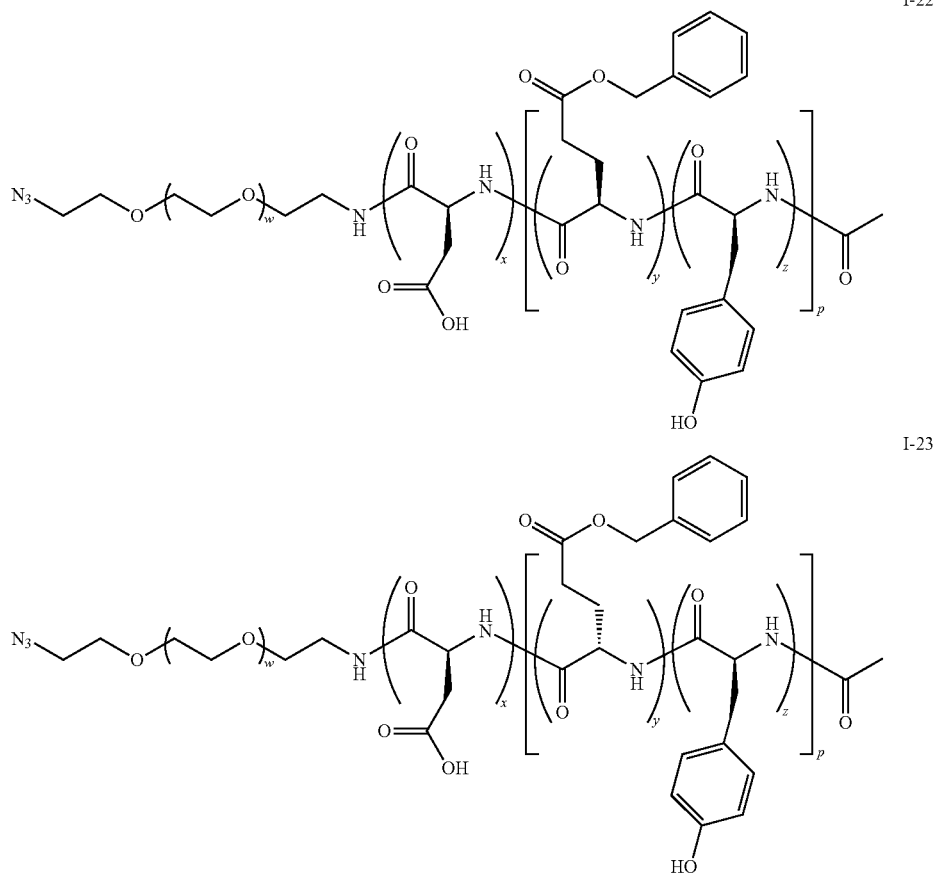

I-14
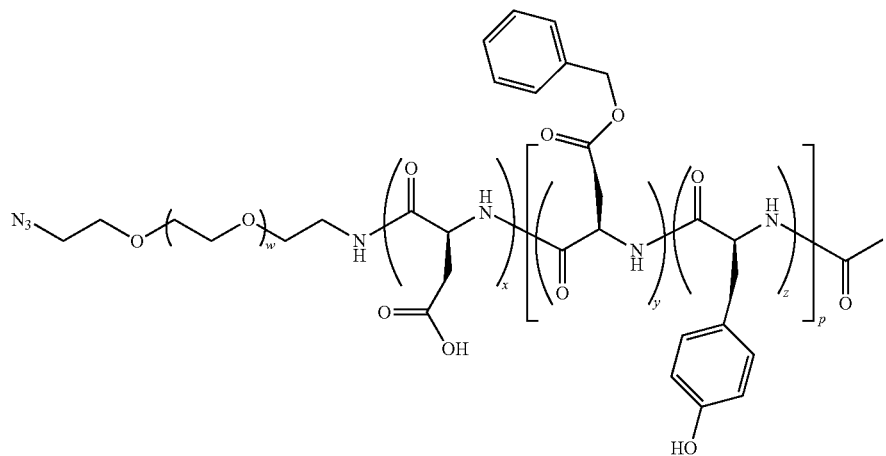
I-25
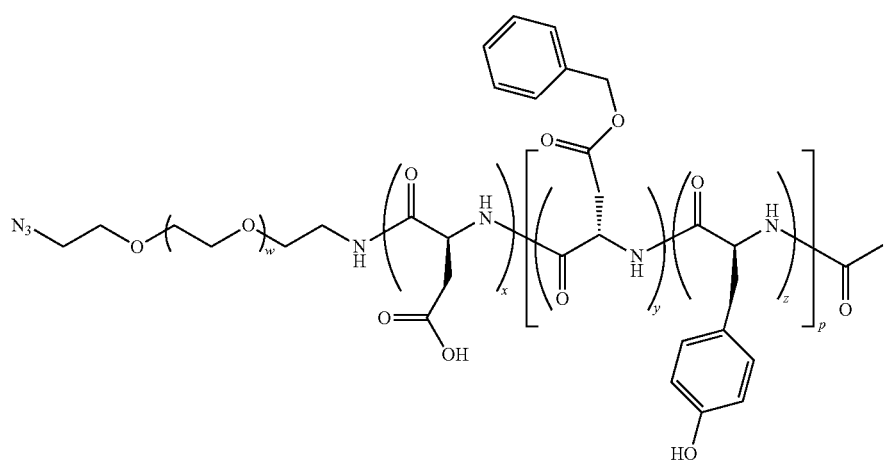
I-26
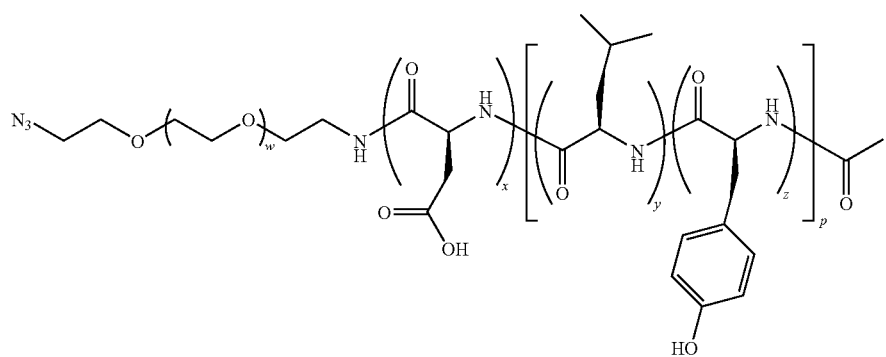
I-27
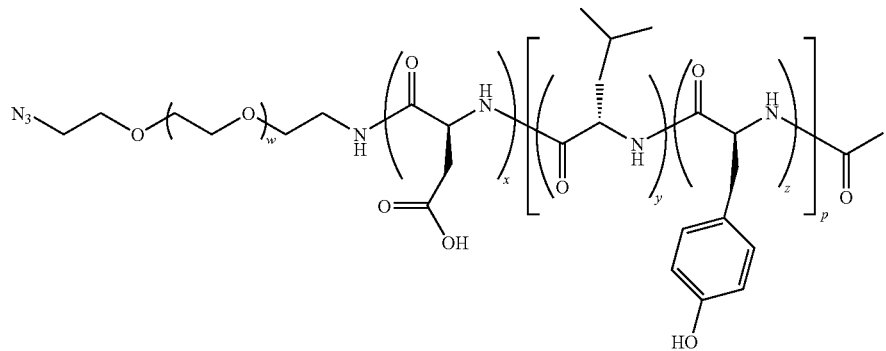

-continued
I-28
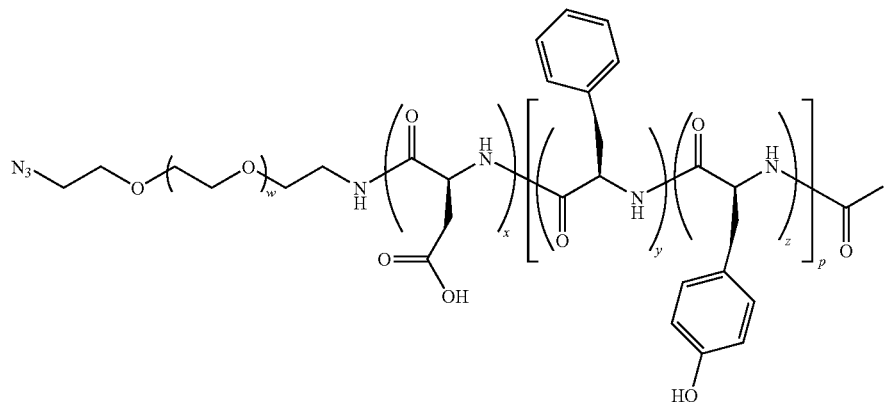
I-29
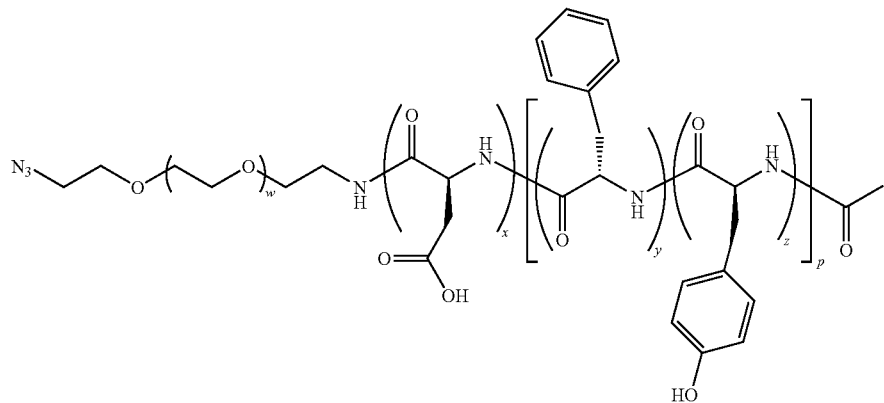
wherein each of w is 150-350, x is 3-20, y is 3-50, z is 3-50, and p is y+z.
In certain embodiments, the present invention provides a micelle having a contrast agent encapsulated therein, wherein the micelle comprises a multiblock copolymer selected from:
I-30
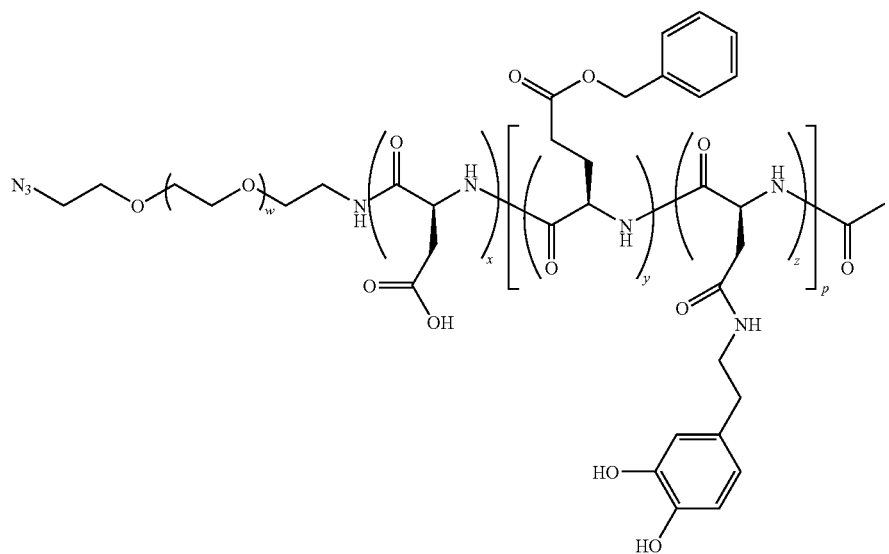

I-31
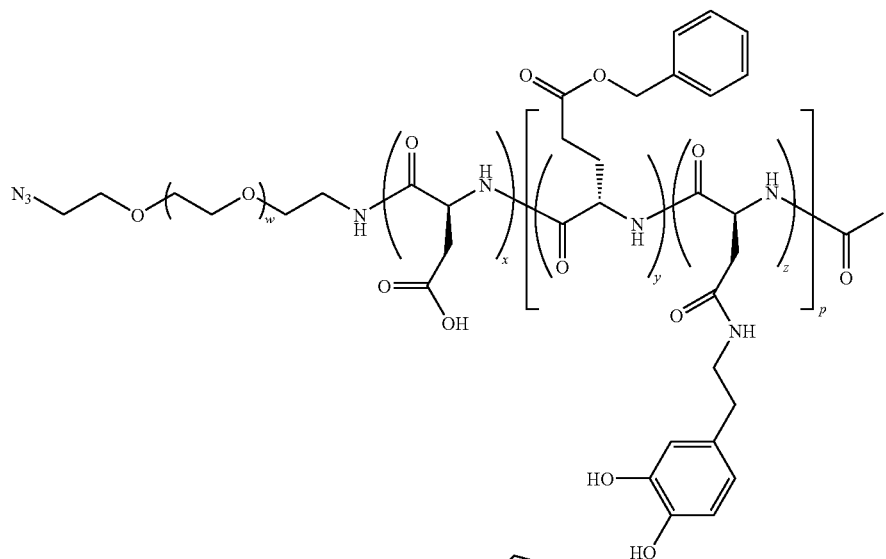
I-32
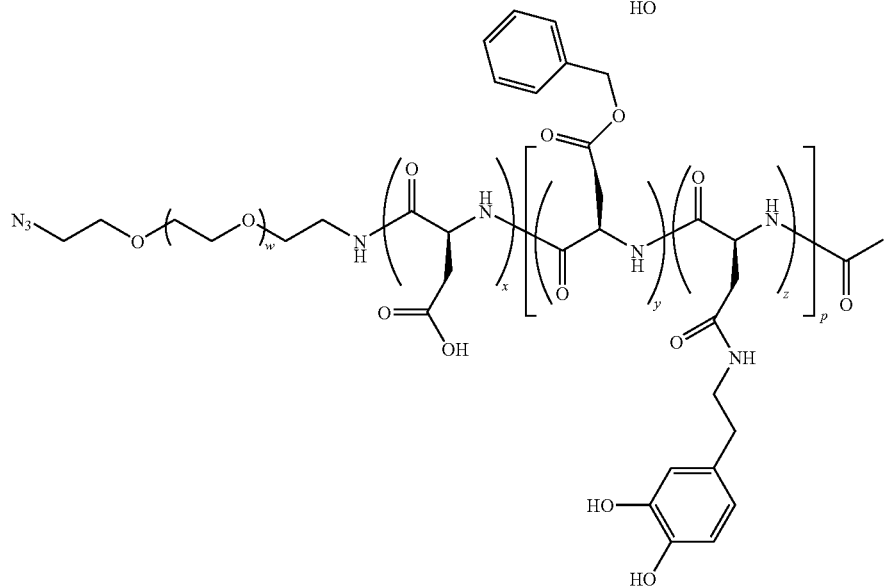
I-33
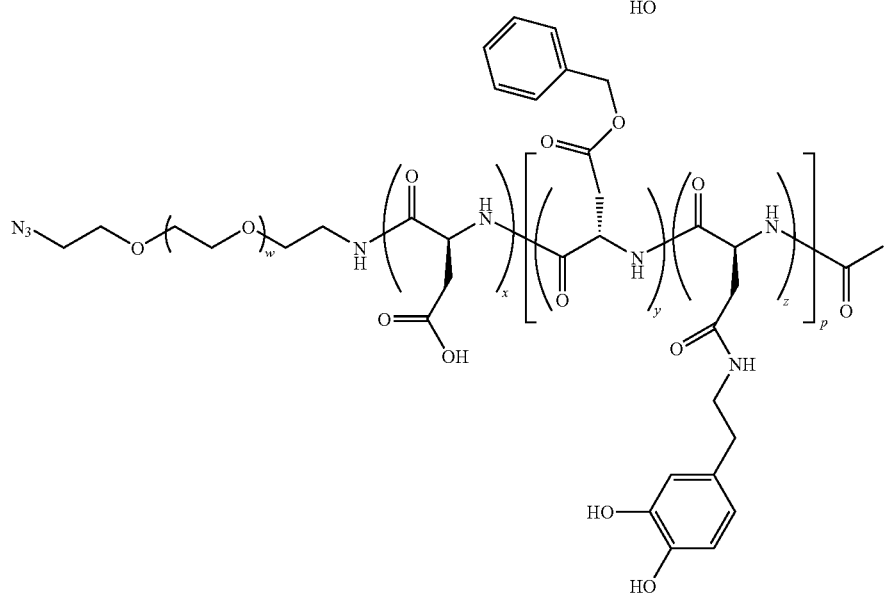

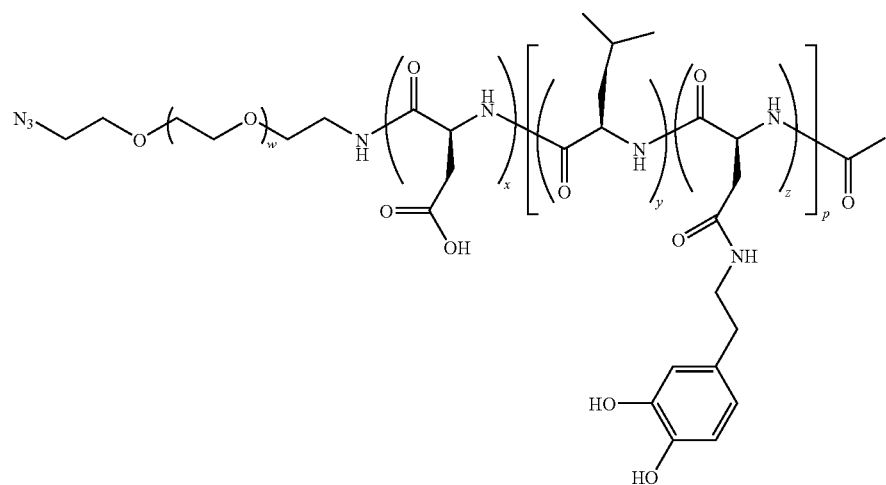
I-34
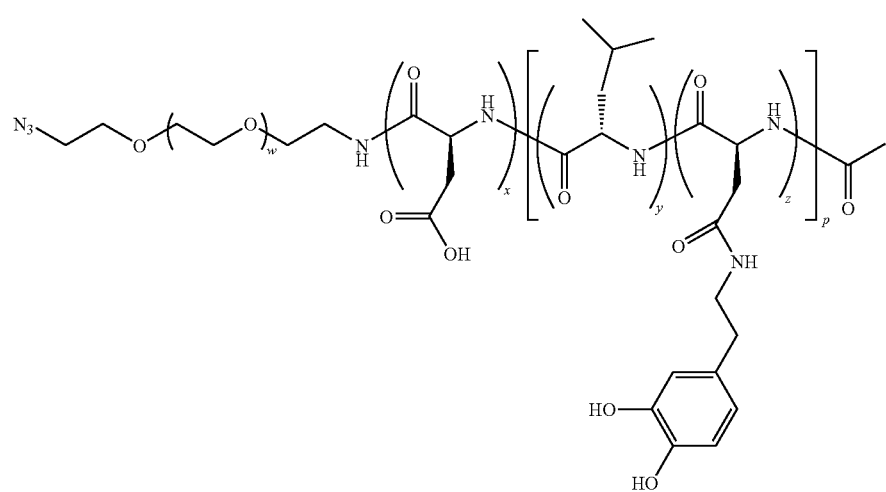
I-35
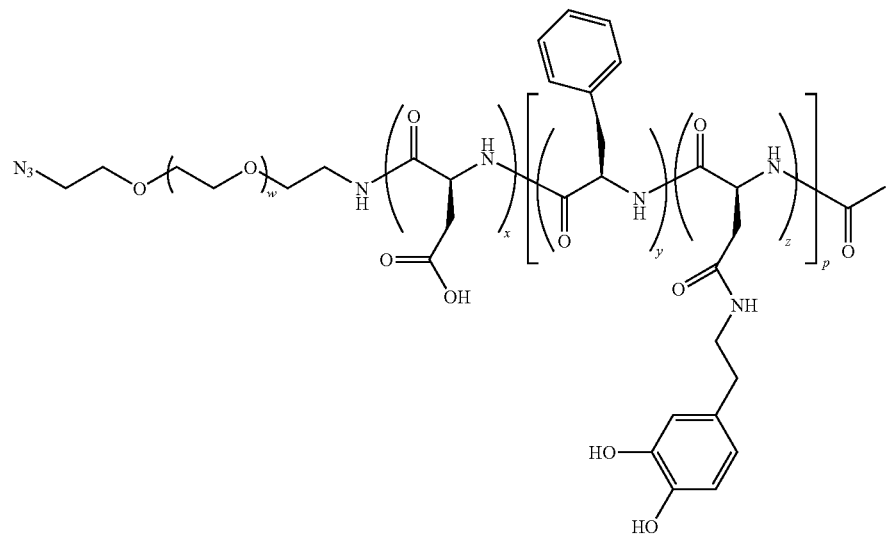
I-36

I-37

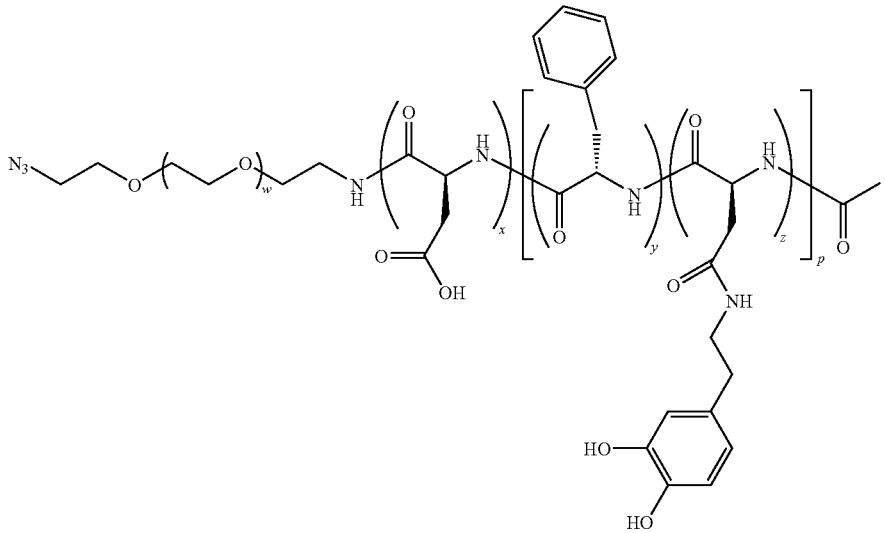

wherein each of w is 150-350, x is 3-20, y is 3-50, z is 3-50, and p is y+z.

B. Crosslinking Chemistries

As described generally above, in certain embodiments, micelles of the present invention, having a contrast agent encapsulated therein, comprise a crosslinkable or crosslinked "outer core." The crosslinking of poly(amino acid) groups is known in the art and includes methods described in detail in WO2006/107903.

In certain embodiments, micelles of the present invention, having a contrast agent encapsulated therein, comprise a crosslinked multiblock polymer of formula III:

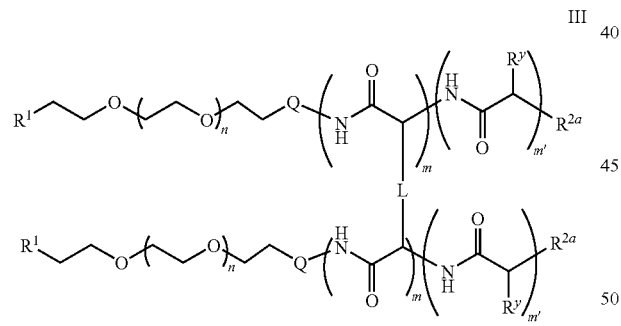

III wherein:
n is 10-2500;
m is 1 to 1000;
m' is 1 to 1000;
L is a bivalent, saturated or unsaturated, straight or branched $C_{1-12}$ hydrocarbon chain, wherein 0-6 methylene units of L are independently replaced by -M-, -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:
-M- is a suitable bivalent metal;
-Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;

$R^y$ is a hydrophobic or ionic, natural or unnatural amino acid side-chain group;

$R^1$ is -Z(CH$_2$CH$_2$Y)$_p$(CH$_2$)$_t$R$^3$, wherein:
Z is —O—, —S—, —C≡C—, or —CH$_2$—;
each Y is independently —O— or —S—;
p is 0-10;
t is 0-10; and $R^3$ is hydrogen, —N$_3$, —CN, a mono-protected amine, a di-protected amine, a protected aldehyde, a protected hydroxyl, a protected carboxylic acid, a protected thiol, a 9-30 membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;

Q is a valence bond or a bivalent, saturated or unsaturated, straight or branched $C_{1-12}$ hydrocarbon chain, wherein 0-6 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:
-Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;

$R^{2a}$ is a mono-protected amine, a di-protected amine, —N(R$^4$)$_2$, —NR$^4$C(O)R$^4$, —NR$^4$C(O)N(R$^4$)$_2$, —NR$^4$C(O)OR$^4$, or —NR$^4$SO$_2$R$^4$; and each $R^4$ is independently an optionally substituted group selected from hydrogen, aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety, or:

two $R^4$ on the same nitrogen atom are taken together with said nitrogen atom to form an optionally substituted 4-7 membered saturated, partially unsaturated, or aryl ring having 1-4 heteroatoms independently selected from nitrogen, oxygen, or sulfur.

Embodiments for each of $R^1$, Q, n, m, m', $R^x$, $R^y$, and $R^{2a}$ for compounds of formula III are as described herein for compounds of formula I, singly and in combination.

According to another embodiment, the present invention provides compounds of formula III, as described above, wherein said compounds have a PDI of about 1.0 to about 1.2. According to another embodiment, the present invention provides compounds of formula III, as described above, wherein said compound has a PDI of about 1.03 to about 1.15. According to yet another embodiment, the present invention provides compounds of formula I, as described above, wherein said compound has a PDI of about 1.10 to about 1.20. According to other embodiments, the present invention provides compounds of formula III having a PDI of less than about 1.10.

As defined generally above, the L group of formula III is a bivalent, saturated or unsaturated, straight or branched $C_{1-12}$ alkylene chain, wherein 0-6 methylene units of L are independently replaced by -M-, Cy, —O—, NH—, —S—, —C(O)—, —SO—, —SO$_2$—, NHC(O)—, C(O)NH—, OC(O)NH—, or —NHC(O)O—, wherein -M- is a suitable bivalent metal, and -Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur. It will be appreciated that the L group of formula III represents crosslinked amino acid side-chain groups. In certain embodiments, the crosslinked amino acid side-chain groups correspond to the $R^x$ moiety of compounds of formulae I and II as described herein. In certain embodiments, the L group of formula III represents a metal crosslinked amino acid side-chain group, a hydrazone crosslinked amino acid side-chain group, an ester crosslinked amino acid side-chain group, an amide crosslinked side-chain group, an imine (e.g. Schiff base) crosslinked side-chain group, or a disulfide crosslinked side-chain group.

In certain embodiments, the L group of formula III comprises -M-. In other embodiments, -M- is zinc, calcium, iron or aluminum. In yet other embodiments, -M- is strontium, manganese, palladium, silver, gold, cadmium, chromium, indium, or lead.

In other embodiments, the L group of formula III is a bivalent, saturated or unsaturated, straight or branched $C_{1-12}$ alkylene chain wherein 2 methylene units of L are independently replaced by —C(O)—, —C(O)NH—, —NHC(O)—, —S—, —C(O)O—, —OC(O)—, —C(O)NHN—, =NNHC(O), =N, N=, -M-OC(O)—, or —C(O)O-M-. According to another embodiment, the L group of formula III is a bivalent, saturated or unsaturated, straight or branched $C_{1-6}$ alkylene chain, wherein two methylene units of L are replaced by —C(O)— or —C(O)NH—. In other embodiments, the L group of formula III is a bivalent, saturated or unsaturated, straight or branched $C_{1-12}$ alkylene chain having at least 2 units of unsaturation. According to yet another embodiment, the L group of formula III is a bivalent, saturated or unsaturated, straight or branched $C_{1-12}$ alkylene chain wherein two methylene units of L are replaced by —NH—. According to yet another embodiment, the L group of formula III is a bivalent, saturated or unsaturated, straight or branched $C_{1-12}$ alkylene chain wherein two methylene units of L are replaced by —C(O)NHN.

In certain embodiments, the -M- moiety of the L group of formula III is zinc. In other embodiments, L forms a zinc-dicarboxylate crosslinking moiety. In certain embodiments, the crosslinking utilizes zinc-mediated coupling of carboxylic acids, a highly selective and pH-sensitive reaction that is performed in water. This reaction, which is widely used in cough lozenge applications, involves the association of zinc ions with carboxylic acids at basic pH. See Bakar, N. K. A.; Taylor, D. M.; Williams, D. R. *Chem. Spec. Bioavail.* 1999, 11, 95-101; and Eby, G. A. *J. Antimicrob. Chemo.* 1997, 40, 483-493. These zinc-carboxylate bonds readily dissociate in the presence of acid.

Scheme 1

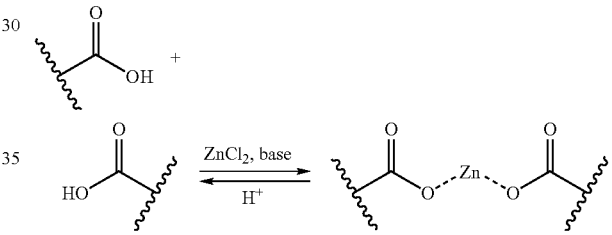

Scheme 1 above illustrates the reaction of an aqueous zinc ion (e.g. from zinc chloride) with two equivalents of an appropriate carboxylic acid to form the zinc dicarboxylate. This reaction occurs rapidly and irreversibly in a slightly basic pH environment but upon acidification, is reversible within a tunable range of pH 4.0-6.8 to reform $ZnX_2$, where X is the conjugate base. One of ordinary skill in the art will recognize that a variety of natural and unnatural amino acid side-chains have a carboxylic acid moiety that can be crosslinked by zinc or another suitable metal.

In certain embodiments, L represents aspartic acid side-chains crosslinked with zinc. Without wishing to be bound by theory, it is believed that the zinc aspartate crosslinks are stable in the blood compartment (pH 7.4), allowing for effective accumulation of the loaded micelles in solid tumors by passive and active targeting mechanisms. In the presence of lactic acid concentrations commonly encountered in solid tumors or in acidic organelles of cancer cells, rapid degradation of the metal crosslinks leading to micelle dissociation and release of the contrast agent at the tumor site. Preliminary, qualitative studies have shown that crosslinked zinc aspartate segments are reversible in the presence of α-hydroxyacids.

In certain embodiments, the -M- moiety of the L group of formula III is zinc. In some embodiments, L forms a zinc-imidazole crosslinking moiety. In certain embodiments, the crosslinking utilizes zinc-mediated coupling of imidazoles.

Scheme 2

Zn(II) +

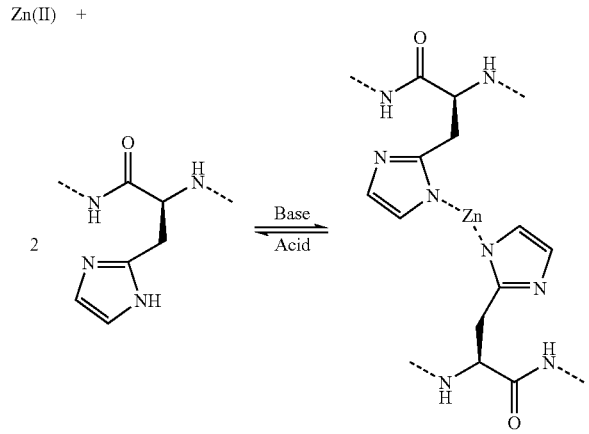

Scheme 2, above, illustrates the reaction of an aqueous zinc (II) ion (e.g. from zinc chloride or zinc acetate) with two equivalents of an appropriate imidazole (e.g. histidine) to form a zinc-histidine complex. This reaction occurs rapidly in a slightly basic pH environment and is reversible upon acidification to pH less than 6. (Tezcan, et. al. J. Am. Chem. Soc. 2007, 129, 13347-13375.)

In certain embodiments, $R^x$ is a histidine side-chain crosslinked with zinc. Without wishing to be bound by any particular theory, it is believed that zinc-histidine crosslinks are stable in the blood compartment (pH 7.4), allowing for effective accumulation of therapeutic loaded micelles in solid tumors by passive and/or active targeting mechanisms. In the presence of lactic acid concentrations commonly encountered in solid tumors or hydrochloric acid in acidic organelles of cancer cells, rapid degradation of the metal crosslinks occurs which leads to micelle dissociation and release of the polynucleotide at the tumor site.

Scheme 3

Zn(II) +

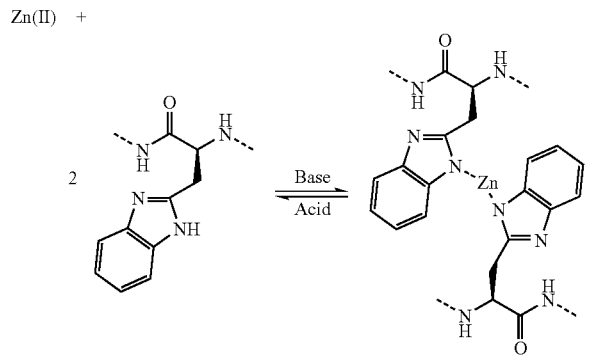

Scheme 3 above illustrates the reaction of an aqueous zinc (II) ion (e.g. from zinc chloride or zinc acetate) with two equivalents of an appropriate imidazole (e.g. benzimidazole) to form a zinc-benzimidazole complex.

In certain embodiments, $R^x$ is a benzimidazole side-chain crosslinked with zinc. Without wishing to be bound by any particular theory, it is believed that zinc-benzimidazole crosslinks are stable in the blood compartment (pH 7.4), allowing for effective accumulation of therapeutic loaded micelles in solid tumors by passive and/or active targeting mechanisms. In the presence of lactic acid concentrations commonly encountered in solid tumors or hydrochloric acid in acidic organelles of cancer cells, rapid degradation of the metal crosslinks occurs which leads to micelle dissociation and release of the polynucleotide at the tumor site.

The choice of zinc as a crosslinking metal is advantageous for effective micelle crosslinking. Zinc chloride and the zinc lactate by-product are generally recognized as non-toxic, and other safety concerns are not anticipated. Pharmaceutical grade zinc chloride is commonly used in mouthwash and as a chlorophyll stabilizer in vegetables while zinc lactate is used as an additive in toothpaste and drug preparation. The reaction is reversible within a tunable pH range, selective toward carboxylic acids, and should not alter the encapsulated chemotherapy agents. While zinc has been chosen as an exemplary metal for micelle crosslinking, it should be noted that many other metals undergo acid sensitive coupling with carboxylic acids. These metals include calcium, iron and aluminum, to name but a few. One or more of these metals can be substituted for zinc.

The ultimate goal of metal-mediated crosslinking is to ensure micelle stability when diluted in the blood (pH 7.4) followed by rapid dissolution and contrast agent release in response to a finite pH change such as those found in cancer cells. Previous reports suggest a widely variable and tunable dissociation pH for zinc-acid bonds (from approximately 2.0 to 7.0) depending on the carboxylic acid used and number of bonds formed. See Cannan, R. K.; Kibrick, A. *J. Am. Chem. Soc.* 1938, 60, 2314-2320. Without wishing to be bound by theory, it is believed that the concentration of zinc chloride and the number of aspartic acid, or other carboxylic acid-containing amino acid, repeat units in the crosslinking block will ultimately control the pH at which complete micelle disassembly occurs. The synthetic versatility of the block copolymer design is advantageous since one or more variables are tuned to achieve the desired pH reversibility. By simple adjustment of zinc chloride/polymer stoichiometry, pH-reversible crosslinking is finely tuned across the pH range of interest. For example, higher zinc concentrations yield more zinc crosslinks which require higher acid concentrations (i.e. lower pH) to dissociate. Adjustments in zinc/polymer stoichiometry will yield the desired pH reversibility, however other variables such as increasing the poly(aspartic acid) block length (i.e. 15-25 repeat units) further tune the reversible crosslinking reaction if necessary.

In other embodiments, L comprises a mixture of crosslinked hydrophilic amino acid side-chain groups. Such mixtures of amino acid side-chain groups include those having a carboxylic acid functionality, a hydroxyl functionality, a thiol functionality, and/or amine functionality. It will be appreciated that when L comprises a mixture of crosslinked hydrophilic amino acid side-chain functionalities, then multiple crosslinking can occur. For example, when L comprises a carboxylic acid-containing side-chain (e.g., aspartic acid or glutamic acid) and a thiol-containing side-chain (e.g., cysteine), then the amino acid block can have both zinc crosslinking and cysteine crosslinking (dithiol). This sort of mixed crosslinked block is advantageous for the delivery of contrast agent to the cytosol of diseased cells because a second stimuli must be present to allow for drug release. For example, micelles possessing both carboxylic acid-zinc crosslinking and cysteine dithiol crosslinking would be required to enter an acidic environment (e.g. a tumor) and enter an environment with a high concentration of glutathione (e.g. in the cell cytoplasm). When L comprises an amine-containing side-chain (e.g., lysine or arginine) and a thiol-containing side-chain (e.g., cysteine), then the amino acid block can have both imine (e.g. Schiff base) crosslinking and cysteine crosslinking (dithiol). The zinc and ester crosslinked carboxylic acid functionality and the imine (e.g. Schiff base) crosslinked amine functionality are reversible in acidic organelles (i.e. endosomes, lysosome) while disulfides are reduced in the cytosol by glutathione or other reducing agents resulting in contrast agent release exclusively in the cytoplasm.

Exemplary $R^1$ groups of any of formulae I, II, and III are set forth in Table 12, below.

TABLE 12

Representative $R^1$ Groups

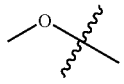
a

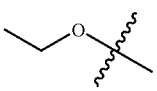
b

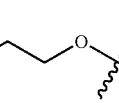
c

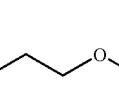
d

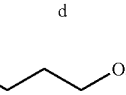
e

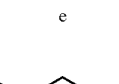
f

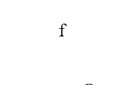
g

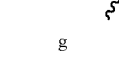
h

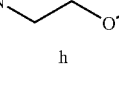
i

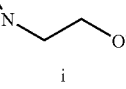
j

TABLE 12-continued

Representative $R^1$ Groups

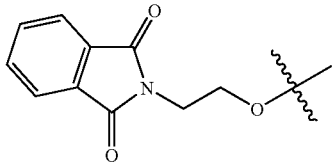
k

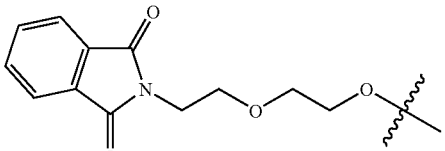
l

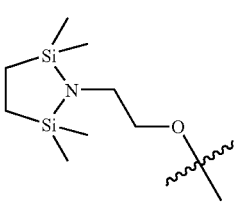
m

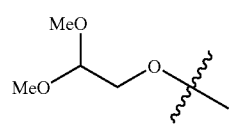
n

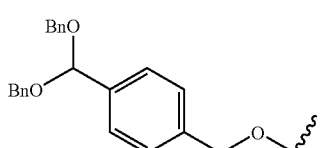
o

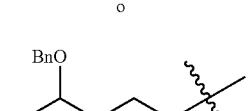
p

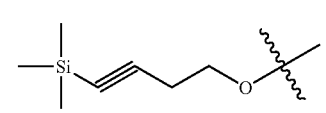
q

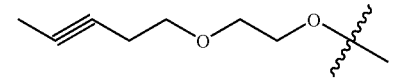
r

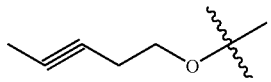
s

TABLE 12-continued
Representative R¹ Groups
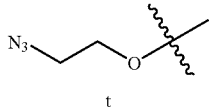
t
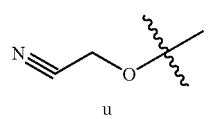
u
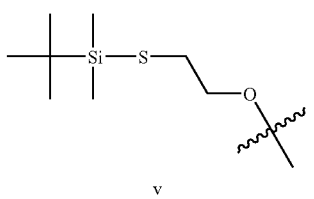
v
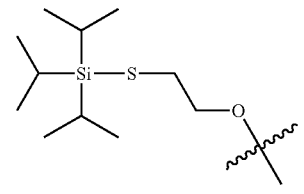
w
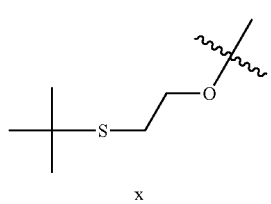
x
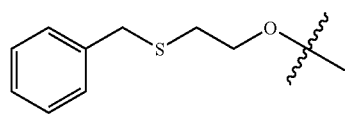
y
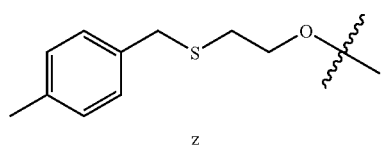
z
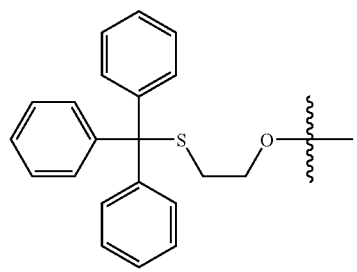
aa
TABLE 12-continued
Representative R¹ Groups
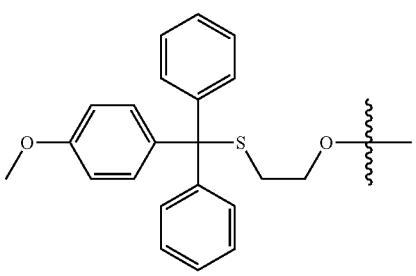
bb
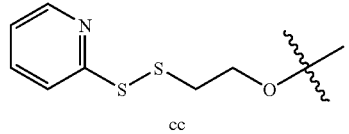
cc
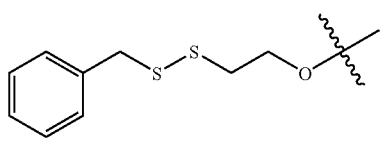
dd
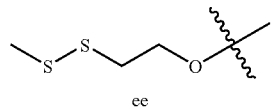
ee
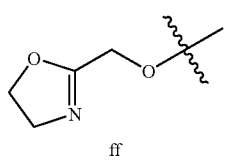
ff
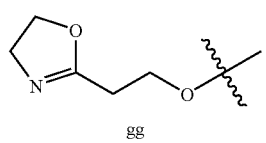
gg
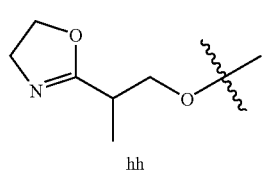
hh
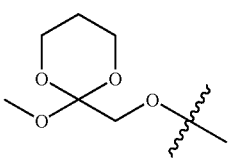
ii TABLE 12-continued
Representative R¹ Groups
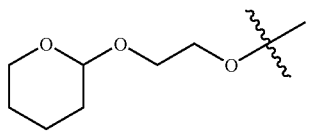
jj
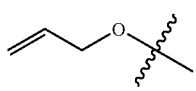
kk
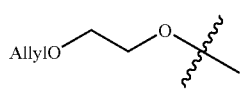
ll
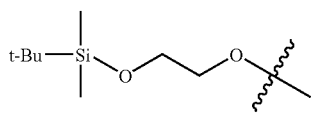
mm
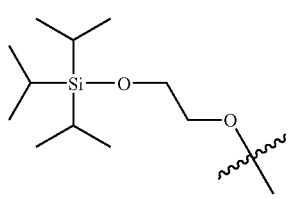
nn
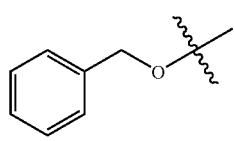
oo
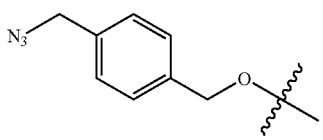
pp
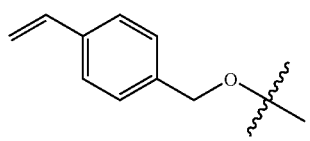
qq
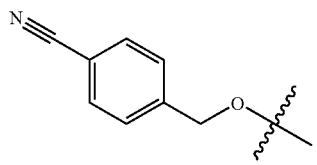
rr
TABLE 12-continued
Representative R¹ Groups
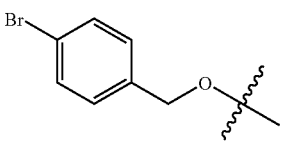
ss
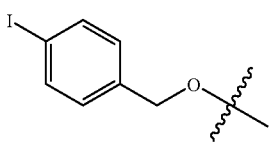
tt
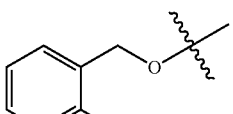
uu
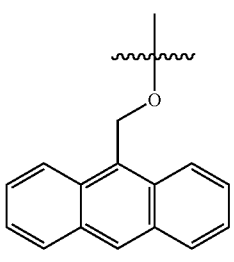
vv
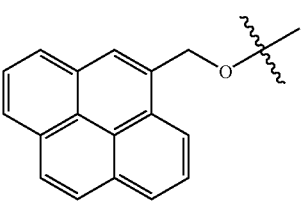
ww
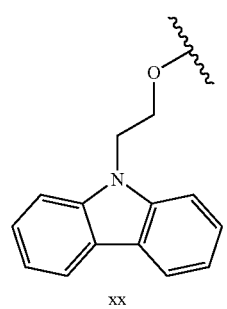
xx
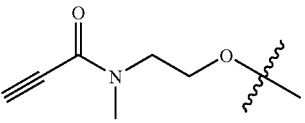
yy TABLE 12-continued
Representative R[1] Groups
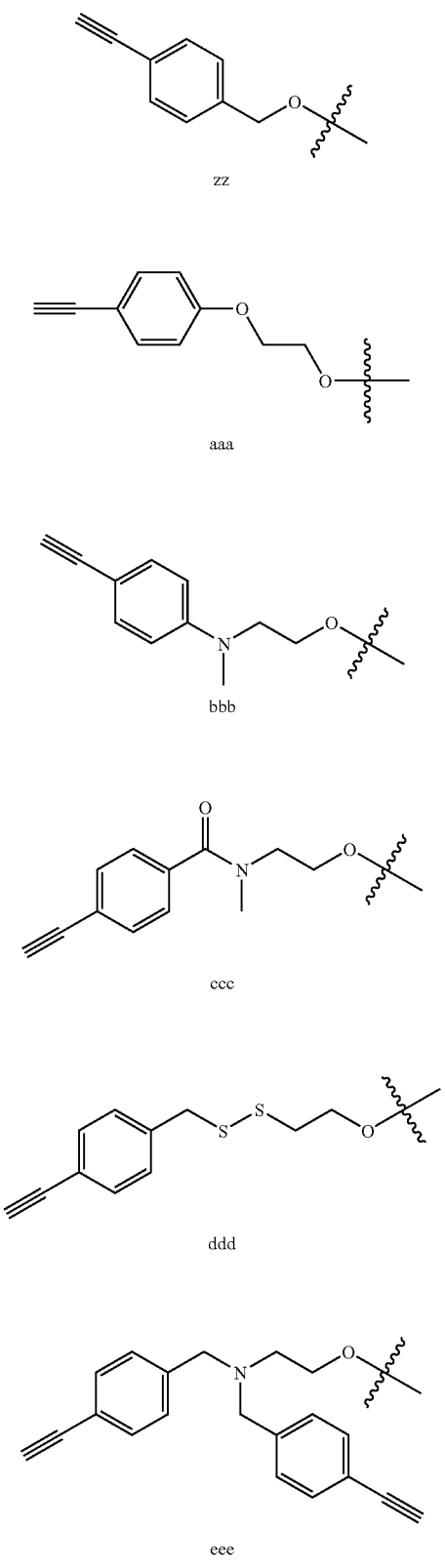
zz
aaa
bbb
ccc
ddd
eee
TABLE 12-continued
Representative R[1] Groups
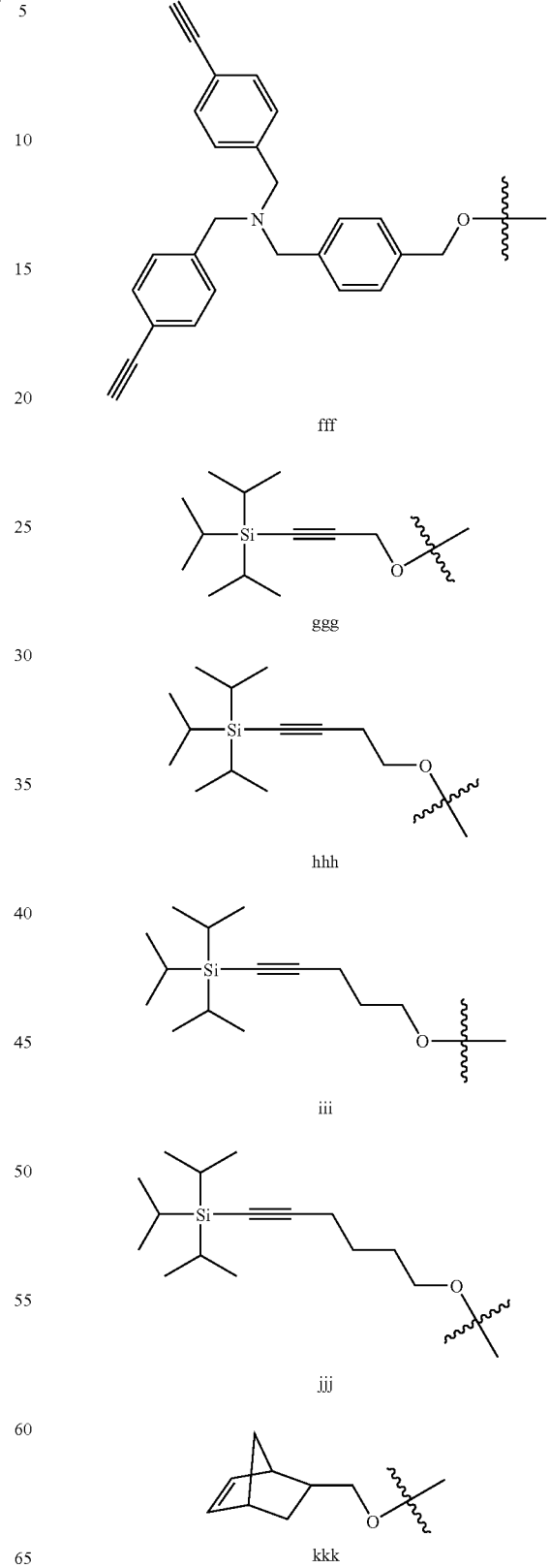
fff
ggg
hhh
iii
jjj
kkk

TABLE 12-continued

Representative R[1] Groups

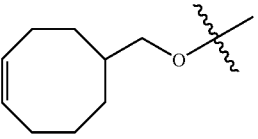
lll

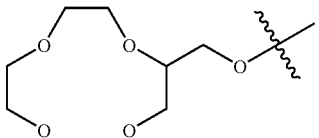
mmm

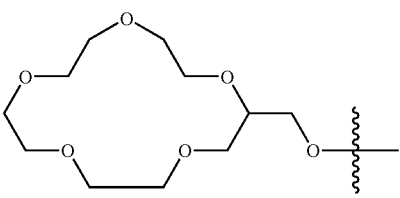
nnn

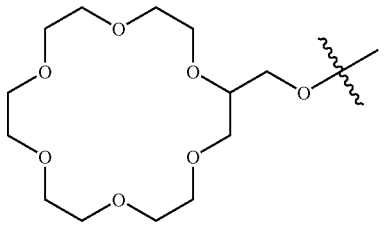
ooo

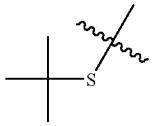
ppp

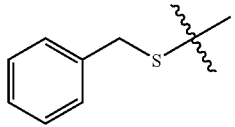
qqq

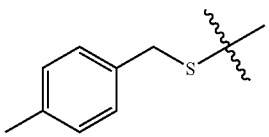
rrr

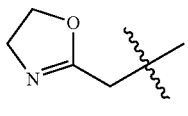
sss

TABLE 12-continued

Representative R[1] Groups

ttt

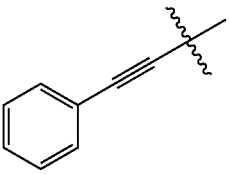
uuu

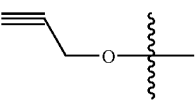
vvv

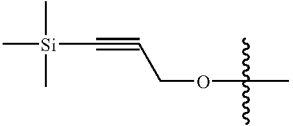
www

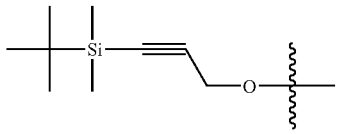
xxx

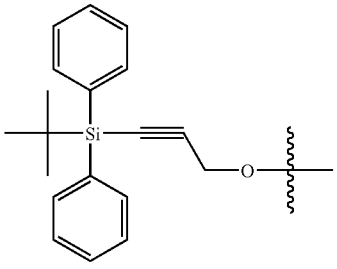
yyy

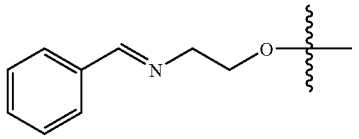
zzz

One of ordinary skill in the art would recognize that certain R[1] groups depicted in Table 12 are protected groups, e.g. protected amine, protected hydroxyl, protected thiol, protected carboxylic acid, or protected alkyne groups. Each of these protected groups is readily deprotected (see, for example, Green). Accordingly, the deprotected groups corresponding to the protected groups set forth in Table 12 are also contemplated. According to another embodiment, the R[1] group of any of formulae I, II, and III is selected from a deprotected group of Table 12.

Additional exemplary R¹ groups of any of formulae I, II, and III are set forth in Table 12a, below.
TABLE 12a
Representative R¹ Groups
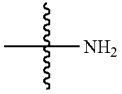
a
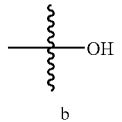
b
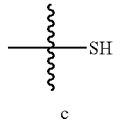
c
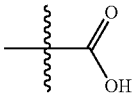
d
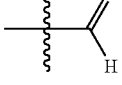
e
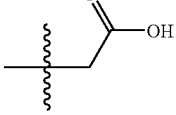
f
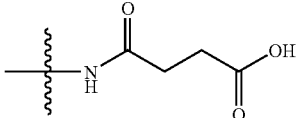
g
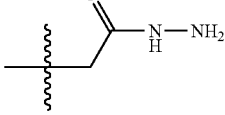
h
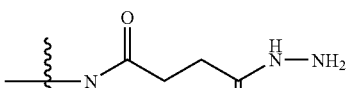
i
TABLE 12a-continued
Representative R¹ Groups
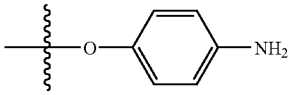
j
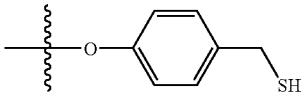
k
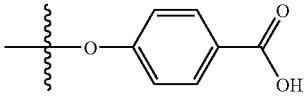
l
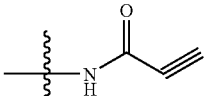
m
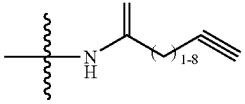
n
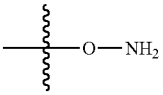
o
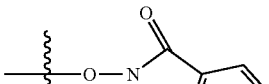
p
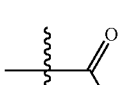
q
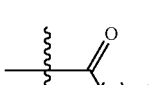
r TABLE 12a-continued
Representative R¹ Groups
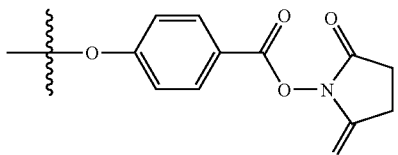
s
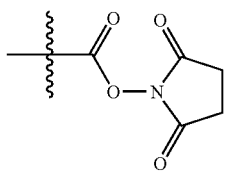
t
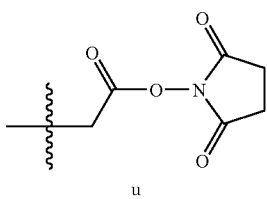
u
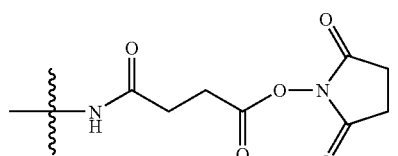
v
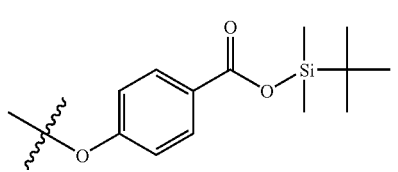
w
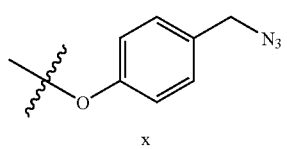
x
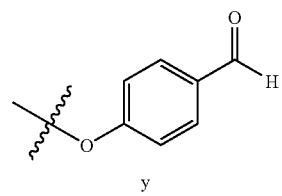
y
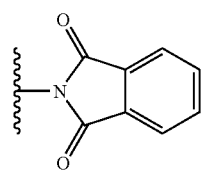
z
TABLE 12a-continued
Representative R¹ Groups
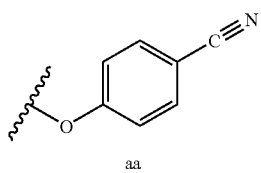
aa
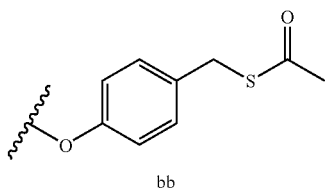
bb
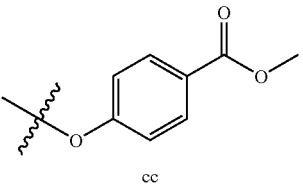
cc
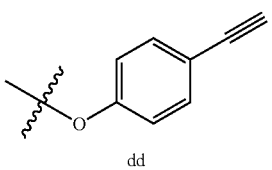
dd
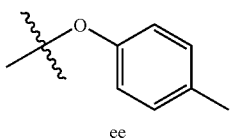
ee
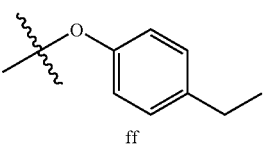
ff
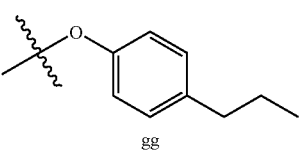
gg
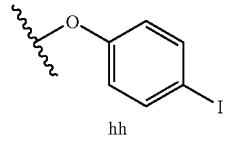
hh
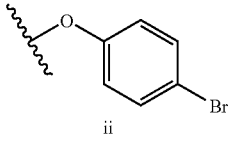
ii TABLE 12a-continued
Representative R¹ Groups
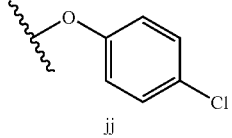
jj
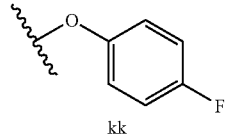
kk
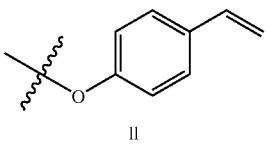
ll
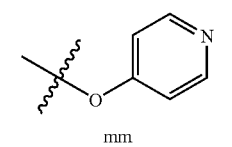
mm
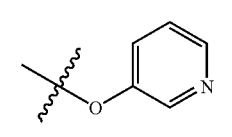
nn
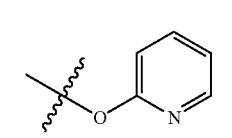
oo
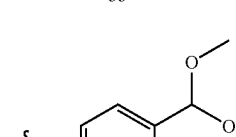
pp
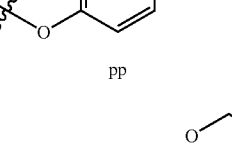
qq
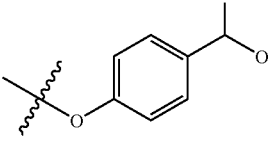
rr
TABLE 12a-continued
Representative R¹ Groups
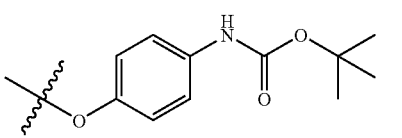
ss
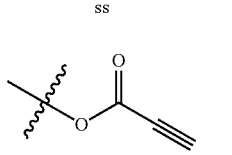
tt
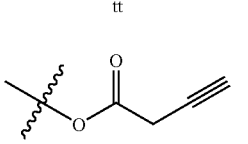
uu
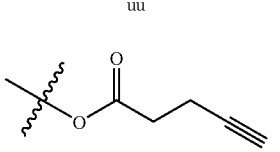
vv
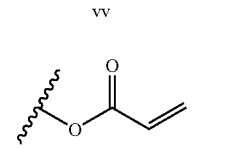
ww
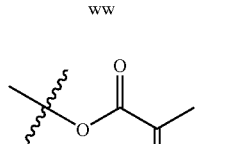
xx
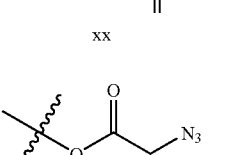
yy
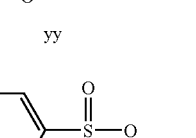
zz
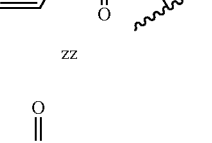
aaa
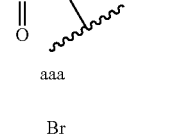
bbb TABLE 12a-continued
Representative R[1] Groups
ccc
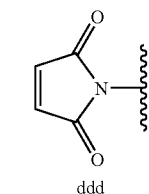
ddd
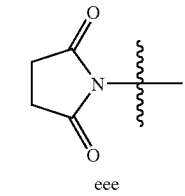
eee
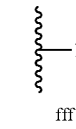
fff
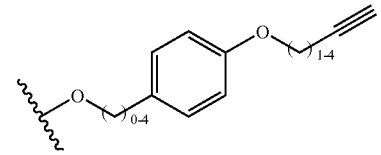
ggg
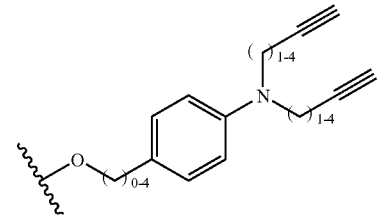
hhh
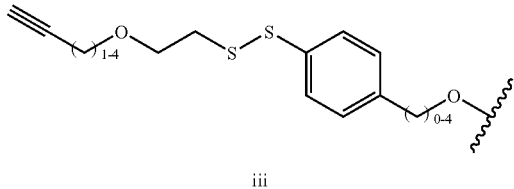
iii
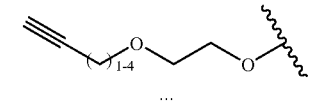
jjj
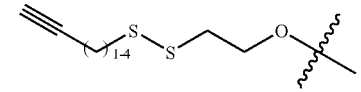
kkk
TABLE 12a-continued
Representative R[1] Groups
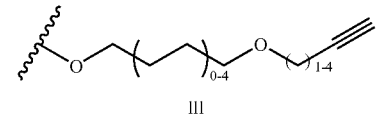
lll
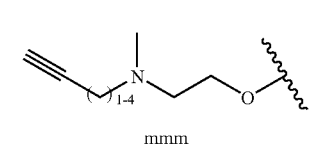
mmm
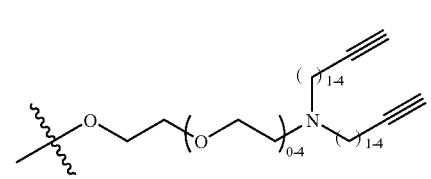
nnn
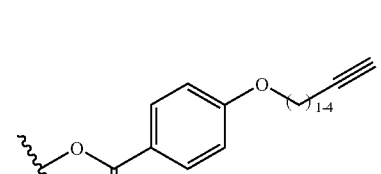
ooo
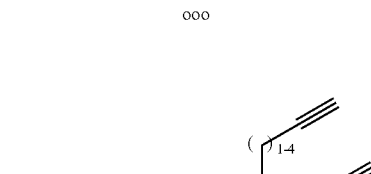
ppp
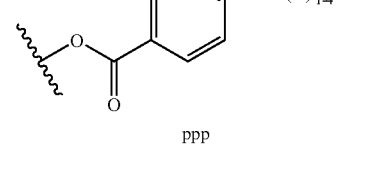
qqq
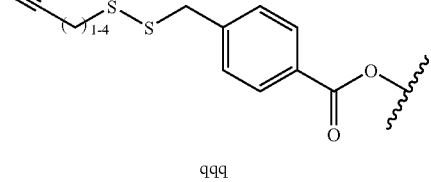
rrr TABLE 12a-continued Representative R¹ Groups sss ttt In certain embodiments, the R¹ group of any of formulae I, II, and III is selected from any of those R¹ groups depicted in Table 12, supra. In other embodiments, the R¹ group of any of formulae I, II, and III is group k or l. In yet other embodiments, the R¹ group of any of formulae I, II, and III is n, o, cc, dd, ee, ff hh, h, ii, jj, ll, or uu. In still other embodiments, the R¹ group of any of formulae I, II, and III is h, aa, yy, zz, or aaa.

According to another aspect of the present invention, the R¹ group of any of formulae I, II, and III is q, r, s, t, www, xxx, or yyy.

In other embodiments, the R¹ group of any of formulae I, II, and III is selected from any of those R¹ groups depicted in Tables 1-11, supra.

Exemplary R$^{2a}$ groups of any of formulae I, II, and III are set forth in Table 13, below.

TABLE 13

Representative R$^{2a}$ Groups i ii iii

TABLE 13-continued

Representative R$^{2a}$ Groups iv v vi vii viii ix x x xi

TABLE 13-continued

Representative R²ᵃ Groups xii, xiii, xiv, xv, xvi, xvii, xviii, xix, xx, xxi, xxii, xxiii, xxiv, xxv, xxvi, xxvii, xxviii TABLE 13-continued
Representative R²ᵃ Groups
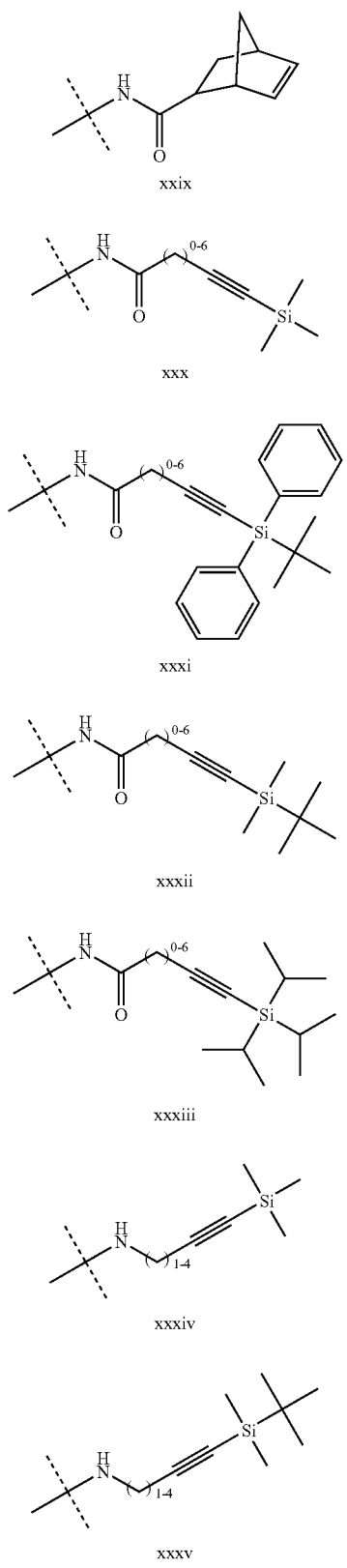
xxix
xxx
xxxi
xxxii
xxxiii
xxxiv
xxxv
TABLE 13-continued
Representative R²ᵃ Groups
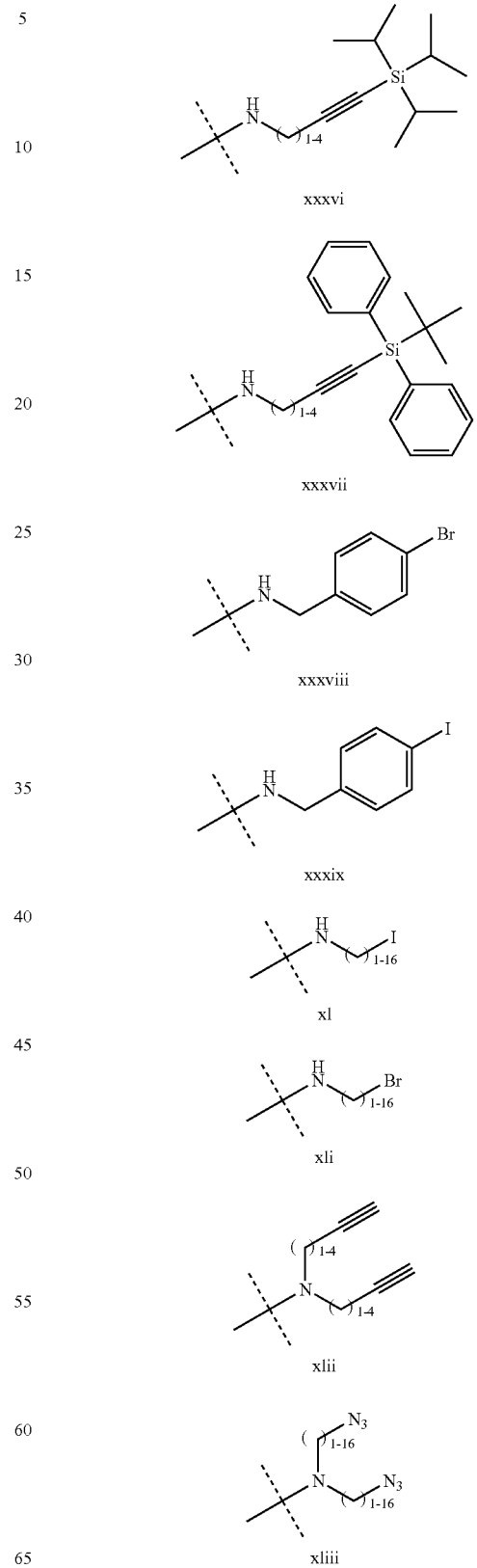
xxxvi
xxxvii
xxxviii
xxxix
xl
xli
xlii
xliii TABLE 13-continued Representative $R^{2a}$ Groups

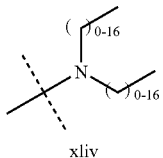

xliv

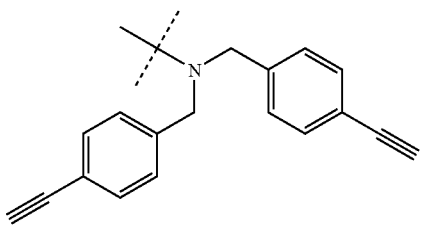

xlv

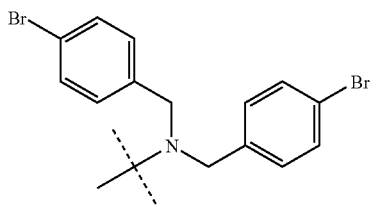

xlvi

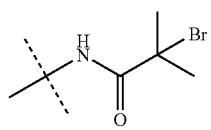

xlvii

In certain embodiments, the $R^{2a}$ group of any of formulae I, II, and III is selected from any of those $R^{2a}$ groups depicted in Table 13, supra. In other embodiments, the $R^{2a}$ group of any of formulae I, II, and III is group v, viii, xvi, xix, xxii, xxx, xxxi, xxxii, xxxiii, xxxiv, xxxv, xxxvi, xxxvii, or xlii. In yet other embodiments, the $R^{2a}$ group of any of formulae I, II, and III is xv, xviii, xx, xxi, xxxviii, or xxxix. In certain embodiments, the $R^{2a}$ group of any of formulae I, II, and III is xxxiv.

According to another embodiment, the $R^{2a}$ group of any of formulae I, II, and III is selected from any of those $R^{2a}$ groups depicted in Tables 1-1, supra.

One of ordinary skill in the art would recognize that certain $R^{2a}$ groups depicted in Table 13 are protected groups, e.g. protected amine, protected hydroxyl, protected thiol, protected carboxylic acid, or protected alkyne groups. Each of these protected groups is readily deprotected (see, for example, Green). Accordingly, the deprotected groups corresponding to the protected groups set forth in Table 13 are also contemplated. According to another embodiment, the $R^{2a}$ group of any of formulae I, II, and III is selected from a deprotected group of Table 13.

C. Contrast Agent Encapsulation

As described generally above, in certain embodiments the present invention provides a micelle having a contrast agent encapsulated therein, comprising a multiblock copolymer which comprises a polymeric hydrophilic block, optionally a crosslinkable or crosslinked poly(amino acid block), and a poly(amino acid block), characterized in that said micelle has a contrast agent-loaded inner core, optionally a crosslinkable or crosslinked outer core, and a hydrophilic shell. In some embodiments the present invention provides a micelle having a contrast agent encapsulated therein, comprising a multiblock copolymer which comprises a polymeric hydrophilic block, crosslinked poly(amino acid block), and a poly(amino acid block), characterized in that said micelle has a contrast agent-loaded inner core, crosslinked outer core, and a hydrophilic shell. As described herein, micelles of the present invention can be loaded with any contrast agent.

The use of various nanoparticles has been demonstrated to be useful in a number of in vitro and in vivo medical fields ranging from the tagging of biological species, in vitro cell separation, immunoassays, immunomagnetic array, in vivo contrast agents for MRI, PET, ultrasound, X-ray, computed tomography, fluorescence, disease treatment, targeted therapeutic delivery. See: Jeong, U.; Teng, X.; Wang, Y.; Yang, H.; Xia, Y. "Superparamagnetic Colloids: Controlled Synthesis and Niche Applications" Adv. Mater.; 2007, 19, 33-60.

In order to fully exploit these nanoparticles, delivery systems must be developed that can encapsulate the nanoparticles and impart properties such as long circulation time following injection by reducing RES uptake, accumulation in a targeted region of the body, and functionality for attachment to specific biological molecules. They must be administered in a biocompatible delivery vehicle that does not elicit cytotoxic or immunological responses but can improve their solubility and stability in biological media. The versatility of the triblock copolymer micelle described herein allows for a wide range of nanoparticles to be encapsulated, solubilized, stabilized, and targeted for in vitro and in vivo applications.

Semiconductor nanoparticles, such as CdSe, CdS, CdTe, PdSe, InP, InAs, PbS, CdSe/CdS, CdSe/ZnS, CdS/ZnS, and CdTe/ZnS have been shown to be potentially useful in both in vitro and in vivo as diagnostic agents. Their narrow emission, broad absorption profiles, and resistance to photo-bleaching make them ideal for in vitro and in vivo biological tagging, especially in multiplexing applications. Sizes of such semiconducting nanoparticles typically range from 2 to 50 nm (See Brus, L. "Chemical Approaches to Semiconducting Nanoparticles" J. Phy. Chem. Solids 1998, 59, 459-465. Wang, D.; He, J.; Rosenzweig, N.; Rosenzweig, Z. "Superparamagnetic $Fe_2O_3$ Beads-CdSe/ZnS Quantum Dots Core-Shell Nanocomposite Particles for Cell Separation" Nano Letters 2004, 4, 409-413. Yu, W. W.; Falkner, J. C.; Shih, B. S.; Colvin, V. L.; "Preparation and Characterization of Monodisperse PbSe Semiconductor Nanocrystals in a Noncoordinating Solvent" Chem. Mater. 2004, 16, 3318-3322).

Magnetic nanoparticles, such as: Fe, $Fe_2O_3$, $Fe_3O_4$, $MnFe_2O_4$, $CoFe_2O_4$, $NiFe_2O_4$, Co, Ni, FePt, CoPt, CoO, $Fe_3Pt$, $Fe_2Pt$, $CO_3Pt$, $CO_2Pt$, FeOOH, have also been useful for in vitro and in vivo diagnostics and treatments. Nanoparticles of this type, with sizes ranging from 2 nm-100 nm, have been successfully utilized as contrast agents for magnetic resonance, magnetically-controlled drug delivery vehicles, and in hyperthermia treatments. See: Jeong, U.; Teng, X.; Wang, Y.; Yang, H.; Xia, Y. "Superparamagnetic Colloids: Controlled Synthesis and Niche Applications" Adv. Mater.; 2007, 19, 33-60. Niederberger, M.; Garnweitner, G. "Organic Reaction Pathways in the Nonaqueos Synthesis of Metal Oxide Nanoparticles" 2006, 12, 7282-7302. Sun, S.; Zeng, H.; "Size-controlled Synthesis of Magnetite Nanoparticles" 2002, 124, 8204-8205.

While magnetic nanoparticles have shown a great deal of potential as contrast agents; their application in vivo has been limited in some cases by their limited aqueous solubility, poor biocompatibility, and short circulation lifetime following injection. One approach to address these two problems has been to alter the periphery of the nanoparticles with poly(ethylene glycol) ligands or to encapsulate the nanoparticles in the core of a polymeric micelle. See: Kumagai, M.; Imai, Y.; Nakamura, T.; Yamasaki, Y.; Sekino, M.; Ueno, S.; Hanaoka, K.; Kikuchi, K.; Nagano, T.; Kaneko, E.; Shimokado, K.; Kataoka, K. "Iron Hydroxide Nanoparticles Coated with Poly(ethylene glycol)-poly(aspartic acid) block copolymer as novel magnetic resonance contrast agents for in vivo cancer imaging" *Colloids and Surfaces B: Biointerfaces*, 2007, 56, 174-181. Kim, D. K.; Mikhaylova, M.; Zhang, Y.; Muhammed, M. "Protective Coating of Superparamagnetic Iron Oxide Nanoparticle" *Chem. Mater.* 2003, 15, 1617-1627. Ai, H.; Flask, C.; Weinberg, B.; Shuai, X.; Pagel, M.D.; Farrell, D.; Duerk, J.; Gao, J. "Magnetite-Loaded Polymeric Micelles as Ultrasensitive Magnetic-Resonance Probes" *Adv. Mater.*, 2005, 17, 1949-1952. While these approaches have had some limited success in improving nanoparticle solubility, they do not address the inherent instability of the nanoparticle-loaded micelles following administration and dilution in the body. Furthermore, the accumulation of the nanoparticles in a specified area of the body (e.g. solid tumor, lymph nodes, etc.) requires long circulation times which can be improved through crosslinking strategies to improve micelle stability and reduction in uptake by the reticuloendothelial system (RES). Both of these attributes can be imparted using micelles of the present invention which can possess chemical cross-linking in the micelle outer core and stealth properties imparted by the poly(ethylene glycol) corona. Thus, the crosslinked polymer micelles described herein are resistant to dissociation and instability resulting from post-injection dilution and destabilizing blood components.

In addition to the optional crosslinking procedure described above, certain inner core blocks can function as a ligand for the encapsulated nanoparticle. Without wishing to be bound by any particular theory, it is believed that when the inner core block contains certain residues, these residues can function as a multi-dentate ligand for the nanoparticle. For examine, when $R^y$ comprises an aspartic acid or glutamic acid functionality, a tyrosine functionality, or a DOPA functionality, the resulting inner core will function as a multi-dentate ligand for the nanoparticle. Amino-functionalized $R^y$ moieties, such as lysine, ornithine, histidine, and arginine also function as a multi-dentate ligand for the nanoparticle. Thus, in certain embodiments, the present invention provides a micelle having aspartic acid or glutamic acid functionality which functions as a multi-dentate ligand for the encapsulated nanoparticle. In other embodiments, tyrosine containing inner core blocks will function as a multi-dentate ligand for the encapsulated nanoparticle. In yet other embodiments, DOPA containing inner core blocks will function as a multi-dentate ligand for the encapsulated nanoparticle. Without wishing to be bound to any particular theory, in the case where the inner core block contains a moiety capable of functioning as a ligand for the encapsulated nanoparticle, it is believed that the large number of ligand-nanoparticle interactions acts to stabilize the micelle, with the nanoparticle itself acting as the crosslinking agent.

D. Polymer Conjugation

The ability to target the nanoparticles is of importance in allowing for specific imaging of unhealthy cells, e.g. tumors. In order to accomplish this several groups have shown that over expressed receptors can be used as targeting groups. Examples of these targeting groups include Folate, Her-2 peptide, etc. The shortfalls of attaching these targeting units directly to the nanoparticle surface through ligand attachment are that this bonding is not permanent. The ligands have the tendency to debond from the nanoparticle surface, especially as the nanoparticles are diluted. The attachment of targeting moieties directly to the nanoparticle surface in many cases does not advantageously increase the size of the nanoparticle (typically 2-20 nm) to the optimal size range, 50-200 nm, to avoid the endo-reticular system. In contrast, by encapsulating a number of nanoparticles in a given micelle one can deliver a much greater amount of contrast agent with one delivery event. The encapsulated micelles also allow for the generation of a wide range of size ranges from 40 nm to 500 nm. See: Lee, J.; Huh, Y.; Jun, Y. Seo, J.; Jang, J.; Song, H.; Kim, S.; Cho, E.; Yoon, H.; Suh, J.; Cheon, J. "Artificially Engineered Magnetic Nanoparticles for Ultra-sensitive Molecule Imaging" *Nature Medicine*, 2007, 13, 95-99.

In addition to their core-shell morphology, polymer micelles can be modified to enable passive and active cell-targeting to maximize the benefits of current and future therapeutic agents and contrast agents. Because contrast agent-loaded micelles typically possess diameters greater than 20 nm, they exhibit dramatically increased circulation time when compared to stand-alone contrast agents due to minimized renal clearance. This unique feature of nanovectors and polymeric delivery systems leads to selective accumulation in diseased tissue, especially cancerous tissue due to the enhanced permeation and retention effect ("EPR"). The EPR effect is a consequence of the disorganized nature of the tumor vasculature, which results in increased permeability of polymer therapeutics and contrast agent retention at the tumor site. In addition to passive cell targeting by the EPR effect, micelles are designed to actively target tumor cells through the chemical attachment of targeting groups to the micelle periphery. The incorporation of such groups is most often accomplished through end-group functionalization of the hydrophilic block using chemical conjugation techniques. Like viral particles, micelles functionalized with targeting groups utilize receptor-ligand interactions to control the spatial distribution of the micelles after administration, further enhancing cell-specific delivery of therapeutics. In cancer therapy, targeting groups are designed to interact with receptors that are over-expressed in cancerous tissue relative to normal tissue such as folic acid, oligopeptides, sugars, and monoclonal antibodies. See Pan, D.; Turner, J. L.; Wooley, K. L. *Chem. Commun.* 2003, 2400-2401; Gabizon, A.; Shmeeda, H.; Horowitz, A. T.; Zalipsky, S. *Adv. Drug Deliv. Rev.* 2004, 56, 1177-1202; Reynolds, P. N.; Dmitriev, I.; Curiel, D. T. Vector. Gene Ther. 1999, 6, 1336-1339; Derycke, A. S. L.; Kamuhabwa, A.; Gijsens, A.; Roskams, T.; De Vos, D.; Kasran, A.; Huwyler, J.; Missiaen, L.; de Witte, P. A. M. T *J. Nat. Cancer Inst.* 2004, 96, 1620-30; Nasongkla, N., Shuai, X., Ai, H.,; Weinberg, B. D. P., J.; Boothman, D. A.; Gao, J. *Angew. Chem. Int. Ed.* 2004, 43, 6323-6327; Jule, E.; Nagasaki, Y.; Kataoka, K. *Bioconj. Chem.* 2003, 14, 177-186; Stubenrauch, K.; Gleiter, S.; Brinkmann, U.; Rudolph, R.; Lilie, H. *Biochem. J.* 2001, 356, 867-873; Kurschus, F. C.; Kleinschmidt, M.; Fellows, E.; Dommair, K.; Rudolph, R.; Lilie, H.; Jenne, D. E. *FEBS Lett.* 2004, 562, 87-92; and Jones, S. D.; Marasco, W. A. *Adv. Drug Del. Rev.* 1998, 31, 153-170.

Compounds of any of formulae I, II, and III having $R^3$ moieties suitable for Click chemistry are useful for conjugating said compounds to biological systems or macromolecules such as proteins, viruses, and cells, to name but a few. The Click reaction is known to proceed quickly and selectively under physiological conditions. In contrast, most conjugation reactions are carried out using the primary amine functionality on proteins (e.g. lysine or protein end-group). Because most proteins contain a multitude of lysines and arginines, such conjugation occurs uncontrollably at multiple sites on the protein. This is particularly problematic when lysines or arginines are located around the active site of an enzyme or other biomolecule. Thus, another embodiment of the present invention provides a method of conjugating the $R^1$ groups of a compound of any of formulae I, II, and III to a macromolecule via Click chemistry. Yet another embodiment of the present invention provides a macromolecule conjugated to a compound of any of formulae I, II, and III via the $R^1$ group.

After incorporating the poly(amino acid) block portions into the multi-block copolymer of the present invention resulting in a multi-block copolymer of the form W—X—X', the other end-group functionality, corresponding to the $R^1$ moiety of any of formulae I, II, and III, can be used to attach targeting groups for cell specific delivery including, but not limited to, attach targeting groups for cell specific delivery including, but not limited to, proteins, oliogopeptides, antibodies, monosaccharides, oligosaccharides, vitamins, or other small biomolecules. Such targeting groups include, but or not limited to monoclonal and polyclonal antibodies (e.g. IgG, IgA, IgM, IgD, IgE antibodies), sugars (e.g. mannose, mannose-6-phosphate, galactose), proteins (e.g. Transferrin), oligopeptides (e.g. cyclic and acylic RGD-containing oligopeptides), and vitamins (e.g. folate). Alternatively, the $R^1$ moiety of any of formulae I, II, and III is bonded to a biomolecule, drug, cell, or other suitable substrate.

In other embodiments, the $R^1$ moiety of any of formulae I, II, and III is bonded to biomolecules which promote cell entry and/or endosomal escape. Such biomolecules include, but are not limited to, oligopeptides containing protein transduction domains such as the HIV Tat peptide sequence (GRKKRRQRRR) or oligoarginine (RRRRRRRRR). Oligopeptides which undergo conformational changes in varying pH environments such oligohistidine (HHHHH) also promote cell entry and endosomal escape.

In other embodiments, the $R^1$ moiety of any of formulae I, II, and III is bonded to detectable moieties, such as fluorescent dyes or labels for positron emission tomography including molecules containing radioisotopes (e.g. $^{18}F$) or ligands with bound radioactive metals (e.g. $^{62}Cu$). In other embodiments, the $R^1$ moiety of any of formulae I, II, and III is bonded to a contrast agents for magnetic resonance imaging such as gadolinium, gadolinium chelates, or iron oxide (e.g. $Fe_3O_4$ and $Fe_2O_3$) particles. In other embodiments, the $R^1$ moiety of any of formulae I, II, and III is bonded to a semiconducting nanoparticle such as cadmium selenide, cadmium sulfide, or cadmium telluride or bonded to other metal nanoparticles such as colloidal gold. In other embodiments, the $R^1$ moiety of any of formulae I, II, and III is bonded to natural or synthetic surfaces, cells, viruses, dyes, drugs, chelating agents, or used for incorporation into hydrogels or other tissue scaffolds.

In one embodiment, the $R^1$ moiety of any of formulae I, II, and III is an acetylene or an acetylene derivative which is capable of undergoing [3+2] cycloaddition reactions with complementary azide-bearing molecules and biomolecules. In another embodiment, the $R^1$ moiety of any of formulae I, II, and III is an azide or an azide derivative which is capable of undergoing [3+2] cycloaddition reactions with complementary alkyne-bearing molecules and biomolecules (i.e. click chemistry).

Click chemistry has become a popular method of bioconjugation due to its high reactivity and selectivity, even in biological media. See Kolb, H. C.; Finn, M. G.; Sharpless, K. B. *Angew. Chem. Int. Ed.* 2001, 40, 2004-2021; and Wang, Q.; Chan, T. R.; Hilgraf, R.; Fokin, V. V.; Sharpless, K. B.; Finn, M. G. *J. Am. Chem. Soc.* 2003, 125, 3192-3193. In addition, currently available recombinant techniques permit the introduction of azides and alkyne-bearing non-canonical amino acids into proteins, cells, viruses, bacteria, and other biological entities that consist of or display proteins. See Link, A. J.; Vink, M. K. S.; Tirrell, D. A. *J. Am. Chem. Soc.* 2004, 126, 10598-10602; Deiters, A.; Cropp, T. A.; Mukherji, M.; Chin, J. W.; Anderson, C.; Schultz, P. G. *J. Am. Chem. Soc.* 2003, 125, 11782-11783.

In another embodiment, the [3+2] cycloaddition reaction of azide or acetylene-bearing nanovectors and complimentary azide or acetylene-bearing biomolecules are transition metal catalyzed. Copper-containing molecules which catalyze the "click" reaction include, but are not limited to, copper bromide (CuBr), copper chloride (CuCl), copper sulfate ($CuSO_4$), copper iodide (CuI), [$Cu(MeCN)_4$](OTf), and [$Cu(MeCN)_4$]($PF_6$). Organic and inorganic metal-binding ligands can be used in conjunction with metal catalysts and include, but are not limited to, sodium ascorbate, tris(triazolyl)amine ligands, tris(carboxyethyl)phosphine (TCEP), and sulfonated bathophenanthroline ligands.

In another embodiment, the $R^1$ moiety of any of formulae I, II, and III is an hydrazine or hydrazide derivative which is capable of undergoing reaction with biomolecules containing aldehydes or ketones to form hydrazone linkages. In another embodiment, the $R^1$ moiety of any of formulae I, II, and III is an aldehyde or ketone derivative which is capable of undergoing reaction with biomolecules containing a hydrazine or hydrazide derivative to form hydrazone linkages.

In another embodiment, the $R^1$ moiety of any of formulae I, II, and III is a hydroxylamine derivative which is capable of undergoing reaction with biomolecules containing aldehydes or ketones. In another embodiment, the $R^1$ moiety of any of formulae I, II, and III is an aldehyde or ketone which is capable of undergoing reaction with biomolecules containing a hydroxylamine, or a hydroxylamine derivative.

In yet another embodiment, the $R^1$ moiety of any of formulae I, II, and III is an aldehyde or ketone derivative which is capable of undergoing reaction with biomolecules containing primary or secondary amines to form imine linkages. In another embodiment, the $R^1$ moiety of any of formulae I, II, and III is a primary or secondary amine which is capable of undergoing reaction with biomolecules containing an aldehyde or ketone functionality to form imine linkages. It will be appreciated that imine linkages can be further converted to stable amine linkages by treatment with a suitable reducing agent (e.g. lithium aluminum hydride, sodium borohydride, sodium cyanoborohydride, etc.)

In yet another embodiment, the $R^1$ moiety of any of formulae I, II, and III is an amine (primary or secondary) or alcohol which is capable of undergoing reaction with biomolecules containing activated esters (e.g. 4-nitrophenol ester, N-hydroxysuccinimide, pentafluorophenyl ester, ortho-pyridylthioester), to form amide or ester linkages. In still other embodiments, the $R^1$ moiety of any of formulae I, II, and III is an activated ester which is capable of undergoing reaction with biomolecules possessing amine (primary or secondary) or alcohols to form amide or ester linkages.

In still other embodiments, the $R^1$ moiety of any of formulae I, II, and III is an amine or alcohol which is bound to biomolecules with carboxylic acid functionality using a suitable coupling agent. In still other embodiments, the $R^1$ moiety of any of formulae I, II, and III is a carboxylic acid functionality which is bound to biomolecules containing amine or alcohol functionality using a suitable coupling agent. Such coupling agents include, but are not limited to, carbodiimides (e.g. 1-ethyl-3-(3-dimethylaminopropyl)-carbodiimide (EDC), diisopropyl carbodiimide (DIC), dicyclohexyl carbodiimide (DCC)), aminium or phosphonium derivatives (e.g.

PyBOP, PyAOP, TBTU, HATU, HBTU), or a combination of 1-hydroxybenzotriazole (HOBt) and a aminium or phosphonium derivative.

In another embodiment, the $R^1$ moiety of any of formulae I, II, and III is an electrophile such as maleimide, a maleimide derivative, or a bromoacetamide derivative, which is capable of reaction with biomolecules containing thiols or amines. In another embodiment, the $R^1$ moiety of any of formulae I, II, and III is a nucleophile such as an amine or thiol which is capable or reaction with biomolecules containing electrophilic functionality such as maleimide, a maleimide derivative, or a bromoacetamide derivative.

In still other embodiments, the $R^1$ moiety of any of formulae I, II, and III is a ortho-pyridyl disulfide moiety which undergoes disulfide exchange with biomolecules containing thiol functionality. In still other embodiments, the $R^1$ moiety of any of formulae I, II, and III is a thiol or thiol derivative which undergoes disulfide exchange with biomolecules containing ortho-pyridyl disulfide functionality. It will be appreciated that such exchange reactions result in a disulfide linkage which is reversible in the presence of a suitable reducing agent (e.g. glutathione, dithiothreitol (DTT), etc.).

In certain embodiments, micelles of the present invention are mixed micelles comprising one or more compounds of formula I, II, or III. It will be appreciated that mixed micelles having different $R^1$ groups, as described herein, can be conjugated to multiple other compounds and/or macromolecules. For example, a mixed micelle of the present invention can have one $R^1$ group suitable for Click chemistry and another $R^1$ group suitable for covalent attachment via a variety of coupling reactions. Such a mixed micelle can be conjugated to different compounds and/or macromolecules via these different $R^1$ groups. Such conjugation reactions are well known to one of ordinary skill in the art and include those described herein.

4. General Methods for Providing Compounds of the Present Invention

Multiblock copolymers of the present invention are prepared by methods known to one of ordinary skill in the art and those described in detail in U.S. patent application Ser. No. 11/325,020 filed Jan. 4, 2006 and published as US 20060172914 on Aug. 3, 2006, the entirety of which is hereby incorporated herein by reference. Generally, such multiblock copolymers are prepared by sequentially polymerizing one or more cyclic amino acid monomers onto a hydrophilic polymer having a terminal amine salt wherein said polymerization is initiated by said amine salt. In certain embodiments, said polymerization occurs by ring-opening polymerization of the cyclic amino acid monomers. In other embodiments, the cyclic amino acid monomer is an amino acid NCA, lactam, or imide.

Scheme 4

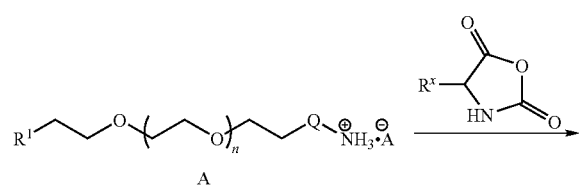

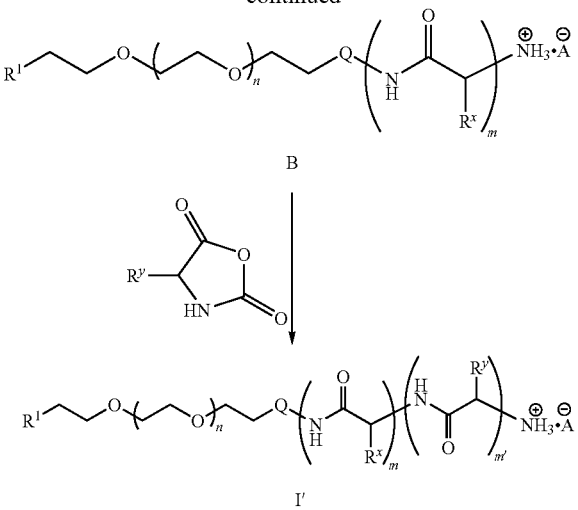

Scheme 4 above depicts a general method for preparing multiblock polymers of the present invention. A macroinitiator of formula A is treated with a first amino acid NCA to form a compound of formula B having a first amino acid block. The second amino acid NCA is added to the living polymer of formula B to form a compound of formula I' having two differing amino acid blocks. Each of the $R^1$, A, n, Q, $R^x$, $R^y$, m, and m' groups depicted in Scheme 4 are as defined and described in classes and subclasses, singly and in combination, herein.

One step in the preparation of a compound of formula I comprises terminating the living polymer chain-end of the compound of formula I' with a suitable polymerization terminator to afford a compound of formula I. One of ordinary skill in the art would recognize that the polymerization terminator provides the R group of formula I. Accordingly, embodiments directed to the $R^{2a}$ group of formula I as set forth above and herein, are also directed to the suitable polymerization terminator itself, and similarly, embodiments directed to the suitable polymerization terminator, as set forth above and herein, are also directed to the $R^{2a}$ group of formula I.

As described above, compounds of formula I are prepared from compounds of formula I' by treatment with a suitable terminating agent. One of ordinary skill in the art would recognize that compounds of formula I are also readily prepared directly from compounds of formula I'. In such cases, and in certain embodiments, the compound of formula I' is treated with a base to form the freebase compound prior to, or concurrent with, treatment with the suitable terminating agent. For example, it is contemplated that a compound of formula I' is treated with a base and suitable terminating agent in the same reaction to form a freebase of that compound. In such cases, it is also contemplated that the base may also serve as the reaction medium.

One of ordinary skill in the art would also recognize that the above method for preparing a compound of formula I may be performed as a "one-pot" synthesis of compounds of formula I that utilizes the living polymer chain-end to incorporate the $R^{2a}$ group of formula I. Alternatively, compounds of formula I may also be prepared in a multi-step fashion. For example, the living polymer chain-end of a compound of formula I' may be quenched to afford an amino group which may then be further derivatized, according to known methods, to afford a compound of formula I.

One of ordinary skill in the art will recognize that a variety of polymerization terminating agents are suitable for the present invention. Such polymerization terminating agents include any $R^{2a}$-containing group capable of reacting with the living polymer chain-end of a compound of formula I', or the free-based amino group of formula I', to afford a compound of formula I. Thus, polymerization terminating agents include anhydrides, and other acylating agents, and groups that contain a suitable leaving group LG that is subject to nucleophilic displacement.

Alternatively, compounds of formula I' may be coupled to carboxylic acid-containing groups to form an amide thereof. Thus, it is contemplated that the amine group of formula I' or freebase thereof, may be coupled with a carboxylic acid moiety to afford compounds of formula I wherein $R^{2a}$ is —NHC(O)$R^4$. Such coupling reactions are well known in the art. In certain embodiments, the coupling is achieved with a suitable coupling reagent. Such reagents are well known in the art and include, for example, DCC and EDC, among others. In other embodiments, the carboxylic acid moiety is activated for use in the coupling reaction. Such activation includes formation of an acyl halide, use of a Mukaiyama reagent, and the like. These methods, and others, are known to one of ordinary skill in the art, e.g., see, "Advanced Organic Chemistry," Jerry March, 5$^{th}$ Ed., pp. 351-357, John Wiley and Sons, N.Y.

A "suitable leaving group that is subject to nucleophilic displacement" is a chemical group that is readily displaced by a desired incoming chemical moiety. Suitable leaving groups are well known in the art, e.g., see, March. Such leaving groups include, but are not limited to, halogen, alkoxy, sulphonyloxy, optionally substituted alkylsulphonyloxy, optionally substituted alkenylsulfonyloxy, optionally substituted arylsulfonyloxy, and diazonium moieties. Examples of suitable leaving groups include chloro, iodo, bromo, fluoro, methanesulfonyloxy (mesyloxy), tosyloxy, triflyloxy, nitrophenylsulfonyloxy (nosyloxy), and bromo-phenylsulfonyloxy (brosyloxy).

According to an alternate embodiment, the suitable leaving group may be generated in situ within the reaction medium. For example, a leaving group may be generated in situ from a precursor of that compound wherein said precursor contains a group readily replaced by said leaving group in situ.

Alternatively, when the $R^{2a}$ group of formula I is a mono- or di-protected amine, the protecting group(s) is removed and that functional group may be derivatized or protected with a different protecting group. It will be appreciated that the removal of any protecting group of the $R^{2a}$ group of formula I is performed by methods suitable for that protecting group. Such methods are described in detail in Green.

In other embodiments, the $R^{2a}$ group of formula I is incorporated by derivatization of the amino group of formula I', or freebase thereof, via anhydride coupling, optionally in the presence of base as appropriate. One of ordinary skill in the art would recognize that anhydride polymerization terminating agents containing an azide, an aldehyde, a hydroxyl, an alkyne, and other groups, or protected forms thereof, may be used to incorporate said azide, said aldehyde, said protected hydroxyl, said alkyne, and other groups into the $R^{2a}$ group of compounds of formula I. It will also be appreciated that such anhydride polymerization terminating agents are also suitable for terminating the living polymer chain-end of a compound of formula I', or freebase thereof. Such anhydride polymerization terminating agents include, but are not limited to, those set forth in Table 14, below.

TABLE 14

Representative Anhydride Polymerization Terminating Agents

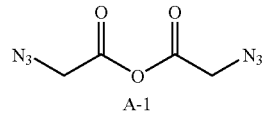

A-1

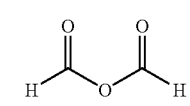

A-2

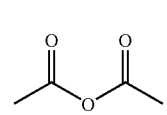

A-3

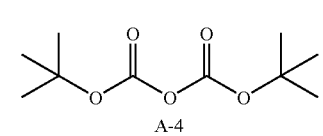

A-4

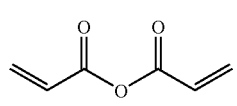

A-5

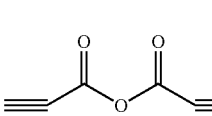

A-6

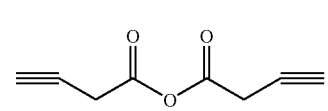

A-7

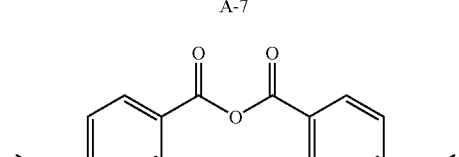

A-8

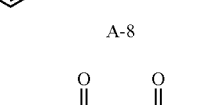

A-9

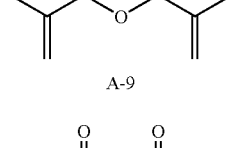

A-10

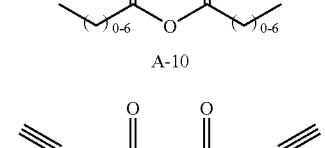

A-11

TABLE 14-continued

Representative Anhydride Polymerization Terminating Agents

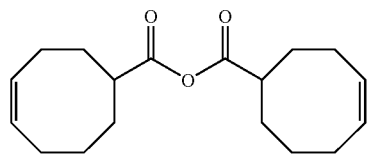

A-12

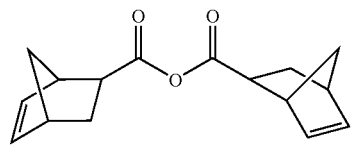

A-13

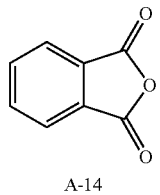

A-14

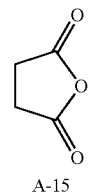

A-15

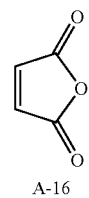

A-16

In other embodiments, the $R^4$ moiety of the $R^{2a}$ group of formula III is incorporated by derivatization of the amino group of formula I', or freebase thereof, via reaction with a polymerization terminating agent having a suitable leaving group. It will also be appreciated that such polymerization terminating agents are also suitable for terminating the living polymer chain-end of a compound of formula I', or freebase thereof. Examples of these polymerization terminating agents include, but are not limited to, those set forth in Table 15, below.

TABLE 15

Representative Polymerization Terminating Agents

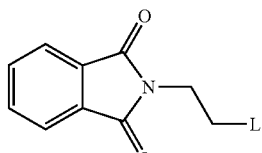

L-1

TABLE 15-continued

Representative Polymerization Terminating Agents

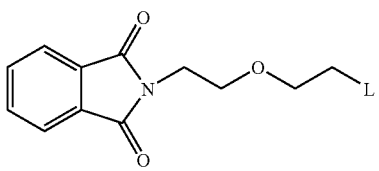

L-2

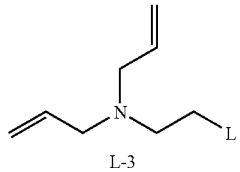

L-3

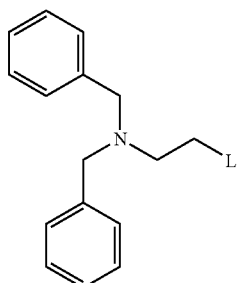

L-4

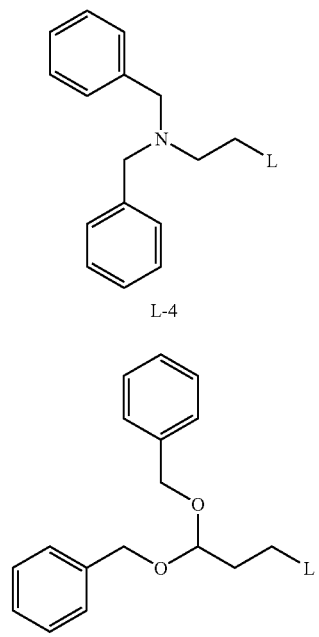

L-5

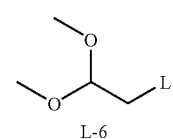

L-6

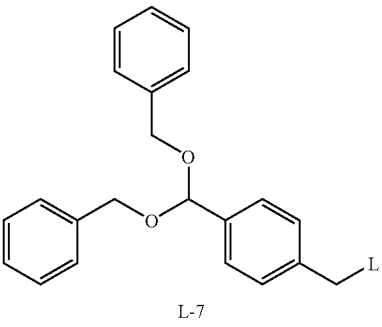

L-7

TABLE 15-continued

Representative Polymerization Terminating Agents

L-8, L-9, L-10, L-11, L-12, L-13, L-14, L-15, L-16, L-17, L-18, L-19, L-20, L-21, L-22, L-23, L-24, L-25, L-26, L-27

TABLE 15-continued

Representative Polymerization Terminating Agents

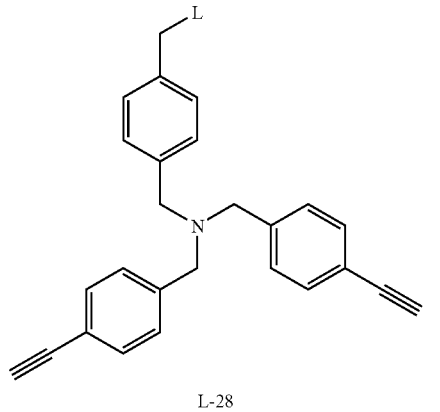
L-28

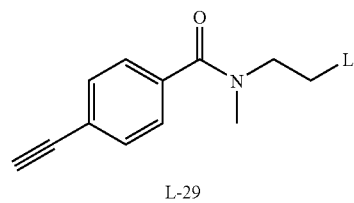
L-29

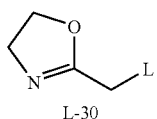
L-30

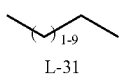
L-31

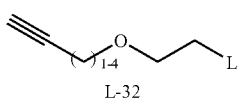
L-32

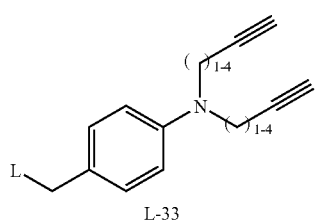
L-33

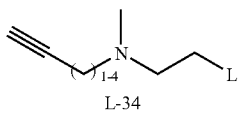
L-34

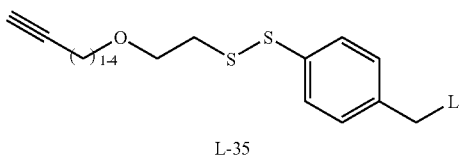
L-35

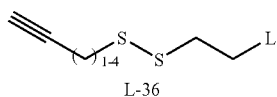
L-36

TABLE 15-continued

Representative Polymerization Terminating Agents

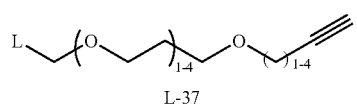
L-37

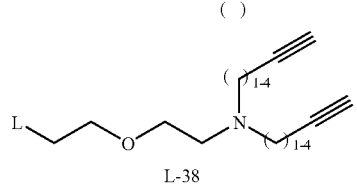
L-38

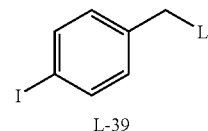
L-39

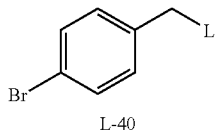
L-40

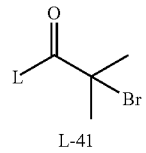
L-41

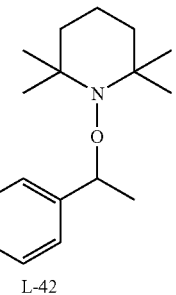
L-42 wherein each L is a suitable leaving group as defined above and in classes and subclasses as described above and herein.

In certain embodiments, the hydrophilic polymer block is poly(ethylene glycol) (PEG) having a terminal amine salt ("PEG macroinitiator"). This PEG macroinitiator initiates the polymerization of NCAs to provide the multiblock copolymers of the present invention. Such polymers having a terminal amine salt may be prepared from synthetic polymers having a terminal amine. Such synthetic polymers having a terminal amine group are known in the art and include PEG-amines. PEG-amines may be obtained by the deprotection of a suitably protected PEG-amine. Preparation of such suitably protected PEG-amines, and methods of deprotecting the same, is described in detail in U.S. patent application Ser. No. 11/256,735, filed Oct. 24, 2005 and published as US 20060142506 on Jun. 29, 2006, the entirety of which is hereby incorporated herein by reference.

As described in US 20060142506, suitably protected PEG-amines may be formed by terminating the living polymer chain end of a PEG with a terminating agent that contains a suitably protected amine. The suitably protected amine may then be deprotected to generate a PEG that is terminated with a free amine that may subsequently be converted into the corresponding PEG-amine salt macroinitiator. In certain embodiments, the PEG-amine salt macroinitiator of the present invention is prepared directly from a suitably protected PEG-amine by deprotecting said protected amine with an acid. Accordingly, in other embodiments, the terminating agent has suitably protected amino group wherein the protecting group is acid-labile.

Alternatively, suitable synthetic polymers having a terminal amine salt may be prepared from synthetic polymers that contain terminal functional groups that may be converted to amine salts by known synthetic routes. In certain embodiments, the conversion of the terminal functional groups to the amine salts is conducted in a single synthetic step. In other embodiments, the conversion of the terminal functional groups to the amine salts is achieved by way of a multi-step sequence. Functional group transformations that afford amines, amine salts, or protected amines are well known in the art and include those described in Larock, R. C., "Comprehensive Organic Transformations," John Wiley & Sons, New York, 1999.

compounds of the invention can be prepared according to the methods described generally above using appropriate starting materials by methods generally available to one of ordinary skill in the art. Additional embodiments are exemplified in more detail herein.

Methods of preparing micelles are known to one of ordinary skill in the art. Micelles can be prepared by a number of different dissolution methods. In the direct dissolution method, the block copolymer is added directly to an aqueous medium with or without heating and micelles are spontaneously formed up dissolution. The dialysis method is often used when micelles are formed from poorly aqueous soluble copolymers. The copolymer is dissolved in a water miscible organic solvent such as N-methylpyrollidinone, dimethylformamide, dimethylsulfoxide, tetrahydrofuran, or dimethylacetamide, and this solution is then dialyzed against water or another aqueous medium. During dialysis, micelle formation is induced and the organic solvent is removed. Alternatively, the block copolymer can be dissolved in a water miscible organic solvent such as N-methylpyrollidinone, dimethylformamide, dimethylsulfoxide, tetrahydrofuran, or dimethylacetamide and added dropwise to water or another aqueous medium. Micelles prepared by these methods can be sterilized by sterile filtration and then isolated by lyophilization.

Scheme 5

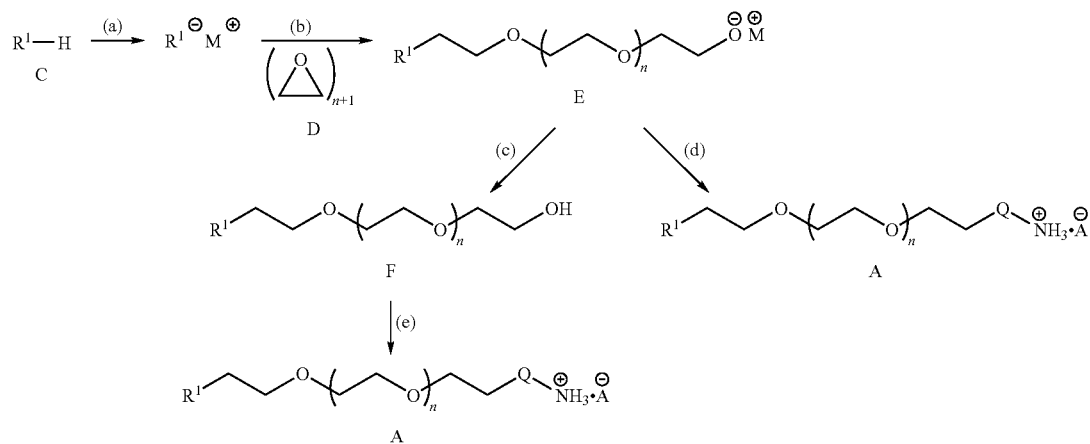

Scheme 5 above shows one exemplary method for preparing the bifunctional PEGs used to prepare the multiblock copolymers of the present invention. At step (a), the polymerization initiator is treated with a suitable base to form D. A variety of bases are suitable for the reaction at step (a). Such bases include, but are not limited to, potassium naphthalenide, diphenylmethyl potassium, triphenylmethyl potassium, and potassium hydride. At step (b), the resulting anion is treated with ethylene oxide to form the polymer E. Polymer E can be transformed at step (d) to a compound of formula A directly by terminating the living polymer chain-end of E with a suitable polymerization terminator to afford a compound of formula A. Alternatively, polymer E may be quenched at step (c) to form the hydroxyl compound F. Compound F is then derivatized to afford a compound of formula A by methods known in the art, including those described herein. Each of the $R^1$, A, n, and Q groups depicted in Scheme 5 are as defined and described in classes and subclasses, singly and in combination, herein.

Although certain exemplary embodiments are depicted and described above and herein, it will be appreciated that In one embodiment, inventive micelles having a contrast agent encapsulated therein and possessing carboxylic acid functionality in the outer core are optionally crosslinked by addition of zinc chloride to the micelle solution along with a small amount of sodium bicarbonate to neutralize any hydrochloric acid by-product. In this basic pH environment, the reaction of zinc chloride with the poly(aspartic acid) crosslinking block is rapid and irreversible.

In another embodiment, inventive micelles having a contrast agent encapsulated therein and possessing amine functionality in the outer core are optionally crosslinked by the addition of a bifunctional, or multi-functional aldehyde-containing molecule which forms pH-reversible imine crosslinks. In another embodiment, micelles, having a contrast agent encapsulated therein, possessing aldehyde functionality in the outer core are optionally crosslinked by the addition of a bifunctional, or multi-functional amine-containing molecule which forms pH-reversible imine crosslinks.

In another embodiment, inventive micelles having a contrast agent encapsulated therein and possessing alcohol or amine functionality in the outer core are optionally crosslinked by the addition of a bifunctional, or multi-functional carboxylic acid-containing molecules and a coupling agent to form amide or ester crosslinks. In yet another embodiment, inventive micelles having a contrast agent encapsulated therein and possessing carboxylic acid functionality in the outer core are optionally crosslinked by the addition of a bifunctional, or multi-functional amine or alcohol-containing molecules and a coupling agent to form amide or ester crosslinks. Such coupling agents include, but are not limited to, carbodiimides (e.g. 1-ethyl-3-(3-dimethylamino-propyl)-carbodiimide (EDC), diisopropyl carbodiimide (DIC), dicyclohexyl carbodiimide (DCC)), aminium or phosphonium derivatives (e.g. PyBOP, PyAOP, TBTU, HATU, HBTU), or a combination of 1-hydroxybenzotriazole (HOBt) and a aminium or phosphonium derivative.

In another embodiment, inventive micelles having a contrast agent encapsulated therein and possessing aldehyde or ketone functionality in the outer core are optionally crosslinked by the addition of a bifunctional, or multifunctional hydrazine or hydrazide-containing molecule to form pH-reversible hydrazone crosslinks. In still other embodiments, inventive micelles having a contrast agent encapsulated therein and hydrazine or hydrazide-functionality in the outer core are optionally crosslinked by the addition of a bifunctional, or multifunctional aldehyde or ketone-containing molecule to form pH-reversible hydrazone crosslinks.

In another embodiment, inventive micelles having a contrast agent encapsulated therein and possessing thiol functionality in the outer core are optionally crosslinked by the addition of an oxidizing agent (e.g. metal oxides, halogens, oxygen, peroxides, ozone, peroxyacids, etc.) to form disulfide crosslinks. It will be appreciated that disulfide crosslinks are reversible in the presence of a suitable reducing agent (e.g. glutathione, dithiothreitol (DTT), etc.).

In yet another embodiment, inventive micelles having a contrast agent encapsulated therein and possessing both carboxylic acid and thiol functionality in the outer core can be dual crosslinked by the addition of an oxidizing agent (e.g. metal oxides, halogens, oxygen, peroxides, ozone, peroxyacids, etc.) to form disulfide crosslinks followed by the addition of zinc chloride to the micelle solution along with a small amount of sodium bicarbonate to neutralize any hydrochloric acid by-product. It will be appreciated that such a dual-crosslinked micelle is reversible only in the presence of acid and a reducing agent (e.g. glutathione, dithiothreitol (DTT), etc.).

According to another aspect, the present invention provides a method for preparing a micelle having a contrast agent encapsulated therein, comprising a multiblock copolymer which comprises a polymeric hydrophilic block, a crosslinked poly(amino acid block), and a poly(amino acid) block, characterized in that said micelle has an inner core, a crosslinked outer core, and a hydrophilic shell, said method comprising the steps of:

(a) providing a multiblock copolymer of formula I:

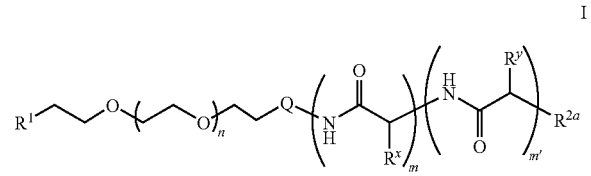

I wherein:
  n is 10-2500;
  m is 1 to 1000;
  m' is 1 to 1000;
  $R^x$ is a natural or unnatural amino acid side-chain group that is capable of crosslinking;
  $R^y$ is a hydrophobic or ionic, natural or unnatural amino acid side-chain group;
  $R^1$ is -Z(CH$_2$CH$_2$Y)$_p$(CH$_2$)$_t$R$^3$, wherein:
    Z is —O—, —S—, —C≡C—, or —CH$_2$—;
    each Y is independently —O— or —S—;
    p is 0-10;
    t is 0-10; and
  $R^3$ is hydrogen, —N$_3$, —CN, a mono-protected amine, a di-protected amine, a protected aldehyde, a protected hydroxyl, a protected carboxylic acid, a protected thiol, a 9-30 membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;
  Q is a valence bond or a bivalent, saturated or unsaturated, straight or branched C$_{1-12}$ hydrocarbon chain, wherein 0-6 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:
    -Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;
  $R^{2a}$ is a mono-protected amine, a di-protected amine, —N(R$^4$)$_2$, —NR$^4$C(O)R$^4$, —NR$^4$C(O)N(R$^4$)$_2$, —NR$^4$C(O)OR$^4$, or —NR$^4$SO$_2$R$^4$; and
  each $R^4$ is independently an optionally substituted group selected from hydrogen, aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety, or:
    two $R^4$ on the same nitrogen atom are taken together with said nitrogen atom to form an optionally substituted 4-7 membered saturated, partially unsaturated, or aryl ring having 1-4 heteroatoms independently selected from nitrogen, oxygen, or sulfur, (b) combining said compound of formula I with a contrast agent; and
(c) treating the resulting micelle with a crosslinking reagent to crosslink $R^x$.

In one embodiment, contrast agents are loaded into the micelle inner core by adding an aliquot of a copolymer solution in water to the contrast agent to be incorporated. For example, a stock solution of the contrast agent in a polar organic solvent is made and the solvent is allowed to evaporate. The copolymer/water solution is subsequently added and loading can be achieved through stirring, vortex mixing, sonication, and the like. In another embodiment, the contrast agent is incorporated using an oil in water emulsion technique. In this case, the contrast agent is dissolved in a water immiscible organic solvent and added dropwise to the agitated micelle solution in water, and the contrast agent is incorporated into the micelle during solvent evaporation. In another embodiment, the contrast agent and polymer can be dissolved in a water immiscible organic solvent and added dropwise to water while stirring, vortex mixing, or other methods of agitation. The contrast agent is incorporated into the micelle during solvent evaporation. In another embodiment, the contrast agent is dissolved with the copolymer in a common polar organic solvent and dialyzed against water or another aqueous medium. See Allen, C.; Maysinger, D.; Eisenberg A. *Colloid Surface B* 1999, 16, 3-27.

In still another embodiment, the loading and crosslinking of contrast agent-filled micelles is carried out by dissolving the contrast agent and the block copolymer in a polar solvent such as acetone or ethanol, followed by slow addition to water or buffer solution. Due to the limited solubility of the contrast agent in water, the contrast agent is forced into the core of the micelle, effectively encapsulating the contrast agent.

5. Uses, Methods, and Compositions

Although bones are easily visualized using x-ray imaging, many other organs and tissues cannot be easily imaged without contrast enhancement. Contrast agents, also known as contrast media or diagnostic agents, are often used during medical imaging examinations to highlight specific parts of the body (e.g. tissues and organs) and make them easier to visualize and improve disease diagnosis. Contrast agents can be used with many types of imaging examinations, including x-ray exams, computed tomography scans, magnetic resonance imaging, and positron emission tomography to name but a few.

As described herein, micelles of the present invention can encapsulate a wide variety of contrast agents. In certain embodiments, the present invention provides a micelle having a contrast agent encapsulated therein, as described herein, wherein said micelle is useful for enhancing the visualization of tissues and organs. Such visualization is useful for diagnosing various diseases and injuries.

In certain embodiments, the present invention provides a method for imaging at least one tissue in a patient said method comprising administering to said patient a provided micelle having a contrast agent encapsulated therein, or composition thereof, and detecting the contrast agent. One of ordinary skill in the art will recognize that various imaging methods are useful for the detecting step. Exemplary imaging methods include x-ray, magnetic resonance, ultrasound, optical imaging, sonoluminescence, photoacoustic imaging, nuclear imaging, positron emission tomography, absorption, light scattering, and computed tomography.

In certain embodiments, the present invention provides a diagnostic imaging method comprising the steps of: (a) administering to a patient a provided micelle having a contrast agent encapsulated therein, or composition thereof, and (b) imaging the contrast agent after administration of the micelle to the patient. In some embodiments, the present invention provides a diagnostic imaging method comprising the steps of: (a) administering to a patient a provided micelle having a contrast agent encapsulated therein wherein the micelle is conjugated to a targeting group, or composition thereof, and (b) imaging the contrast agent after administration of the micelle to the patient.

In certain embodiments, the imaging step is selected from magnetic resonance imaging, ultrasound imaging, optical imaging, sonoluminescence imaging, photoacoustic imaging, or nuclear imaging.

In certain embodiments, the present invention provides a method of imaging at least one tissue in a patient comprising administering a provided micelle, or composition thereof, and performing an imaging procedure.

Compositions

According to another embodiment, the invention provides a composition comprising a micelle of this invention or a pharmaceutically acceptable derivative thereof and a pharmaceutically acceptable carrier, adjuvant, or vehicle. In certain embodiments, the composition of this invention is formulated for administration to a patient in need of such composition. In other embodiments, the composition of this invention is formulated for oral administration to a patient. In some embodiments, compositions of the present invention are formulated for parenteral administration.

The term "patient", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and N+(C1-4 alkyl)4 salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added. In certain embodiments, pharmaceutically acceptable compositions of the present invention are enterically coated.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the agent. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In certain embodiments, the pharmaceutically acceptable compositions of this invention are formulated for oral administration.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the contrast agent can be administered to a patient receiving these compositions.

It will be appreciated that dosages typically employed for the encapsulated contrast agent are contemplated by the present invention. In certain embodiments, a patient is administered a contrast agent-loaded micelle of the present invention wherein the dosage of the contrast agent is equivalent to what is typically administered for that contrast agent. In other embodiments, a patient is administered a contrast agent-loaded micelle of the present invention wherein the dosage of the drug is lower than is typically administered for that contrast agent.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

In order that the invention described herein may be more fully understood, the following examples are set forth. It will be understood that these examples are for illustrative purposes only and are not to be construed as limiting this invention in any manner.

EXAMPLES

Preparation of Bifunctional Pegs and Multiblock Copolymers of the Present Invention As described generally above, multiblock copolymers of the present invention are prepared using the heterobifunctional PEGs described herein and in U.S. patent application Ser. No. 11/256,735, filed Oct. 24, 2005 and published as US20060142506 on Jun. 29, 2006, the entirety of which is hereby incorporated herein by reference. The preparation of multiblock polymers in accordance with the present invention is accomplished by methods known in the art, including those described in detail in U.S. patent application Ser. No. 11/325,020, filed Jan. 4, 2006 and published as US 20060172914 on Aug. 3, 2006, the entirety of which is hereby incorporated herein by reference.

Example 1

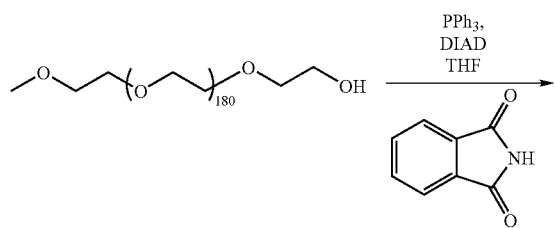

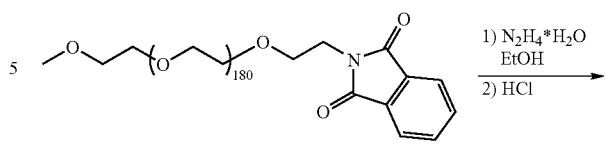

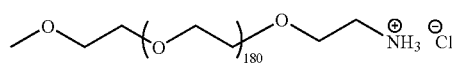

mPEG-hydrochloride

To a 500 mL 2-neck round bottom flask was added mPEG (40 g, 5 mmol), phthalimide (4.41 g, 30 mmol) and triphenyl phosphine (6.55 g, 25 mmol). The reagents were dissolved in anhydrous THF (300 mL) and stirred at room temperature. Once a homogeneous solution was present, DIAD (4.04 g, 20 mmol) was added and the solution stirred for 16 h. The solvent was evaporated and the residue purified by solid phase extraction (3% MeOH in $CHCl_3$ (1 L) followed by 10% MeOH in $CHCl_3$ (1 L) which contained the polymer product). The solvent was removed and the resulting liquid dissolved in ethanol (200 mL) and hydrazine hydrate (10 mL). The solution was stirred at reflux for 14 h, allowed to cool, then concentrated HCl (15 mL) was added dropwise to the solution. The solution was filtered and the solvent evaporated. The residue was dissolved in water and the polymer product extracted with $CHCl_3$ (4×500 mL). The combined organic layers were dried over $MgSO_4$, filtered and the solvent evaporated. The resulting liquid was diluted with a minimal amount of methanol and precipitated in to diethyl ether. A white powder (28.2 g, 71%) was isolated following filtration. $^1$H NMR (400 MHz, DMSO-$d_6$, δ) 7.79 br-s, 3.7-3.3 br-m, 2.96 t. GPC (DMF, PEG standards) $M_n$=7,800; PDI=1.03.

Example 2

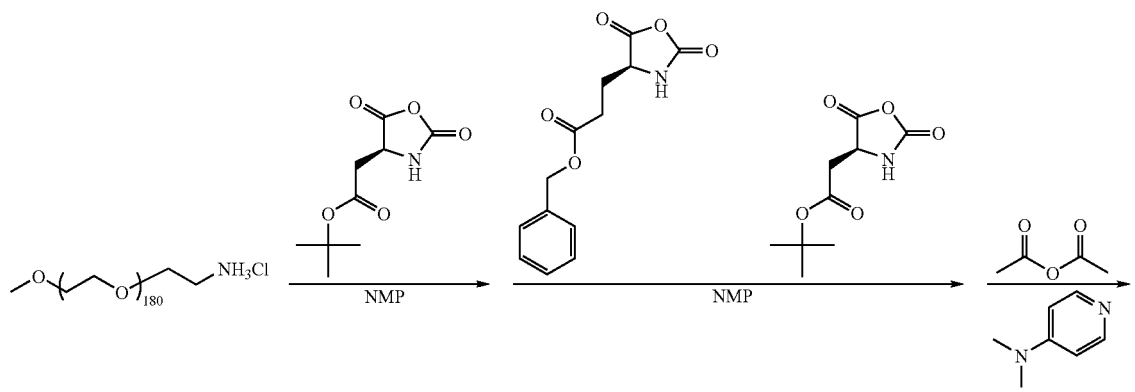

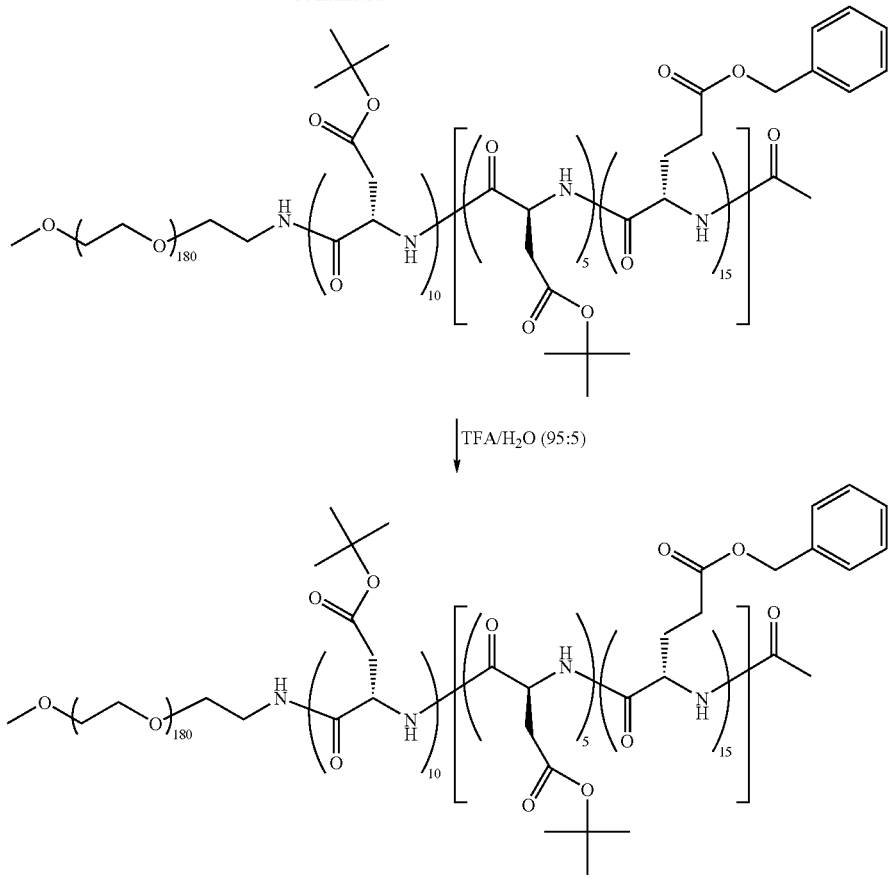

mPEG-PAsp-(PAsp-co-PBLG)-Ac

To a 100 mL round bottom flask was added mPEG-hydrochloride (1.04 g, 0.14 mmol) and t-butyl aspartic acid NCA (0.3 g, 1.4 mmol). The reagents were dried under vacuum for 1 hour, then NMP (15 mL) added. The solution was degassed under vacuum the backfilled with $N_2$, and stirred at 80° C. After 48 h, benzyl glutamate NCA (0.54 g, 2.1 mmol) and t-butyl aspartic acid NCA (0.15 g, 0.70 mmol) was dissolved in NMP (10 mL) and added to the reaction. After an additional 48 h, the solution was allowed to cool, then DMAP (0.17 g, 1.4 mmol) and acetic anhydride (0.14 g, 1.4 mmol) added to the stirred solution. After 1 hour, the solution was precipitated into diethyl ether/hexanes (3:2, 300 mL). A white solid was recovered after filtration, which was dissolved in TFA/$H_2O$ (95:5, 40 mL) and stirred for 4 hours at room temperature. The solvent was evaporated and the residue precipitated into ether (300 mL). A white powder (1.15 g, 68% yield) was recovered following filtration. $^1H$ NMR (400 MHz, DMSO-$d_6$, δ) 12.21, 8.19, 7.36, 5.08, 4.50, 3.7-3.3, 3.16, 2.67, 2.38, 2.01, 1.80.

Example 3

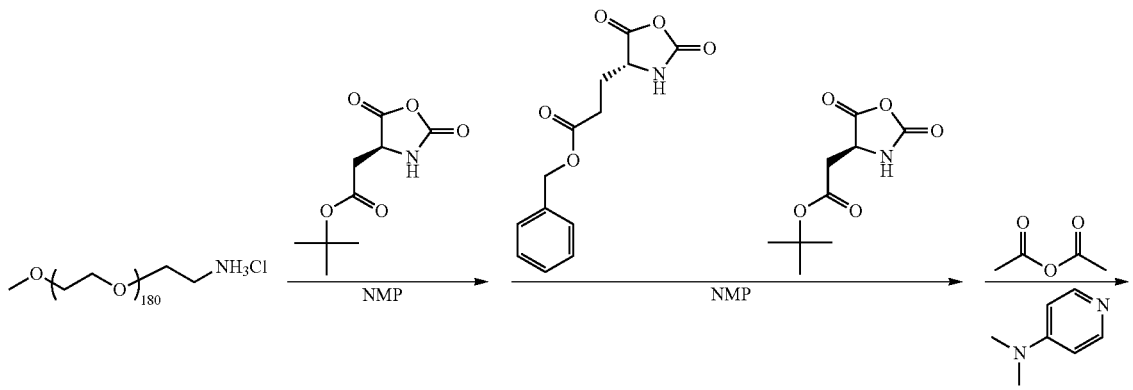

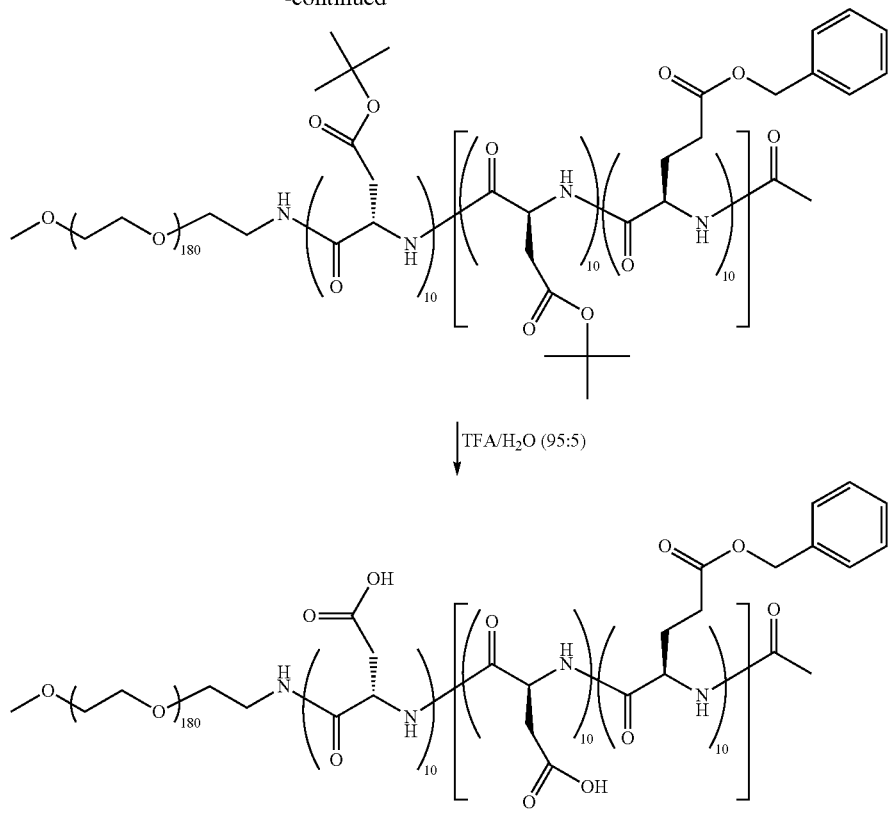

mPEG-PAsp-(PAsp-co-DBzGlu)-Ac

To a 100 mL round bottom flask was added mPEG-hydrochloride (1.0 g, 0.13 mmol) and t-butyl aspartic acid NCA (0.28 g, 1.3 mmol). The reagents were dried under vacuum for 1 hour, then NMP (10 mL) added. The solution was degassed under vacuum the backfilled with $N_2$, and stirred at 80° C. After 48 h, D-benzyl glutamate NCA (0.34 g, 1.3 mmol) and t-butyl aspartic acid NCA (0.28 g, 1.3 mmol) was dissolved in NMP (5 mL) and added to the reaction. After an additional 48 h, the solution was allowed to cool, then DMAP (0.16 g, 1.3 mmol) and acetic anhydride (0.13 g, 1.3 mmol) added to the stirred solution. After 1 hour, the solution was precipitated into diethyl ether/hexanes (3:2, 300 mL). A white solid was recovered after filtration, which was dissolved in TFA/$H_2O$ (95:5, 40 mL) and stirred for 4 hours at room temperature. The solvent was evaporated and the residue precipitated into ether (300 mL). A white powder (0.7 g, 52% yield) was recovered following filtration. $^1H$ NMR (400 MHz, DMSO-$d_6$, δ) 12.37, 8.23, 7.97, 7.55, 7.34, 6.97, 5.06, 4.51, 4.27, 3.7-3.3, 3.19, 2.67, 2.35, 2.01, 1.83.

Example 4

4 nm $Fe_3O_4$ nanoparticles (2.5 mg) (prepared according to Sun, S.; Zeng, H. "Size-Controlled Synthesis of Magnetite Nanoparticles" J. Am. Chem. Soc. 2002, 124, 8204-8205.) dissolved in $CH_2Cl_2$ (1 mL) was added to PEG-b-PAsp-b-P (Phe-co-Tyr) (50 mg) dissolved in water. The biphasic mixture was agitated in an incubated shaker for 3 hours. The homogenous solution was lyophilized and the dry powder was stored at 4° C.

Example 5

Figure 2:
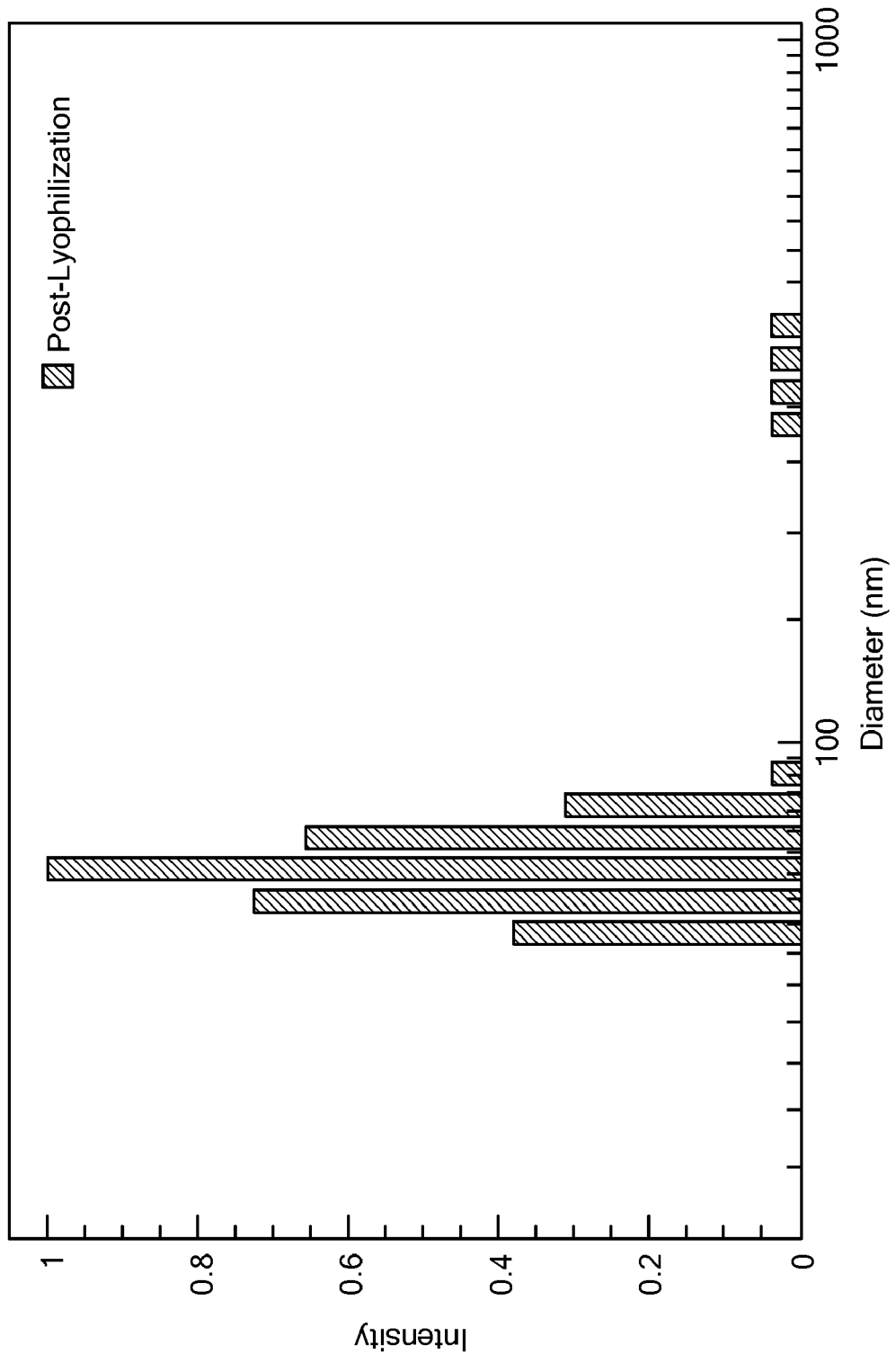
FIG. 2 depicts the results of dynamic light scattering on an exemplary iron oxide nanoparticle-loaded micelle after lyophilization and reconstitution in deionized water.

A solution of 4 nm $Fe_3O_4$ nanoparticles (2.5 mg) and mPEG-PAsp-(PAsp-co-DBzGlu)-Ac (25 mg) dissolved in $CHCl_3$ (1 mL) was added dropwise to a vortexing flask containing water (20 mL). The mixture was vortexed until a homogenous solution was formed. The homogenous solution was analyzed by dynamic light scattering (FIG. 1) then lyophilized and the dry powder was stored at 4° C. A small portion of the powder (5 mg) was reconstituted in water and again analyzed by dynamic light scattering (FIG. 2). Diameter=60+/−8.8 nm pre-lyophilization, 65+/−9.7 nm post-lyophilization.

Example 6

Figure 3:
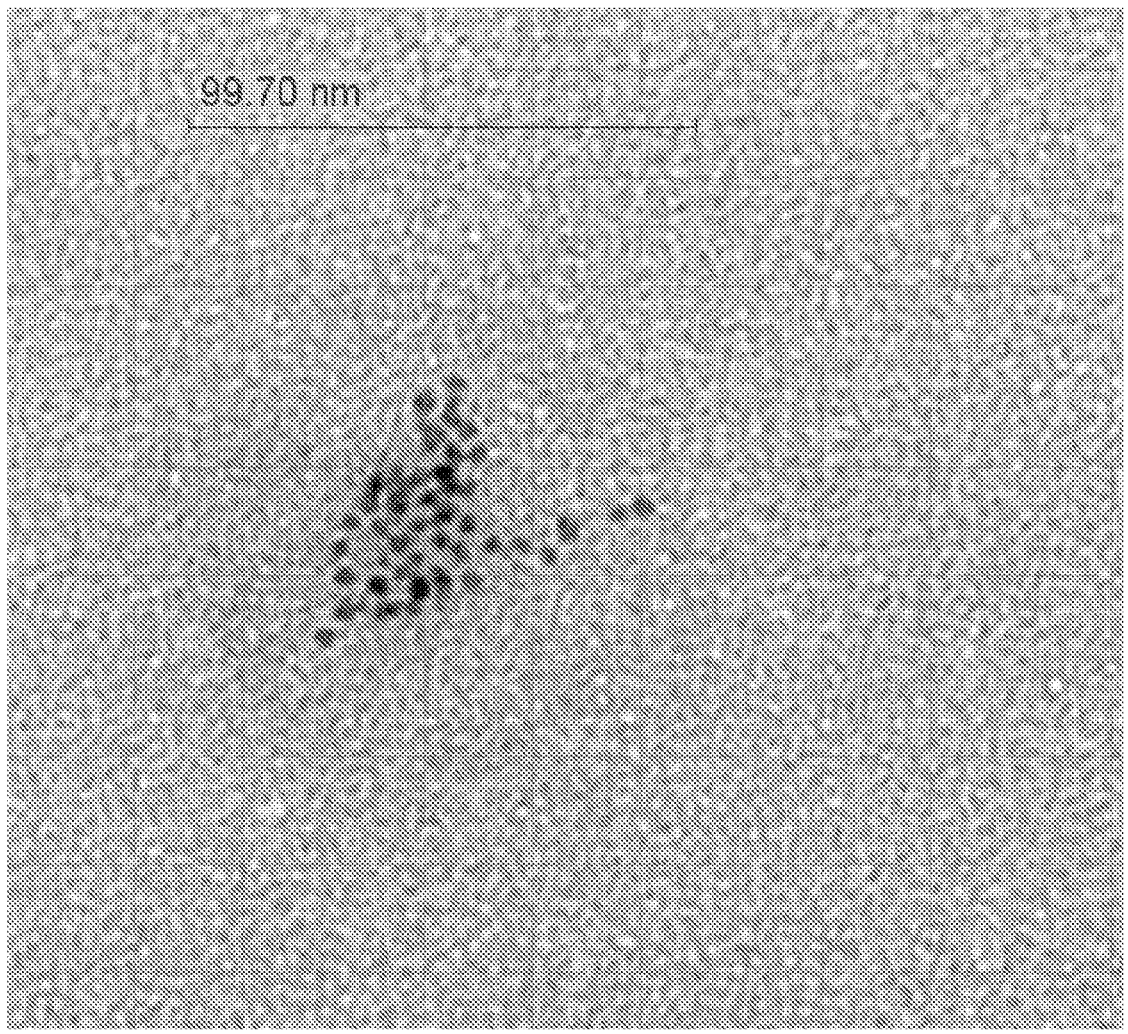
FIG. 3 depicts the 100 kV transmission electron microscope image of an exemplary iron oxide nanoparticle-loaded micelle following drying.

A portion of the iron oxide encapsulated nanoparticles (Example 5, 5 mg) were reconstituted in water (0.5 mL). One drop was added to a carbon-coated, 400 Mesh copper TEM grid. The encapusalted nanoparticles were then imaged on a 100 kV transmission electron microscope (FIG. 3).

Example 7

Figure 4:
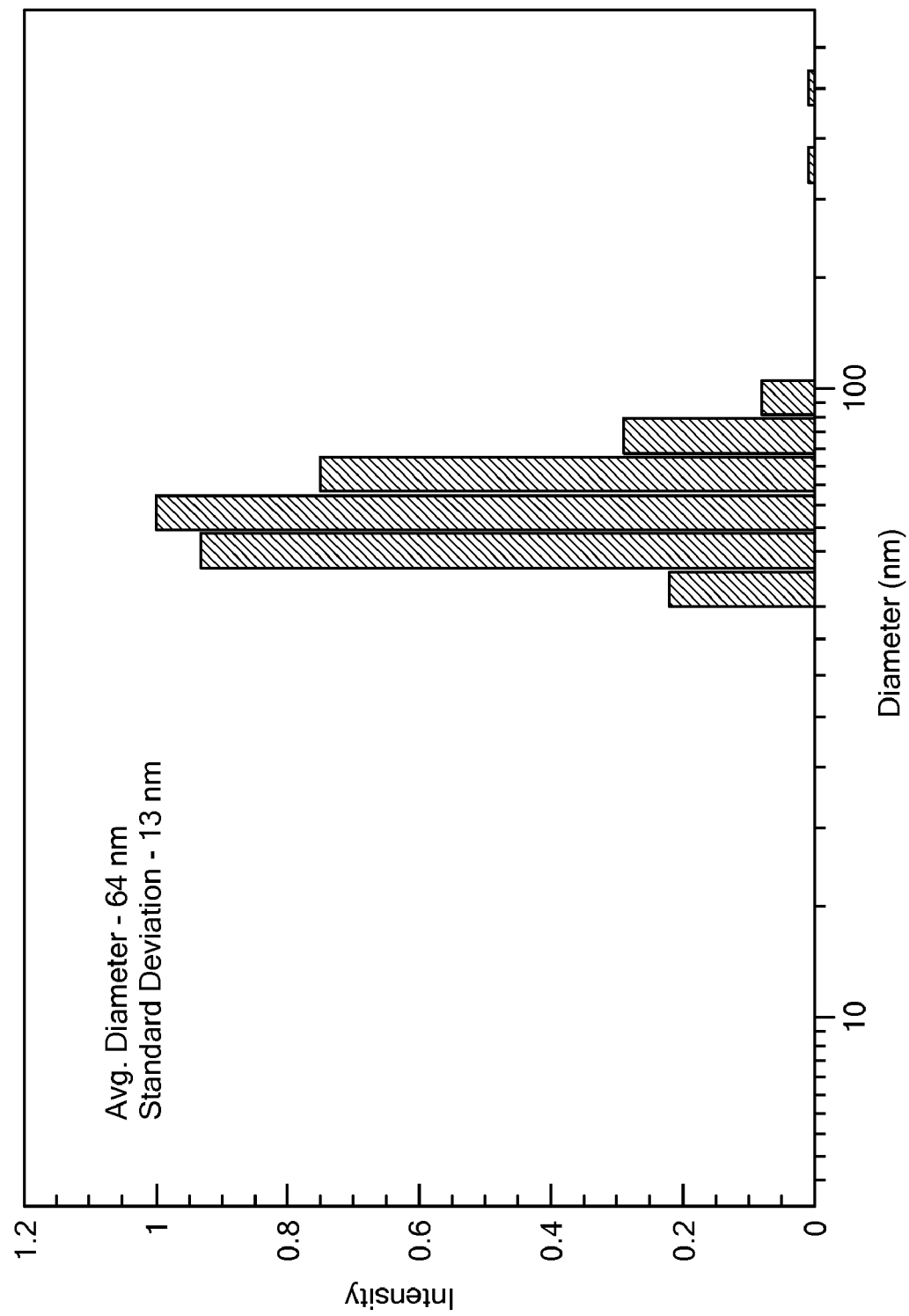
FIG. 4 depicts the results of dynamic light scattering on an exemplary iron oxide nanoparticle-loaded micelle in deionized water.

A solution consisting of 4 nm $Fe_3O_4$ nanoparticles (6.35 mg) and mPEG-PAsp-(PAsp-co-PBLG)-Ac (63.5 mg) dissolved in $CHCl_3$ (1 mL) was added dropwise to a vortexing flask containing water (12.5 mL). The mixture was vortexed until a homogenous solution was formed. An aqueous solution of zinc chloride (0.1 M, 12.5 μL) was added and vortexing was continued for 5 minutes, followed by 30 minutes of sonication. The pH of the solution was then adjusted to 7.8 with dilute aqueous sodium hydroxide. The solution was lyophilized and the dry powder was stored at 4° C. A small portion of the powder (5 mg) was reconstituted in water (1 mL) and analyzed by dynamic light scattering (FIG. 4). Diameter=64+/−13 nm.

Example 8

Figure 5:
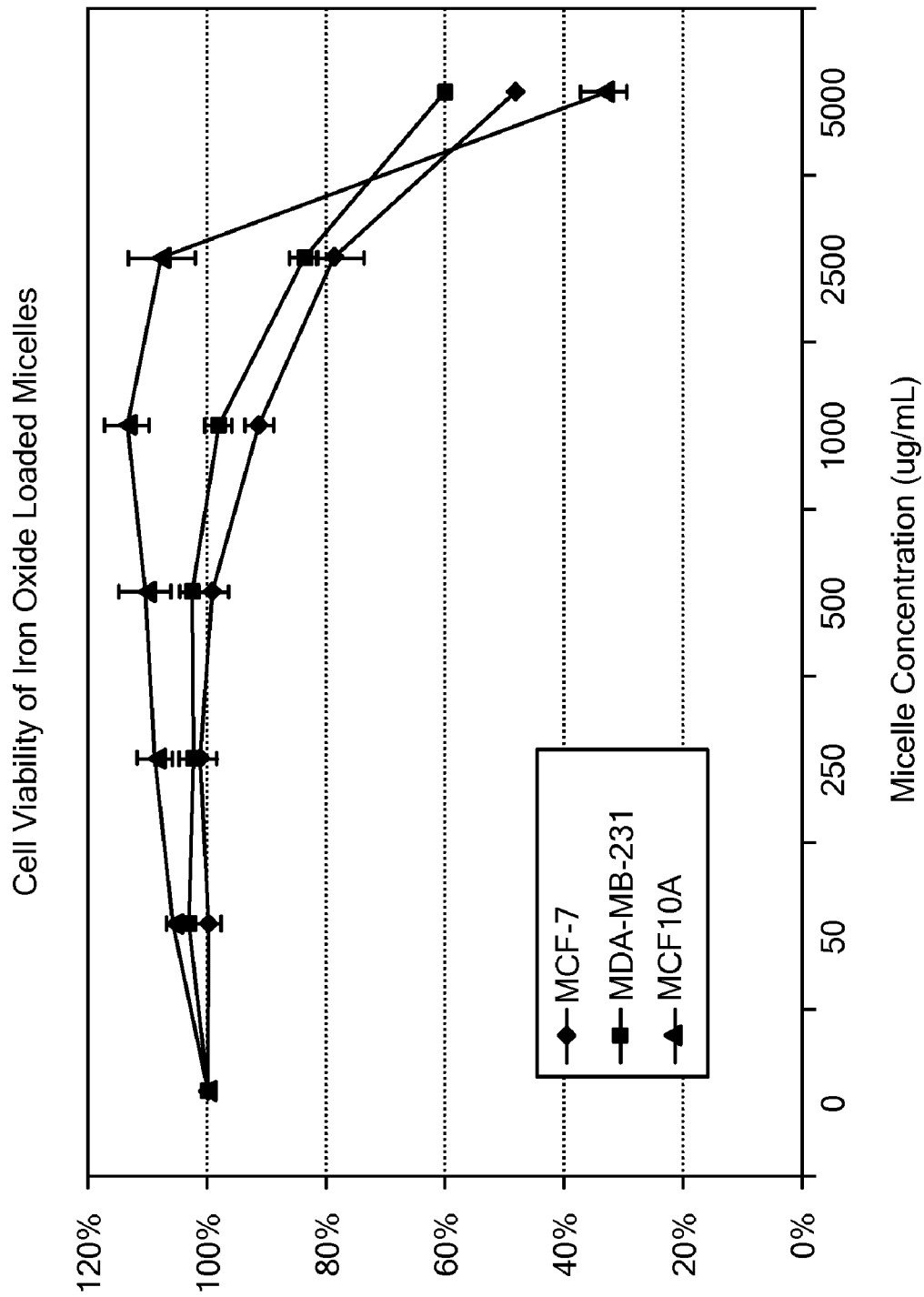
FIG. 5 depicts the results of a cell viability assay performed on an exemplary iron oxide nanoparticle-loaded micelle.

Iron Oxide micelle cytotoxicity assay: $1.5 \times 10^4$ MCF-7, $1.5 \times 10^4$ MDA-MB-231, or $3 \times 10^3$ MCF10A cells were plated in 96 well-plates. Twenty-four hours later, growth media was replaced with 0, 50, 250, 500, 1000, 2500, or 5000 μg/mL of iron oxide-loaded micelles. After incubation at 37 degrees Celsius for 72 h, cell viability was determined using Cell-Titer Glo reagent. Experiments were performed in triplicate and are shown in FIG. 5.

Example 9

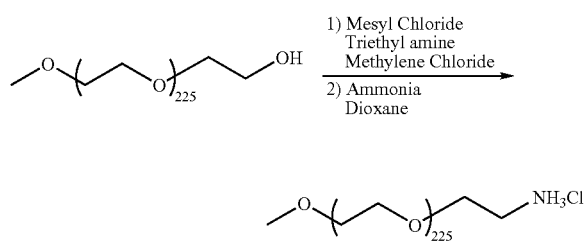

To a 2 L 2-neck round bottom flask was added mPEG (180 g, 15 mmol) and anhydrous methylene chloride (1 L). Once a homogeneous solution was present, methane sulfonyl chloride (2.3 mL, 30 mmol) was added, followed by triethyl amine (4.2 mL, 30 mmol) and the solution stirred for 16 h at room temperature. The solvent was evaporated and the residue purified by solid phase extraction (3% MeOH in $CHCl_3$ (2 L) followed by 10% MeOH in $CHCl_3$ (3 L) which contained the polymer product). The solvent was removed and the resulting liquid dissolved in ammonia in methanol (7M, 600 mL). The solution was stirred at 60° C. for 48 h and allowed to cool. The solution was concentrated and redissolved in brine/0.1N HCl solution. The aqueous phase was washed with ether (1 L), then the polymer product extracted with $CHCl_3$ (4×1 L). The combined organic layers were dried over $MgSO_4$, filtered and the solvent evaporated. The resulting liquid was diluted with a minimal amount of methanol and precipitated in to diethyl ether. A white powder (110 g, 69%) was isolated following filtration. $^1$H NMR (400 MHz, DMSO-d6, δ) 7.84 br-s, 3.7-3.3 br-m, 2.97 t. GPC (DMF, PEG standards) Mn=10,600; PDI=1.06.

Example 10

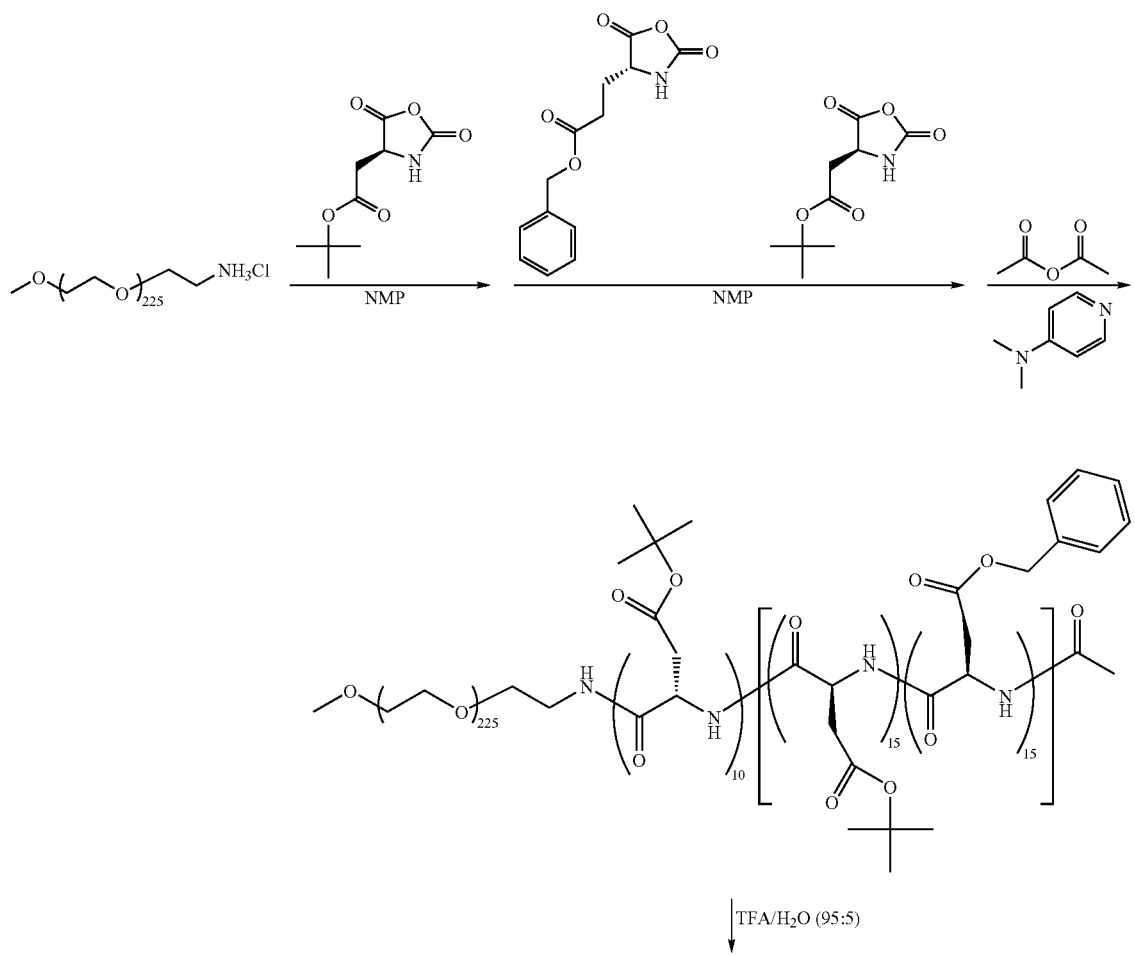

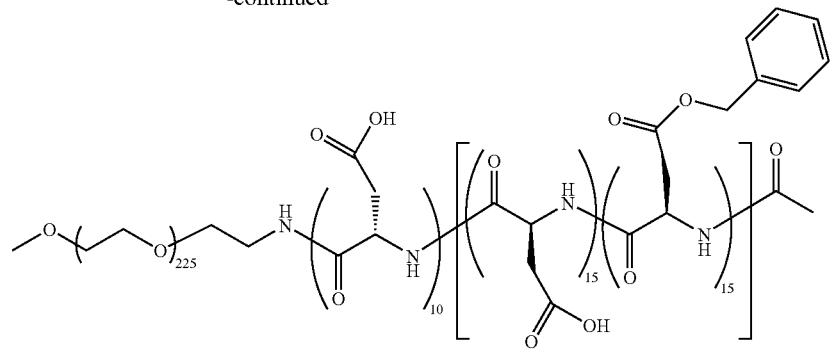

mPEG$_{227}$-b-(PAsp)$_{10}$-b-(PAsp$_{15}$-co-PLBzAsp$_{15}$)-Ac To a 100 mL round bottom flask was added mPEG-hydrochloride (1.0 g, 0.13 mmol) and t-butyl aspartic acid NCA (0.28 g, 1.3 mmol). The reagents were dried under vacuum for 1 hour, then NMP (10 mL) added. The solution was degassed under vacuum the backfilled with N$_2$, and stirred at 80° C. After 48 h, d-benzyl aspartate NCA (0.48 g, 1.95 mmol) and t-butyl aspartic acid NCA (0.41 g, 1.95 mmol) was dissolved in NMP (5 mL) and added to the reaction. After an additional 48 h, the solution was allowed to cool, then DMAP (0.16 g, 1.3 mmol) and acetic anhydride (0.13 g, 1.3 mmol) added to the stirred solution. After 1 hour, the solution was precipitated into diethyl ether/hexanes (3:2, 300 mL). A white solid was recovered after filtration, which was dissolved in TFA/H$_2$O (95:5, 40 mL) and stirred for 4 hours at room temperature. The solvent was evaporated and the residue precipitated into ether (300 mL). A white powder (0.75 g, 54% yield) was recovered following filtration. $^1$H NMR (400 MHz, DMSO-d$_6$, δ) 12.38, 8.26, 7.97, 7.54, 7.34, 6.92, 5.08, 4.53, 4.28, 3.7-3.3, 3.19, 2.32, 2.05, 1.84.

Example 11

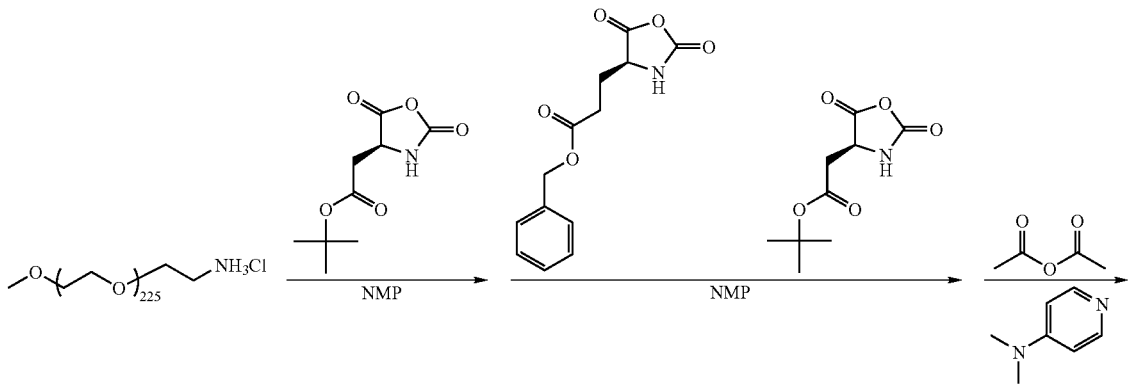

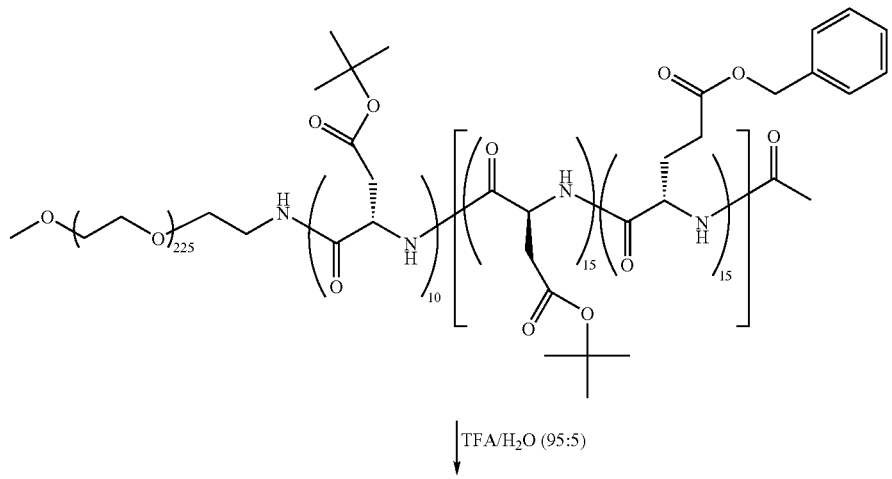

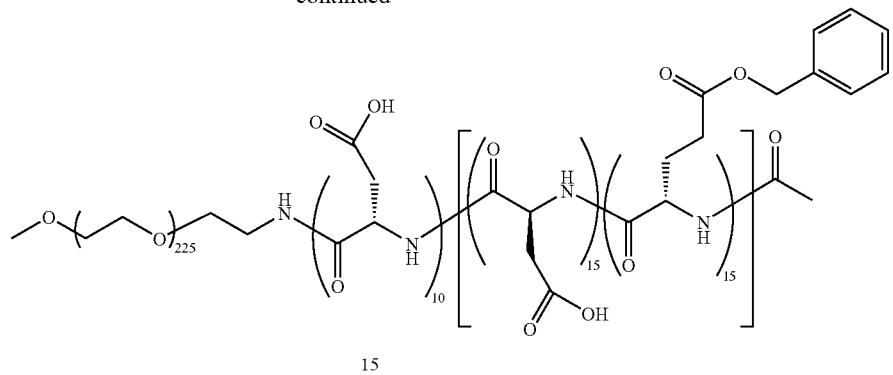

mPEG$_{227}$-b-(PAsp)$_{10}$-b-(PAsp$_{15}$-co-PBzGlu$_{15}$)-Ac To a 100 mL round bottom flask was added mPEG-hydrochloride (1.0 g, 0.13 mmol) and t-butyl aspartic acid NCA (0.28 g, 1.3 mmol). The reagents were dried under vacuum for 1 hour, then NMP (10 mL) added. The solution was degassed under vacuum the backfilled with N$_2$, and stirred at 80° C. After 48 h, benzyl glutamate NCA (0.52 g, 1.95 mmol) and t-butyl aspartic acid NCA (0.41 g, 1.95 mmol) was dissolved in NMP (5 mL) and added to the reaction. After an additional 48 h, the solution was allowed to cool, then DMAP (0.16 g, 1.3 mmol) and acetic anhydride (0.13 g, 1.3 mmol) added to the stirred solution. After 1 hour, the solution was precipitated into diethyl ether/hexanes (3:2, 300 mL). A white solid was recovered after filtration, which was dissolved in TFA/H$_2$O (95:5, 40 mL) and stirred for 4 hours at room temperature. The solvent was evaporated and the residue precipitated into ether (300 mL). A white powder (0.9 g, 58% yield) was recovered following filtration. $^1$H NMR (400 MHz, DMSO-d$_6$, δ) 12.38, 8.25, 7.97, 7.54, 7.34, 6.93, 5.11, 4.52, 4.27, 3.7-3.3, 3.19, 2.66, 2.32, 1.99, 1.80.

Example 12

HS-2-165 mPEG$_{227}$-b-(PAsp)$_{10}$-b-(PAsp$_{15}$-co-PLBzAsp$_{15}$)-Ac (0.5 g) and 11 nm MnFe$_2$O$_4$ nanoparticles (56.4 mg in 2 mL hexanes) were dissolved in 5 mL CH$_2$Cl$_2$. The homogenous CH$_2$Cl$_2$ solution was added dropwise to a vortexing flask filled with 100 mL of water. The flask was vortexed for 10 minutes until no odor could be detected and the solution became homogenous. The solution was filtered through a 0.22 micron filter. A brown/black solid was obtained after the sample was lyophilzed.

Example 13

HS-2-166 mPEG$_{227}$-b-(PAsp)$_{10}$-b-(PAsp$_{15}$-co-PLBzAsp$_{15}$)-Ac (0.5 g) and 15 nm MnFe$_2$O$_4$ nanoparticles (56.4 mg in 2 mL hexanes) were dissolved in 5 mL CH$_2$Cl$_2$. The homogenous CH$_2$Cl$_2$ solution was added dropwise to a vortexing flask filled with 100 mL of water. The flask was vortexed for 10 minutes until no odor could be detected and the solution became homogenous. The solution was filtered through a 0.22 micron filter. A brown/black solid was obtained after the sample was lyophilzed.

Example 14

HS-2-113 mPEG$_{227}$-b-(PAsp)$_{10}$-b-(PAsp$_{15}$-co-PBzGlu$_{15}$)-Ac (0.5 g) and 4 nm Fe$_3$O$_4$ nanoparticles (50.0 mg) were dissolved in 8.78 mL CH$_2$Cl$_2$. The homogenous CH$_2$Cl$_2$ solution was added dropwise to a vortexing flask filled with 100 mL of water. The flask was vortexed for 10 minutes until no odor could be detected and the solution became homogenous. The solution was filtered through a 0.22 micron filter. A brown/black solid was obtained after the sample was lyophilzed.

Example 15

HS-2-177 mPEG$_{227}$-b-(PAsp)$_{10}$-b-(PAsp$_{15}$-co-PLBzAsp$_{15}$)-Ac (3.5 g) and 15 nm MnFe$_2$O$_4$ nanoparticles (875 mg in 20 mL of a 2/1 solution of hexanes/CH$_2$Cl$_2$) were dissolved in 30 mL CH$_2$Cl$_2$. The homogenous CH$_2$Cl$_2$ solution was added dropwise to a stirring beaker filled with 700 mL of water. The beaker was stirred at 1700 rpm for 60 minutes until no odor could be detected and the solution became homogenous. The solution was filtered through a 0.22 micron filter. A brown/black solid was obtained after the sample was lyophilzed.

Example 16

The focus of this study was to measure the R1 and R2 relativities of HS-2-113 as a function of concentration using MRI. HS-2-113 was determined to have R1 relaxivity of 0.012 s−1 mmol Fe-1, and an R2 relaxivity of 14.1 s−1 mmol Fe-1. The R1, and R2 relaxivities are lower than that of Feridex (0.68 s−1 mmol Fe-1, and 100 s$^{-1}$ mol Fe-1 respectively), based on MIR historical data.

HS-2-113 was serially diluted with sterile saline for relaxivity imaging in 1/10, 1/50, 1/200, 1/1000, and 1/5000, dilutions with water. Test dilutions were contained in 0.2 ml Eppendorf tubes.

Imaging

Each set of diluted sample tubes was arranged such that all the tubes could be imaged simultaneously. A tube of sterile water was also included to use as a benchmark for minimal relaxivity. The tubes were imaged using the following scans and scan parameters:

| MRI scans used, with associated variable parameters | | |
|---|---|---|
| Relaxivity Type | Image Scan Type | Variable Parameters |
| R1 | Spin-echo | Repetition Time (TR) = 0.1, 0.2, 0.4, 0.7, 1, 2, 5, 7.5, 10, 15, 20 s |
| R2 | Spin-echo | Echo time (TE) = 8.4, 10, 12.5, 15, 20, 25, 30, 40, 50, 75, 150, 300, 600 ms |

For the R1 measurements, an echo time of 8 ms was used, and for the R2 measurements, a repetition time of 2 s was used. All images were acquired using three 1.5 mm thick transaxial slices through the tubes. The images were manually segmented by defining regions-of-interest (ROIs) for each tube in each slice of each image, and calculating the signal intensity time courses for each tube, averaged over all three slices.

The R2 data were then fitted to a decaying exponential to calculate R2:

$$S=S0*\exp(-R2*t)+C$$

where S=signal intensity, t=time, S0=signal intensity for t=0, C=constant (offset).

The R1 data were fitted to an exponential recovery:

$$S=S_{eq}*(1-\exp(-R1*t))+C$$

where S=signal intensity, $S_{eq}$=asymptotic signal value, t=time, C=constant (offset).

All fitting was performed using the Sigmaplot mathematical package. R1 and R2 relaxivity were then calculated as a function of Fe concentration by performing a linear regression over the relaxivity (R1 or R2) vs. concentration curve, and expressed in the standard units of s-1 mmol $Fe^{-1}$. Historical data for the FDA approved Fe-based contrast agent, Feridex, was used as a relaxivity benchmark.

Figure 6:
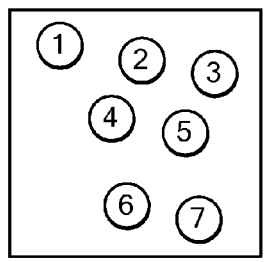
FIG. 6 depicts individual images showing signal increase with repetition time for R1 determination for HS-2-113.
Figure 6:
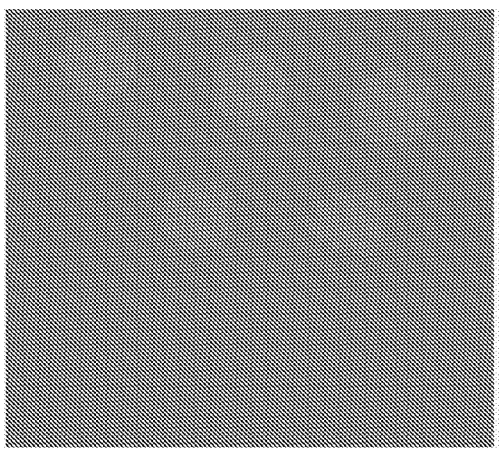
Figure 6:
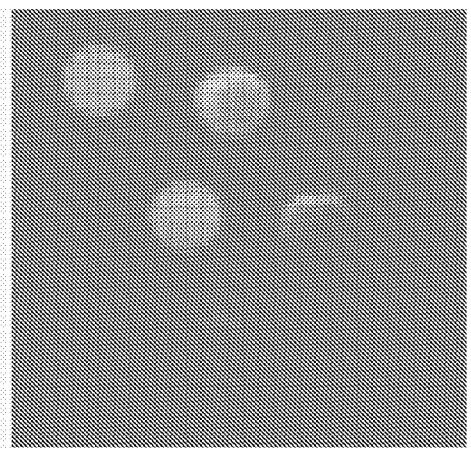
Figure 6:
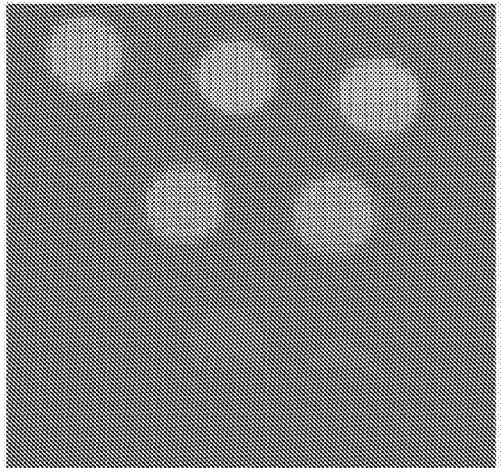
Figure 6:
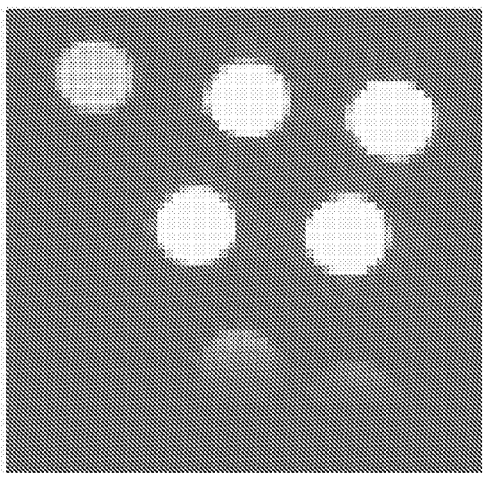
Figure 7:
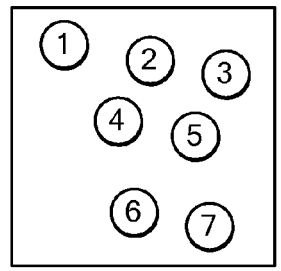
FIG. 7 depicts individual images showing decrease with echo time for R2 determinations for HS-2-113.
Figure 7:
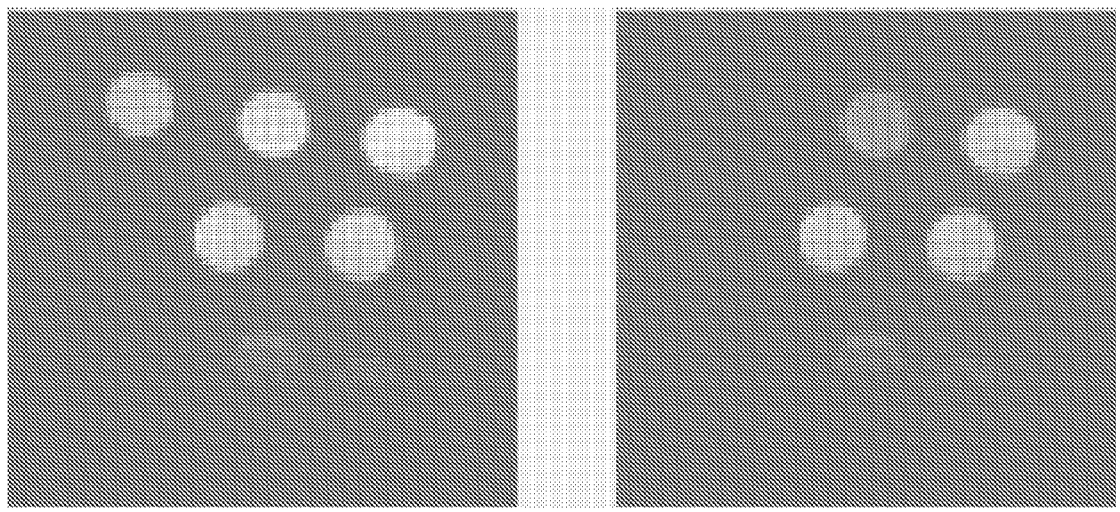
Figure 7:
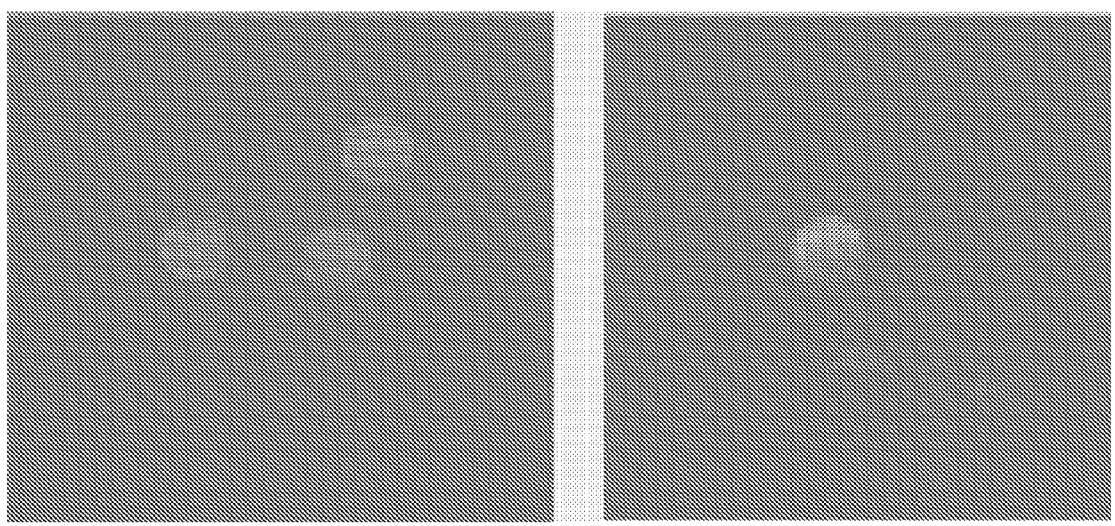
Figure 8:
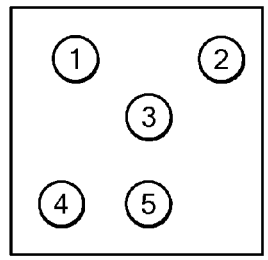
FIG. 8 depicts individual images showing signal increase with repetition time for R1 determination for HS-2-165.
Figure 8:
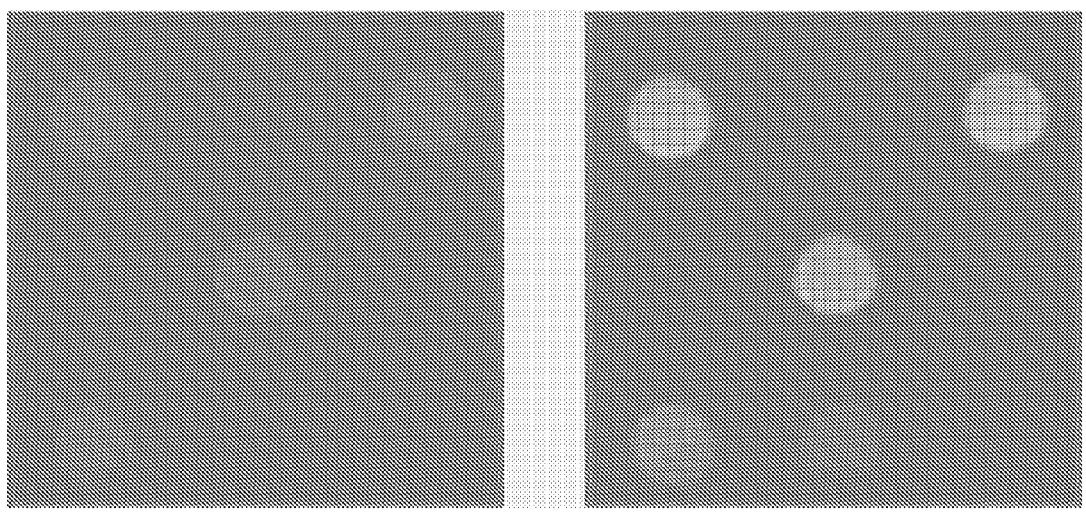
Figure 8:
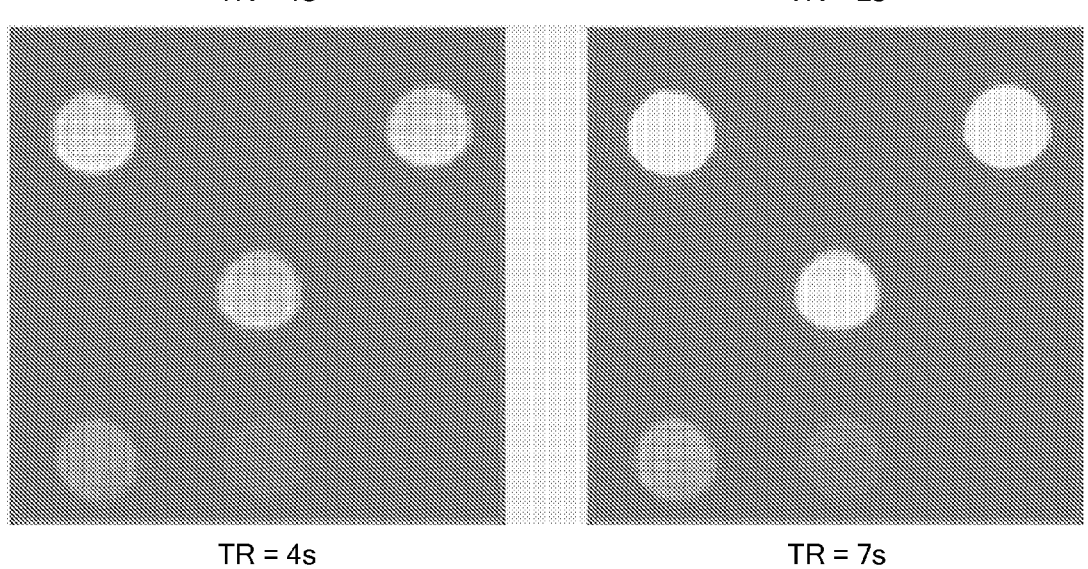
Figure 9:
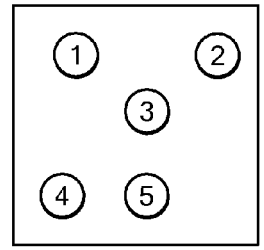
FIG. 9 depicts individual images showing signal increase with repetition time for R1 determination for HS-2-166.
Figure 9:
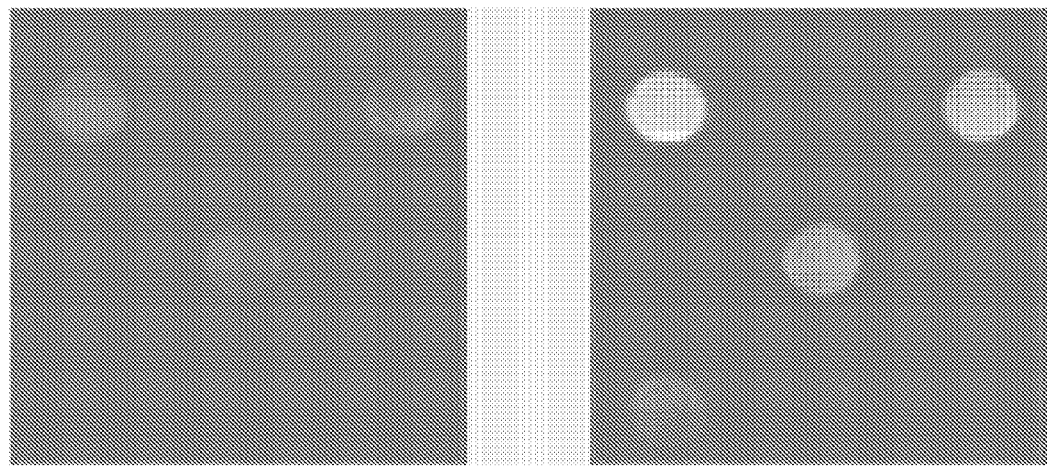
Figure 9:
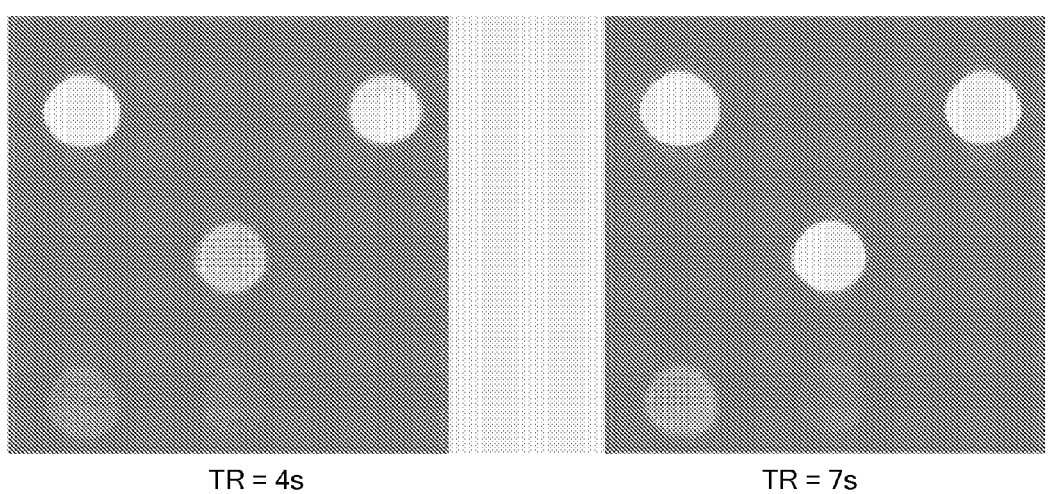
Figure 10:
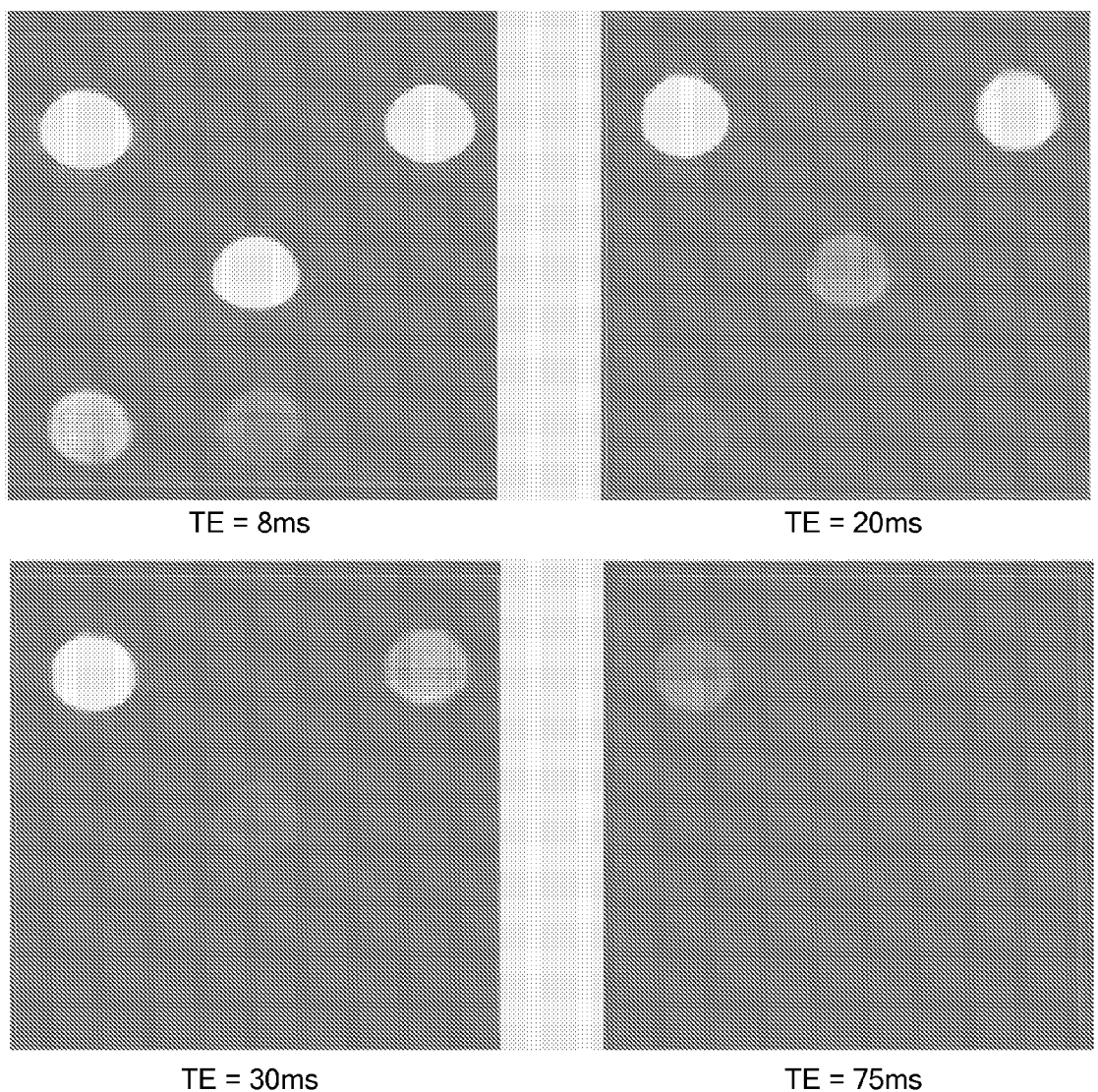
FIG. 10 depicts individual images showing decrease with echo time for R2 determinations for HS-2-165.
Figure 11:
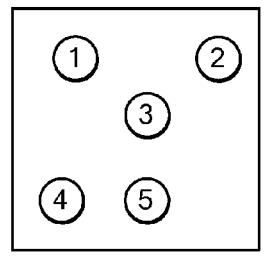
FIG. 11 depicts individual images showing decrease with echo time for R2 determinations for HS-2-166.
Figure 11:
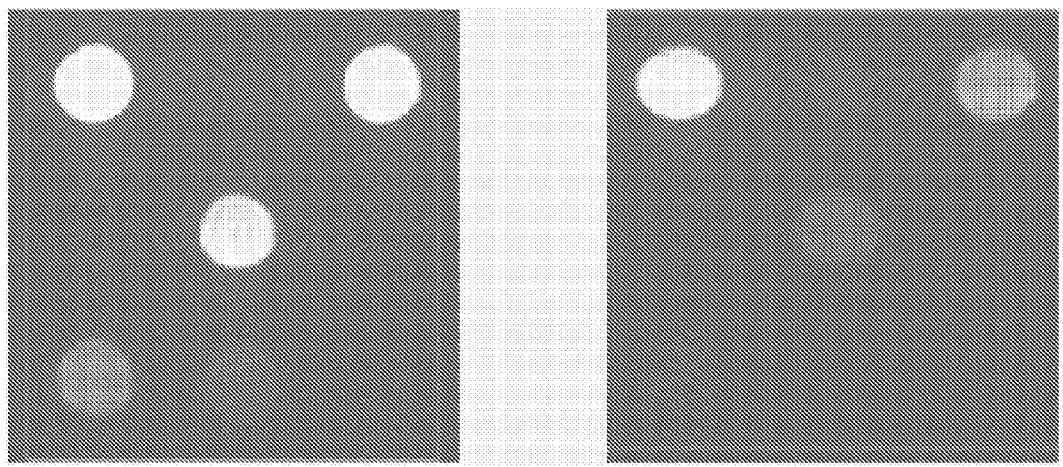
Figure 11:
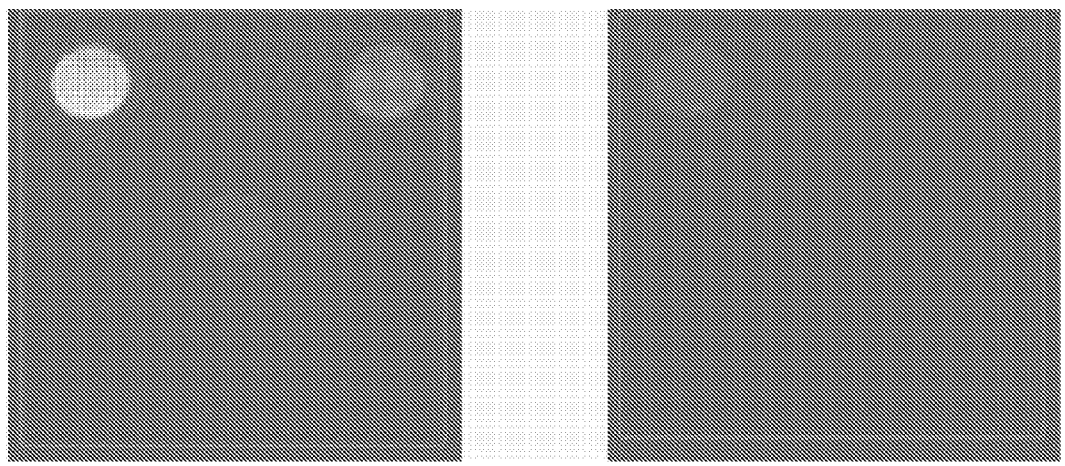

Individual images showing signal decrease with echo time (for R2 determinations) and signal increase with repetition time (for R1 determination) are displayed in FIG. 6 and FIG. 7. The calculated relaxivities for the dilutions used are shown in Table 9 below.

TABLE 9

Calculated relaxivities for each dilution of HS-2-113 and water

| Dilution | R1 (s$^{-1}$) | R2 (s$^{-1}$) |
|---|---|---|
| 1/10 | 0.244 | 77.3 |
| 1/50 | 0.244 | 17.8 |
| 1/200 | 0.202 | 5.9 |
| 1/500 | 0.179 | 2.9 |
| 1/1000 | 0.187 | 1.1 |
| 1/5000 | 0.192 | 3.6 |
| Water | 0.152 | 0.9 |

Table 10, below, shows the linear correlations between relaxivity and concentration for HS-2-113 and Feridex, for R1 and R2. Linear regressions on these curves provided quantification.

TABLE 10

Concentration-dependent relaxivity comparisons between HS-2-113 and Feridex

| Relaxivity Parameter | HS-2-113 | Feridex |
|---|---|---|
| R1 (s$^{-1}$ mmol Fe$^{-1}$) | 0.012 | 0.68 |
| R2 (s$^{-1}$ mmol Fe$^{-1}$) | 14.1 | 100 |

The measured relaxivity values show that R1 for HS-2-113 was significantly less than that of Feridex, while R2 was about one seventh that of Feridex. While HS-2-113 has lower relaxivity than Feridex, the R2 relaxivity is estimated to be in the range required to obtain in vivo contrast. The lower R1 relaxivity compared with that of Feridex is favorable for a negative contrast agent as it reduces the potential for R1-mediated positive contrast effects which could offset and reduce the overall negative contrast induced by the agent.

Example 17

The focus of this study was to measure the R1 and R2 relaxivities of HS-2-165 and HS-2-166 as a function of concentration using MRI.

HS-2-165 was determined to have R1 relaxivity of 0.038 s−1 mmol $Fe^{-1}$, and R2 relaxivity of 31 s−1 mmol $Fe^{-1}$. The R1 and R2 relaxivities are lower than that of Feridex (0.68 s$^{-1}$ mmol $Fe^{-1}$, and 100 s−1 mmol $Fe^{-1}$ respectively), based on MIR historical data.

HS-2-166 was determined to have R1 relaxivity of 0.017s$^{-1}$ mmol $Fe^{-1}$, and an R2 relaxivity of 156 s$^{-1}$ mmol $Fe^{-1}$. For HS-2-166, the R1 relaxivity was found to be lower than that of Feridex (0.68 s$^{-1}$ mmol $Fe^{-1}$), and the R2 relaxivity was found to be higher than that of Feridex (100 s$^{-1}$ mmol $Fe^{-1}$).

HS-2-165 and HS-2-166 were serially diluted with sterile saline for relaxivity imaging, beginning with a 15 mg/ml solution (top concentration, TC), then diluting to obtain additional 0.1×TC, 0.067×TC, 0.04×TC, and 0.02×TC dilutions. Test dilutions were contained in 0.2 ml Eppendorf tubes.

Imaging

Each set of diluted sample tubes was arranged such that all the tubes could be imaged simultaneously. A tube of sterile water was also included to use as a benchmark for minimal relaxivity. The tubes were imaged using the following scans and scan parameters set forth in Table 11, below:

TABLE 11

MRI Scans Used with Associated Variable Parameters

| Relaxivity Type | Image Scan Type | Variable Parameters |
|---|---|---|
| R1 | Spin-echo | Repetition Time (TR) = 0.1, 0.2, 0.4, 0.7, 1, 2, 5, 7.5, 10, 15, 20 s |
| R2 | Spin-echo | Echo time (TE) = 8.4, 10, 12.5, 15, 20, 25, 30, 40, 50, 75, 150, 300, 600 ms |

For the R1 measurements, an echo time of 8 ms was used, and for the R2 measurements, a repetition time of 2s was used. All images were acquired using three 1.5 mm thick transaxial slices through the tubes. The images were manually segmented by defining regions-of-interest (ROIs) for each tube in each slice of each image, and calculating the signal intensity time courses for each tube, averaged over all three slices.

The R2 data were then fitted to a decaying exponential to calculate R2:

$$S=S0*\exp(-R2*t)+C$$

where S=signal intensity, t=time, S0=signal intensity for t=0, C=constant (offset).

The R1 data were fitted to an exponential recovery:

$$S=S_{eq}*(1-\exp(-R1*t))+C$$

where S=signal intensity, $S_{eq}$=asymptotic signal value, t=time, C=constant (offset).

All fitting was performed using the Sigmaplot mathematical package. R1 and R2 relaxivity were then calculated as a function of Fe concentration by performing a linear regression over the relaxivity (R1 or R2) vs. concentration curve, and expressed in the standard units of s-1 mmol $Fe^{-1}$. Historical data for the FDA approved Fe-based contrast agent, Feridex, was used as a relaxivity benchmark.

Results

Individual images showing signal decrease with echo time (for R2 determinations) and signal increase with repetition time (for R1 determination) for HS-2-165 and HS-2-166 are displayed in FIGS. 8-11. The calculated relaxivities for the dilutions used are shown in Table 12, below.

TABLE 12

Calculated Relaxivities for Each Dilution of HS-2-165 and HS-2-166

| Concentration Relative to Top Concentration (15 mg/ml) | R1 (s$^{-1}$) HS-2-165 | R2 (s$^{-1}$) HS-2-165 | R1 (s$^{-1}$) HS-2-166 | R2 (s$^{-1}$) HS-2-166 |
|---|---|---|---|---|
| 0.01x | 0.267 | 31 | 0.349 | 258 |
| 0.02x | 0.267 | 63 | 0.373 | 442 |
| 0.04x | 0.346 | 120 | 0.414 | 698 |
| 0.067x | 0.420 | 190 | 0.453 | 1011 |
| 0.1x | 0.592 | 308 | 0.462 | 1294 |

Table 13, below, shows the linear correlations between relaxivity and concentration for HS-2-165 and HS-2-166 and Feridex, for R1 and R2. Linear regressions on these curves provided quantification of the relaxivity for HS-2-165 and HS-2-166, compared with Feridex in the standard units of s$^{-1}$ mmol Fe$^{-1}$.

TABLE 13

Concentration-Dependent Relaxivity Comparisons: HS-2-165, HS-2-166, and Feridex

| Relaxivity Parameter | HS-2-165 | HS-2-166 | Feridex |
|---|---|---|---|
| R1 (s$^{-1}$ mmol Fe$^{-1}$) | 0.038 | 0.017 | 0.68 |
| R2 (s$^{-1}$ mmol Fe$^{-1}$) | 31 | 156 | 100 |

The measured relaxivity values show that R1 for HS-2-165 was significantly less than that of Feridex, while R2 was about one third that of Feridex. R1 for HS-2-166 was significantly less than that of Feridex, while the R2 value was about 50% higher than that of Feridex. While HS-2-165 has lower R2 than Feridex, the R2 relaxivity is estimated to be in the range required to obtain in vivo contrast given a tolerated dosage of approximately 400 mg/kg. The R2 relaxivity for HS-2-166 suggests that it would provide greater in vivo contrast than HS-2-165 at a similar dosage level. The lower R1 relaxivity for both particles compared with that of Feridex is favorable for a negative contrast agent as this reduces the potential for R1-mediated positive contrast effects which could offset and reduce the overall negative contrast induced by the agent.

Example 18

The purpose of this study was to determine the maximum tolerated dose for the contrast agent HS-2-113. HS-2-113 was well tolerated at the single, maximal dosage tested in Fischer 344 rats.

The test compound, HS-2-113, was obtained as a powder and stored at room temperature in a cool dry cabinet protected from light. It was first formulated in saline at a concentration of 100 mg/ml. The concentration was slowly increased to a final concentration of 164.6 mg/ml. It was observed that the powder did not dissolve immediately when added to saline, but did dissolve after several hours, without vortexing, sonication or heat. The dosing solution was made on Day 1 of treatment. All dosage levels in this report are expressed in terms of parent compound.

Animals and Husbandry

Female Fischer 344 rats were obtained from Harlan. They were 6 weeks old on Day 1 of the experiment. The animals were fed irradiated Rodent Diet 5053 (LabDiet™) and water ad libitum. Rats were housed in Thoren™ microisolator caging with Bed-O'Cobs™ bedding. All treatments, body weight determinations, and tumor measurements were carried out in laminar down flow cabinets. All procedures carried out in this experiment were conducted in compliance with all the laws, regulations and guidelines of the National Institutes of Health (NIH).

Treatment was administered on Day 1, after the animals were housed and their body weights measured. All animals weighed ≧134.8 g at the initiation of therapy. Mean group body weights at treatment were well matched (range, 135.6-140.2 g). All animals were dosed according to individual body weight on the day of treatment (0.2 ml/20g). The HS-2-113 solution was administered via slow injection (over 3 minutes).

Assessment of Side Effects

All animals were observed for one hour following the dose for signs of acute toxicity. Throughout the study, all animals were observed for clinical signs at least once daily. Animals were weighed on the day of treatment and twice weekly thereafter. Individual body weights were recorded twice weekly. Treatment-related weight loss in excess of 20% is generally considered unacceptably toxic. In this report, a dosage level is described as tolerated if treatment-related weight loss (during and two weeks after treatment) is <20% and mortality during this period in the absence of potentially lethal tumor burdens is ≦10%.

Dosing and Toxicity

The treated animals in this study showed no signs of toxicity from the treatments. The animals in the Treatment Group experienced no weight loss; however, their weight gain was slightly slower than that of the Untreated Group. Given the small group sizes (n=3), this difference is not thought to be significant. Animal 2 of the Treatment Group displayed slight discoloration of the tail. This occurred one week after treatment and remained until the end of treatment, and was likely due to leakage of the agent from the tail vein into the subdermal space.

HS-2-113 was well tolerated at the dosage level tested. The only unusual occurrence was discoloration of the tail in one treated animal. This discoloration was closely monitored and although it did not disappear, it also did not get any worse. This animal survived through the duration of the experiment and did not show any other adverse clinical signs.

Example 19

HS-2-177 was well tolerated at 150 mg/ml and showed significant in vivo contrast enhancement in the 9L intracranial glioma rat model for all three animals studied.

HS-2-177 is an iron-oxide based nanoparticle that is under development as an MRI contrast agent. The current study was designed to verify a tolerated dose in vivo, and to test in vivo contrast enhancement of a newly synthesized nanoparticle, HS-2-177, in the 9L orthotopic rat brain tumor model.

Animals and Husbandry

Intracranial 9L tumors were implanted in male Fischer 344 rats weighing between 125 and 150 g. 9L cells (105) were implanted in the right forebrain at a depth of 3 mm through a 1 mm burr hole on Day 0. The surgical field was cleaned with 70% ethanol and the burr hole was filled with bone wax to prevent extracranial extension of the tumor. Animals were imaged using MRI beginning at 15 days post cell implantation to select tumors for in vivo nanoparticle (NP) studies. A total of 3 animals were selected for the study from 5 that were implanted. The animals imaged in this study had tumors in the range 40-89 µl in volume.

Nanoparticle Preparation and Administration

HS-2-177 was supplied as a powder, and formulated in saline at a concentration of 150 mg/ml to create a fine, opaque black suspension ready for injection. Tolerance of IV injection of HS-2-177 at 10 ml/kg using the 150 mg/ml formulation was initially tested in a triage rat (Fischer 344) from the tumor pool, but further testing could not be done as the remaining triage animals had succumbed to tumor burden at the time of injection. HS-2-177 was therefore tested in one additional Female Dark Agouti rat that was available. For both animals, HS-2-177 was dosed intravenously over approximately 180 seconds. Animals were observed for acute signs of toxicity for 30 minutes, and then monitored every 15 minutes for a further hour. Additional monitoring of the animals was done over the next 4 days while the imaging was done. Nanoparticle administration began on Day 21. All animals weighed >240 g at the time of administration. HS-2-177 was dosed (10 ml/kg) by tail vein injection of the formulated material. An Angiocath™ Teflon catheter was placed in the tail vein of the animal and flushed with 0.2 ml heparin in saline (10 units/ml). A pre-primed infusion line was connected to the Angiocath™. The HS-2-177 was injected over 30 seconds using a Harvard syringe pump during dynamic MR scanning (see below).

In vivo MRI

After animal preparation and anesthesia induction using 1.5% isoflurane, an anatomical T2-weighted scout image was obtained to locate the tumor using a multi-slice fast spinecho protocol with a 25×25 mm field of view (FOV), 128×128 image matrix, TR=4s, echo spacing=15 ms, and 8 echoes with k-space centered on the 4th echo. To determine the distribution and preliminary pharmacokinetic behavior of HS-2-177, MR images were obtained using T2*-weighted gradient echo MRI. For imaging nanoparticle uptake, gradient echo images were acquired using a 25×25 mm field of view over a 64×64 matrix, in contiguous 1 mm axial slices which covered the entire region of the tumor. Pre-IV bolus scans were obtained with TR=2s/TE=15 ms (referred to as TR2k protocol). During IV injection of the nanoparticle suspension, a dynamic gradient-echo sequence with a time resolution of 10.24 sec (TR=80 ms/TE=7.5 ms) was used to characterize the uptake of the particle into normal tissue and the tumor over 7 minutes. Post-IV-injection TR2k gradient-echo scans were then acquired at approximately 3 hours to examine the rate clearance of HS-2-177.

Measurements and Endpoints

Images were analyzed by measuring signal intensity time courses within manually drawn regions of interest (ROIs) in vessel, normal brain, and tumor. Relative concentration of the contrast agents is a measure of the relative change in tissue contrast agent concentration over time and can be derived from the tissue signal intensity:

$$\text{Relative concentration} \propto \Delta R_2^* \propto \log(S/S0)/TE$$

where $R_2^*$ (i.e. inverse of $T_2^*$) is the transverse relaxation rate or relaxivity and $\Delta R_2^*$ is the change in $R_2^*$ after injection of the contrast agent, S is signal intensity following administration of the contrast agent, S0 is the initial signal intensity and TE is the echo time. Exponential nanoparticle clearance was assumed and therefore, the extended time courses of relative concentration (nanoparticle washout curves), were fitted to decaying exponentials and half-lives derived for clearance of the nanoparticles from vasculature, contralateral normal brain tissue and tumor tissue.

The contrast-to-noise ratio (CNR) was also determined from the uptake data according to the relation:

$$CNR = [S(\text{brain}) - S(\text{tumor})]/N,$$

where S(brain) and S(tumor) are the average signal intensities of normal brain and tumor, respectively, and N is the average noise signal level. The CNR between normal brain and tumor were calculated at baseline (pre-injection) and maximum (postinjection).

A second parameter used to quantify the level of contrast is the Brain/Tumor Signal ratio defined as:

Brain/Tumor Signal ratio=[signal intensity in contralateral brain tissue]/[signal intensity in tumor].

Results

The 9L rat glioma model was chosen because it provides an excellent model for showing contrast enhancement (through contrast between tumor and normal brain tissue) using MRI, and is especially suited toward proof of principle studies. This study was preceded by the following studies:

1. Tested tolerance of HS-2-113 and showed that a 164.6 mg/ml formulation was well tolerated at the maximal dose volume of 10 ml/kg.

2. Tested in vitro relaxivity of HS-2-113 and determined that the relaxivity of HS-2-113 was approximately 7 times lower than that of Feridex.

3. Tested in vitro relaxivity of HS-2-165 and HS-2-166. It was determined that HS-2-166 had R2 relaxivity approximately 1.5 times greater than that of Feridex, while HS-2-165 R2 relaxivity was approximately 3 times lower than that of Feridex.

Figure 12:
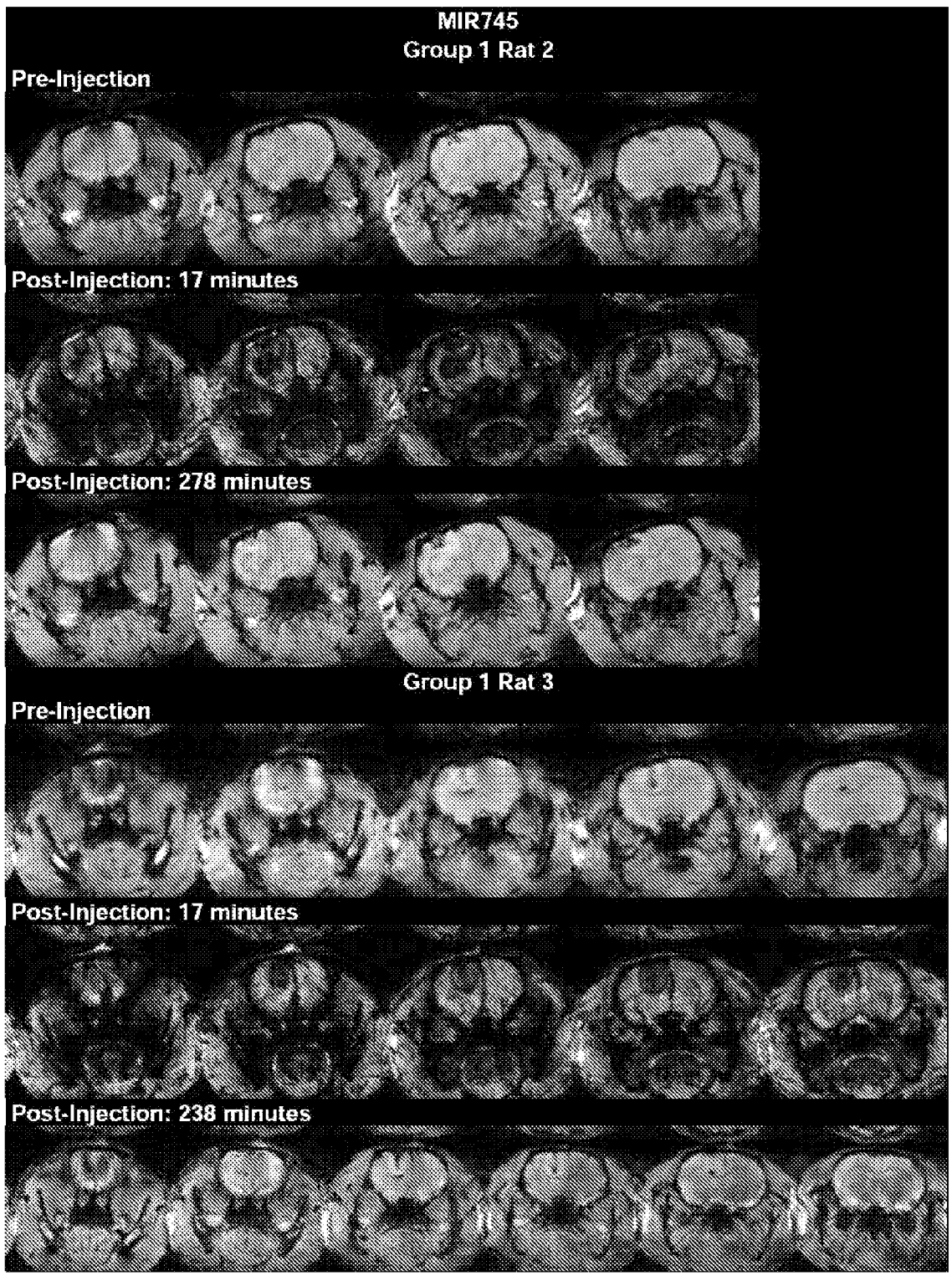
FIG. 12 depicts contrast enhancement in the brains of two animals studied following intravenous administration of HS-2-177.
Figure 13:
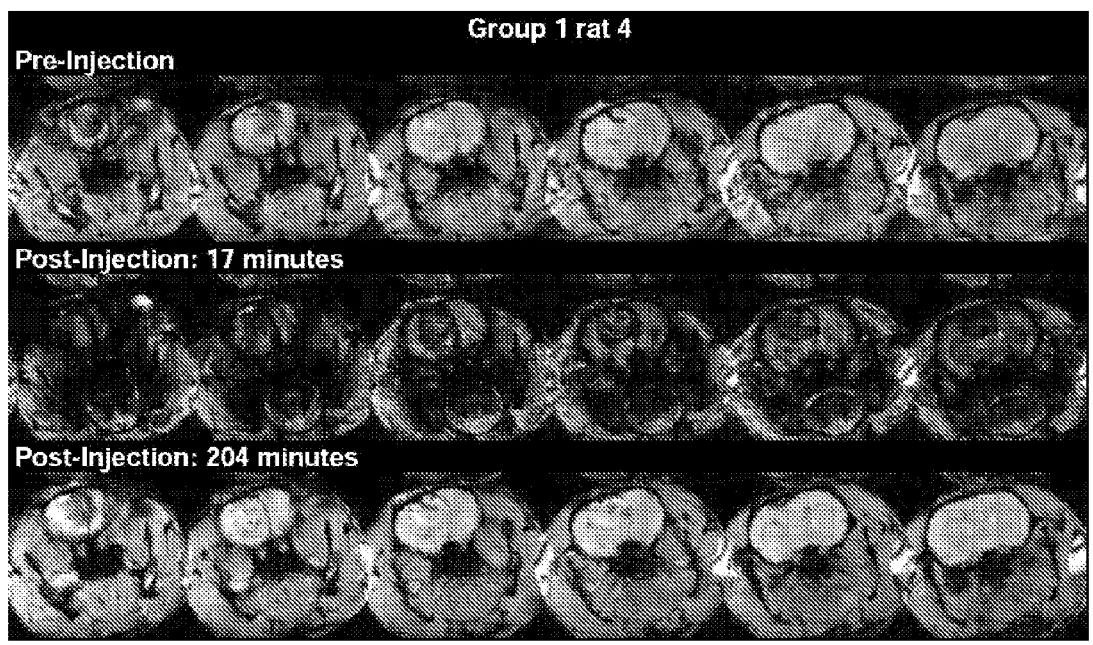
FIG. 13 depicts contrast enhancement in the brain of one animal studied following intravenous administration of HS-2-177.

Significant contrast enhancement was detected in the brains of three animals studied following intravenous administration of HS-2-177. See FIG. 12 and FIG. 13. The tumor signal was approximately decreased to the noise level 1-2 minutes after the injection. Heterogeneity was observed across the tumor in all cases, which is typical due to normal tumor heterogeneity. The mean tumor CNR value obtained was 10 (averaged over the entire tumor in each case), with two animals showing CNR values of 13 (range=4-13). The commercial standard in this agent class has shown peak CNR of 50-60. The mean brain/tumor signal ratio for HS-2-177 was calculated to be 2.1 (range=1.9-2.5). In previous work, Feridex produced a brain/tumor signal ratio of approximately 3.

Based on a comparison of a single image acquired at approximately 90 minutes after the HS-2-177 administration with the images acquired immediately after administration, it was estimated by relative concentration exponential decay analyses that the half life for HS-2-177 was approximately 26 minutes. This is less then the half life that has been measured for Feridex (46 minutes). In summary, this study demonstrated that HS-2-177 was well tolerated and had favorable in vivo contrast enhancement properties that approximate those of Feridex in the 9L tumor model.

Example 20

Figure 14:
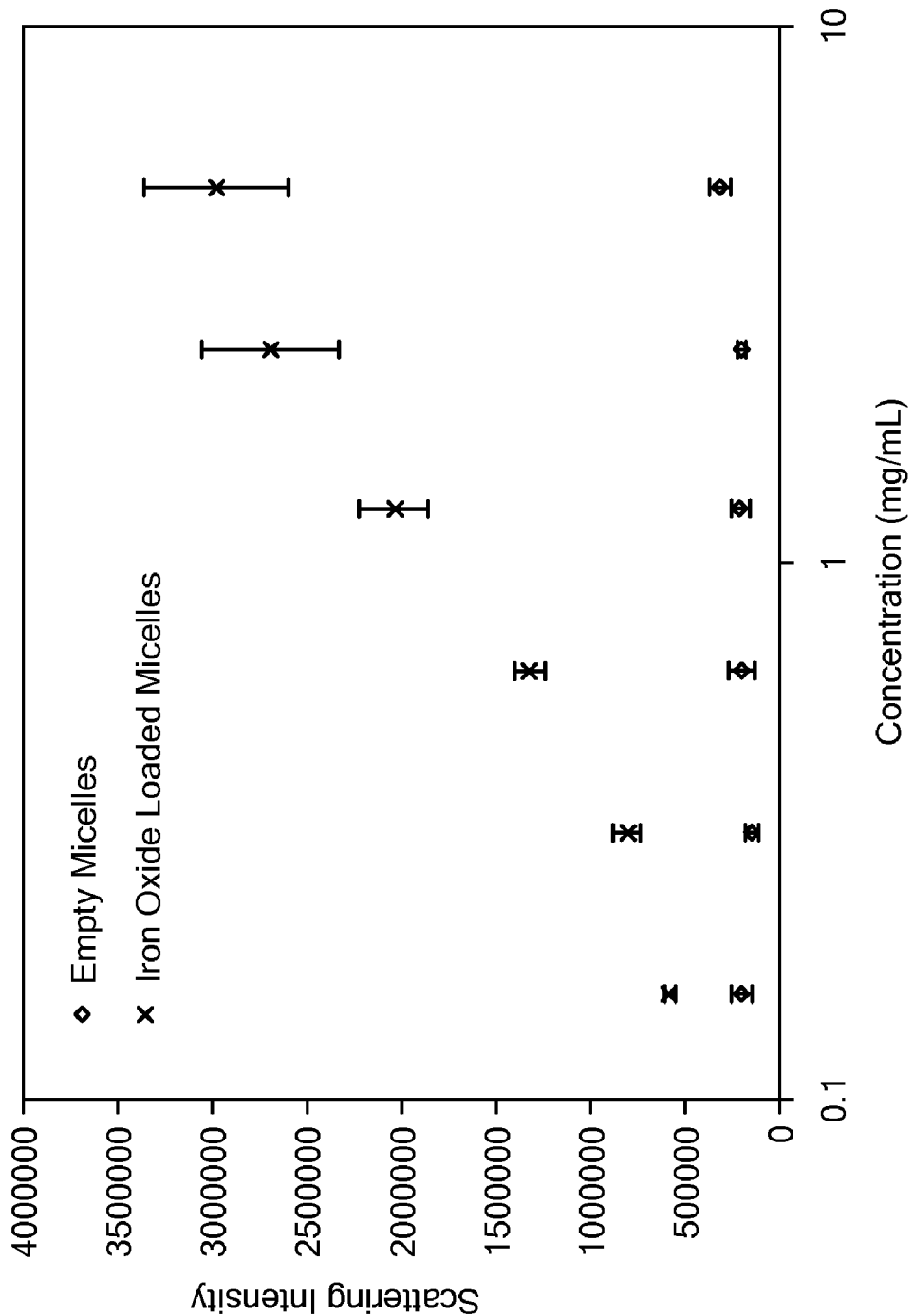
FIG. 14 depicts light scattering of iron oxide loaded micelles (HS-2-177) as compared to empty micelles.
Figure 15:
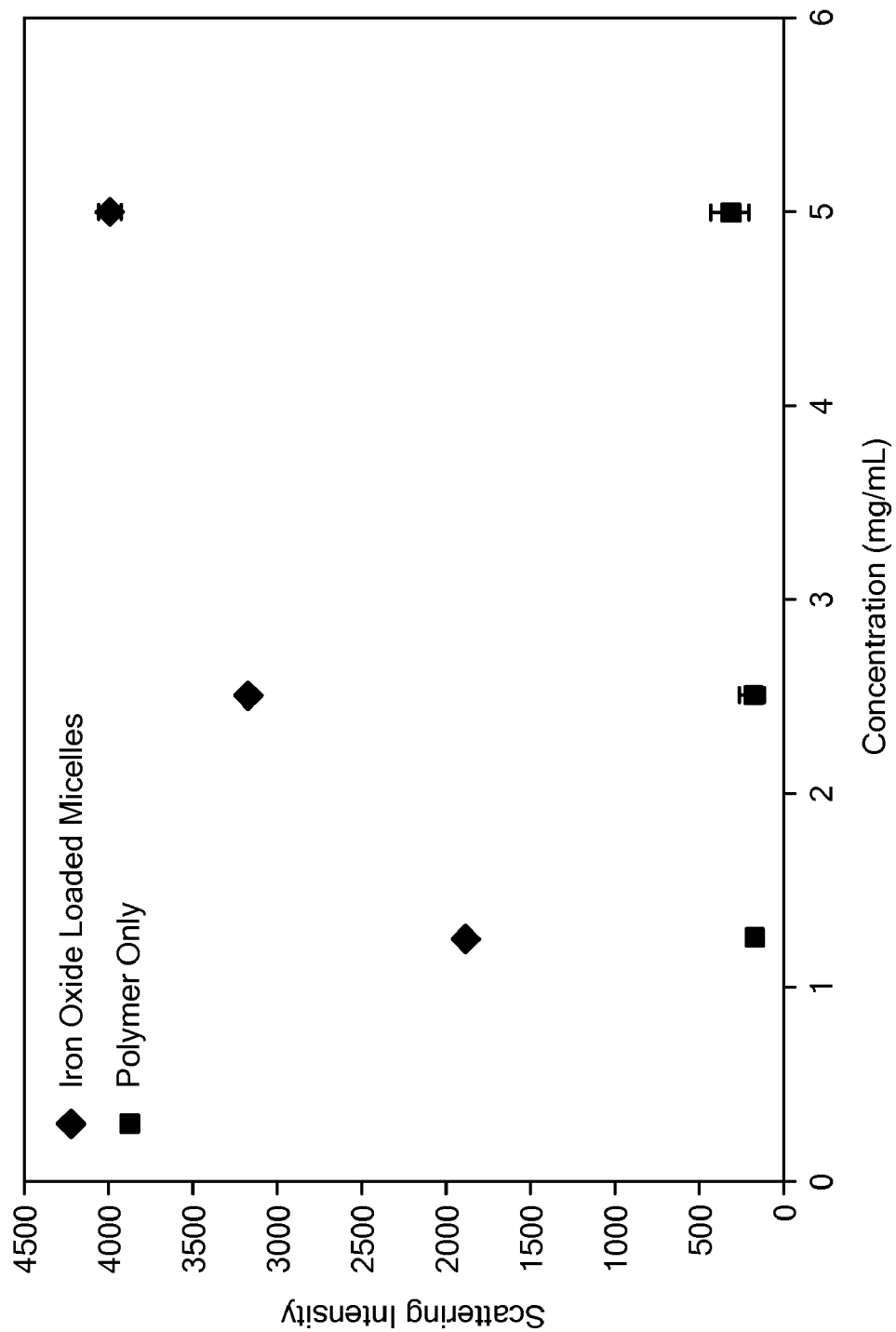
FIG. 15 depicts light scattering of iron oxide loaded micelles (HS-2-113) as compared to polymer.

As depicted in FIGS. 14 and 15, empty micelles and iron oxide loaded micelles were dissolved at various concentrations in an aqueous solution of sodium dodecyl sulfate (5 mg/mL) and the scattering intensity recorded for each solution. FIG. 14 depicts HS-2-177 compared to mPEG227-b-(PAsp)$_{10}$-b-(PAsp$_{15}$-co-PLBzAsp$_{15}$)-Ac). FIG. 15 depicts HS-2-113 compared to (mPEG227-b-(PAsp)$_{10}$-b-(PAsp$_{15}$-co-PBzGlu$_{15}$)-Ac). The significantly higher scattering intensity for the iron oxide loaded micelles suggests the persistence of the micellar structure throughout dilution. Dynamic light scattering of the iron oxide loaded micelle solutions exhibited a size distribution centered around 60 nm, confirming the presence of micelles throughout the dilution. DLS sizing of the empty micelle solution exhibited a size distribution of less than ten nanometers, indicating free polymer and the disruption of the micelle structure.

Example 21

The focus of this study was to measure the R1 and R2 relaxivities of HS-2-177 as a function of concentration using MRI, and to benchmark the measured relaxivity values against those measured for Feridex in a previous study.

HS-2-177 was obtained as a brown powder and was stored in a dark dry cabinet. It was serially diluted with sterile saline for relaxivity imaging, resulting in suspensions that varied from an opaque black appearance (highest concentration) to a transparent appearance (lowest concentration). The intermediate concentrations were transparent in appearance with varying shades of brown. The various concentrations of the test agent were contained in 0.2 ml Eppendorf tubes. The concentrations formulated were:
Tube 1: 0.300 mg/ml; Tube 2: 0.200 mg/ml
Tube 3: 0.120 mg/ml
Tube 4: 0.060 mg/ml
Tube 5: 0.030 mg/ml Imaging The sample tubes containing the concentrations listed above were arranged such that all the tubes could be imaged simultaneously. The tubes were imaged using the following scans and scan parameters:

TABLE 14

MRI Scans Used with Associated Variable Parameters

| Relaxivity Type | Image Scan Type | Variable Parameters |
|---|---|---|
| R1 | Spin-echo | Repetition Time (TR) = 0.1, 0.2, 0.4, 0.7, 1, 2, 5, 7.5, 10, 15, 20 s |
| R2 | Spin-echo | Echo time (TE) = 8.4, 10, 12.5, 15, 20, 25, 30, 40, 50, 75, 150, 300, 600 ms |

For the R1 measurements, an echo time of 8 ms was used, and for the R2 measurements, a repetition time of 2 s was used. All images were acquired using three 1.5 mm thick transaxial slices through the tubes. The images were manually segmented by defining regions-of-interest (ROIs) for each tube in each slice of each image, and calculating the signal intensity time courses for each tube, averaged over all three slices.

The R2 data were then fitted to a decaying exponential to calculate R2:

$$S = S0 * \exp(-R2 * t) + C$$

where S=signal intensity, t=time, S0=signal intensity for t=0, C=constant (offset).

The R1 data were fitted to an exponential recovery:

$$S = Seq * (1 - \exp(-R1 * t)) + C$$

where S=signal intensity, Seq=asymptotic signal value, t=time, C=constant (offset).

All fitting was performed using the Sigmaplot mathematical package. R1 and R2 relaxivity were then calculated as a function of Fe concentration by performing a linear regression over the relaxivity (R1 or R2) vs. concentration curve, and expressed in the standard units of $s^{-1}$ mmol $Fe^{-1}$. Historical data for the FDA approved Fe-based contrast agent, Feridex, was used as a relaxivity benchmark.

Results

Figure 16:
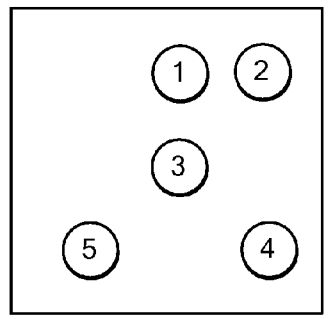
FIG. 16 depicts individual images showing signal increase with repetition time for R1 determination for HS-2-177.
Figure 16:
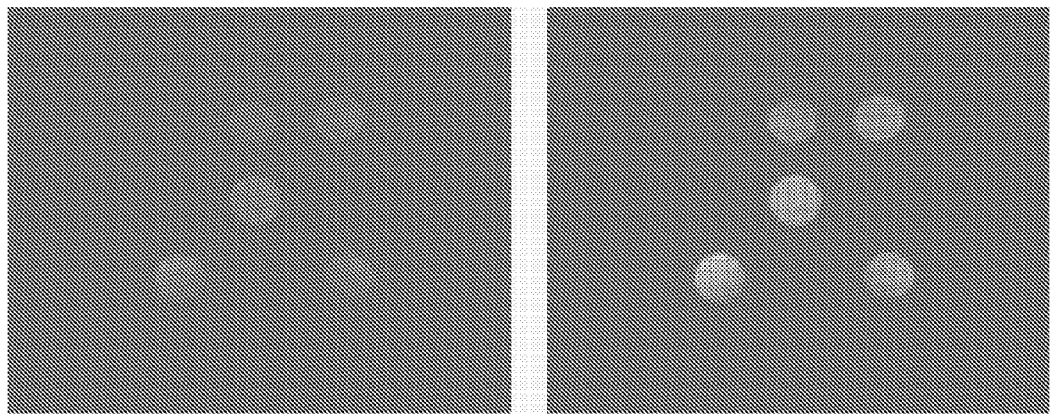
Figure 16:
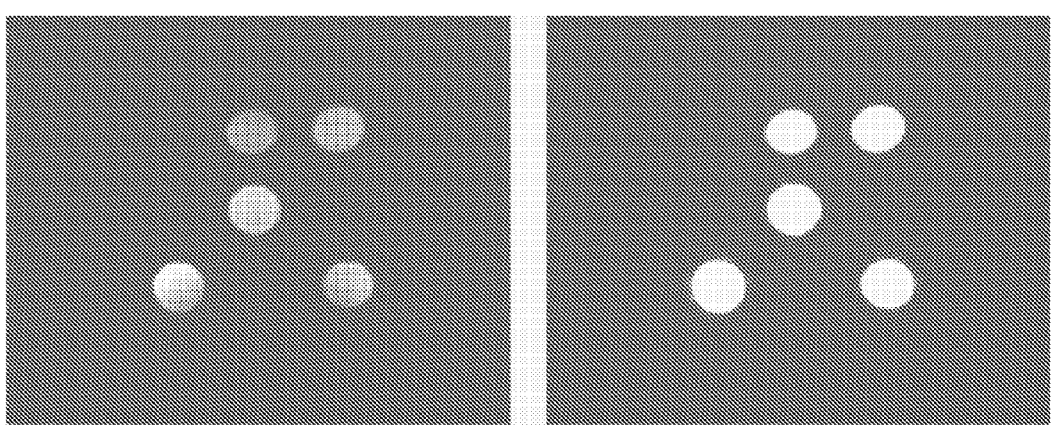
Figure 17:
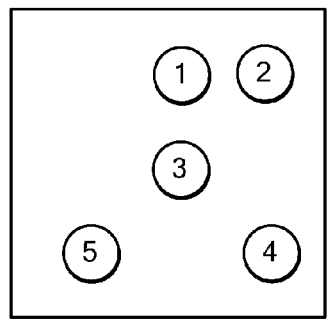
FIG. 17 depicts individual images showing decrease with echo time for R2 determinations for HS-2-177.
Figure 17:
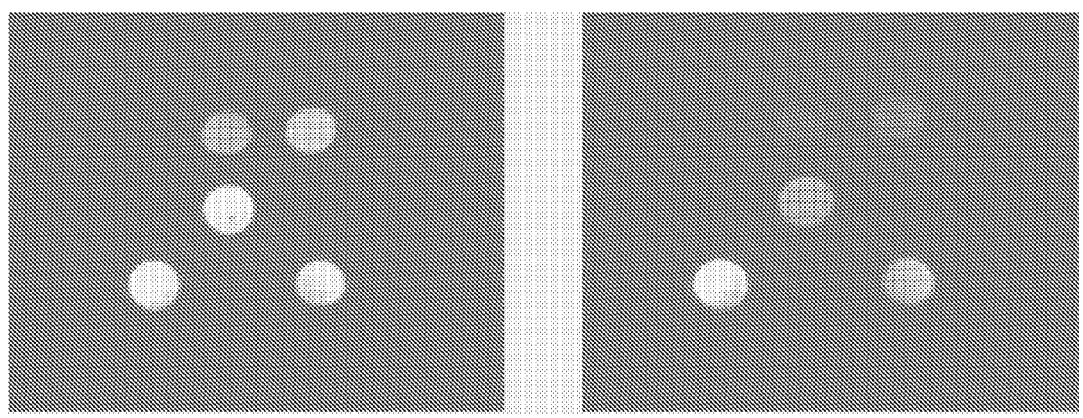
Figure 17:
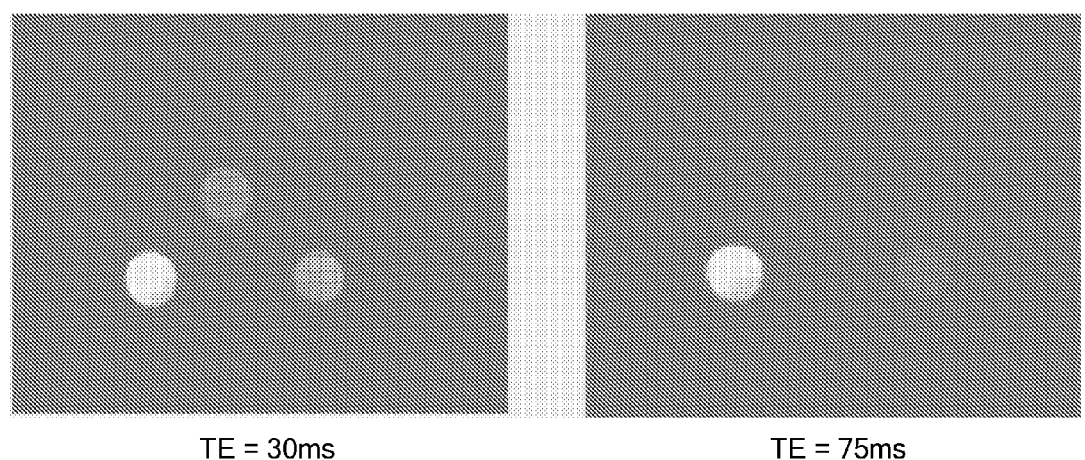

Individual images showing signal decrease with echo time (for R2 determinations) and signal increase with repetition time (for R1 determination) are displayed in FIGS. 16 and 17.

TABLE 15

Calculated Relaxivities for Each Dilution of HS-2-177

| Concentration (mg/ml) | R1 ($s^{-1}$) HS-2-177 | R2 ($s^{-1}$) HS-2-177 |
|---|---|---|
| 0.300 | 1.49 | 159.07 |
| 0.200 | 2.52 | 104.48 |
| 0.120 | 0.98 | 51.94 |
| 0.060 | 0.57 | 28.46 |
| 0.03 | 0.36 | 4.34 |

Table 16, below, shows the linear correlations between relaxivity and concentration for HS-2-177 and Feridex, for R1 and R2.

TABLE 16

Concentration-Dependent Relaxivity Comparisons Between HS-2-177 and Feridex

| Relaxivity Parameter | HS-2-17 | Feridex |
|---|---|---|
| R1 ($s^{-1}$ mmol $Fe^{-1}$) | 3.3 | 0.68 |
| R2 ($s^{-1}$ mmol $Fe^{-1}$) | 237 | 100 |

As reported in Table 16, above, the measured relaxivity values show that R1 and R2 relaxivities for HS-2-177 were higher than those of Feridex.

Example 22

The purpose of this study was to determine the effect of particle size and weight loading on R1 and R2 relaxivity of $MnFe_2O_4$ loaded micelles. These nanoparticle-loaded micelles were prepared with 7 nm, 11 nm, and 15 nm $MnFe_2O_4$ particles with feed ratios of 20%, 50%, 60% or 80% by mass with respect to the polymer. $MnFe_2O_4$ loaded micelles were prepared according to Example 14. The actual Fe concentration was determined by fully dissolving the micelles in 10% $HNO_3$ then subjecting this solution to ICP-MS analysis.

Samples for relaxivity measurements were prepared by dissolving ca. 2 mg of micelle in 10% $D_2O$ in $H_2O$, then serially diluting the samples four times to give a range of Fe concentrations. R1 and R2 values were calculated for each Fe concentration from measurements performed on a 400 MHz NMR under the following conditions:

$T_1$ measurements performed using an inversion recovery pulse sequence with recovery times of 0.1000, 0.1479, 0.2169, 0.3234, 0.4782, 0.7071, 1.0456, 1.5463, 2.2865, 3.3812, and 5.0000 seconds. The $T_1$ value was calculated by the VNMRJ 2.2C software package. The $R_1$ value for each sample was calculated by the following equation:

$$R1 = \frac{1}{T_1}$$

The R1 values were plotted against the iron concentration in mmol/L and a linear regression (y=mx) fit to the data, where the slope of the line is equal to the R1 relaxivity.

R2 measurements were performed using a Carr-Purcell pulse sequence with echo times of 0.00500, 0.00793, 0.01257, 0.01994, 0.03162, 0.05014, 0.07952, 0.1261, and 0.2000 seconds. The amplitude of the H$_2$O resonance was recorded for each echo time and plotted against the echo time. The data was fitted to the following equation:

$$y = a * e^{-R2x}$$

The R2 values for each sample were plotted against Fe concentration in mmol/L and the data fit to a linear regression (y=mx), where the slope of the line is equal to the R2 relaxivity.

A summary of the results is found in Table 17.

TABLE 17

| Micelle | Target wt % | ICP wt % | R1 | R2 | Contrast (R2/R1) |
|---|---|---|---|---|---|
| 7 nm particles | | | | | |
| HS-2-235-20 | 20 | 4.13 | 3.00 | 85.0 | 28 |
| HS-2-235-50 | 50 | 4.76 | 3.07 | 108.0 | 35 |
| 11 nm particles | | | | | |
| HS-2-236-20 | 20 | 7.27 | 2.66 | 146.6 | 55 |
| HS-2-236-50 | 50 | 11.84 | 2.23 | 381.7 | 171 |
| 15 nm particles | | | | | |
| HS-2-237-20 | 20 | 15.69 | 1.07 | 177.2 | 166 |
| HS-2-237-50 | 50 | 22.07 | 0.87 | 711.7 | 818 |
| HS-2-237-60 | 60 | 25.96 | 0.68 | 605.0 | 890 |
| HS-2-237-80 | 80 | 24.88 | 0.51 | 491.1 | 963 |

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A micelle, having a contrast agent encapsulated therein, comprising a multiblock copolymer of formula I:

wherein:
  n is 10-2500;
  m is 5-50;
  m' is 5-50;
  $R^x$ is a natural or unnatural amino acid side-chain group that is capable of crosslinking;
  $R^y$ is a hydrophobic or ionic, natural or unnatural amino acid side-chain group;
  $R^1$ is —Z(CH$_2$CH$_2$Y)$_p$(CH$_2$)$_t$R$^3$, wherein:
    Z is —O—, —S—, —C≡C—, or —CH$_2$—;
    each Y is independently —O— or —S—;
    p is 0-10;
    t is 0-10; and $R^3$ is hydrogen, —N$_3$, —CN, a mono-protected amine, a di-protected amine, a protected aldehyde, a protected hydroxyl, a protected carboxylic acid, a protected thiol, a 9-30 membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;

Q is a valence bond or a bivalent, saturated or unsaturated, straight or branched C$_{1-12}$ hydrocarbon chain, wherein 0-6 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:
  -Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;

$R^{2a}$ is a mono-protected amine, a di-protected amine, —N(R$^4$)$_2$, —NR$^4$C(O)R$^4$, —NR$^4$C(O)N(R$^4$)$_2$, —NR$^4$C(O)OR$^4$, or —NR$^4$SO$_2$R$^4$; and each $R^4$ is independently an optionally substituted group selected from hydrogen, aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety, or:
  two $R^4$ on the same nitrogen atom are taken together with said nitrogen atom to form an optionally substituted 4-7 membered saturated, partially unsaturated, or aryl ring having 1-4 heteroatoms independently selected from nitrogen, oxygen, or sulfur.

2. The micelle according to claim 1, wherein $R^3$ is an optionally substituted aliphatic group.

3. The micelle according to claim 1, wherein $R^3$ is an azide-containing group or an alkyne-containing group.

4. The micelle according to claim 1, wherein Q is a valence bond.

5. The micelle according to claim 1, wherein Q is a bivalent, saturated C$_{1-12}$ alkylene chain, wherein 0-6 methylene units of Q are independently replaced by -Cy-, —O—, —NH—, —S—, —OC(O)—, —C(O)O—, or —C(O)—, wherein -Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur.

6. The micelle according to claim 1, wherein $R^x$ is a natural or unnatural amino acid side-chain group selected from a glutamic acid side-chain, an aspartic acid side-chain, a cysteine side-chain, a serine side-chain, an aldehyde containing side-chain, an imidazole containing side-chain, a benzimidazole containing side-chain, a lysine side-chain, an arginine side-chain, or a histidine side-chain.

7. The micelle according to claim 1, wherein $R^y$ is a hydrophobic amino acid side-chain selected from a suitably protected aspartic acid, a suitably protected glutamic acid, a suitably protected tyrosine side-chain, a suitably protected serine side-chain, a suitably protected threonine side-chain, a phenylalanine side-chain, an alanine side-chain, a valine side-chain, a leucine side-chain, a tryptophan side-chain, a proline side-chain, or a mixture thereof.

8. The micelle according to claim 1, wherein $R^y$ comprises a mixture of hydrophobic and hydrophilic amino acid side-chain groups such that the overall poly(amino acid) block comprising $R^y$ is hydrophobic.

9. The micelle according to claim 1, wherein $R^y$ consists of a mixture of D-hydrophobic and L-hydrophilic amino acid side-chain groups such that the overall poly(amino acid) block comprising $R^y$ is hydrophobic and is a mixture of D- and L-configured amino acids.

10. The micelle according to claim 1, wherein $R^y$ consists of a mixture of hydrophobic amino acid side-chain groups selected from D-leucine, D-phenylalanine, D-alanine, D-benzyl aspartate, or D-benzyl glutamate, and one or more of L-tyrosine, L-cysteine, L-aspartic acid, L-glutamic acid, L-DOPA, L-histidine, L-lysine, or L-ornithine.

11. The micelle according to claim 9, wherein the mixture of D-hydrophobic and L-hydrophilic amino acid side-chain groups is selected from D-leucine/L-tyrosine, D-leucine/L-aspartic acid, D-leucine/L-glutamic acid, D-phenylalanine/L-tyrosine, D- phenylalanine/L-aspartic acid, D-phenylalanine/L-glutamic acid, D-phenylalanine/L-serine, D-benzyl aspartate/L-tyrosine, D-benzyl aspartate/L-aspartic acid, D-benzyl aspartate/L-glutamic acid, D-benzyl glutamate/L-tyrosine, D-benzyl glutamate/L-aspartic acid.

12. The micelle according to claim 2, wherein $R^{2a}$ is —NHC(O)R$^4$, —NHR$^4$ or —N(R$^4$)$_2$, wherein each R$^4$ is an optionally substituted aliphatic group.

13. The micelle according to claim 1, wherein $R^{2a}$ is —NHR$^4$ or —N(R$^4$)$_2$, wherein each R$^4$ is independently methyl, ethyl, propyl, butyl, pentyl, hexyl, 2-(tetrahydropyran-2-yloxy)ethyl, pyridin-2-yldisulfanylmethyl, methyldisulfanylmethyl, (4-acetylenylphenyl)methyl, 3-(methoxycarbonyl)-prop-2-ynyl, methoxycarbonylmethyl, 2-(N-methyl-N-(4-acetylenylphenyl)carbonylamino)-ethyl, 2-phthalimidoethyl, 4-bromobenzyl, 4-chlorobenzyl, 4-fluorobenzyl, 4-iodobenzyl, 4-propargyloxybenzyl, 2-nitrobenzyl, 4-(bis-4-acetylenylbenzyl)aminomethyl-benzyl, 4-propargyloxy-benzyl, 4-dipropargylamino-benzyl, 4-(2-propargyloxy-ethyldisulfanyl)benzyl, 2-propargyloxy-ethyl, 2-propargyldisulfanyl-ethyl, 4-propargyloxy-butyl, 2-(N-methyl-N-propargylamino)ethyl, 2-(2-dipropargylaminoethoxy)-ethyl, vinyl, allyl, crotyl, 2-propenyl, but-3-enyl, —CH$_2$CN, —CH$_2$CH$_2$CN, —CH$_2$CH(OCH$_3$)$_2$, 4-(bisbenzyloxymethyl)phenylmethyl, —C≡CH, —CH$_2$C≡CH, —CH$_2$C≡CCH$_3$, or —CH$_2$CH$_2$C≡CH.

14. The micelle according to claim 1, wherein the contrast agent is selected from a magnetic nanoparticle or a semiconductor nanoparticle.

15. The micelle according to claim 1, wherein the contrast agent is selected from Fe, Fe$_2$O$_3$, Fe$_3$O$_4$, MnFe$_2$O$_4$, CoFe$_2$O$_4$, NiFe$_2$O$_4$, Co, Ni, FePt, CoPt, CoO, Fe$_3$Pt, Fe$_2$Pt, CO$_3$Pt, CO$_2$Pt, or FeOOH.

\* \* \* \* \*